US010025187B2

(12) United States Patent
Nagahara et al.

(10) Patent No.: US 10,025,187 B2
(45) Date of Patent: Jul. 17, 2018

(54) PHOTOSENSITIZATION CHEMICAL-AMPLIFICATION TYPE RESIST MATERIAL, METHOD FOR FORMING PATTERN USING SAME, SEMICONDUCTOR DEVICE, MASK FOR LITHOGRAPHY, AND TEMPLATE FOR NANOIMPRINTING

(71) Applicants: TOKYO ELECTRON LIMITED, Tokyo (JP); OSAKA UNIVERSITY, Osaka (JP)

(72) Inventors: Seiji Nagahara, Tokyo (JP); Seiichi Tagawa, Suita (JP); Akihiro Oshima, Suita (JP)

(73) Assignees: TOKYO ELECTRON LIMITED, Tokyo (JP); OSAKA UNIVERSITY, Osaka (JP)

( * ) Notice: Subject to any disclaimer, the term of this patent is extended or adjusted under 35 U.S.C. 154(b) by 14 days.

(21) Appl. No.: 15/117,686

(22) PCT Filed: Feb. 17, 2015

(86) PCT No.: PCT/JP2015/054325
§ 371 (c)(1),
(2) Date: Aug. 9, 2016

(87) PCT Pub. No.: WO2015/125788
PCT Pub. Date: Aug. 27, 2015

(65) Prior Publication Data
US 2016/0357103 A1 Dec. 8, 2016

(30) Foreign Application Priority Data

Feb. 21, 2014 (JP) ................................. 2014-032281
Feb. 17, 2015 (JP) ................................. 2015-028423

(51) Int. Cl.
G03F 7/004 (2006.01)
G03F 7/039 (2006.01)
(Continued)

(52) U.S. Cl.
CPC .......... *G03F 7/0397* (2013.01); *C07C 303/32* (2013.01); *C07C 309/07* (2013.01);
(Continued)

(58) Field of Classification Search
CPC ...... G03F 7/004; G03F 7/2002; G03F 7/0397; G03F 7/32; G03F 7/38; H01L 21/0274;
(Continued)

(56) References Cited

U.S. PATENT DOCUMENTS 8,124,326 B2 * 2/2012 Shirley ................ G03F 7/2022
430/322
8,900,791 B2 * 12/2014 Tsuchimura .......... C07C 309/29
430/270.1
(Continued)

FOREIGN PATENT DOCUMENTS

EP 0 622 682 A1 3/1994
EP 2 960 926 12/2015
(Continued)

OTHER PUBLICATIONS

Machine translation of JP 2014-224984 (no date).*
(Continued)

Primary Examiner — Amanda C Walke
(74) Attorney, Agent, or Firm — Squire Patton Boggs (US) LLP

(57) ABSTRACT

A photosensitization chemical-amplification type resist material according to the present invention is used for a two-stage exposure lithography process, and contains (1) a developable base component and (2) a component generating a photosensitizer and an acid through exposure. Among (Continued)

three components consisting of (a) an acid-photosensitizer generator, (b) a photosensitizer precursor, and (c) a photoacid generator, the above component contains only the component (a), any two components, or all of the components (a) to (c).

41 Claims, 13 Drawing Sheets

(51) Int. Cl.
| | | |
|---|---|---|
| G03F 7/32 | (2006.01) | |
| C07C 381/12 | (2006.01) | |
| C07C 309/07 | (2006.01) | |
| C07C 303/32 | (2006.01) | |
| H01L 21/027 | (2006.01) | |
| C08F 220/14 | (2006.01) | |
| C08F 220/22 | (2006.01) | |
| C08F 220/38 | (2006.01) | |
| C08F 220/28 | (2006.01) | |
| G03F 7/38 | (2006.01) | |
| G03F 7/038 | (2006.01) | |
| G03F 7/20 | (2006.01) | |
| G03F 1/20 | (2012.01) | |
| G03F 1/24 | (2012.01) | |
| G03F 1/26 | (2012.01) | |
| G03F 7/16 | (2006.01) | |

(52) U.S. Cl.
CPC .......... *C07C 381/12* (2013.01); *C08F 220/14* (2013.01); *C08F 220/22* (2013.01); *C08F 220/28* (2013.01); *C08F 220/38* (2013.01); *G03F 1/20* (2013.01); *G03F 1/24* (2013.01); *G03F 1/26* (2013.01); *G03F 7/0045* (2013.01); *G03F 7/0382* (2013.01); *G03F 7/16* (2013.01); *G03F 7/2002* (2013.01); *G03F 7/2022* (2013.01); *G03F 7/2041* (2013.01); *G03F 7/32* (2013.01); *G03F 7/322* (2013.01); *G03F 7/38* (2013.01); *H01L 21/0274* (2013.01)

(58) Field of Classification Search
CPC ... C07C 381/12; C07C 303/32; C07C 309/07; C08F 220/14; C08F 220/28; C08F 220/38; C08F 220/22
USPC ............ 430/270.1, 322, 325, 330, 331, 913; 560/1, 103, 149, 9, 83; 526/243, 281
See application file for complete search history.

(56) References Cited

U.S. PATENT DOCUMENTS

| 9,045,398 | B2* | 6/2015 | Suzuki | C07C 309/06 |
|---|---|---|---|---|
| 9,156,785 | B2* | 10/2015 | Aqad | C07C 63/72 |
| 9,244,347 | B2* | 1/2016 | Komuro | C07C 381/12 |
| 9,720,323 | B2* | 8/2017 | Kotake | G03F 7/0392 |
| 2006/0269879 | A1 | 11/2006 | Elian | G03F 7/203 |
| | | | | 430/394 |
| 2011/0151540 | A1* | 6/2011 | Taran | C12N 9/16 |
| | | | | 435/197 |
| 2013/0224659 | A1* | 8/2013 | Ohashi | C08F 220/18 |
| | | | | 430/285.1 |
| 2013/0344435 | A1* | 12/2013 | Utsumi | G03F 7/039 |
| | | | | 430/270.1 |
| 2014/0377706 | A1* | 12/2014 | Hatakeyama | G03F 7/32 |
| | | | | 430/296 |
| 2015/0086926 | A1* | 3/2015 | Ohashi | C07C 381/12 |
| | | | | 430/285.1 |
| 2016/0004160 | A1* | 1/2016 | Tagawa | G03F 7/38 |
| | | | | 430/296 |
| 2016/0194300 | A1* | 7/2016 | Enomoto | H01L 21/0271 |
| | | | | 216/87 |
| 2016/0195809 | A1* | 7/2016 | Ochiai | G03F 7/038 |
| | | | | 430/270.1 |

FOREIGN PATENT DOCUMENTS

| JP | H4-151156 | 5/1992 |
|---|---|---|
| JP | H4-162040 | 6/1992 |
| JP | H5-005995 | 1/1993 |
| JP | H5-197148 | 8/1993 |
| JP | H5-249676 | 9/1993 |
| JP | H6-194834 | 7/1994 |
| JP | H8-146608 | 6/1996 |
| JP | H10-083079 | 3/1998 |
| JP | 2002-174894 | 6/2002 |
| JP | 2006-039129 | 2/2006 |
| JP | 2007-126582 | 5/2007 |
| JP | 2010-077377 | 4/2010 |
| JP | 2010-219456 | 9/2010 |
| JP | 2013-228526 | 11/2013 |
| JP | 2014-224984 | 12/2014 |
| TW | 201438059 A | 10/2014 |
| WO | WO 2010/058656 | 9/2009 |
| WO | WO 2012/033138 | 3/2012 |
| WO | WO 2014/129556 | 2/2014 |
| WO | WO 2014/208076 | 12/2014 |
| WO | WO 2014/208102 | 12/2014 |
| WO | WO 2015/019616 | 2/2015 |

OTHER PUBLICATIONS

International Search Report of PCT application PCT/JP2015/054325, dated Mar. 31, 2015.

Jiang, Jing et al., "Metal Oxide Nanoparticle Photoresists for EUV Patterning," Journal of Photopolymer Science and Technology, vol. 27, No. 5, Aug. 1, 2014, pp. 663-666.

Nakagawa, Hisashi et al., "Recent EUV Resists toward High Volume Manufacturing," Journal of Photopolymer Science and Technology, vol. 27, No. 6, 2014, Jan. 7, 2015, pp. 739-746.

Tagawa, Seiichi et al., "A technology increasing the speed of the next-generation semiconductor manufacturing ten times or more has been established. Big step toward realization of extreme ultra violet (EUV) Lithography (Jisedai no Handotai Seize no Sokudo o 10 Bailjo ni suru Gijutsu o Kakuritsu)", Internet URL: http://www.sanken.osaka-u.ac.jp/jp/operationlpdfi'press/tagawa20130619.pdf press Release, OsEika University, Jun. 19, 23, press release Jun. 24, 2013, announced on Jun. 28, 2013 at the 3oth InternationIII Conference ofPhotopolymer Science end Technology[retrievel date Mar. 13, 2015), Jun. 19, 2013. Partial Translation.

Tagawa, Seiichi et al., "Super High Sensitivity Enhancement by Photo-Sensitized Chemically Amplified Resist (PS-CAR) Process," Journal of Photopolymer Science and Technology, vol. 26, No. 6, Jan. 8, 2014, pp. 825-830.

Trikeriotis, et al., "Nanoparticle photoresists from HfO$_2$ and ZrO$_2$ for EUV patterning," Journal ofPhotopolynner Science and Technology, vol. 25, No. 5, Jul. 26, 2012, pp. 583-586.

* cited by examiner

PHOTOSENSITIZATION CHEMICAL-AMPLIFICATION TYPE RESIST MATERIAL, METHOD FOR FORMING PATTERN USING SAME, SEMICONDUCTOR DEVICE, MASK FOR LITHOGRAPHY, AND TEMPLATE FOR NANOIMPRINTING

TECHNICAL FIELD

The present invention relates to a photosensitization chemical-amplification type resist material, a method for forming a pattern using the same, a semiconductor device, a mask for lithography, and a template for nanoimprinting.

BACKGROUND ART

As one of the fundamental techniques for manufacturing next-generation semiconductor devices, extreme ultraviolet ray (EUV) lithography is drawing attention. EUV lithography is a pattern forming technique using BUY light having a wavelength of 13.5 nm as an exposure light source. EUV lithography has been demonstrated to be able to form an extremely fine pattern (for example, equal to or smaller than 20 nm) in an exposure step of a semiconductor device manufacturing process.

However, because EUV light sources having been developed at this point in time have low power, the exposure treatment takes a long time, and hence EUV lithography has currently not yet been put to practical use. In order to compensate for the low power of an EUV light source, a method of improving the sensitivity of a resist material (photosensitive resin) has been considered (see Patent Literature 1). The problems with EUV are also found in the power and sensitivity of lithography using electron beams, ion beams, or the like as a light source.

CITATION LIST

Patent Literature

[Patent Literature 1] Japanese Unexamined Patent Publication Application No. 2002-174894

SUMMARY OF INVENTION

Technical Problem

With the technique of the related art, it is difficult to achieve both of higher sensitivity and better lithography characteristics (high resolution, low pattern roughness, and the like). If it is possible to improve the sensitivity while maintaining excellent lithography characteristics, not only in lithography using EUV, electron beams, ion beams, or the like as a light source, but also in lithography using a KrF excimer laser or an ArF excimer laser as a light source, the number of pulses of the laser can be decreased, and the maintenance costs can be reduced. Therefore, the present invention aims to provide a resist material which makes it possible to achieve both of high sensitivity and excellent lithography characteristics in a pattern forming technique using ionizing radiation such as EUV, electron beams, or ion beams, or non-ionizing radiation such as a KrF excimer laser or an ArF excimer laser. The present invention also aims to provide a method for forming a pattern using the aforementioned resist material, a semiconductor device, a mask for lithography, and a template for nanoimprinting.

Solution to Problem

A photosensitization chemical-amplification type resist material according to the present invention is used as a photosensitive resin composition in a lithography process including a pattern-exposure step of irradiating a predetermined site of a resist material film formed using the photosensitive resin composition with ionizing radiation or non-ionizing radiation having a wavelength of equal to or less than 400 nm, a flood-exposure step of irradiating the resist material film having undergone the pattern-exposure step with non-ionizing radiation having a wavelength which is longer than the wavelength of the non-ionizing radiation in the pattern-exposure step and is greater than 200 nm, a baking step of heating the resist material film having undergone the flood-exposure step, and a developing step of forming a resist pattern by bringing the resist material film having undergone the baking step into contact with a developer. The photosensitization chemical-amplification type resist material contains (1) a base component making a portion subjected to the pattern-exposure soluble or insoluble in the developer after the baking step and (2) a component generating a photosensitizer and an acid by exposure.

The component (2) is the following component (a), contains any two components among the following components (a) to (c), or contains all of the following components (a) to (c).

(a) An acid-photosensitizer generator generating an acid and a photosensitizer, which absorbs non-ionizing radiation having a wavelength of greater than 200 nm, by being irradiated with ionizing radiation or non-ionizing radiation having a wavelength of equal to or less than 400 nm.

(b) A photosensitizer precursor becoming a photosensitizer, which absorbs non-ionizing radiation having a wavelength of greater than 200 nm, by being irradiated with ionizing radiation or non-ionizing radiation having a wavelength of equal to or less than 400 nm.

(c) A photoacid generator generating an acid by being irradiated with ionizing radiation or non-ionizing radiation having a wavelength of equal to or less than 400 nm.

According to the photosensitization chemical-amplification type resist material, both of high sensitivity and excellent lithography characteristics can be sufficiently achieved. Accordingly, even in a case where a low-power light source is used in the pattern-exposure step, a fine pattern can be formed.

Advantageous Effects of Invention

According to the present invention, there is provided a chemical-amplification type resist material which makes it possible to achieve both of high sensitivity and extremely excellent lithography characteristics in a pattern forming technique using ionizing radiation such as EUV light, electron beams or ion beams, or non-ionizing radiation having a wavelength of equal to or less than 400 nm such as a KrF excimer laser or an ArF excimer laser. Furthermore, according to the present invention, there are provided a method for forming a pattern, a semiconductor device, a mask for lithography, and a template for nanoimprinting using the resist material.

BRIEF DESCRIPTION OF DRAWINGS

FIG. 6A is a cross-sectional view showing a resist pattern forming step, FIG. 6B is a cross-sectional view showing an etching step, and FIG. 6C is a cross-sectional view showing a resist pattern removing step.

DESCRIPTION OF EMBODIMENTS

Figure 1:
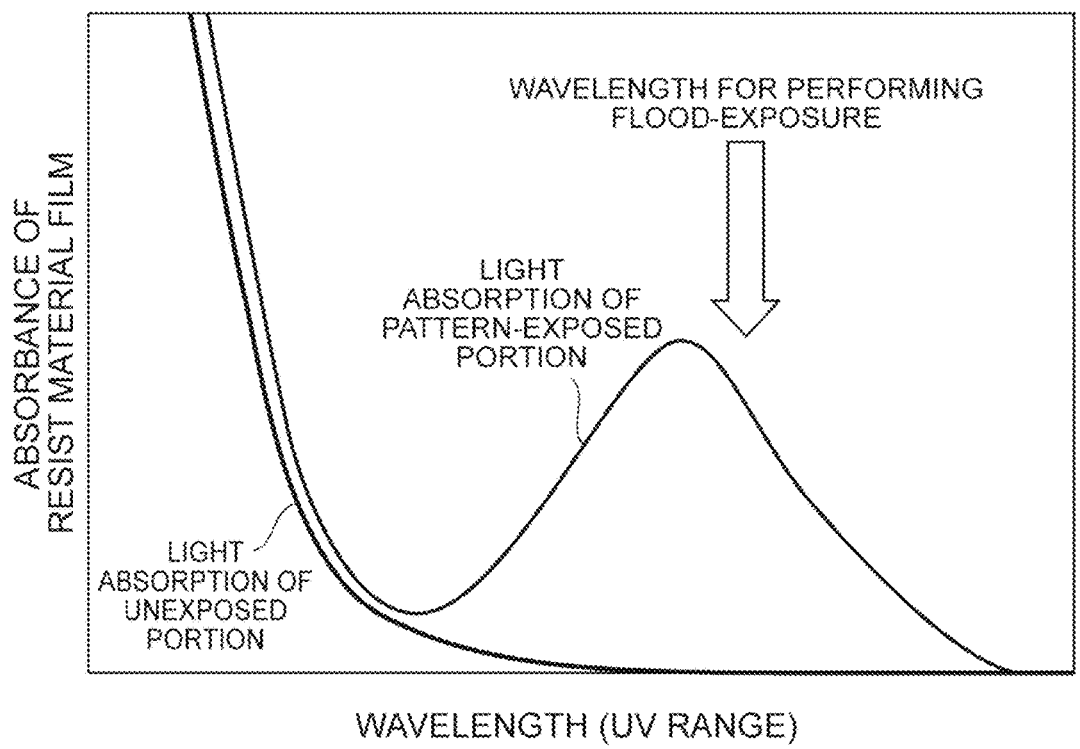
FIG. 1 is a schematic view graphically showing the absorbances of a pattern-exposed portion and an unexposed portion of a resist material film.

Hereinafter, embodiments of the present invention will be specifically described, but the present invention is not limited to the following embodiments.

<Photosensitization Chemical-Amplification Type Resist Material>

A photosensitization chemical-amplification type resist material according to the present embodiment is used as a photosensitive resin composition in a two-stage exposure lithography process. The two-stage exposure lithography process includes a pattern-exposure step, a flood-exposure step, a baking step, and a developing step.

In the pattern-exposure step, a predetermined site of a resist material film formed using the photosensitive resin composition is irradiated with a first radiation. In the flood-exposure step, the resist material film having undergone the pattern-exposure step is irradiated with a second radiation having energy lower than the energy of the wavelength of the first radiation. The flood-exposure is a process in which a region larger than a pattern of the pattern-exposure in size is exposed in a more uniform exposure amount. In the baking step, the resist material film having undergone the flood-exposure step is heated. In the developing step, a resist pattern is formed by bringing the resist material film having undergone the baking step into contact with a developer.

The ionizing radiation is radiation having energy sufficient for ionizing atoms or molecules. In contrast, the non-ionizing radiation is radiation not having energy sufficient for ionizing atoms or molecules. Specific examples of the ionizing radiation include gamma rays, X-rays, alpha rays, heavy particle beams, proton beams, beta rays, ion beams, electron beams, extreme ultraviolet rays, and the like. The ionizing radiation used in the pattern-exposure is preferably electron beams, extreme ultraviolet rays or ion beams, and more preferably electron beams or extreme ultraviolet rays. Specific examples of the non-ionizing radiation include far ultraviolet rays, near ultraviolet rays, visible rays, infrared rays, micro waves, low-frequency waves, and the like. The non-ionizing radiation used in the pattern-exposure is preferably far ultraviolet rays (wavelength: 190 nm to 300 nm). The non-ionizing radiation used in the flood-exposure is preferably near ultraviolet rays (wavelength: 200 nm to 450 nm).

The first radiation used in the pattern-exposure is ionizing radiation or non-ionizing radiation having a wavelength of equal to or less than 400 nm. The wavelength of the non-ionizing radiation is preferably equal to or less than 250 nm and more preferably equal to or less than 200 nm. Furthermore, the wavelength of the non-ionizing radiation is preferably equal to or greater than 150 nm, and more preferably equal to or greater than 190 nm. In a case where the first radiation is non-ionizing radiation, the second radiation used in flood-exposure has a wavelength longer than the wavelength of the non-ionizing radiation used as the first radiation. The second radiation is non-ionizing radiation having a wavelength of greater than 200 nm and is preferably non-ionizing radiation having a wavelength of greater than 250 nm.

The photosensitization chemical-amplification type resist material according to the present embodiment may be a positive resist material or a negative resist material, and is appropriately selected by selecting the base component, the developer, and the like which will be described later. A resist material in which a pattern-exposed portion is dissolved by exposure while a pattern-unexposed portion (radiation-shielded portion) remains is called a positive resist material. In contrast, a resist material in which an unexposed portion is dissolved while an exposed portion (radiation-shielded portion) remains is called a negative resist.

First Embodiment

The photosensitization chemical-amplification type resist material according to the present embodiment (hereinafter, simply referred to as a "resist material" in some cases) contains (1) a base component and (2) a component generating a photosensitizer and an acid by exposure.

(1) Base Component

In the present embodiment, the (1) base component may be an organic compound or an inorganic compound. The organic compound may be a polymer compound or a low-molecular weight compound. It is desired that the base component does not excessively absorb the first radiation in the pattern-exposure and enables the formation of a resist pattern with a shape having sufficiently high verticality. Furthermore, it is desired that the base component absorbs little the second radiation in the flood-exposure and hardly causes an unnecessary sensitization reaction in an unexposed portion at the time of flood-exposure.

The polymer compound is a compound which has a weight average molecular weight of 1,000 to 200,000, preferably 2,000 to 50,000, and more preferably 2,000 to 20,000, and makes the pattern-exposed portion soluble or insoluble in a developer in the developing step through an acid-catalyzed reaction in the baking step (see FIG. 4) after the flood-exposure.

Examples of the polymer compound include a polymer compound having a polar group (for example, an acidic functional group) and a polymer compound in which the polar group is protected with an acid-labile group. The polymer compound having a polar group is soluble in an alkaline developer. However, by reacting with a cross-linking agent, which will be described later, in the baking step, the polymer compound becomes insoluble in an alkaline developer. In this case, in the developing step, the resist material film of the pattern-unexposed portion can be removed by the alkaline developer. Accordingly, in a case where the resist material film formed using the polymer compound described above is developed using the alkaline developer, the resist material functions as a negative resist material.

The polymer compound in which the polar group is protected with an acid-labile group is soluble in an organic developer but is insoluble or poorly soluble in an alkaline developer. The polymer compound, in which the polar group is protected with an acid-labile group, obtains polarity due to the removal (deprotection) of the acid-labile group in the baking step and becomes soluble in an alkaline developer but insoluble in an organic developer. In this case, the resist material film of the pattern-unexposed portion can be removed by the organic developer, and the pattern-exposed portion can be removed by the alkaline developer. Therefore, in a case where the resist material film formed using the polymer compound described above is developed using an organic developer, the resist material functions as a negative resist material. In contrast, in a case where the resist material film formed using the polymer compound is developed using an alkaline developer, the resist material functions as a positive resist material.

Specific examples of the polymer compound include a phenol resin, a (meth)acryl resin, a polyvinyl acetal resin, a polyurethane resin, a polyamide resin, an epoxy resin, a styrene-based resin, a polyester resin, and the like. The polymer compound is preferably a phenol resin, a (meth)acryl resin, or a styrene-based resin, and more preferably a (meth)acryl resin.

The (meth)acryl resin is preferably a polymer compound containing at least one of the constitutional units represented by the following Formulae (VII) and (VIII).

[Chemical Formula 1]

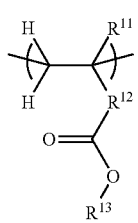

(VII)

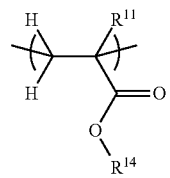

(VIII)

In Formulae (VII) and (VIII), $R^{11}$ represents a hydrogen atom; a fluorine atom; a methyl group; a trifluoromethyl group; a linear, branched or cyclic alkyl group having 1 to 20 carbon atoms that may have a hydroxyl group, an ether bond, an ester bond or a lactone ring; a phenyl group; or a naphthyl group. $R^{12}$ represents a methylene group, a phenylene group, a naphthylene group, or a divalent group represented by C(=O)—O—$R^{12'}$—. $R^{12'}$ represents a linear, branched, or cyclic alkylene group having 1 to 20 carbon atoms that may have any one of a hydroxyl group, an ether bond, an ester bond, and a lactone ring; a phenylene group; or a naphthylene group. Each of $R^{13}$ and $R^{14}$ independently represents a hydrogen atom; a hydroxyl group; a cyano group; a carbonyl group; a carboxyl group; an alkyl group having 1 to 35 carbon atoms; and a protecting group (acid-labile group) having at least one structure selected from the group consisting of an ether bond, an ester bond, a sulfonic acid ester bond, a carbonate bond, a lactone ring, a sultone ring, and two carboxyl groups dehydrated.

The phenol resin is preferably a polymer compound having a constitutional unit represented by the following Formula (XXV).

[Chemical Formula 2]

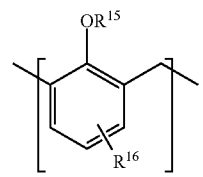

(XXV)

In Formula (XXV), $R^{15}$ represents a hydrogen atom; a hydroxyl group; a cyano group; a carbonyl group; a carboxyl group; an alkyl group having 1 to 35 carbon atoms; and a protecting group (acid-labile group) having at least one structure selected from the group consisting of an ether bond, an ester bond, a sulfonic acid ester bond, a carbonate bond, a lactone ring, a sultone ring, and two carboxyl groups dehydrated.

$R^{16}$ represents a hydrogen atom, an alkyl group having 1 to 35 carbon atoms, or the like. $R^{16}$ is preferably a methyl group and is preferably bonded to a meta-position.

The styrene-based resin is preferably a polyhydroxystyrene resin, and more preferably a polymer compound having a constitutional unit represented by the following Formula (XXVI).

[Chemical Formula 3]

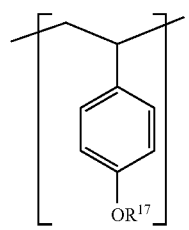

(XXVI)

In Formula (XXVI), $R^{17}$ represents a hydrogen atom; a hydroxyl group; a cyano group; a carbonyl group; a carboxyl group; an alkyl group having 1 to 35 carbon atoms; and a protecting group (acid-labile group) having at least one structure selected from the group consisting of an ether bond, an ester bond, a sulfonic acid ester bond, a carbonate bond, a lactone ring, a sultone ring, and two dehydrated carboxyl groups.

Specific examples of the protecting group represented by $R^{13}$, $R^{14}$, $R^{15}$, and $R^{17}$ include the groups shown below, but the protecting group is not limited thereto. In the following formulae, * represents a binding portion of $R^{13}$, $R^{14}$, $R^{15}$, and $R^{17}$ to oxygen.

[Chemical Formula 4]

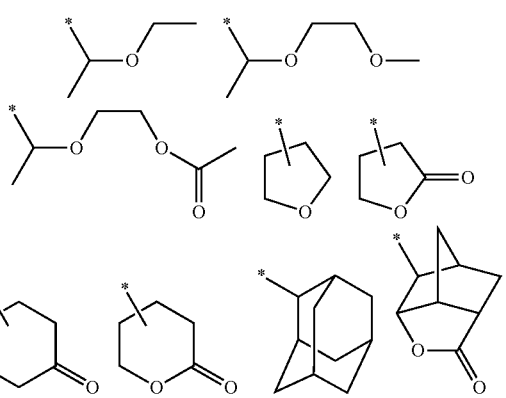

[Chemical Formula 5]

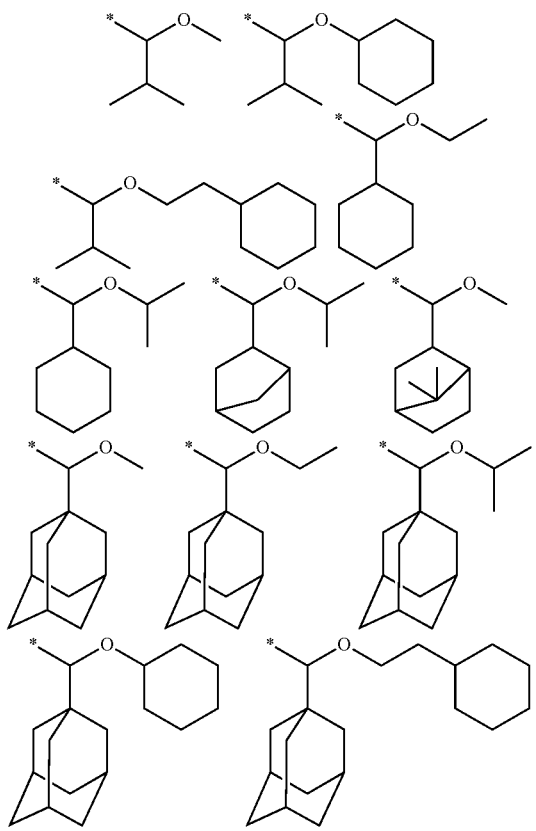

[Chemical Formula 6]

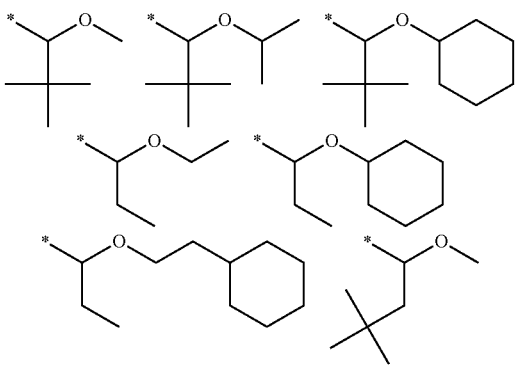

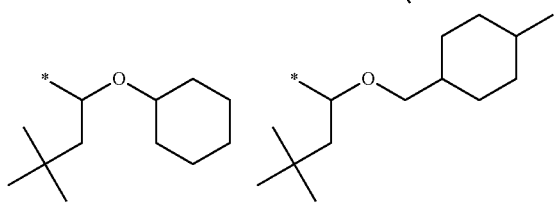

The above constitutional unit may be contained singly in a molecule, or a plurality thereof may be contained in a molecule in combination.

The low-molecular weight compound described above is a compound which has a molecular weight of 300 to 3,000 and preferably 500 to 2,000 and makes a pattern-exposed portion soluble or insoluble in a developer in the developing step through an acid-catalyzed reaction in the baking step (see FIG. 4) after the flood-exposure.

Specific examples of the low-molecular weight compound include a star-shaped molecule such as truxene derivatives, calixarene derivatives, norias, dendrimers, and the like.

Specific examples of the inorganic compound include metal oxide such as cobalt oxide, hafnium oxide and zirconium oxide, and an organic metal compound such as a complex. The metal oxide may be in the form of particles or may be nanoparticles having a nano-order particle size. Furthermore, the metal oxide particles may be coordinated with carboxylic acid or the like. The following is an example of a solubility change caused in a case where an inorganic compound is used as the (1) base component. For example, in a case where nanoparticles of metal oxide coordinated with carboxylic acid are used as the (1) base component, instead of a carboxylate anion, an acid anion generated by exposure is coordinated with the metal oxide, and the interaction between the metal oxide particles is strengthened. Therefore, the resist material can be gelated and inhibited from dissolving in the developing step.

(2) Component Generating Photosensitizer and Acid by Exposure

This is a component generating a photosensitizer and an acid by exposure (radiation irradiation). This component contains, among three components consisting of (a) an acid-photosensitizer generator, (b) a photosensitizer precursor, and (c) a photoacid generator, only the component (a) or any two components, or all of the components (a) to (c). That is, in the resist material, the component (2) is blended with the (1) base component.

(a) Acid-Photosensitizer Generator

The acid-photosensitizer generator is a component which generates both of an acid and a photosensitizer, which absorbs non-ionizing radiation having a wavelength of greater than 200 nm and preferably greater than 250 nm, by being irradiated with ionizing radiation or non-ionizing radiation having a wavelength of equal to or less than 400 nm, preferably equal to or less than 250 nm, and more preferably equal to or less than 200 nm. It is preferable that the non-ionizing radiation the photosensitizer absorbs has a wavelength longer than the wavelength the acid-photosensitizer generator absorbs. It is preferable that the acid-photosensitizer generator is a component which absorbs sufficiently little the non-ionizing radiation having the wavelength for the flood-exposure and does not directly generate an acid.

Examples of the acid-photosensitizer generator include an onium salt compound, a diazomethane compound, a sulfonimide compound, and the like. Examples of the oinum salt compound include a sulfonium salt compound, a tetrahydrothiophenium salt compound, an iodonium salt compound, and the like. The acid-photo sensitizer generator is preferably a sulfonium salt compound or an iodonium salt compound, and more preferably an iodonium salt compound, because these compounds have a high reduction potential.

The sulfonium salt compound is a compound composed of a sulfonium cation and an acid anion. The sulfonium salt compound is preferably at least one compound selected from the group consisting of compounds represented by the following Formulae (I) to (III).

[Chemical Formula 7]

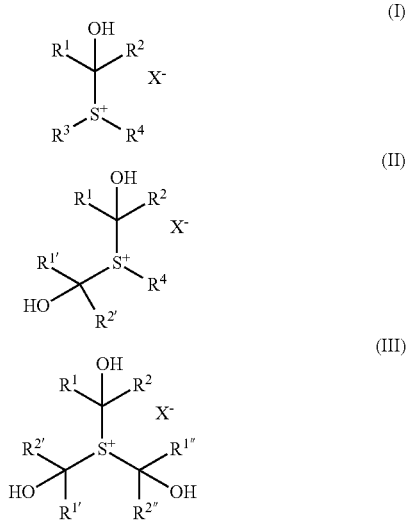

In Formulae (I) to (III), each of $R^1$, $R^2$, $R^{1'}$, $R^{2'}$, $R^{1''}$, $R^{2''}$, $R^3$, and $R^4$ independently represents a hydrogen atom; a phenyl group; a naphthyl group; an anthracenyl group; a phenoxy group; a naphthoxy group; an anthracenoxy group; an amino group; an amide group; a halogen atom; a linear, branched or cyclic and saturated or unsaturated hydrocarbon group (preferably an alkyl group) having 1 to 30 carbon atoms (preferably 1 to 5 carbon atoms); a phenoxy group substituted with an alkoxy group having 1 to 5 carbon atoms, a hydroxyl group, an amino group, an amide group, or an alkyl group having 1 to 5 carbon atoms; a phenyl group substituted with a linear, branched or cyclic and saturated or unsaturated hydrocarbon group (preferably an alkyl group) having 1 to 30 carbon atoms (preferably 1 to 5 carbon atoms), an alkoxy group having 1 to 5 carbon atoms, an amino group, an amide group, or a hydroxyl group; a naphthoxy group substituted with an alkoxy group having 1 to 5 carbon atoms, an alkyl group having 1 to 5 carbon atoms, an amino group, an amide group, or a hydroxyl group; an anthracenoxy group substituted with an alkoxy group having 1 to 5 carbon atoms, an alkyl group having 1 to 5 carbon atoms, an amino group, an amide group, or a hydroxyl group; a linear, branched or cyclic and saturated or unsaturated hydrocarbon group (preferably an alkyl group) having 1 to 30 carbon atoms (preferably 1 to 5 carbon atoms) substituted with an alkoxy group having 1 to 5 carbon atoms, a phenoxy group, a naphthoxy group, an anthracenoxy group, an amino group, an amide group, or a hydroxyl group; or a carbonyl group to which an alkyl group having 1 to 12 carbon atoms is bonded. In Formulae (I) to (III), the hydrogen atom of the hydroxyl group may be substituted with a phenyl group; a halogen atom; a linear, branched or cyclic and saturated or unsaturated hydrocarbon group (preferably an alkyl group) having 1 to 30 carbon atoms (preferably 1 to 5 carbon atoms); or a phenyl group substituted with a linear, branched or cyclic and saturated or unsaturated hydrocarbon group (preferably an alkyl group) having 1 to 30 carbon atoms (preferably 1 to 5 carbon atoms), an alkoxy group having 1 to 5 carbon atoms, or a hydroxyl group. When the hydrogen atom of the hydroxyl group is substituted, the sulfonium salt compound contains a ketal compound group or an acetal compound group. In Formulae (I) to (III), any two or more groups among $R^1$, $R^2$, $R^{1'}$, $R^{2'}$, $R^{1''}$, $R^{2''}$, $R^3$, and $R^4$ may form a cyclic structure by being bonded to each other through a single bond, a double bond, or a bond containing —$CH_2$—, —O—, —S—, —$SO_2$—, —$SO_2NH$—, —C(=O)—, —C(=O)O—, —NHCO—, —NHC(=O)NH—, —$CHR^e$—, —$CR^e{}_2$—, —NH—, or —$NR^e$—. $R^e$ represents a phenyl group; a phenoxy group; a halogen atom; a linear, branched or cyclic and saturated or unsaturated hydrocarbon group (preferably an alkyl group) having 1 to 30 carbon atoms (preferably 1 to 5 carbon atoms); a phenoxy group substituted with an alkoxy group having 1 to 5 carbon atoms, a hydroxyl group, or an alkyl group having 1 to 5 carbon atoms; or a phenyl group substituted with a linear, branched or cyclic and saturated or unsaturated hydrocarbon group (preferably an alkyl group) having 1 to 30 carbon atoms (preferably 1 to 5 carbon atoms), an alkoxy group having 1 to 5 carbon atoms, or a hydroxyl group. Each of $R^1$, $R^2$, $R^{1'}$, $R^{2'}$, $R^{1''}$, $R^{2''}$, $R^3$, and $R^4$ independently preferably represents a phenyl group; a phenoxy group; a phenoxy group substituted with an alkyl group having 1 to 5 carbon atoms; or a phenyl group substituted with an alkoxy group having 1 to 5 carbon atoms or a hydroxyl group. In Formulae (I) to (III), $X^-$ represents an acid anion, preferably represents a strong acid anion, and more preferably a super strong acid anion.

Specific examples of the groups represented by —C(—OH)$R^1R^2$, —C(—OH)$R^{1'}R^{2'}$, —C(—OH)$R^{1''}R^{2''}$, and the like in Formulae (I) to (III) include groups represented by the following formulae. In the following formulae, * represents a binding portion to a sulfur ion in Formulae (I) to (III). In the groups represented by —C(—OH)$R^1R^2$, —C(—OH)$R^{1'}R^{2'}$, and —C(—OH)$R^{1''}R^{2''}$, a hydroxyl group and a carbon atom to which the hydroxyl group is bonded become a carbonyl group by pattern-exposure. In this way, in the compounds represented by Formulae (I) to (III), the groups represented by —C(—OH)$R^1R^2$, —C(—OH)$R^{1'}R^{2'}$, and —C(—OH)$R^{1''}R^{2''}$ are separated after pattern-exposure and generate a photosensitizer.

[Chemical Formula 8]
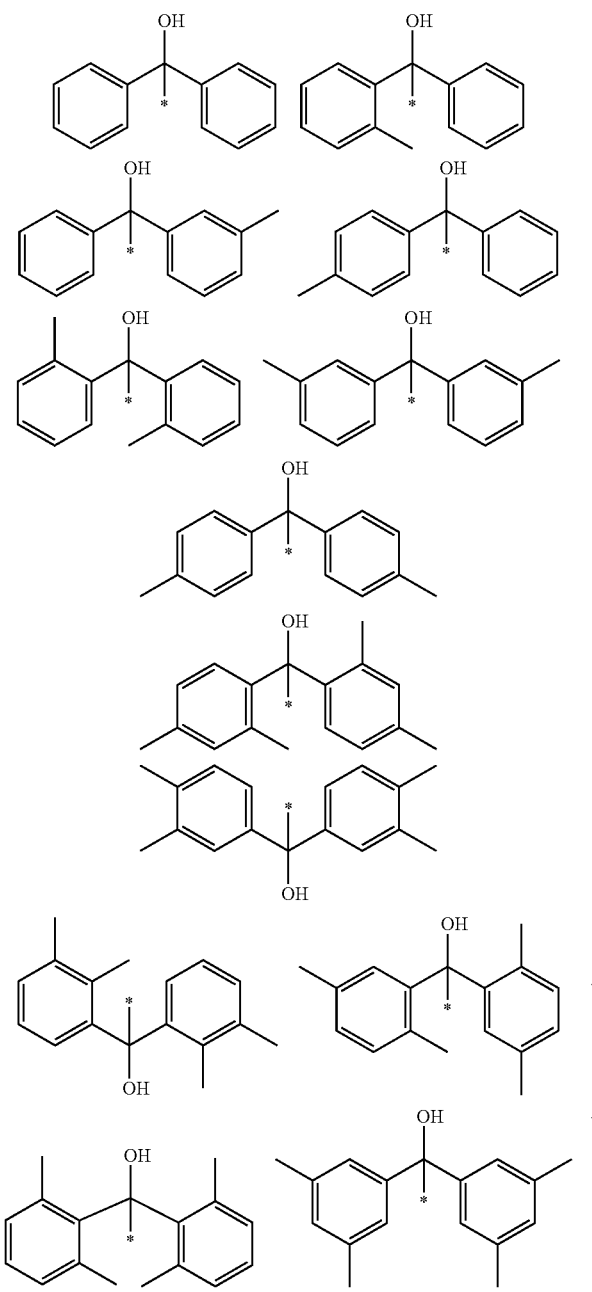
[Chemical Formula 9]
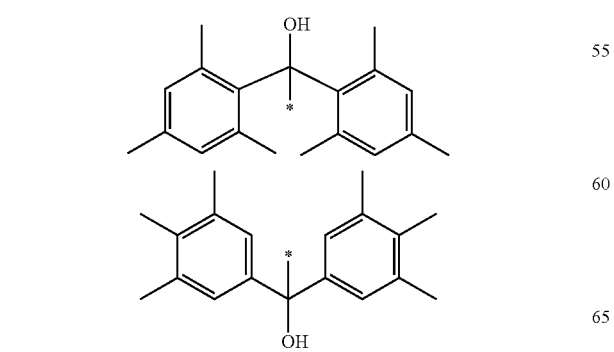
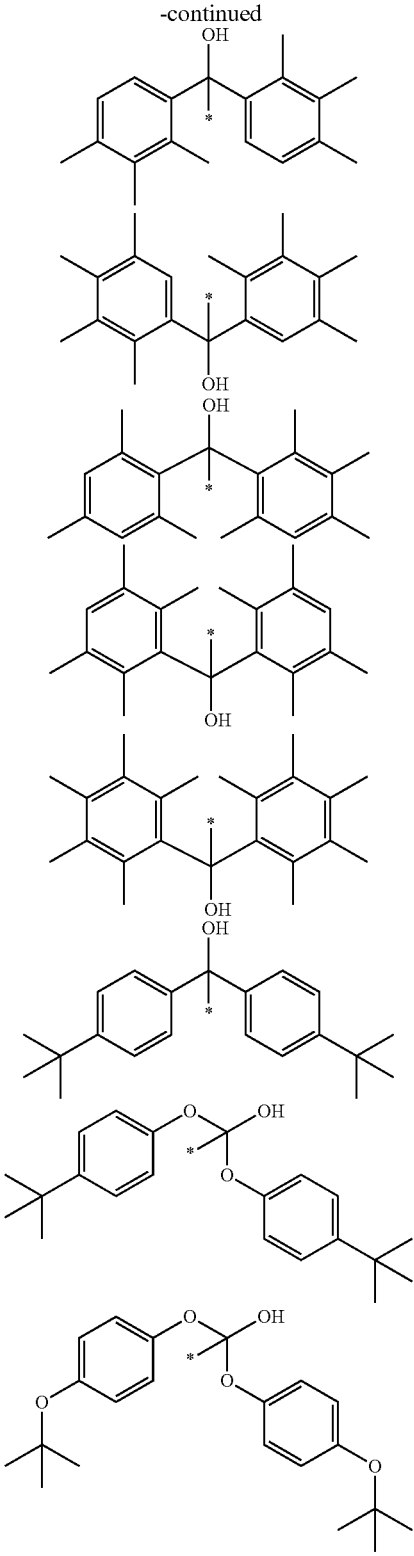
[Chemical Formula 10]
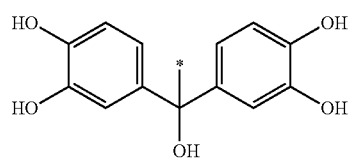

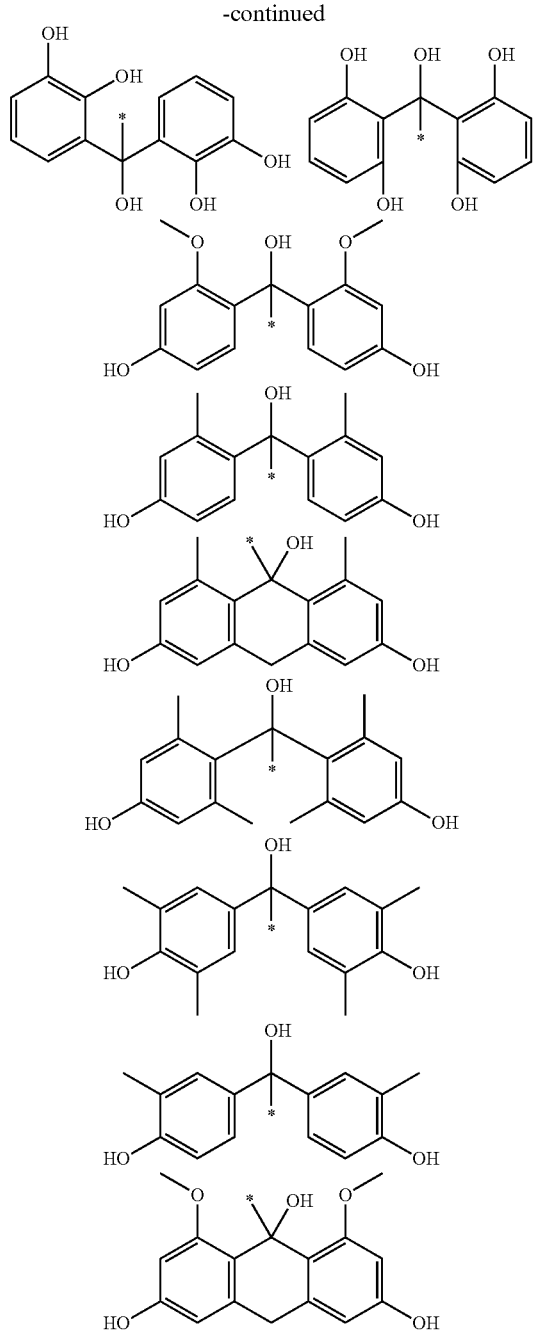
[Chemical Formula 11]
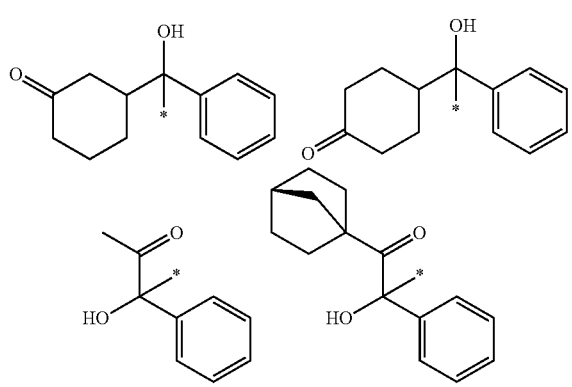
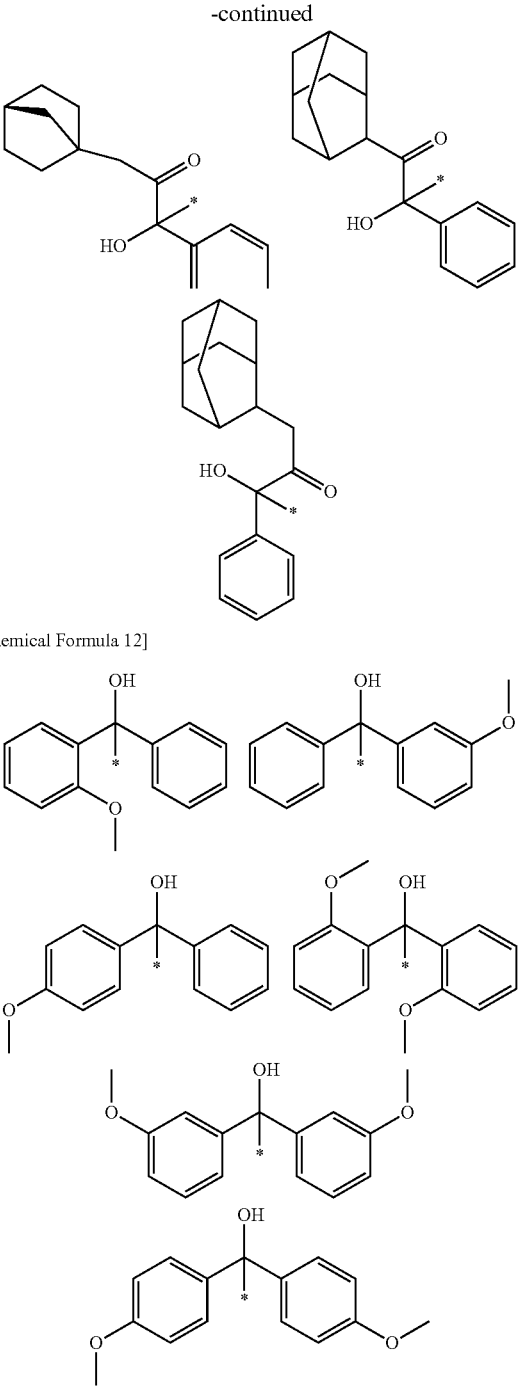
[Chemical Formula 12]
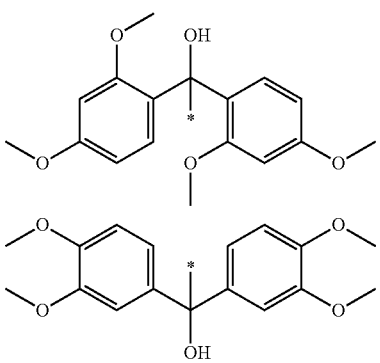

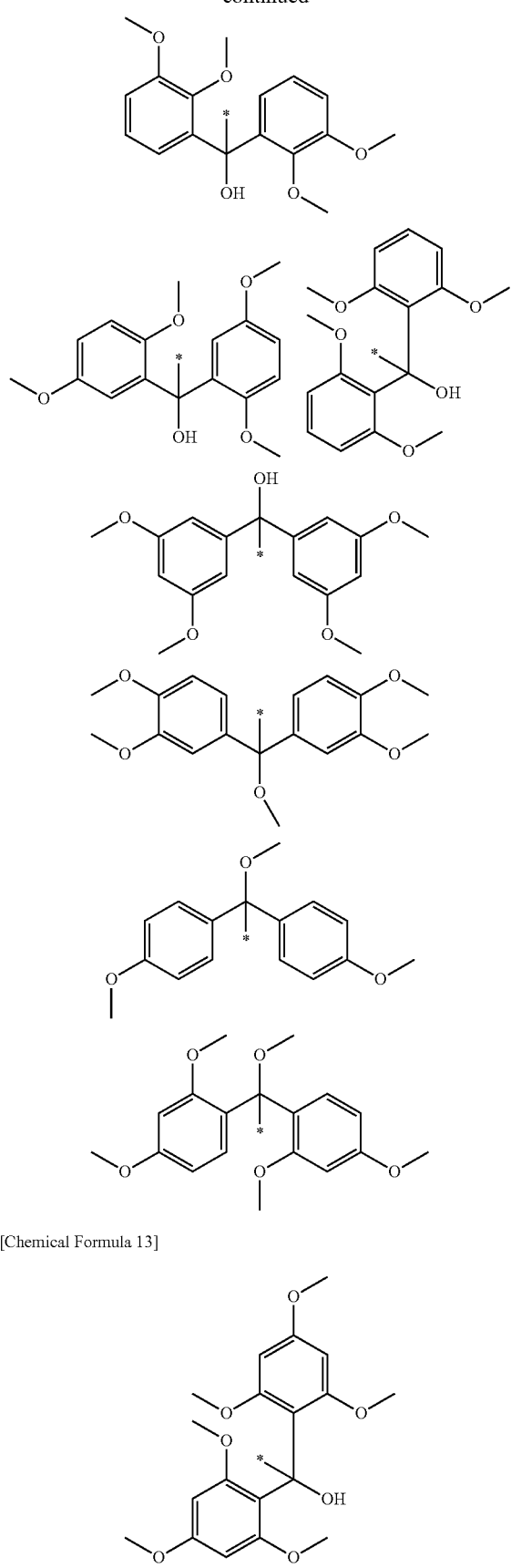
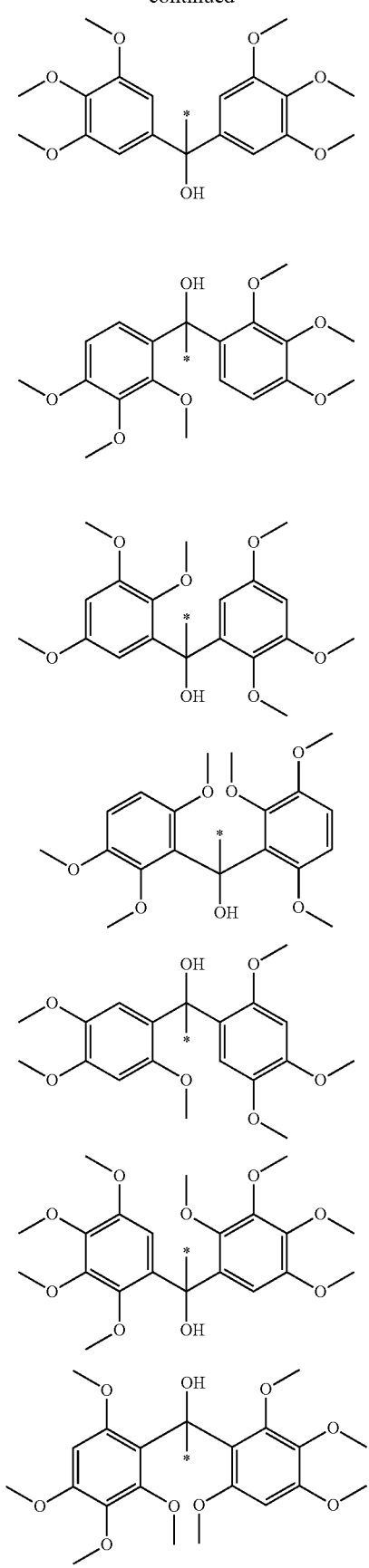
[Chemical Formula 13]

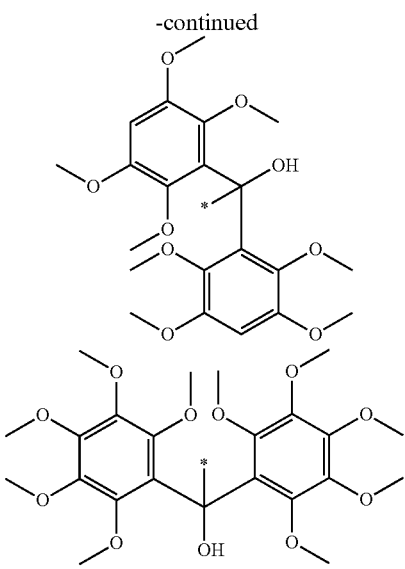
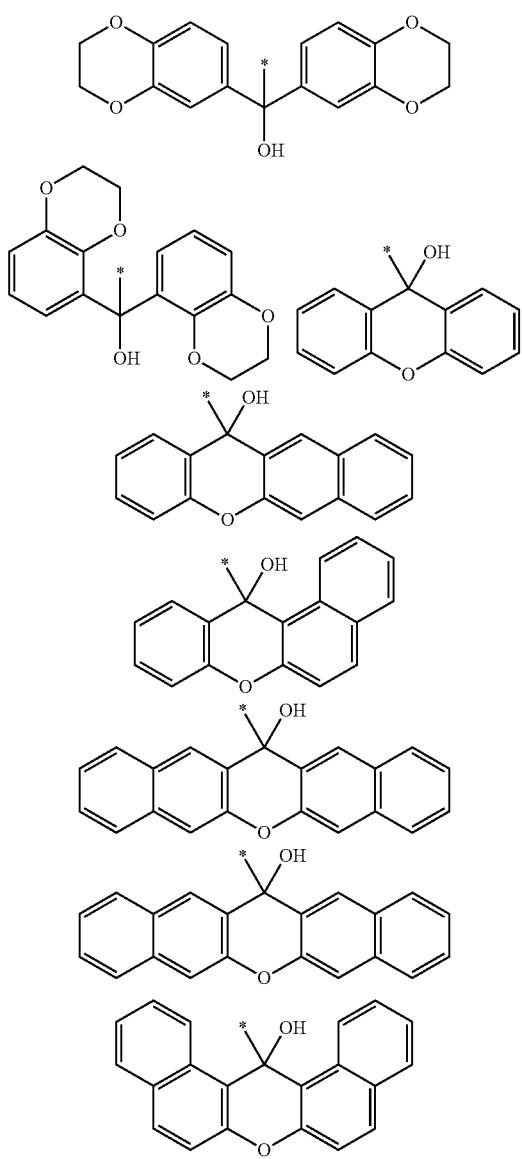
[Chemical Formula 14]
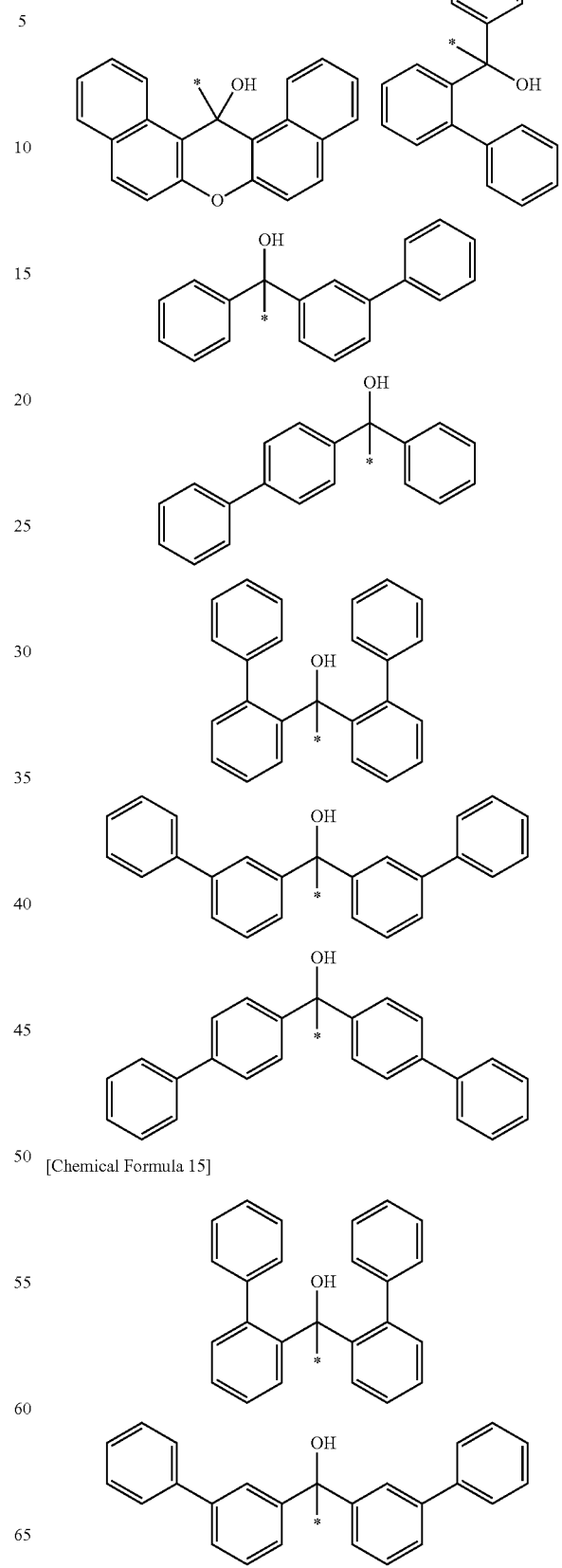
[Chemical Formula 15]

-continued
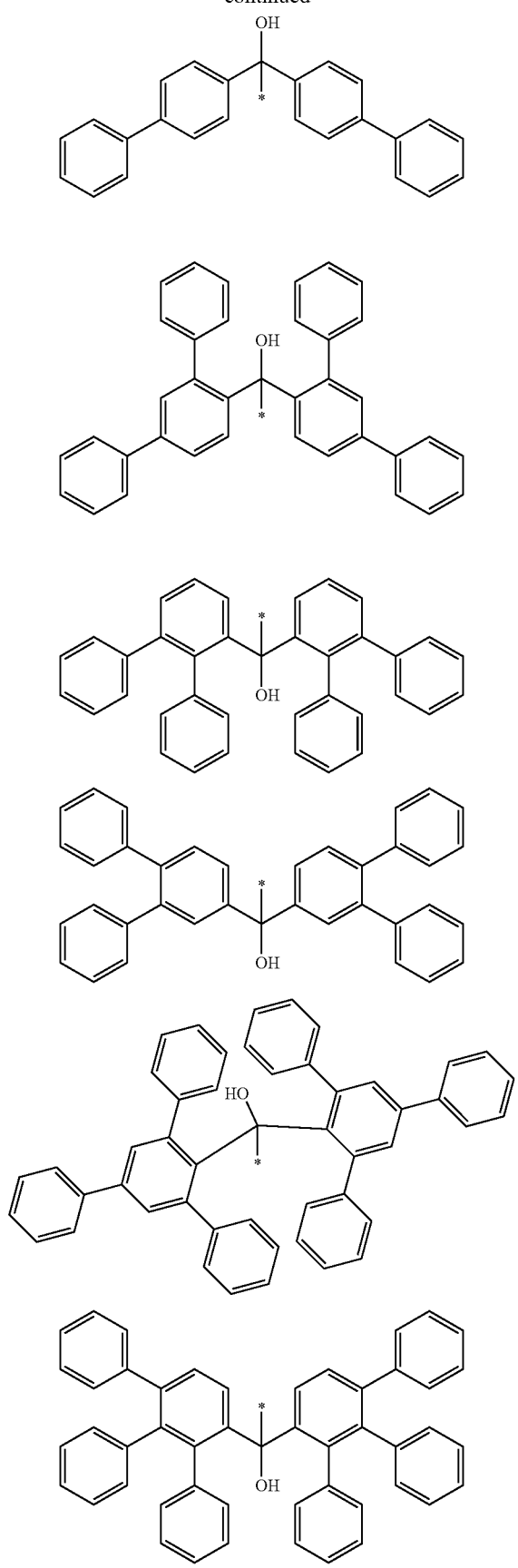
[Chemical Formula 16]
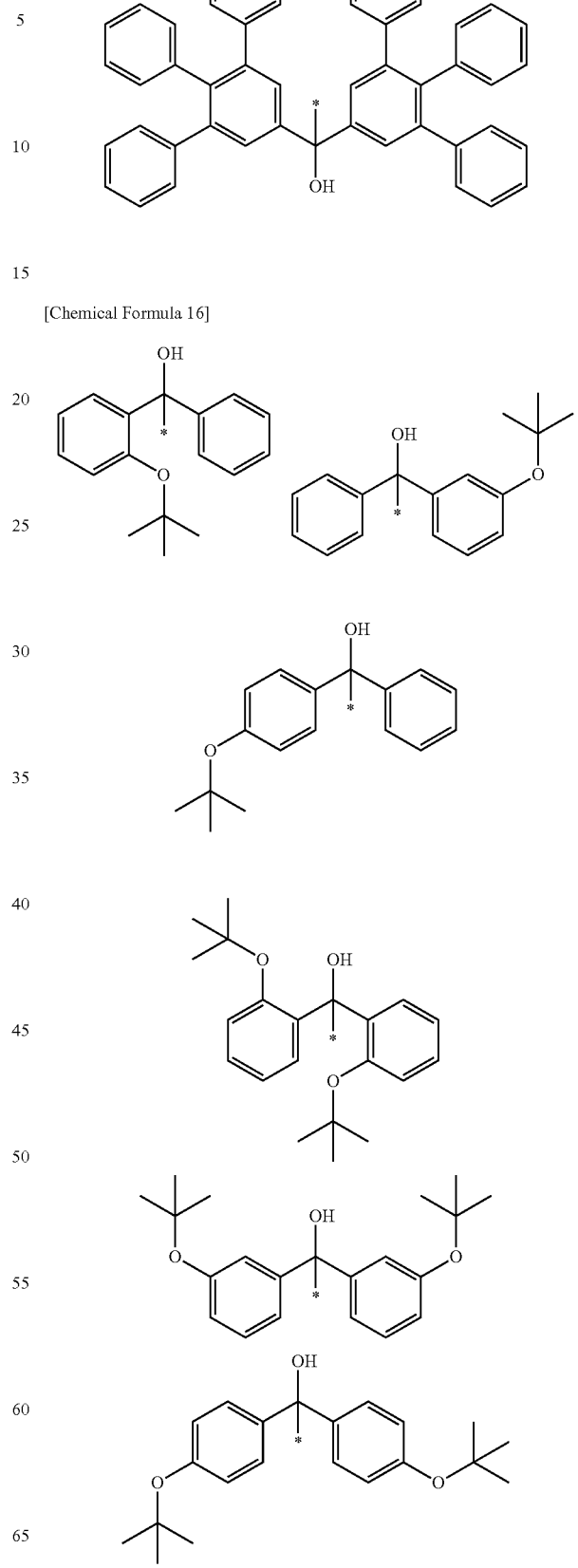

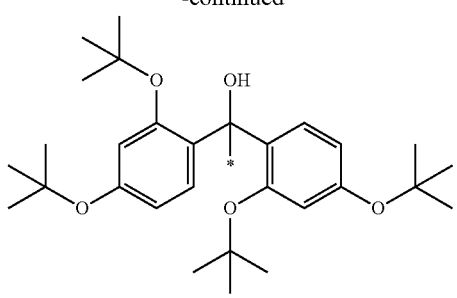
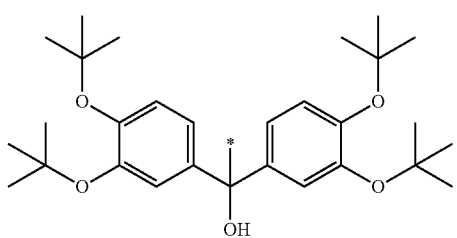
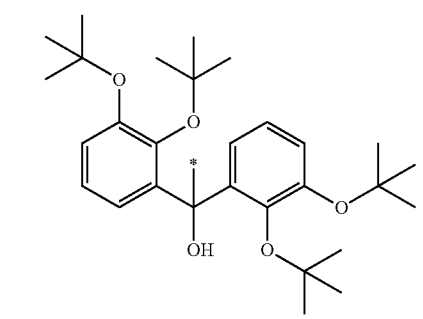
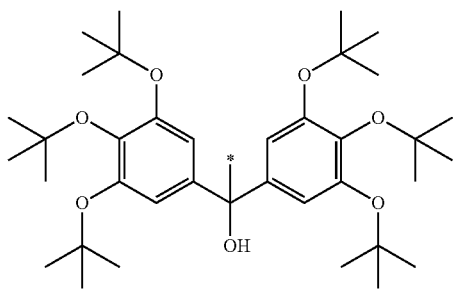
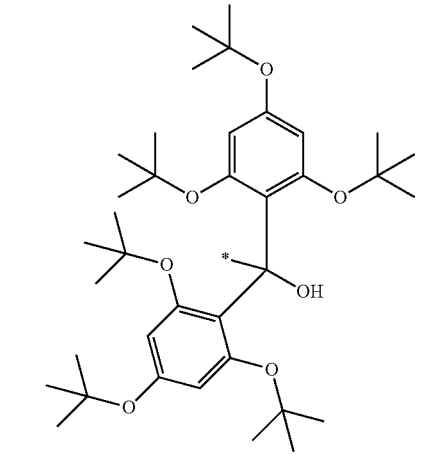
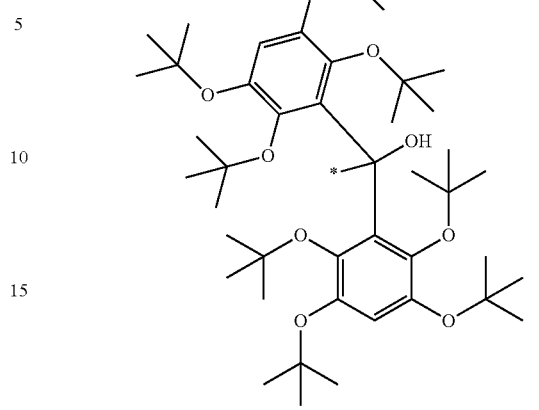
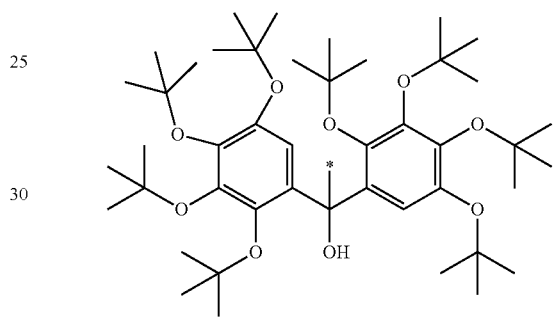
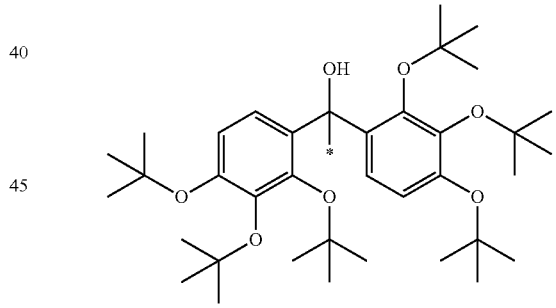
[Chemical Formula 17]
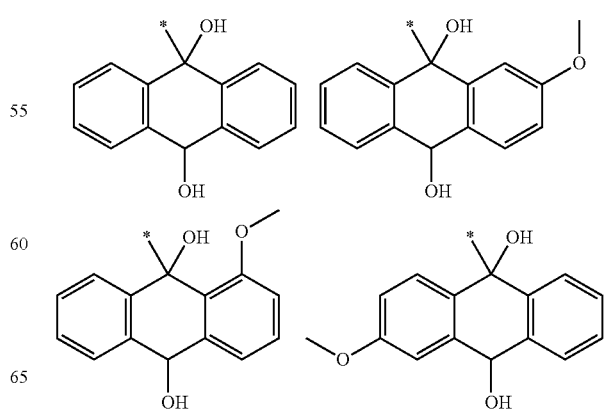

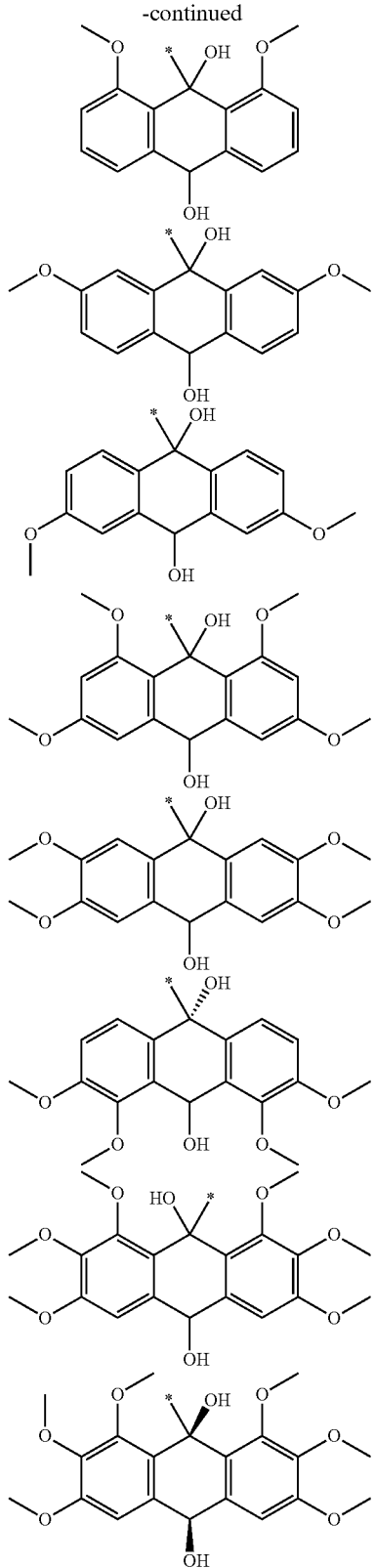

The iodonium salt compound is a compound composed of an iodonium cation and an acid anion. The iodonium salt compound is preferably at least one compound selected from the group consisting of compounds represented by the following Formulae (IV) to (V).

[Chemical Formula 18]

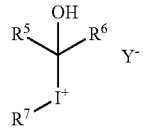

(IV)

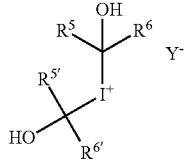

(V)

In Formulae (IV) to (V), each of $R^5$, $R^6$, $R^{5'}$, $R^{6'}$, and $R^7$ independently represents a hydrogen atom; a phenyl group; a naphthyl group; an anthracenyl group; a phenoxy group; a naphthoxy group; an anthracenoxy group; an amino group; an amide group; a halogen atom; a linear, branched or cyclic and saturated or unsaturated hydrocarbon group (preferably an alkyl group) having 1 to 30 carbon atoms (preferably 1 to 5 carbon atoms); a phenoxy group substituted with an alkoxy group having 1 to 5 carbon atoms, a hydroxyl group, an amino group, an amide group, or an alkyl group having 1 to 5 carbon atoms; a phenyl group substituted with a linear, branched or cyclic and saturated or unsaturated hydrocarbon group (preferably an alkyl group) having 1 to 30 carbon atoms (preferably 1 to 5 carbon atoms), an alkoxy group having 1 to 5 carbon atoms, an amino group, an amide group, or a hydroxyl group; a naphthoxy group substituted with an alkoxy group having 1 to 5 carbon atoms, an alkyl group having 1 to 5 carbon atoms, an amino group, an amide group, or a hydroxyl group; an anthracenoxy group substituted with an alkoxy group having 1 to 5 carbon atoms, an alkyl group having 1 to 5 carbon atoms, an amino group, an amide group, or a hydroxyl group; a linear, branched or cyclic and saturated or unsaturated hydrocarbon group (preferably an alkyl group) having 1 to 30 carbon atoms (preferably 1 to 5 carbon atoms) substituted with an alkoxy group having 1 to 5 carbon atoms, a phenoxy group, a naphthoxy group, an anthracenoxy group, an amino group, an amide group, or a hydroxyl group; or a carbonyl group to which an alkyl group having 1 to 12 carbon atoms is bonded. In Formulae (IV) to (V), the hydrogen atom of the hydroxyl group may be substituted with a phenyl group; a halogen atom; a linear, branched or cyclic and saturated or unsaturated hydrocarbon group (preferably an alkyl group) having 1 to 30 carbon atoms (preferably 1 to 5 carbon atoms); or a phenyl group substituted with a linear, branched or cyclic and saturated or unsaturated hydrocarbon group (preferably an alkyl group) having 1 to 30 carbon atoms (preferably 1 to 5 carbon atoms), an alkoxy group having 1 to 5 carbon atoms, or a hydroxyl group. When the hydrogen atom of the hydroxyl group is substituted, the iodonium salt compound contains a ketal compound group or an acetal compound group. In Formulae (IV) to (V), any two or more groups among $R^5$, $R^6$, $R^{5'}$, $R^{6'}$, and $R^7$ may form a cyclic structure through a single bond, a double bond, or a bond containing —$CH_2$—, —O—, —S—, —$SO_2$—, —$SO_2NH$—, —C(=O)—, —C(=O)O—, —NHCO—, —NHC(=O)NH—, —$CHR^f$—, —$CR^f_2$—, —NH—, or —$NR^f$—. $R^f$ represents a phenyl group; a phenoxy group; a halogen atom; a linear, branched or cyclic and saturated or unsaturated hydrocarbon group (preferably an alkyl group) having 1 to 30 carbon atoms (preferably 1 to 5 carbon atoms); a phenoxy group substituted with an alkoxy group having 1 to 5 carbon atoms, a hydroxyl group, or an alkyl group having 1 to 5 carbon atoms; or a phenyl group substituted with a linear, branched or cyclic and saturated or unsaturated hydrocarbon group (preferably an alkyl group) having 1 to 30 carbon atoms (preferably 1 to 5 carbon atoms), an alkoxy group having 1 to 5 carbon atoms, or a hydroxyl group. Each of $R^5$, $R^6$, $R^{5'}$, $R^{6'}$, and $R^7$ independently preferably represents a phenyl group; a phenoxy group; a phenoxy group substituted with an alkoxy group having 1 to 5 carbon atoms, a hydroxyl group, or an alkyl group having 1 to 5 carbon atoms; or a phenyl group substituted with an alkoxy group having 1 to 5 carbon atoms or a hydroxyl group. In Formulae (IV) to (V), Y represents an acid anion, preferably represents a strong acid anion, and more preferably represents a super strong acid anion.

Specific examples of the groups represented by —C(—OH)$R^5R^6$ and —C(—OH)$R^{5'}R^{6'}$ in Formulae (IV) to (V) include the same groups as the groups represented by —C(—OH)$R^1R^2$, —C(—OH)$R^{1'}R^{2'}$, —C(—OH)$R^{1''}R^{2''}$, and the like exemplified above in the above Formulae (I) to (III).

Examples of the acid anion of the sulfonium salt compound and the iodonium salt compound include a sulfonate anion, a carboxylate anion, a bis(alkylsulfonyl)amide anion, a tris(alkylsulfonyl)methide anion, and the like. Among these, acid anion represented by the following Formula (XX), (XXI), or (XXII) is preferable, and an acid anion represented by the following Formula (XX) is more preferable.

[Chemical Formula 19]

(XX)

(XXI)

(XXII)

In Formulae (XX), (XXI), and (XXII), each of $R^{18}$ to $R^{21}$ independently represents an organic group. Specific examples of the organic group include an alkyl group, an aryl group, a group in which a plurality of alkyl or aryl groups is linked to each other, and the like. The organic group is preferably an alkyl group in which the 1-position is substituted with a fluorine atom or a fluoroalkyl group or a phenyl group substituted with a fluorine atom or a fluoroalkyl group. If the organic group has a fluorine atom or a fluoroalkyl group, the acidity of an acid generated by exposure tends to increase, and the sensitivity tends to be improved. It is preferable that the organic group does not contain a fluorine atom as a substituent on the terminal.

It is preferable that the acid anion has at least one anion group selected from the group consisting of a sulfonate anion, a carboxylate anion, a sulfonylimide anion, a bis(alkylsulfonyl)imide anion, and a tris(alkylsulfonyl)methide anion. Specific examples of the acid anion include anions represented by Formula "$R^{22}$—$SO_3^-$" ($R^{22}$ represents a linear, branched or cyclic alkyl group which may have a substituent, a halogenated alkyl group, an aryl group, or an alkenyl group). The linear or branched alkyl group represented by $R^{22}$ preferably has 1 to 10 carbon atoms. In a case where $R^{22}$ represents an alkyl group, examples of the acid anion include alkyl sulfonate such as methane sulfonate, n-propanesulfonate, n-butanesulfonate, n-octanesulfonate, 1-adamantanesulfonate, 2-norbornanesulfonate, and d-camphor-10-sulfonate. The halogenated alkyl group represented by $R^{22}$ is an alkyl group in which some or all of the hydrogen atoms are substituted with a halogen atom, and the alkyl group is preferably an alkyl group having 1 to 10 carbon atoms. Particularly, a linear or branched alkyl group is more preferable, and a methyl group, an ethyl group, a propyl group, an isopropyl group, a n-butyl group, a tert-butyl group, a tert-pentyl group, or an isopentyl group is even more preferable. Examples of the halogen atom substituting the hydrogen atoms include a fluorine atom, a chlorine atom, an iodine atom, a bromine atom, and the like. In the halogenated alkyl group, 50% to 100% of all of the hydrogen atoms of the alkyl group (alkyl group having not yet been halogenated) is preferably substituted with a halogen atom. It is more preferable that all of the hydrogen atoms are substituted with a halogen atom. The halogenated alkyl group is preferably a fluorinated alkyl group. The number of carbon atoms of the fluorinated alkyl group is preferably 1 to 10, more preferably 1 to 8, and most preferably 1 to 4. Furthermore, a fluorination rate of the fluorinated alkyl group is preferably 10% to 100%, and more preferably 50% to 100%. It is particularly preferable that all of the hydrogen atoms are substituted with a fluorine atom because then the acidity is increased. Specific examples of the preferred fluorinated alkyl group include a trifluoromethyl group, a heptafluoro-n-propyl group, and a nonafluoro-n-butyl group.

$R^{22}$ may have a substituent, and the substituent include a divalent linking group containing an oxygen atom. Examples of the linking group include non-hydrocarbon-based oxygen atom-containing linking groups such as an oxygen atom (ether bond: —O—), an ester bond (—C(=O)—O—), an amide bond (—C(=O)—NH—), a carbonyl group (—C(=O)—), a sulfonyl group (—SO$_2$)—, and a carbonate bond (—O—C(=O)—O—).

Specific examples of the acid anion include anions represented by the following formulae, but the acid anion is not limited thereto.

[Chemical Formula 20]

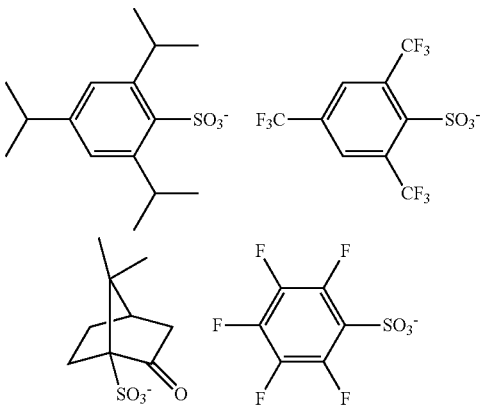

-continued

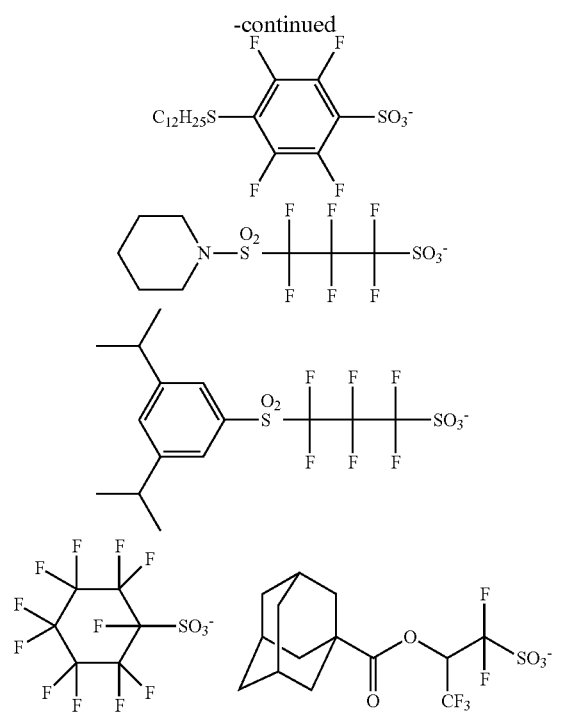

[Chemical Formula 21]

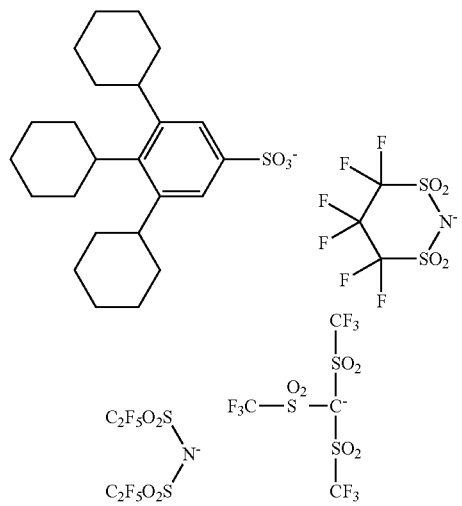

(b) Photosensitizer Precursor

The photosensitizer precursor is a component becoming a photosensitizer, which absorbs non-ionizing radiation having a wavelength of greater than 200 nm and preferably greater than 250 nm, by being irradiated with ionizing radiation or non-ionizing radiation having a wavelength of equal to or less than 400 nm, preferably equal to or less than 250 nm, and more preferably equal to or less than 200 nm. The photosensitizer precursor is a component different from the component (a). It is preferable that the non-ionizing radiation the photosensitizer absorbs has a wavelength longer than the wavelength the photosensitizer precursor absorbs. In the method for forming a pattern according to the present embodiment, the chemical structure of the photosensitizer precursor is changed through a direct or indirect reaction in the pattern-exposure step, and thus a photosensitizer assisting the generation of an acid in the flood-exposure step is generated. The peak of the wavelength of the absorbed non-ionizing radiation shifts before and after the pattern-exposure step, and as a result, it is easy to obtain an absorption contrast of the non-ionizing radiation in the flood-exposure step between an exposed portion, in which the photosensitizer is generated, and an unexposed portion. In a case where the peak of absorption wavelength shifts greatly, the absorption contrast of the non-ionizing radiation in the flood-exposure step becomes greater.

It is preferable that the photosensitizer precursor is a component which becomes a compound (carbonyl compound) having a carbonyl group absorbing non-ionizing radiation having a wavelength of greater than 200 nm and preferably greater than 250 nm by being irradiated with ionizing radiation or non-ionizing radiation having a wavelength of equal to or less than 400 nm, preferably equal to or less than 250 nm, and more preferably equal to or less than 200 nm. Examples of the carbonyl compound include aldehyde, ketone, carboxylic acid, a carboxylic acid ester, and the like. Through the reaction described above, by only the photosensitizer precursor in a pattern-exposed portion, the peak of the absorption wavelength of the radiation shifts. Accordingly, if flood-exposure is performed using radiation having a wavelength that only the pattern-exposed portion can absorb after the pattern-exposure, only the pattern-exposed portion can be selectively sensitized. The photosensitizer precursor is more preferably an alcohol compound represented by the following Formula (VI), and may be a secondary alcohol compound. In the present specification, the alcohol compound is not limited to a compound having an alcoholic hydroxyl group, and may be a ketal compound, an acetal compound, an orthoester compound, or the like obtained by the substitution of a hydrogen atom of an alcoholic hydroxyl group. In a case where the photosensitizer precursor is a ketal compound or an acetal compound, the resist material film may be heated between the pattern-exposure and the flood-exposure so as to speed up a reaction in which the photosensitizer precursor is hydrolyzed into a carbonyl compound by an acid catalyst generated by the pattern-exposure.

[Chemical Formula 22]

(VI)

In Formula (VI), each of $R^8$, $R^9$, and $R^{10}$ independently represents a hydrogen atom; a phenyl group; a naphthyl group; an anthracenyl group; an alkoxy group having 1 to 5 carbon atoms; an alkylthio group having 1 to 5 carbon atoms; a phenoxy group; a naphthoxy group; an anthracenoxy group; an amino group; an amide group; a halogen atom; a linear, branched or cyclic and saturated or unsaturated hydrocarbon group (preferably an alkyl group) having 1 to 30 carbon atoms (preferably 1 to 5 carbon atoms); an alkoxy group having 1 to 5 carbon atoms substituted with a linear, branched or cyclic and saturated or unsaturated hydrocarbon group (preferably an alkyl group) having 1 to 30 carbon atoms (preferably 1 to 5 carbon atoms), an alkoxy group having 1 to 5 carbon atoms, an amino group, an amide group, or a hydroxyl group; an alkylthio group having 1 to 5 carbon atoms substituted with a linear, branched or cyclic and saturated or unsaturated hydrocarbon group (preferably an alkyl group) having 1 to 30 carbon atoms (preferably 1 to 5 carbon atoms), an alkoxy group having 1 to 5 carbon atoms, an amino group, an amide group, or a hydroxyl group; a phenoxy group substituted with an alkoxy group having 1 to 5 carbon atoms, a hydroxyl group, an amino group, an amide group, or an alkyl group having 1 to 5 carbon atoms; a phenyl group substituted with a linear, branched or cyclic and saturated or unsaturated hydrocarbon group (preferably an alkyl group) having 1 to 30 carbon atoms (preferably 1 to 5 carbon atoms), an alkoxy group having 1 to 5 carbon atoms, an amino group, an amide group, or a hydroxyl group; a naphthoxy group substituted with an alkoxy group having 1 to 5 carbon atoms, an alkyl group having 1 to 5 carbon atoms, an amino group, an amide group, or a hydroxyl group; an anthracenoxy group substituted with an alkoxy group having 1 to 5 carbon atoms, an alkyl group having 1 to 5 carbon atoms, an amino group, an amide group, or a hydroxyl group; a linear, branched or cyclic and saturated or unsaturated hydrocarbon group (preferably an alkyl group) having 1 to 30 carbon atoms (preferably 1 to 5 carbon atoms) substituted with an alkoxy group having 1 to 5 carbon atoms, a phenoxy group, a naphthoxy group, an anthracenoxy group, an amino group, an amide group, or a hydroxyl group; or a carbonyl group to which an alkyl group having 1 to 12 carbon atoms is bonded. The alcohol compound may be a thiol compound in which the alcoholic hydroxyl group in Formula (VI) becomes a thiol group. In Formula (VI), the hydrogen atom of the hydroxyl group or thiol group may be substituted with a phenyl group; a halogen atom; a linear, branched or cyclic and saturated or unsaturated hydrocarbon group (preferably an alkyl group) having 1 to 30 carbon atoms (preferably 1 to 5 carbon atoms); or a phenyl group substituted with a linear, branched or cyclic and saturated or unsaturated hydrocarbon group (preferably an alkyl group) having 1 to 30 carbon atoms (preferably 1 to 5 carbon atoms), and alkoxy group having 1 to 5 carbon atoms, or a hydroxyl group. In the formula, any two or more groups among $R^8$, $R^9$, and $R^{10}$ may form a cyclic structure through a single bond, a double bond, or a bond containing —$CH_2$—, —O—, —S—, —$SO_2$—, —$SO_2NH$—, —C(=O)—, —C(=O)O—, —NHCO—, —NHC(=O)NH—, —$CHR^g$—, —$CR^g_2$—, —NH—, or —$NR^g$—. $R^g$ represents a phenyl group; a phenoxy group; a halogen atom; a linear, branched or cyclic and saturated or unsaturated hydrocarbon group (preferably an alkyl group) having 1 to 30 carbon atoms (preferably 1 to 5 carbon atoms); a phenoxy group substituted with an alkoxy group having 1 to 5 carbon atoms, a hydroxyl group, or an alkyl group having 1 to 5 carbon atoms; or a phenyl group substituted with a linear, branched or cyclic and saturated or unsaturated hydrocarbon group (preferably an alkyl group) having 1 to 30 carbon atoms (preferably 1 to 5 carbon atoms), an alkoxy group having 1 to 5 carbon atoms, or a hydroxyl group. Each of $R^8$, $R^9$, and $R^{10}$ independently preferably represents a hydrogen atom; a phenyl group; a phenoxy group; a phenoxy group substituted with an alkoxy group having 1 to 5 carbon atoms, a hydroxyl group, or an alkyl group having 1 to 5 carbon atoms; or a phenyl group substituted with an alkoxy group having 1 to 5 carbon atoms or a hydroxyl group.

It can be said that the ketal compound or the acetal compound obtained by the substitution of the hydrogen atom of the hydroxyl group in Formula (VI) is preferably a compound represented by the following Formula (XXXVI). That is, the photosensitizer precursor may be the compound represented by the following Formula (XXXVI). In a case where either $R^9$ or $R^{10}$ is a hydrogen atom, it can be said that the compound represented by the following Formula (XXXVI) is an acetal compound.

[Chemical Formula 23]

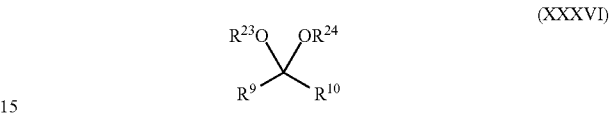

(XXXVI)

In Formula (XXXVI), each of $R^9$ and $R^{10}$ has the same definition as each of $R^9$ and $R^{10}$ in Formula (VI). As described above, $R^9$ and $R^{10}$ may form a cyclic structure. In Formula (XXXVI), each of $R^{23}$ and $R^{24}$ independently represents a phenyl group; a halogen atom; a linear, branched or cyclic and saturated or unsaturated hydrocarbon group (preferably an alkyl group) having 1 to 30 carbon atoms (preferably 1 to 5 carbon atoms); or a phenyl group substituted with a linear, branched or cyclic and saturated or unsaturated hydrocarbon group (preferably an alkyl group) having 1 to 30 carbon atoms (preferably 1 to 5 carbon atoms), an alkoxy group having 1 to 5 carbon atoms, or a hydroxyl group. $R^{23}$ and $R^{24}$ may form a cyclic structure through a single bond, a double bond, or a bond containing —$CH_2$—, —O—, —S—, —$SO_2$—, —$SO_2NH$—, —C(=O)—, —C(=O)O—, —NHCO—, —NHC(=O)NH—, —$CHR^g$—, —$CR^g_2$—, —NH—, or —$NR^g$—. $R^g$ has the same definition as $R^g$ in Formula (VI). The ketal compound or the acetal compound may be a thioketal compound or a thioacetal compound formed by the substitution of an oxygen atom bonded to $R^{23}$ and/or $R^{24}$ in Formula (XXXVI) with sulfur.

The ketal compound and the acetal compound can be obtained by reacting a carbonyl compound with an alcohol. It can be said that the reaction is a reaction for protecting a carbonyl group contributing to photosensitizing action, and $R^{23}$ and $R^{24}$ in Formula (XXXVI) are protecting groups of the carbonyl group. In this case, it can be said that the reaction in which the photosensitizer precursor becomes a photosensitizer by radiation or the like is a deprotection reaction. The reactivity (ease with which the deprotection reaction occurs) of the protecting group will be described below, for example. The reactivity of the protecting group increases toward the right-hand side and decreases toward the left-hand side. For instance, if a methoxy group is used as a protecting group of a carbonyl group (upper right group among the groups shown below), the deprotection reaction tends to exhibit high reactivity and proceed in the presence of an acid catalyst even at normal temperature. It is advantageous for the deprotection reaction to proceed at normal temperature because then image blurring can be prevented. In contrast, if the deprotection reaction occurs in an unexposed portion at the point in time of the pattern-exposure and thus the photosensitizer is generated, the contrast of the resist may deteriorate. In order to prevent the generation of the photosensitizer in the unexposed portion, it is possible to select a protecting group such that the activation energy of the deprotection reaction is increased (the reactivity of the protecting group is decreased). For decreasing the reactivity, for example, it is more preferable to use a cyclic protecting group in which $R^{23}$ and $R^{24}$ in Formula (XXXVI) form a cyclic structure by being bonded to each other. Examples of the cyclic structure include a 6-membered ring and a 5-membered ring. From the viewpoint of decreasing the reactivity, the cyclic structure is preferably a 5-membered ring. In a case where a protecting group having low reactivity is used, the resist material preferably contains a first scavenger which will be described later, and it is desired to bake the resist material film between the pattern-exposure and the flood-exposure. If the resist material film is baked, the unnecessary acid in the unexposed portion can be neutralized by the scavenger, and the contrast of a latent image can be improved. In addition, the baking described above can compensate the reduction of the reactivity of the protecting group, and accordingly, the roughness of the latent image of the acid in the resist material film can be reduced by the diffusion of the substance.

[Chemical Formula 24]

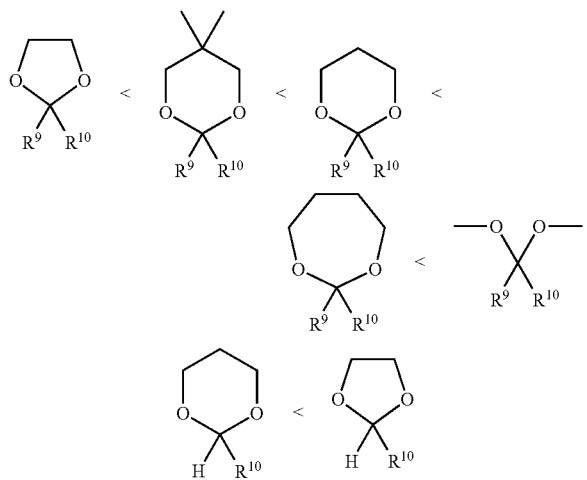

The ketal-type photosensitizer precursor may be a compound represented by any of the following Formulae (XXVII) to (XXX).

[Chemical Formula 25]

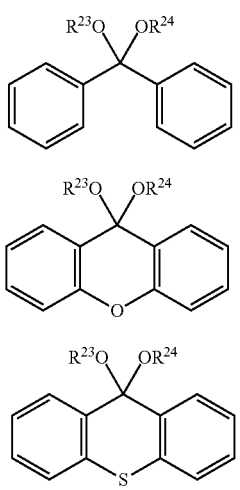

(XXVII)

(XXVIII)

(XXIX)

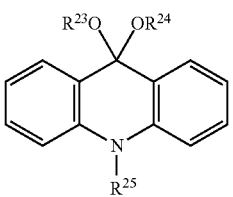

(XXX)

In Formulae (XXVII) to (XXX), each of $R^{23}$ and $R^{24}$ has the same definition as each of $R^{23}$ and $R^{24}$ in Formula (XXXVI). In Formulae (XXVII) to (XXX), the hydrogen atom of the aromatic ring may be substituted with an alkoxy group having 1 to 5 carbon atoms or an alkyl group having 1 to 5 carbon atoms, and the aromatic ring may form a naphthalene ring or an anthracene ring by being bonded to another aromatic ring. $R^{25}$ represents an alkyl group having 1 to 5 carbon atoms. In a case where a compound represented by any of Formulae (XXVII) to (XXX) is used as a photosensitizer precursor, the shift of the absorption wavelength of radiation becomes greater when the photosensitizer precursor turns into a photosensitizer, and a sensitization reaction can be caused in a pattern-exposed portion in a more selective manner.

It can be said that the orthoester compound obtained by the substitution of a hydrogen atom of the hydroxyl group in Formula (VI) is preferably a compound represented by the following Formula (XLVI). That is, the photosensitizer precursor may be a compound represented by the following Formula (XLVI).

[Chemical Formula 26]

(XLVI)

In Formula (XLVI), $R^9$ has the same definition as $R^9$ in Formula (VI). In Formula (XLVI), each of $R^{38}$ to $R^{40}$ independently represents a phenyl group; a halogen atom; a linear, branched or cyclic and saturated or unsaturated hydrocarbon group (preferably an alkyl group) having 1 to 30 carbon atoms (preferably 1 to 5 carbon atoms); or a phenyl group substituted with a linear, branched or cyclic and saturated or unsaturated hydrocarbon group (preferably an alkyl group) having 1 to 30 carbon atoms (preferably 1 to 5 carbon atoms), an alkoxy group having 1 to 5 carbon atoms, or a hydroxyl group. $R^{38}$ to $R^{40}$ may form a cyclic structure through a single bond, a double bond, or a bond containing —$CH_2$—, —O—, —S—, —$SO_2$—, —$SO_2NH$—, —C(=O)—, —C(=O)O—, —NHCO—, —NHC(=O)NH—, —$CHR^g$—, —$CR^g_2$—, —NH—, or —$NR^g$—. $R^g$ has the same definition as $R^g$ in Formula (VI).

The orthoester compound is decomposed through the deprotection reaction in the pattern-exposure and becomes, for example, a carboxylic acid ester or carboxylic acid containing a carbonyl group. The orthoester compound is preferably, for example, an OBO ester compound represented by the following Formula (XLVII) in which the portion of carboxyl group of the photosensitizer having a carboxyl group is substituted (protected) with OBO (for example, 4-methyl2,6,7-trioxabicyclo[2.2.2]-octane-1-yl). The photosensitizer precursor in which a carboxyl group is protected with OBO generates carboxylic acid by an acid catalyst generated at the time of pattern-exposure so as to cause the shift of the absorption wavelength of radiation and functions as a photosensitizer at the time of flood-exposure. Due to the generation of the carboxylic acid from the photosensitizer precursor, the change of polarity of the resist (for example, change of a nonpolar resist to a polar resist) occurs in a pattern-exposed portion. Therefore, the orthoester compound also functions as a dissolution accelerator in the developing step and contributes to the enhancement of resist contrast. If the photosensitizer precursor contains the OBO ester compound, the generation of the photosensitizer and the polarity changing reaction can be caused simultaneously.

[Chemical Formula 27]

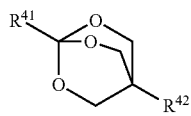

(XLVII)

In Formula (XLVII), each of $R^{41}$ and $R^{42}$ independently represents a hydrogen atom; a phenyl group; a naphthyl group; an anthracenyl group; a phenoxy group; a naphthoxy group; an anthracenoxy group; an amino group; an amide group; a halogen atom; a linear, branched or cyclic and saturated or unsaturated hydrocarbon group (preferably an alkyl group) having 1 to 30 carbon atoms (preferably 1 to 5 carbon atoms); a phenoxy group substituted with an alkoxy group having 1 to 5 carbon atoms, a hydroxyl group, an amino group, an amide group, or an alkyl group having 1 to 5 carbon atoms; a phenyl group substituted with a linear, branched or cyclic and saturated or unsaturated hydrocarbon group (preferably an alkyl group) having 1 to 30 carbon atoms (preferably 1 to 5 carbon atoms), an alkoxy group having 1 to 5 carbon atoms, an amino group, an amide group, or a hydroxyl group; a naphthoxy group substituted with an alkoxy group having 1 to 5 carbon atoms, an alkyl group having 1 to 5 carbon atoms, or a hydroxyl group; an anthracenoxy group substituted with an alkoxy group having 1 to 5 carbon atoms, an alkyl group having 1 to 5 carbon atoms, an amino group, an amide group, or a hydroxyl group; a linear, branched or cyclic and saturated or unsaturated hydrocarbon group (preferably an alkyl group) having 1 to 30 carbon atoms (preferably 1 to 5 carbon atoms) substituted with an alkoxy group having 1 to 5 carbon atoms, a phenoxy group, a naphthoxy group, an anthracenoxy group, an amino group, an amide group, or a hydroxyl group; or a carbonyl group to which an alkyl group having 1 to 12 carbon atoms is bonded. Each of $R^{41}$ and $R^{42}$ preferably independently represents a hydrogen atom; a phenyl group; a phenoxy group; a phenoxy group substituted with an alkoxy group having 1 to 5 carbon atoms, a hydroxyl group, or an alkyl group having 1 to 5 carbon atoms; or a phenyl group substituted with an alkoxy group having 1 to 5 carbon atoms or a hydroxyl group.

Specific examples of the photosensitizer precursor include compounds represented by the following formulae. The followings are compounds resulting from alcohol compounds in which hydrogen atoms of an alcoholic hydroxyl group are not substituted, and turn into ketone compounds through the reaction at the time of pattern-exposure.

[Chemical Formula 28]

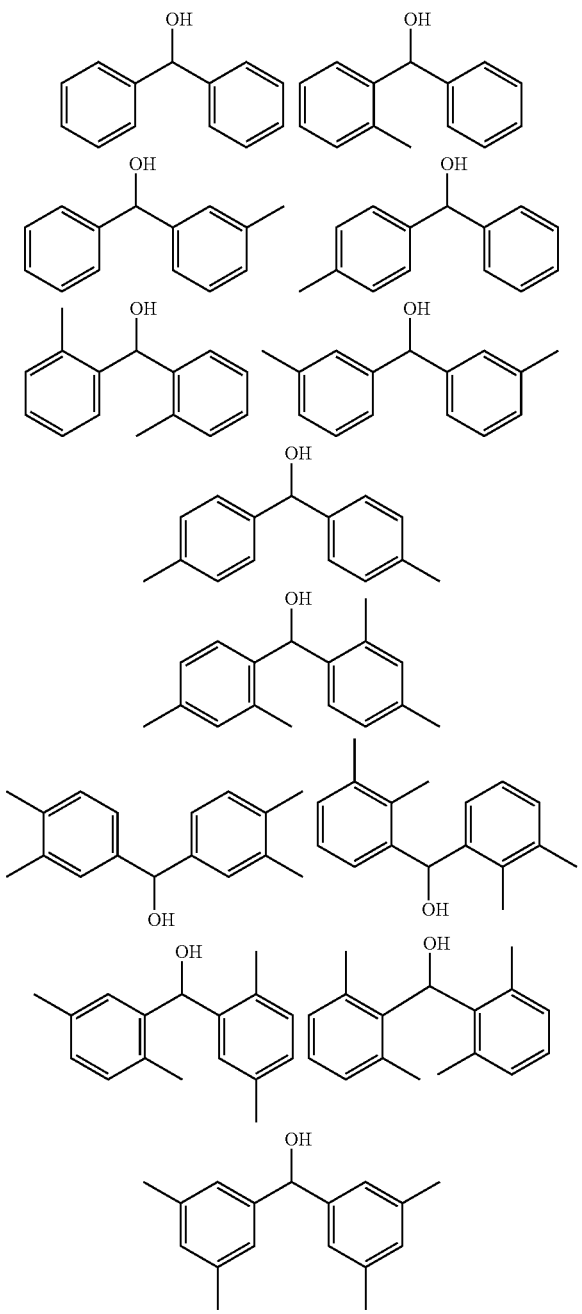

[Chemical Formula 29]

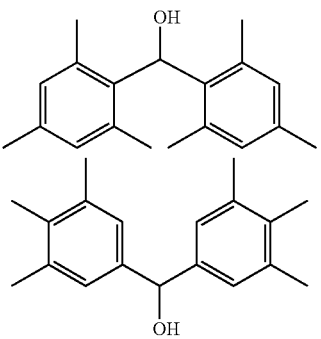

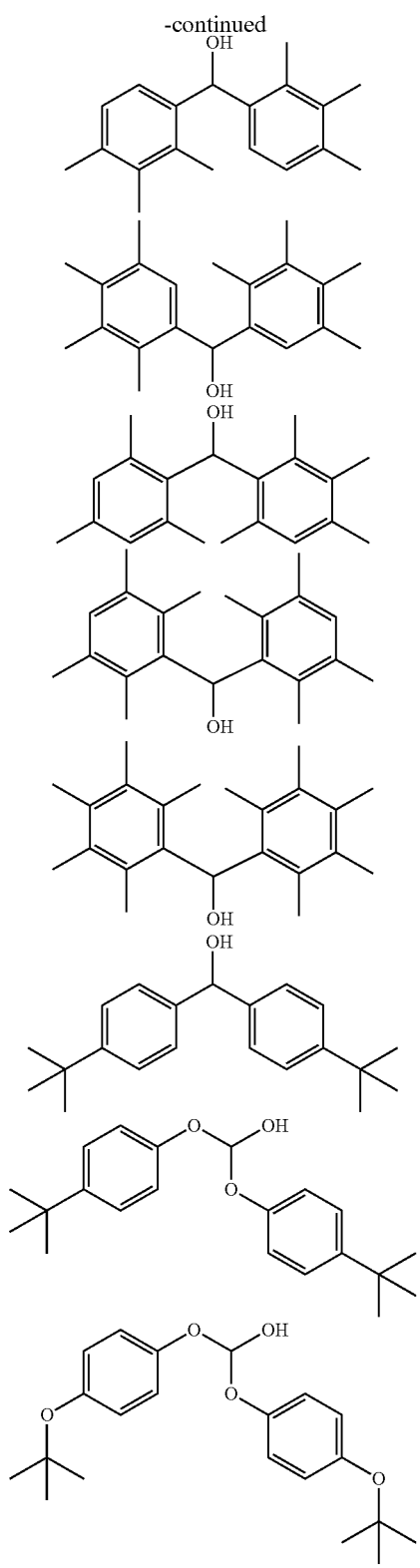
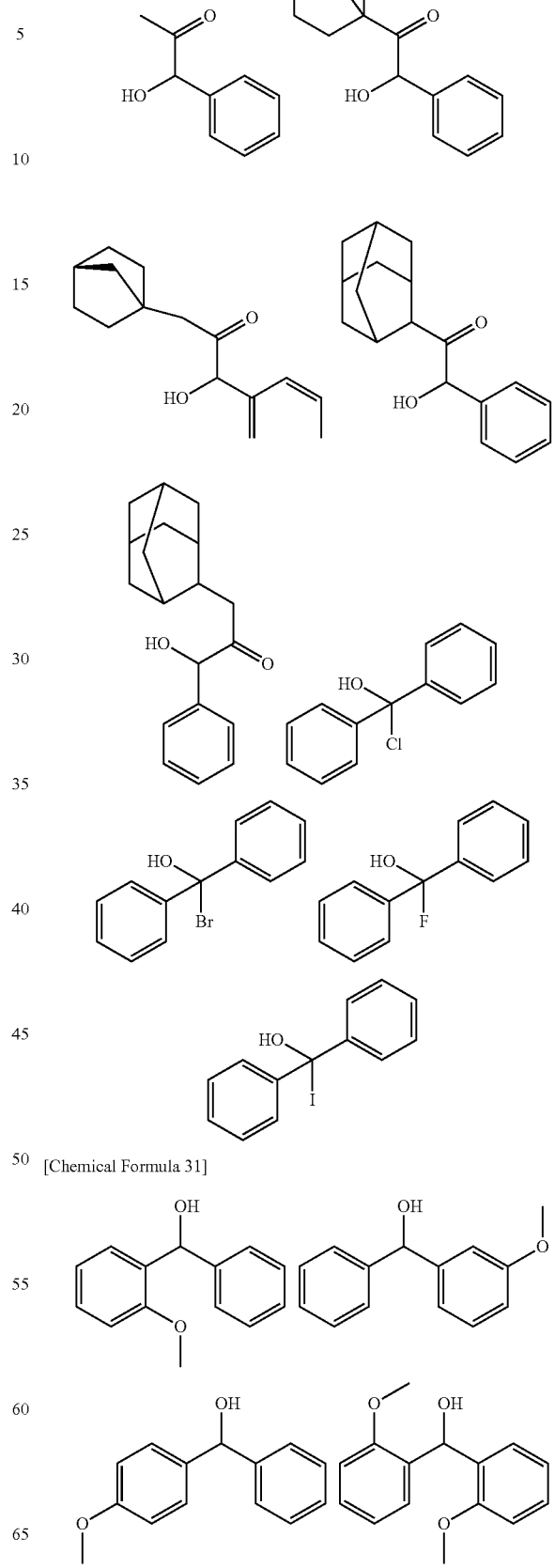
[Chemical Formula 30]
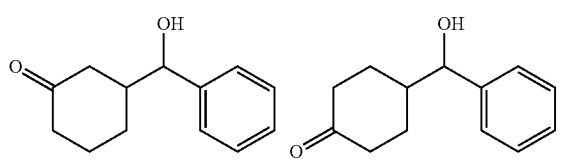
[Chemical Formula 31]

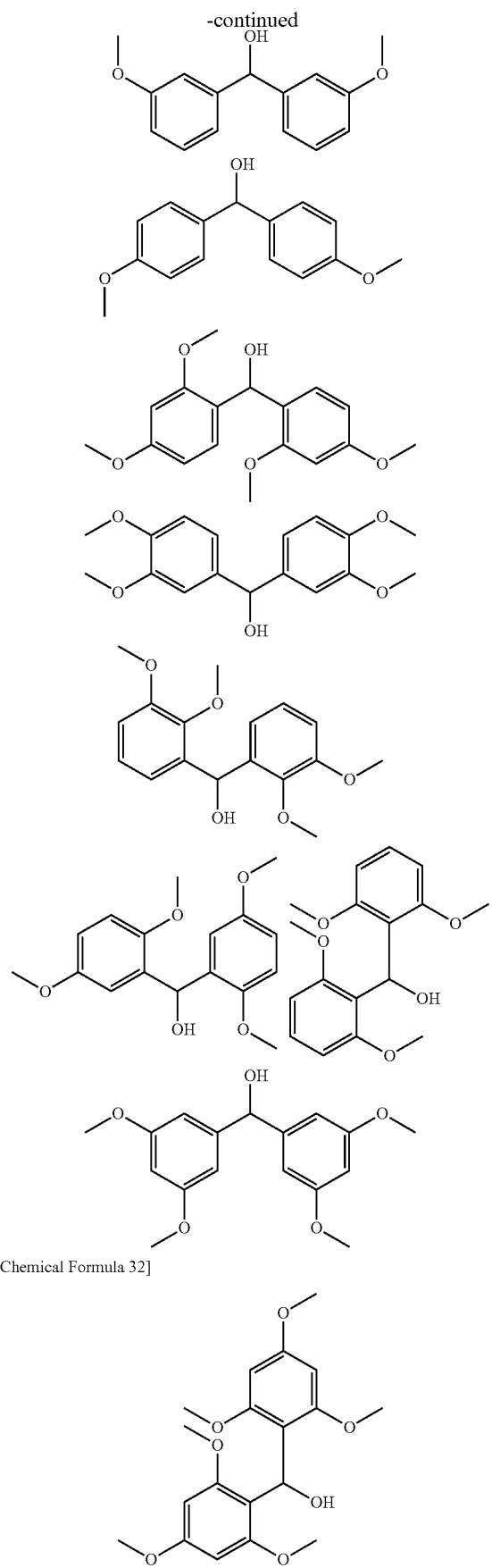

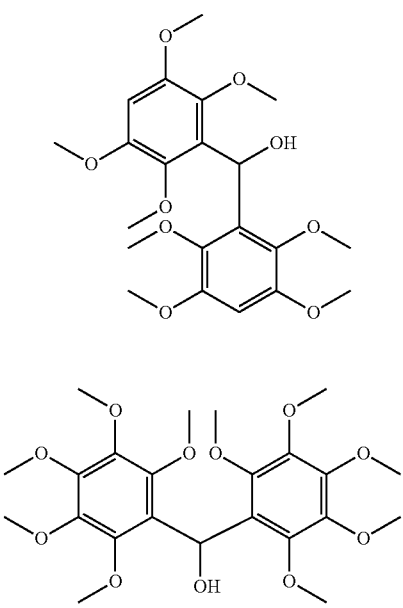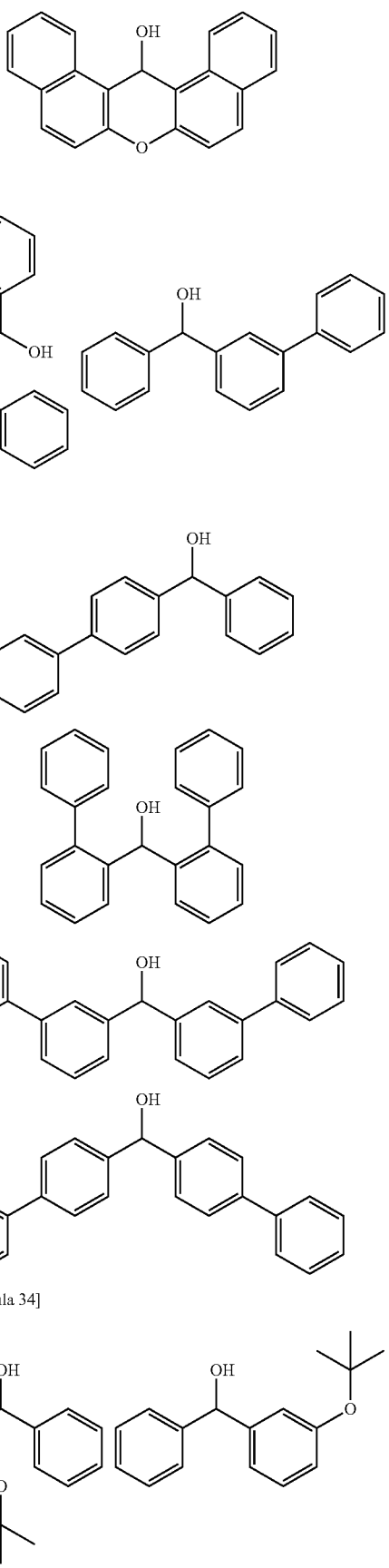

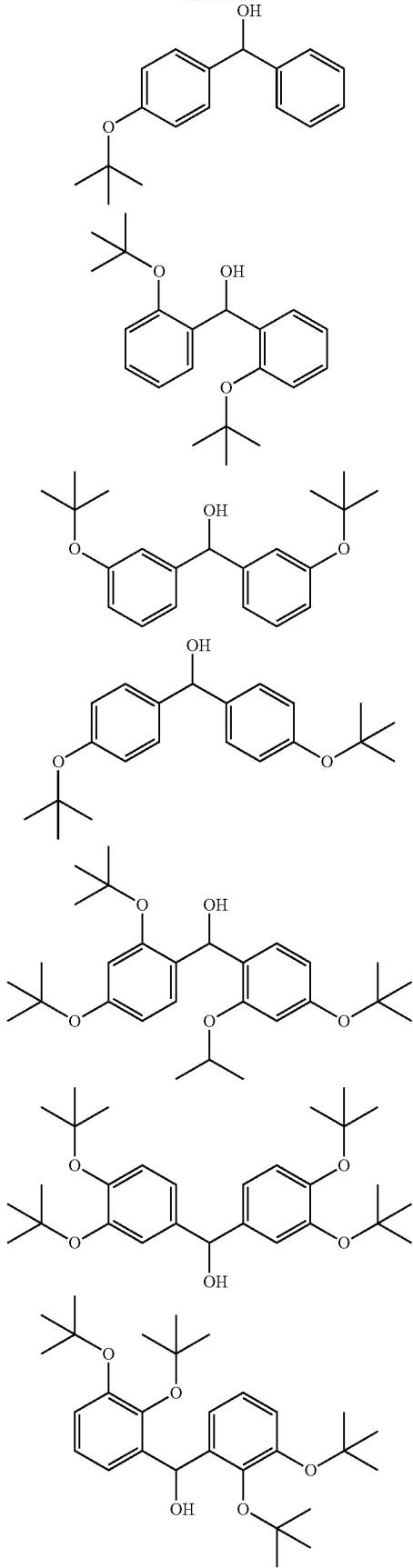
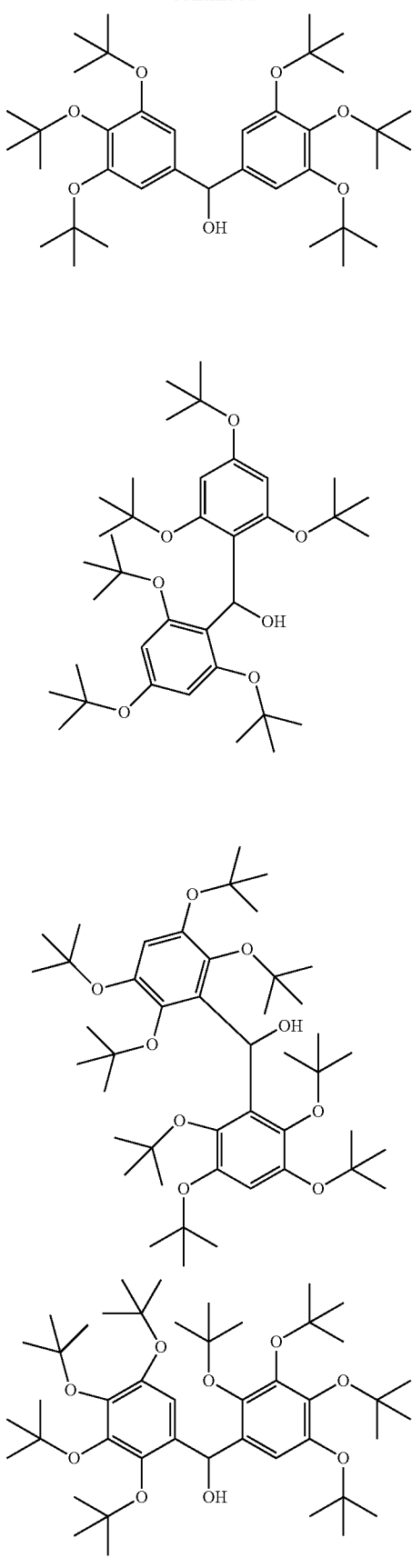

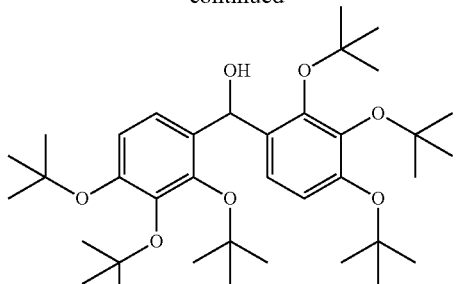
[Chemical Formula 35]
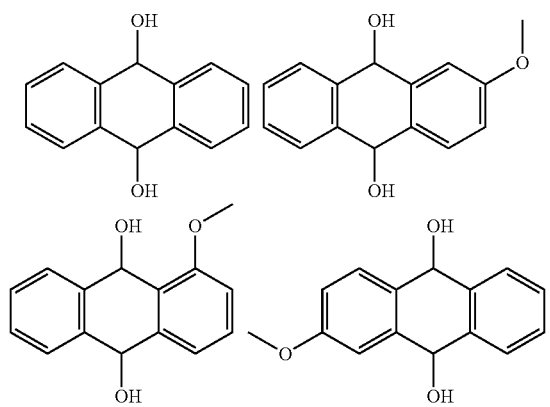
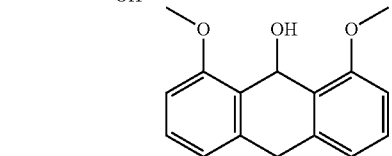
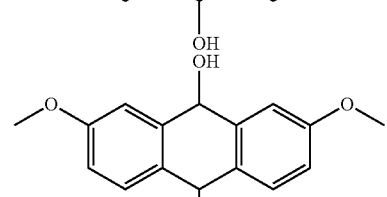
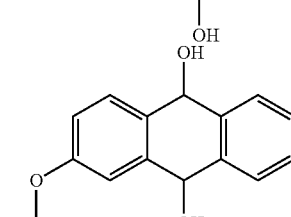
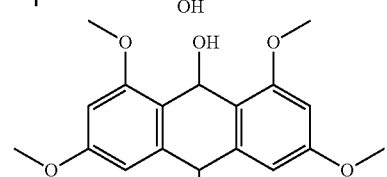
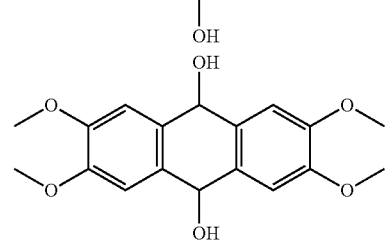
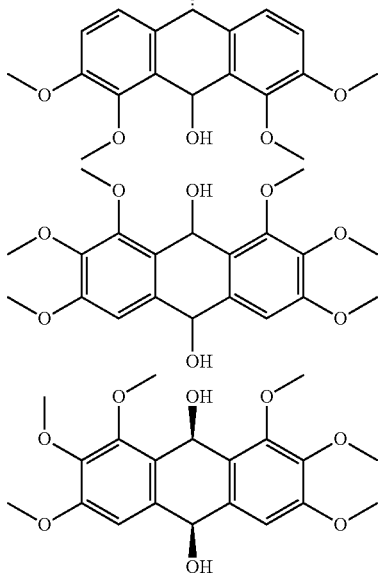
The following compounds are examples of the ketal compound or acetal compound in which a carbonyl group of the photosensitizer is protected and which becomes a ketone-containing photosensitizer in a pattern-exposed portion due to the catalytic action of an acid generated by pattern-exposure.
[Chemical Formula 36]
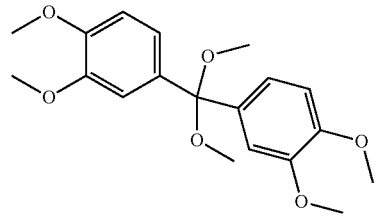
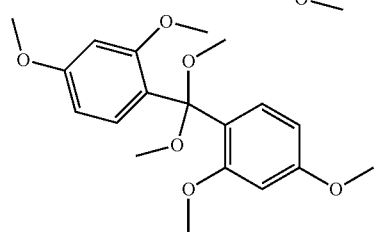
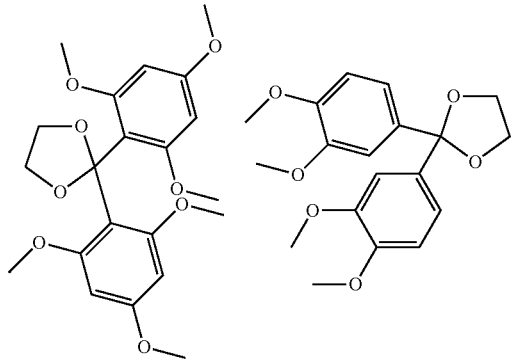

-continued
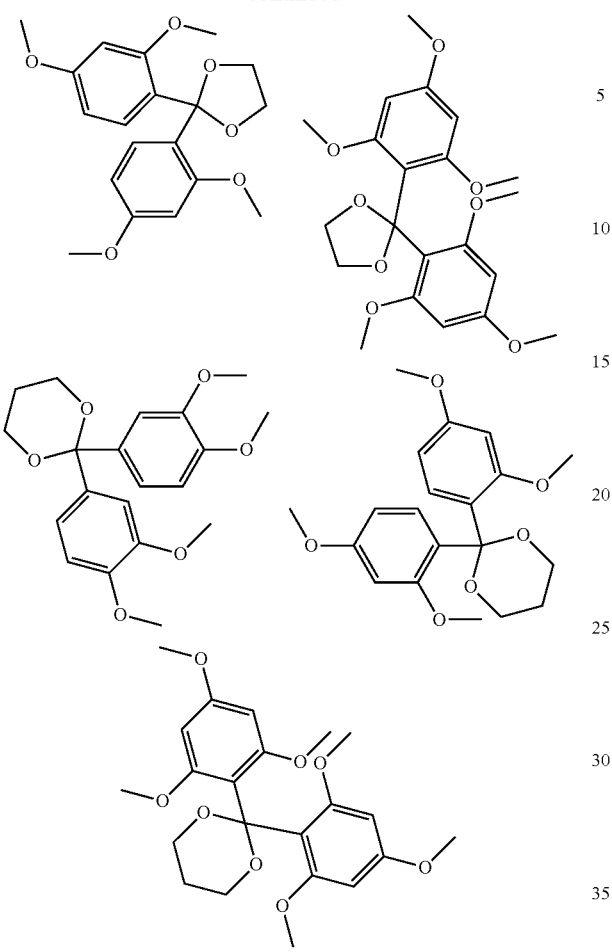
[Chemical Formula 37]
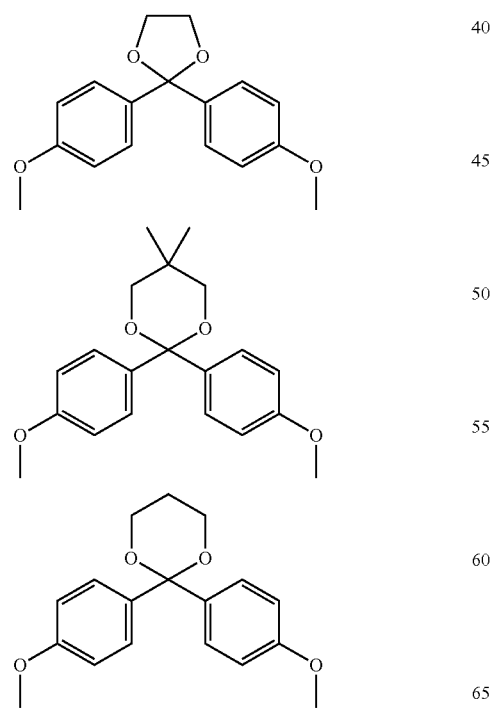
-continued
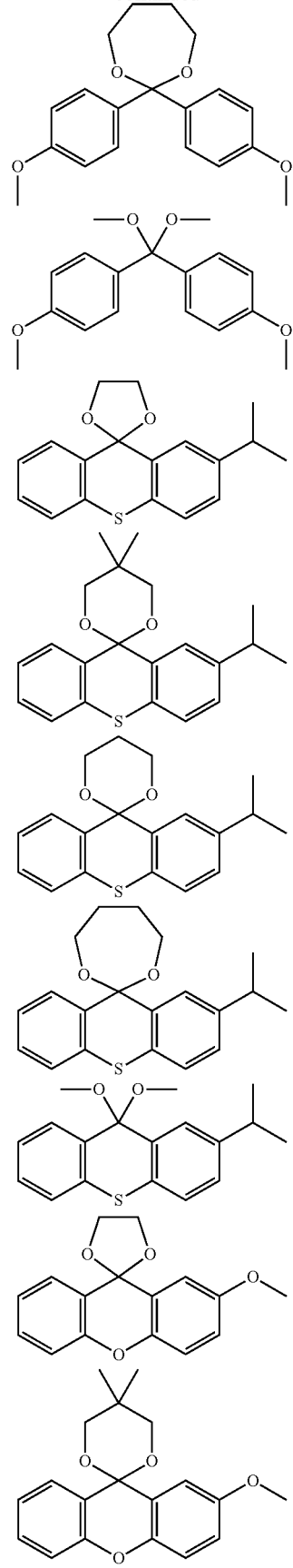

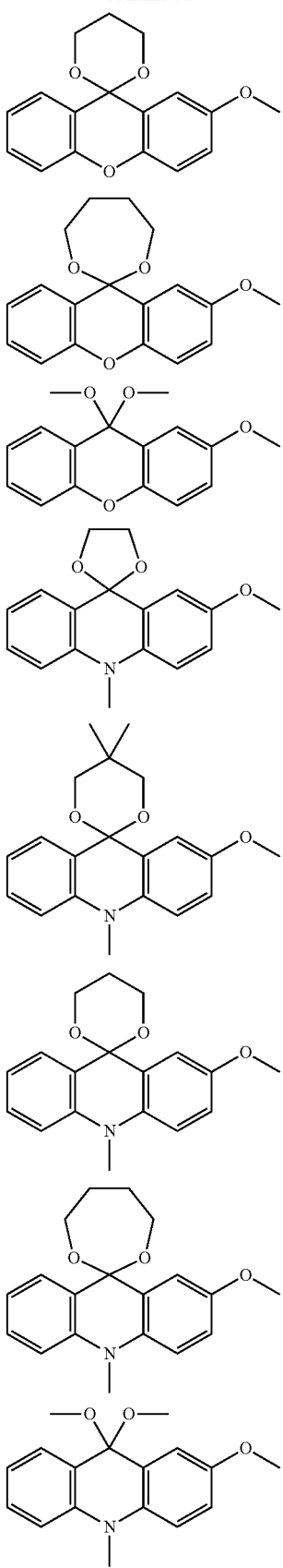
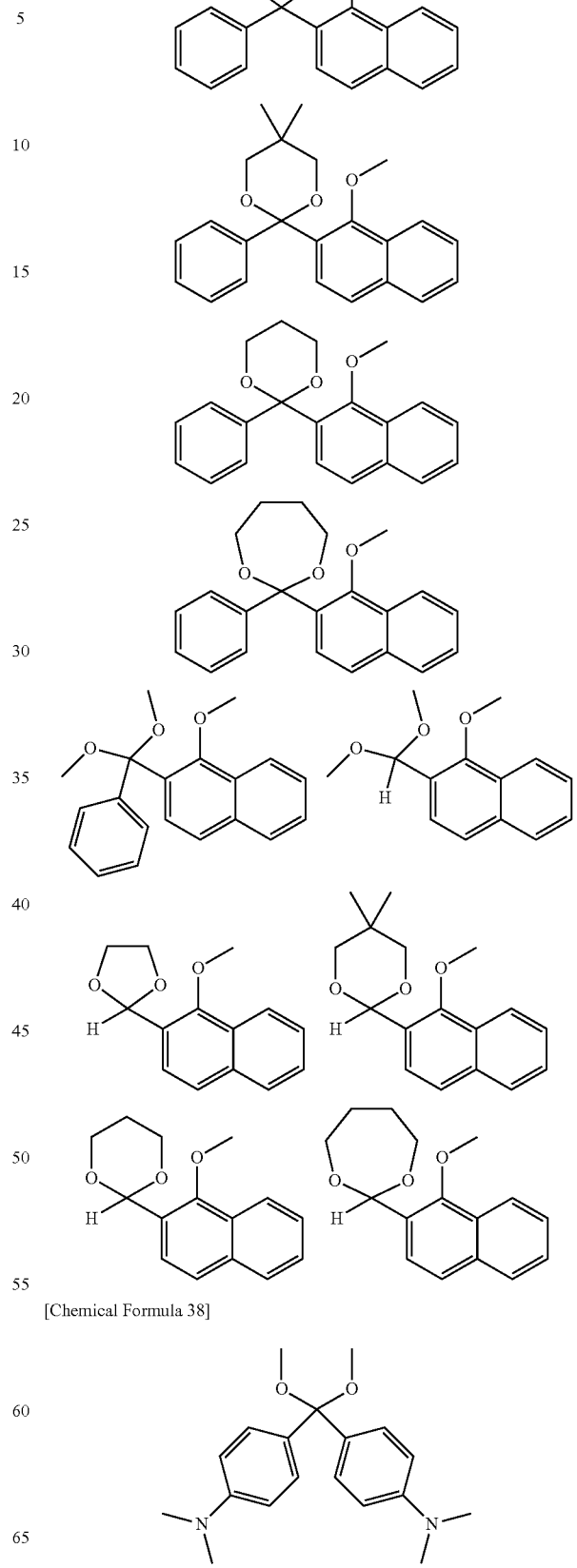
[Chemical Formula 38]

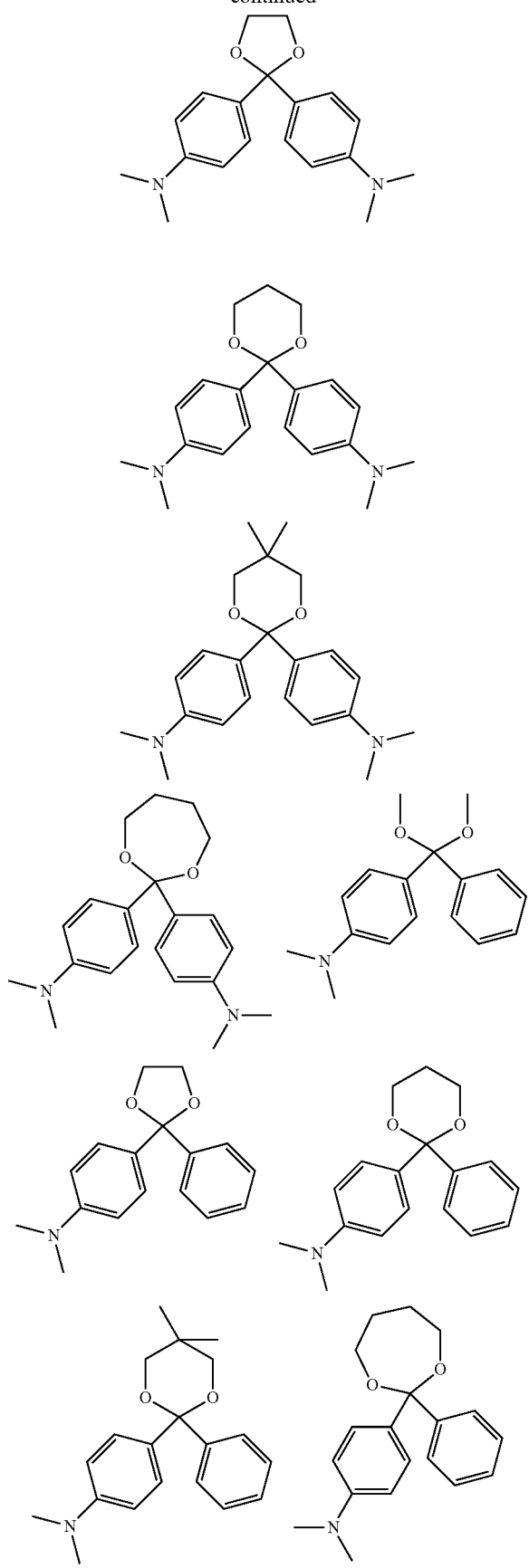
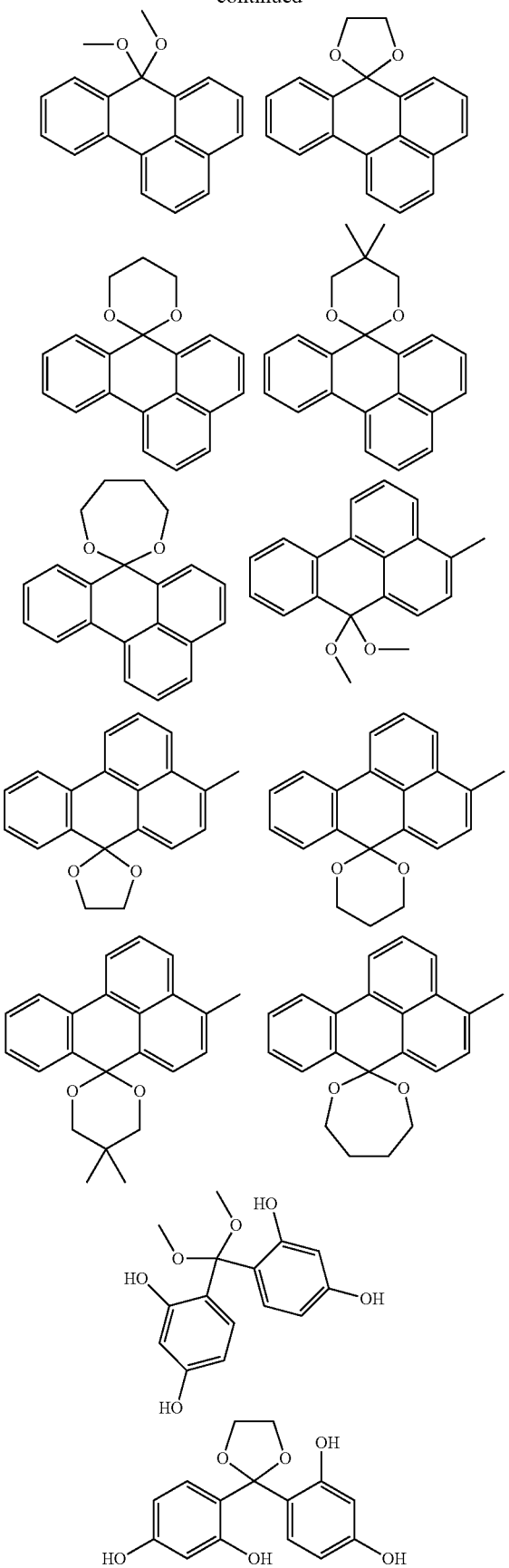

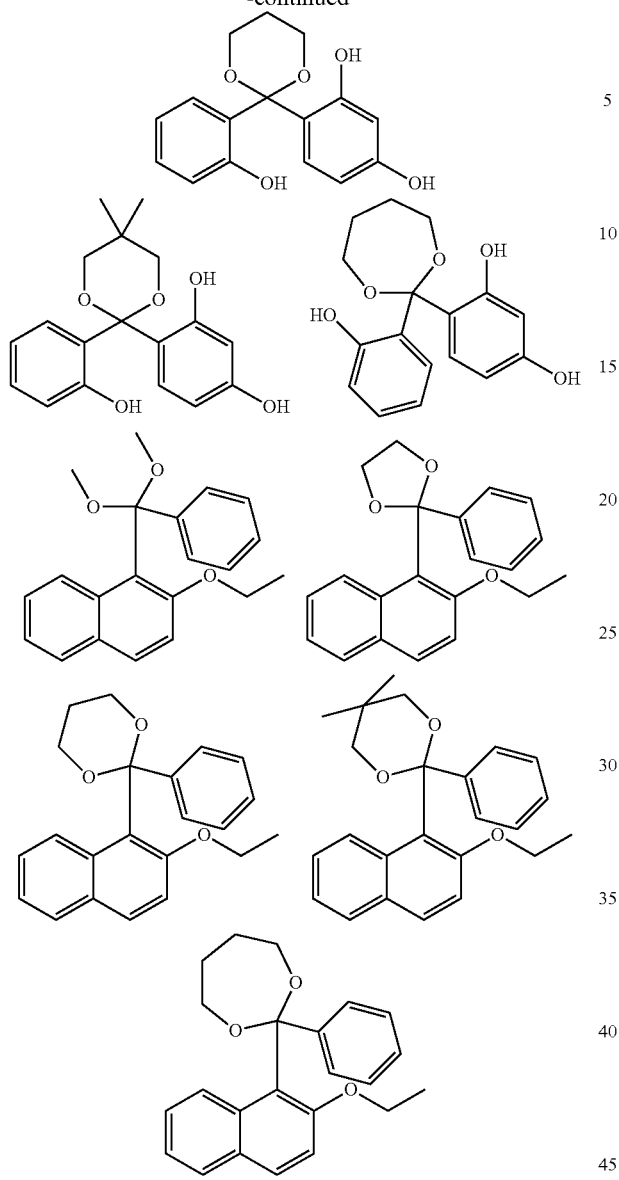
[Chemical Formula 39]
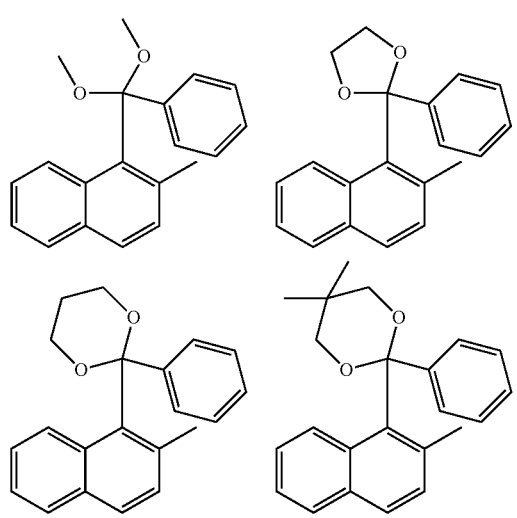
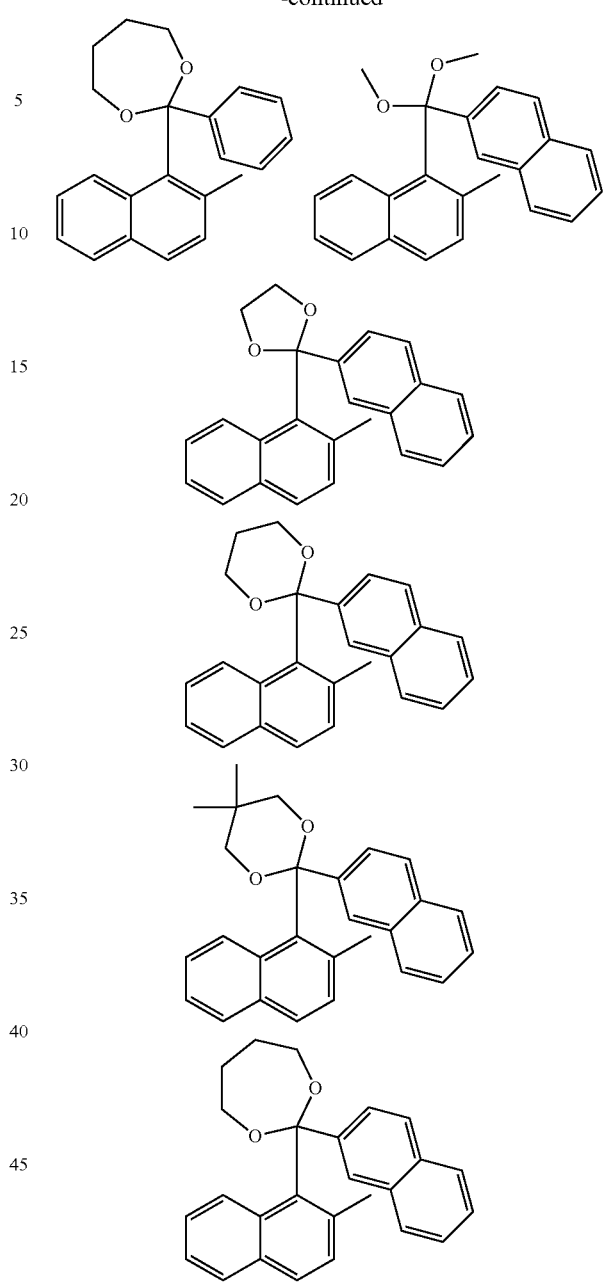
[Chemical Formula 40]
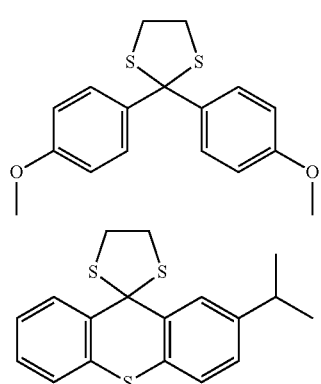

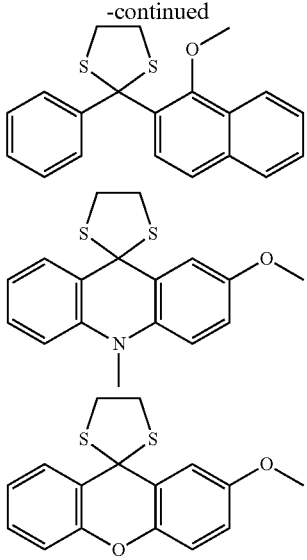
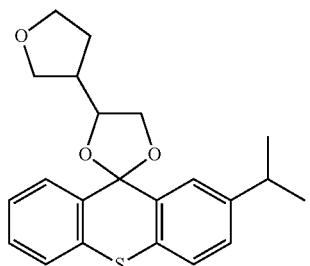
[Chemical Formula 41]
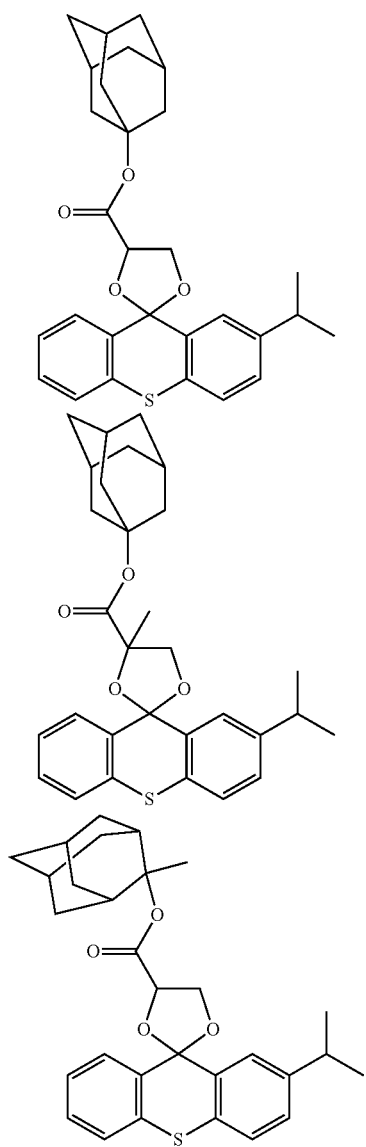
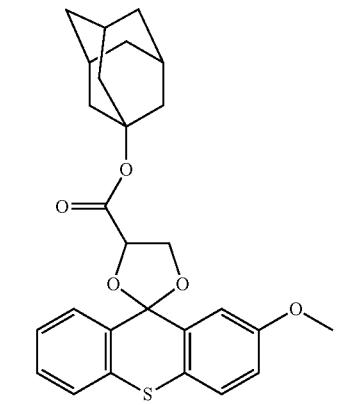
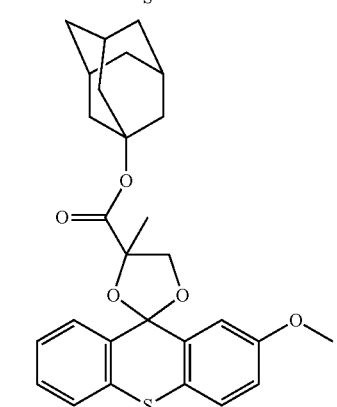
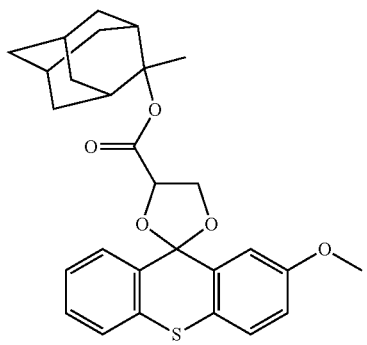
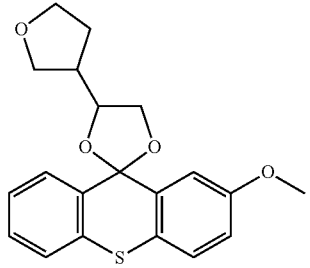

-continued
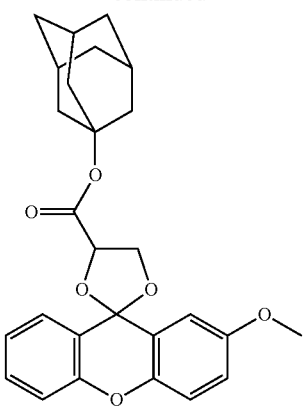
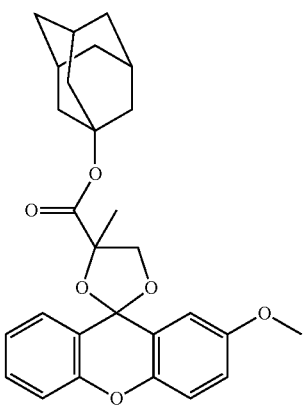
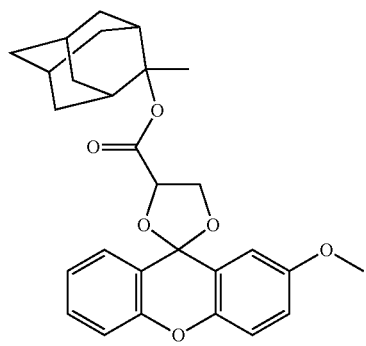
-continued
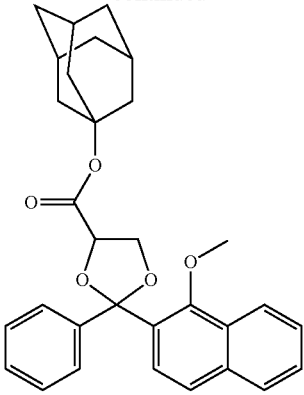
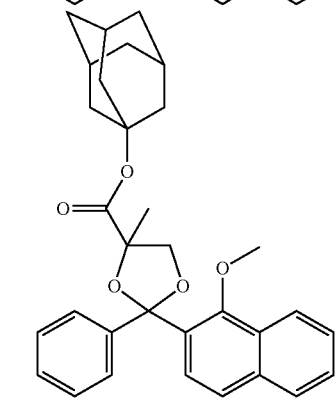
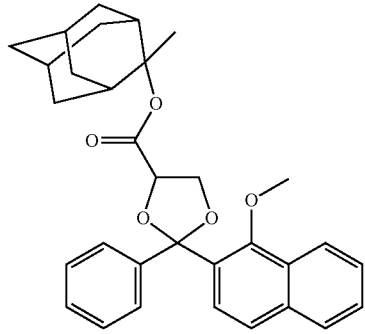
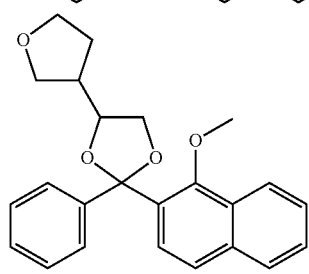
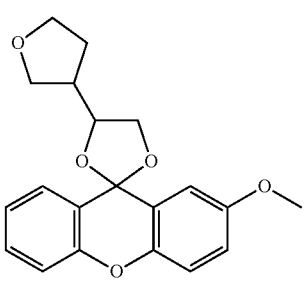
The following compounds are examples of the orthoester compound having a carbon atom substituted with three alkoxy groups.
[Chemical Formula 42]
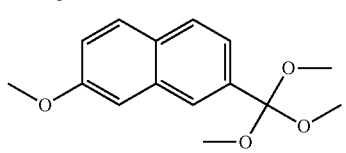

-continued
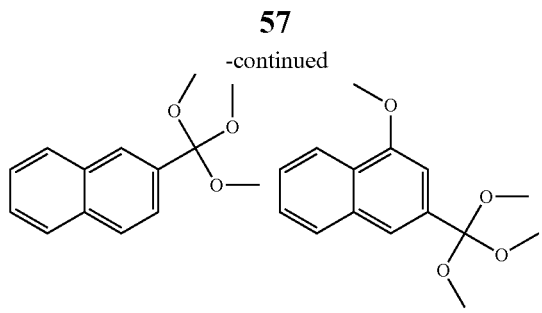
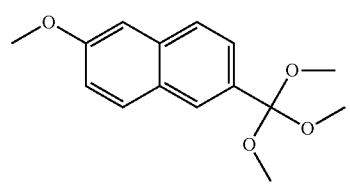
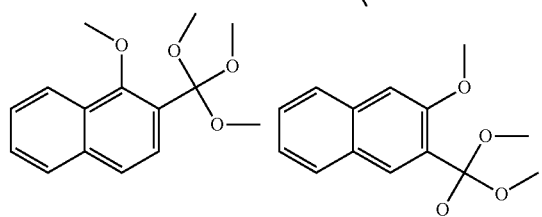
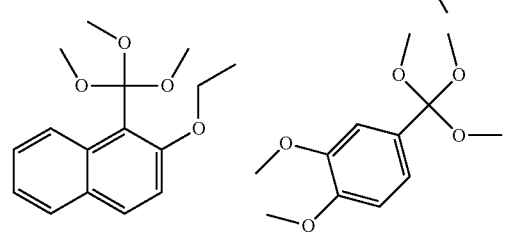
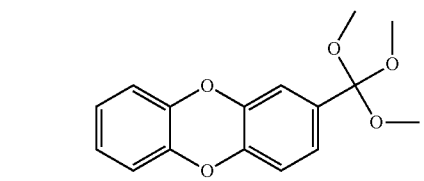
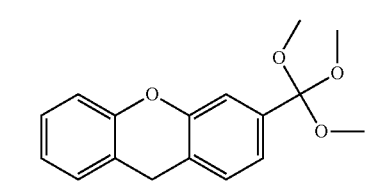
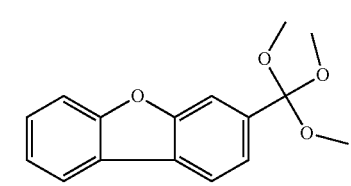
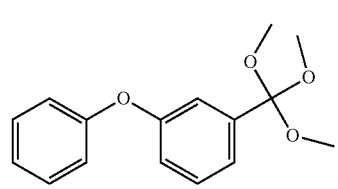
-continued
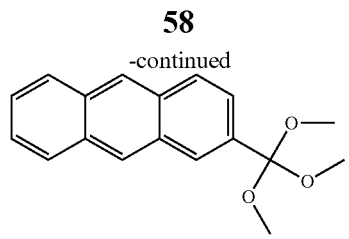
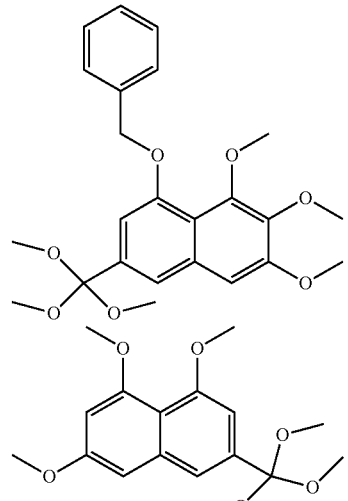
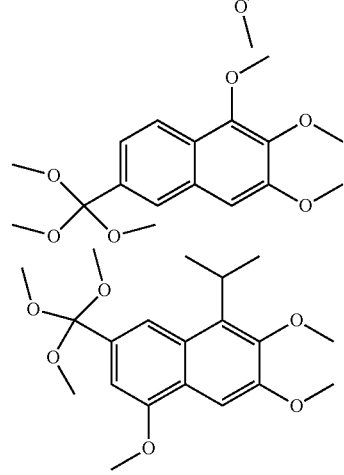
The above orthoester compounds are deprotected due to an acid catalyst generated at the time of pattern-exposure and generate a carbonyl group-containing ester (methyl carboxylate in the following examples).
[Chemical Formula 43]
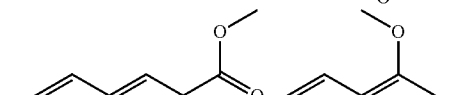

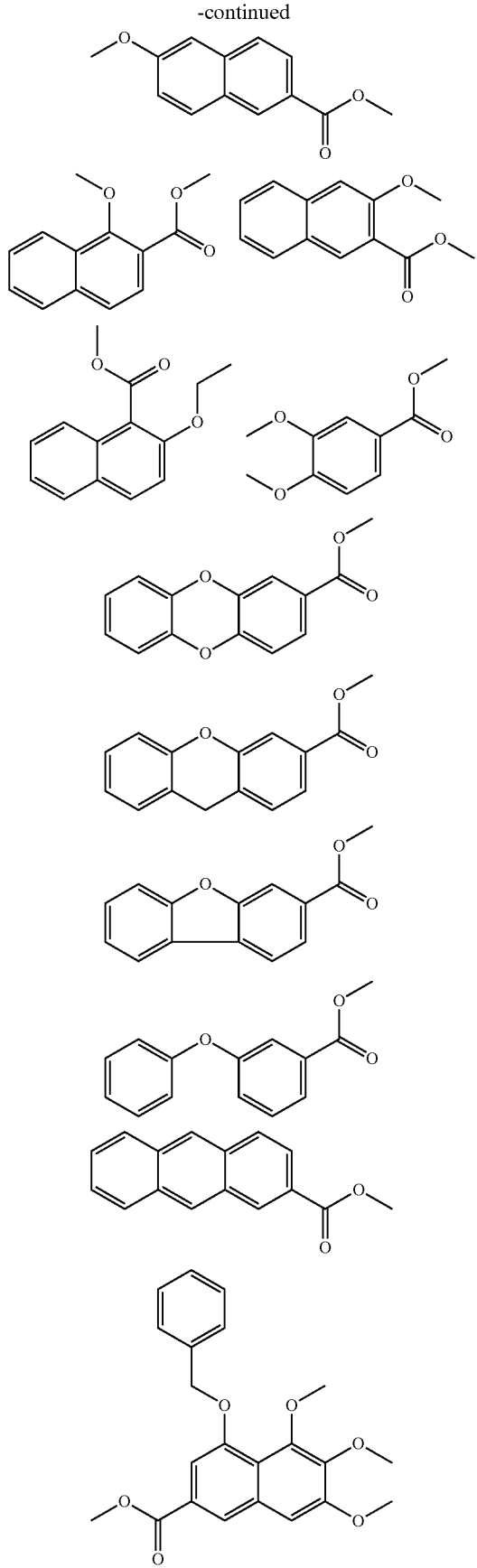
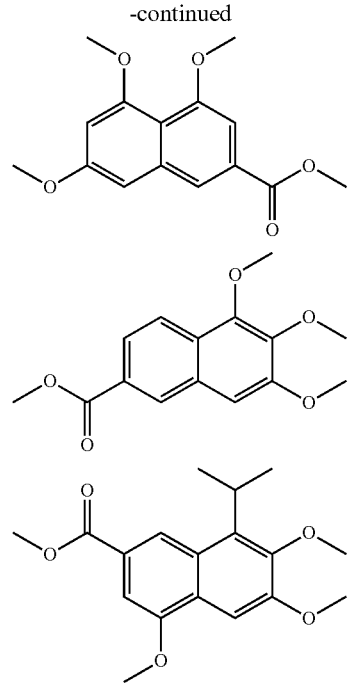
The following chemical formulae show examples of the OBO ester compound as derivatives in which the portion of carboxyl group of the carboxyl group-containing photosensitizer is protected with OBO (for example, 4-methyl-2,6,7-trioxabicyclo[2.2.2]octane-1-yl).
[Chemical Formula 44]
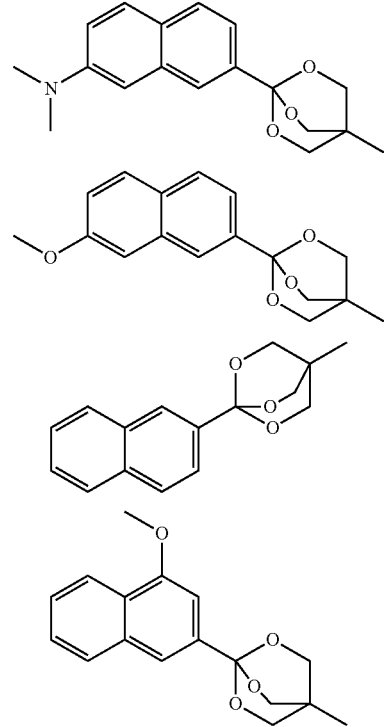

61
-continued
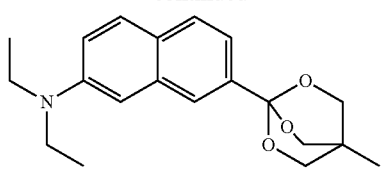
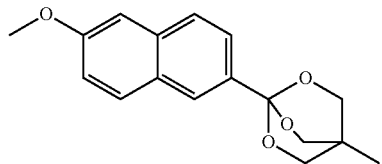
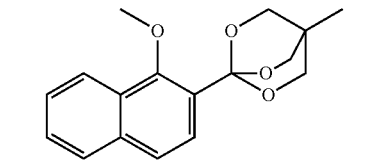
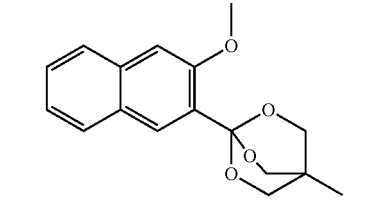
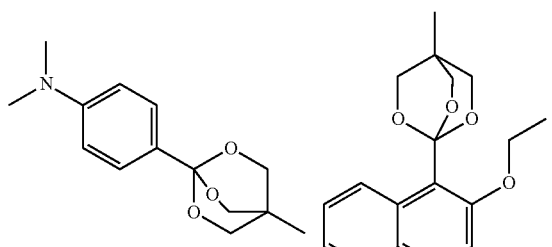
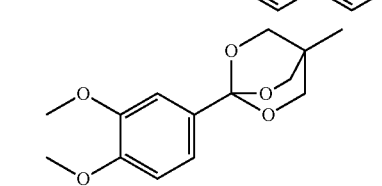
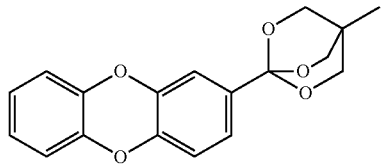
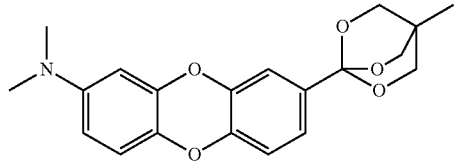
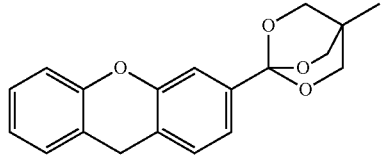
62
-continued
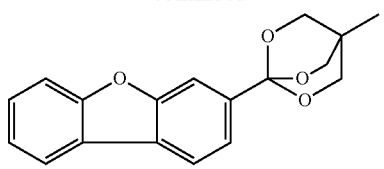
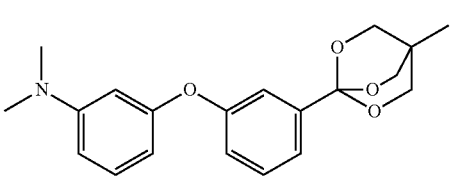
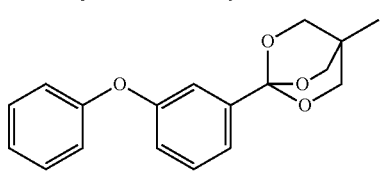
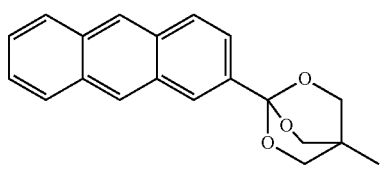
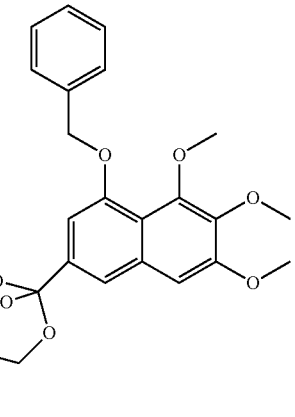
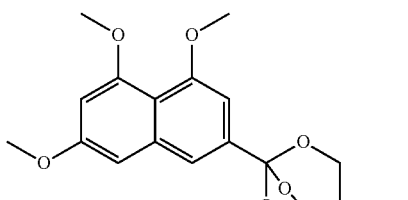
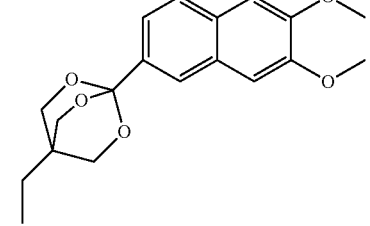

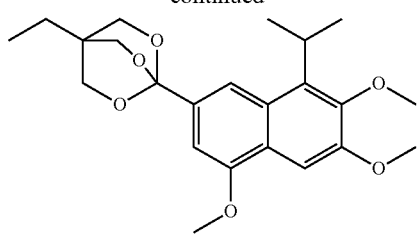
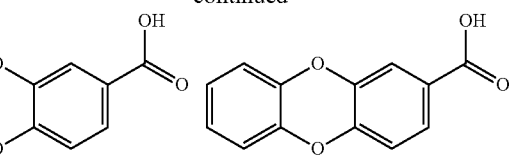
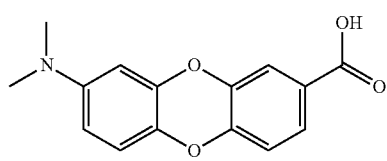
The above OBO ester compounds generate the following carboxylic acids by an acid catalyst generated at the time of pattern-exposure.
[Chemical Formula 45]
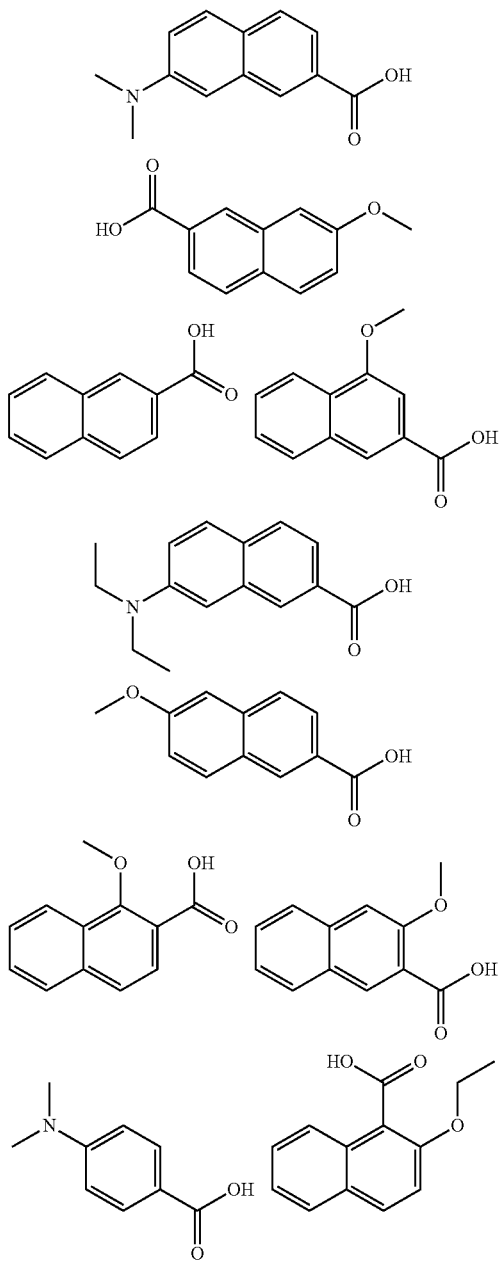
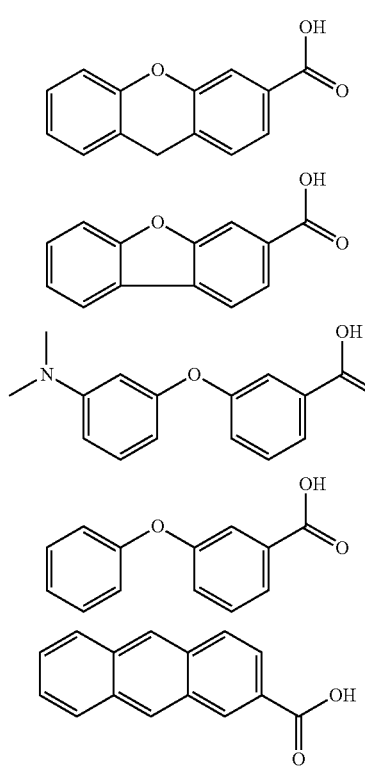
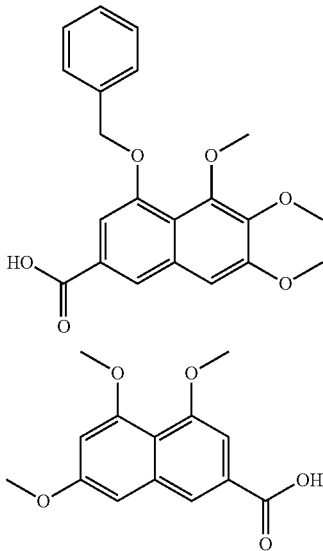

-continued

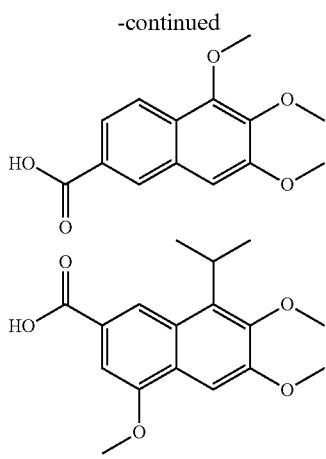

The photosensitizer generated from the component (2) (that is, the components (a) and (b) described above) by exposure should be able to absorb the radiation of flood-exposure to decompose a photoacid generator (PAG). For example, in a case of sensitization by generating an acid through the decomposition of PAG caused by the electron transfer from the photosensitizer to PAG, it is desired for the photosensitizer to satisfy the conditions under which the electron transfer occurs. That is, in order for the electron transfer to occur at the wavelength of the radiation of the flood-exposure, it is desired that the oxidation potential of the photosensitizer is sufficiently low while the reduction potential of PAG is sufficiently high. If such a demand is satisfied, the free energy of the electron transfer reaction of the photosensitization becomes negative, and thus the reaction easily occurs. In a case where a triplet photosensitization reaction from the photosensitizer to PAG is used, it is desired that the photosensitizer can be excited at the wavelength of the radiation of the flood-exposure to a singlet-excited state, and the energy level of the triplet-excited state of the photosensitizer is higher than the energy level of the triplet-excited state of PAG. Examples of the photosensitizer generated from the component (2) (that is, the components (a) and (b) described above) by exposure include chalcone and derivatives thereof, 1,2-diketone and derivatives thereof, benzoin and derivatives thereof, benzophenone and derivatives thereof, fluorene and derivatives thereof, naphthoquinone and derivatives thereof, anthraquinone and derivatives thereof, xanthene and derivatives thereof, thioxanthene and derivatives thereof, xanthone and derivatives thereof, thioxanthone and derivatives thereof, cyanine and derivatives thereof, merocyanine and derivatives thereof, naphthalocyanine and derivatives thereof, subphthalocyanine and derivatives thereof, pyrylium and derivatives thereof, thiopyrylium and derivatives thereof, tetraphylline and derivatives thereof, annulene and derivatives thereof, spiropyran and derivatives thereof, spirooxazine and derivatives thereof, thiospiropyran and derivatives thereof, oxole and derivatives thereof, azine and derivatives thereof, thiazine and derivatives thereof, oxazine and derivatives thereof, indoline and derivatives thereof, azulene and derivatives thereof, azulenium and derivatives thereof, squarylium and derivatives thereof, porphyrin and derivatives thereof, porphyrazine and derivatives thereof, triarylmethane and derivatives thereof, phthalocyanine and derivatives thereof, acridone and derivatives thereof, coumarin and derivatives thereof, ketocoumarin and derivatives thereof, quinolinone and derivatives thereof, benzoxazole and derivatives thereof, acridine and derivatives thereof, thiazine and derivatives thereof, benzothiazole and derivatives thereof, phenothiazine and derivatives thereof, benzotriazole and derivatives thereof, perylene and derivatives thereof, naphthalene and derivatives thereof, anthracene and derivatives thereof, phenanthrene and derivatives thereof, pyrene and derivatives thereof, naphthacene and derivatives thereof, pentacene and derivatives thereof, coronene and derivatives thereof, and the like. Furthermore, it is preferable that the photosensitizer generated from the component (2) through exposure contains a carbonyl compound. It is preferable that the carbonyl compound contains, as a carbonyl group, ketone, aldehyde, carboxylic acid, an ester, amide, enone, carboxylic acid chloride, carboxylic acid anhydride, or the like. In order to enhance the resist contrast by sufficiently separating the wavelength of the radiation at the time of flood-exposure from the wavelength of the radiation at the time of pattern-exposure, the carbonyl compound is preferably a compound absorbing long-wavelength radiation having a wavelength of equal to or greater than 250 nm. Examples of the carbonyl compound include benzophenone derivatives, xanthone derivatives, thioxanthone derivatives, coumarin derivatives, acridone derivatives, and the like. Furthermore, the carbonyl compound may be a naphthalene derivative or an anthracene derivative, and may be an acridone derivative. In the photosensitizer, the hydrogen of an aromatic ring is preferably substituted with an electron-donating group. If the hydrogen of an aromatic ring of the photosensitizer is substituted with an electron-donating group, the efficiency of the electron transfer by the sensitization reaction at the time of flood-exposure tends to be improved, and the sensitivity of the resist tends to be improved. In addition, a greater difference can be made between the absorption wavelength of the radiation of the photosensitizer precursor and the absorption wavelength of the radiation of the photosensitizer, and the photosensitizer can be excited in a more selective manner at the time of flood-exposure. Therefore, the contrast of the latent image of the acid in the resist material tends to be improved. Examples of the electron-donating group include a hydroxyl group, a methoxy group, an alkoxy group, an amino group, an alkylamino group, an alkyl group, and the like.

Examples of benzophenone and derivatives thereof include the following compounds.

[Chemical Formula 46]

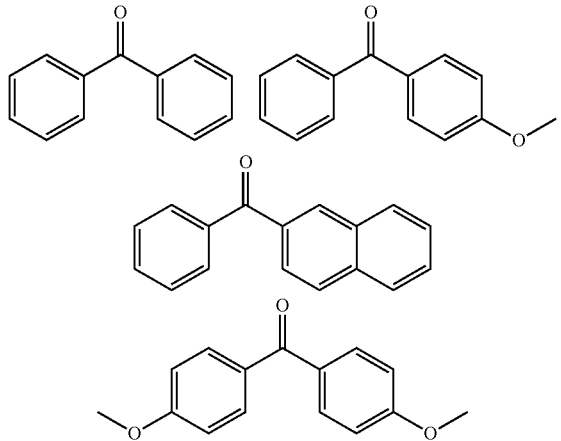

-continued
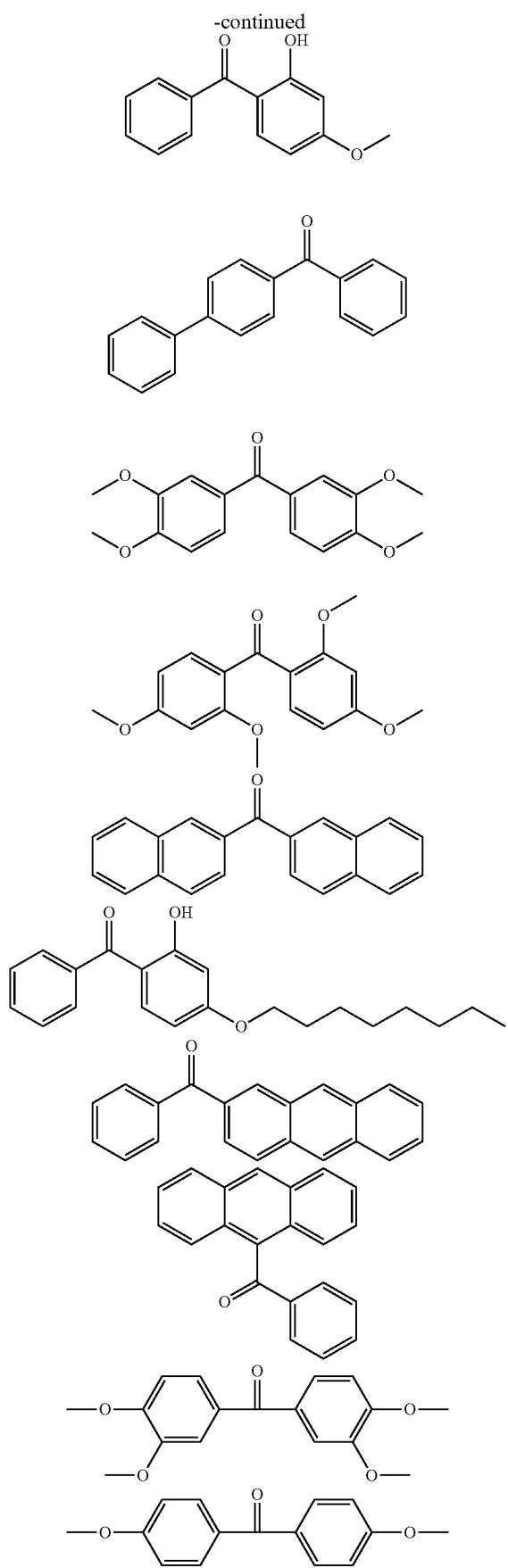
[Chemical Formula 47]
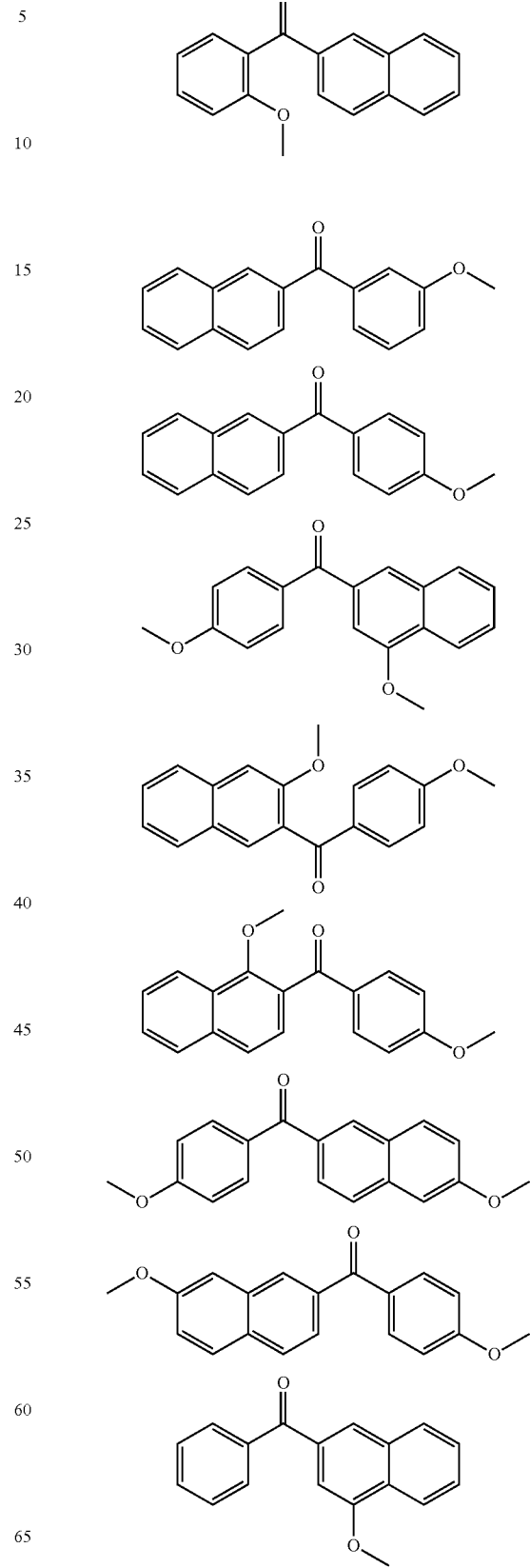

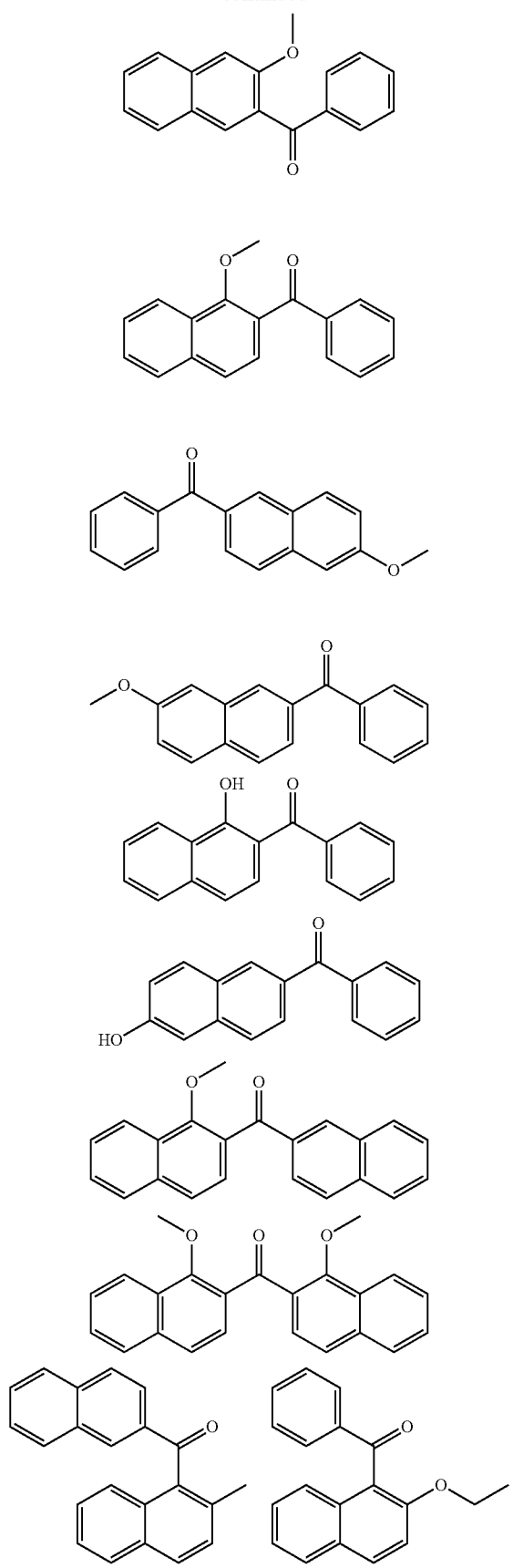
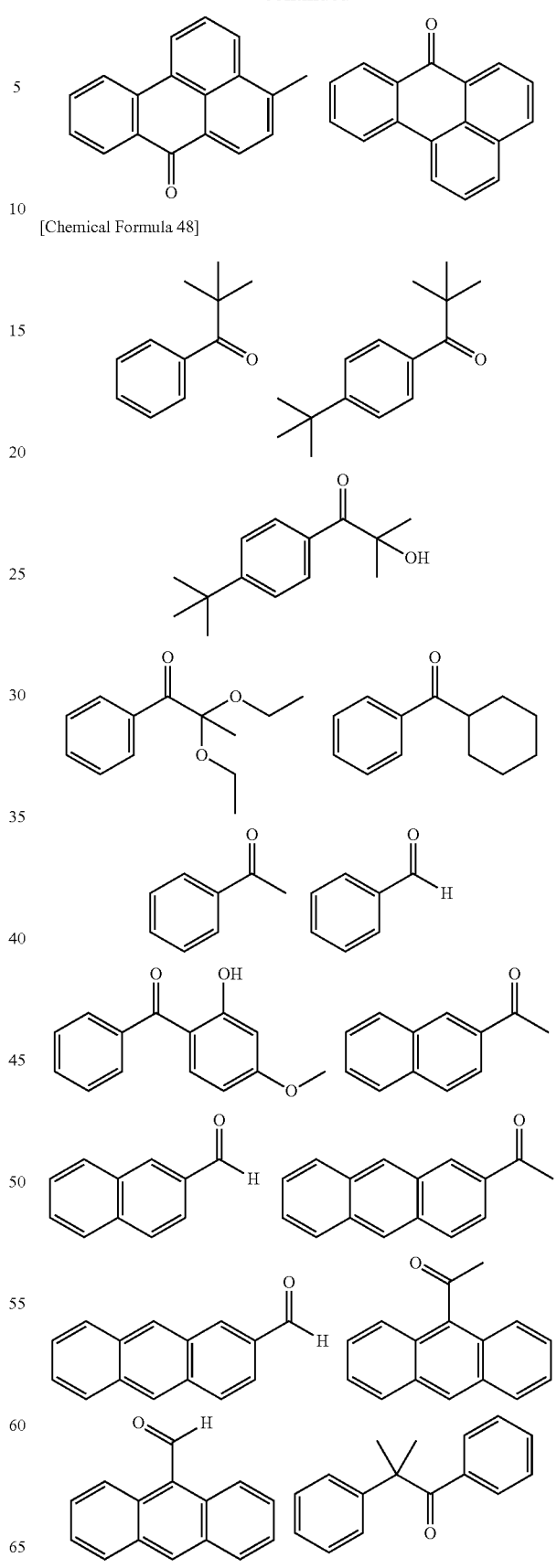
[Chemical Formula 48]

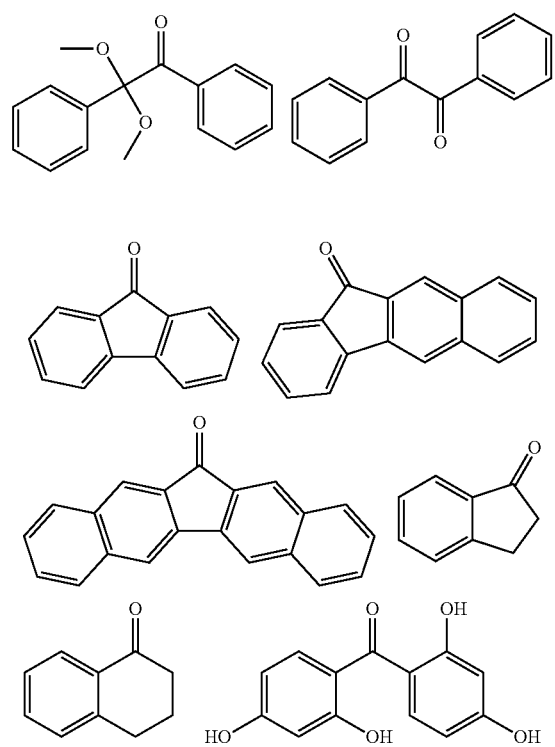
[Chemical Formula 49]
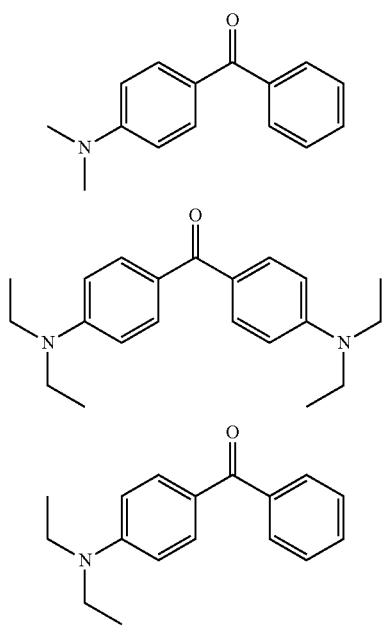
Examples of thioxanthone and derivatives thereof include the following compounds.
[Chemical Formula 50]
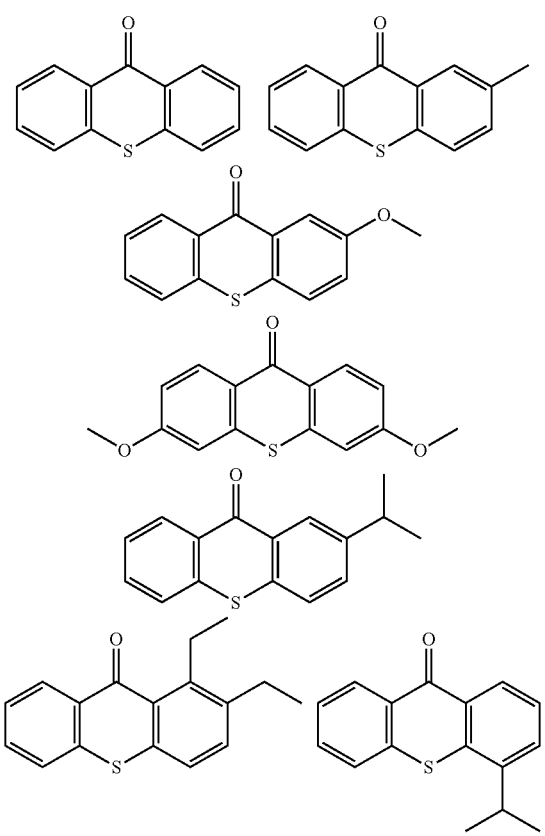
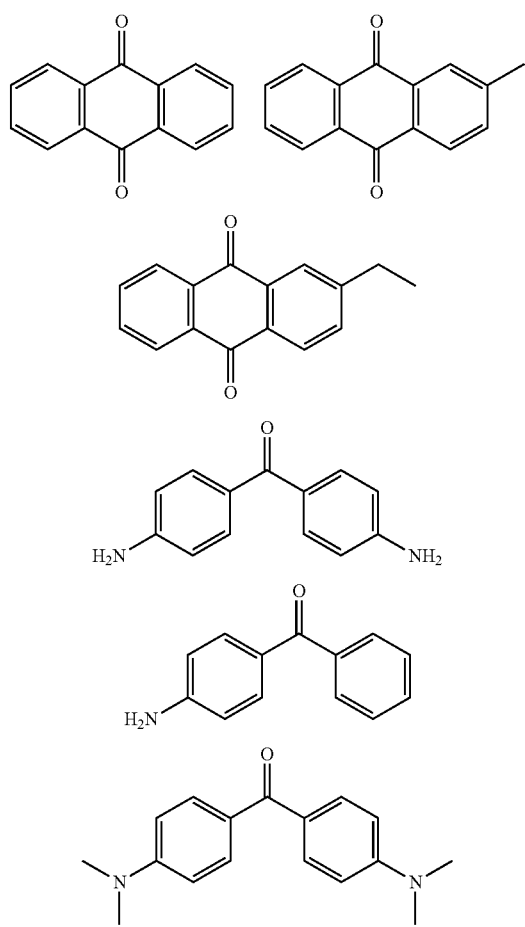
Examples of xanthone and derivatives thereof include the following compounds.

[Chemical Formula 51]
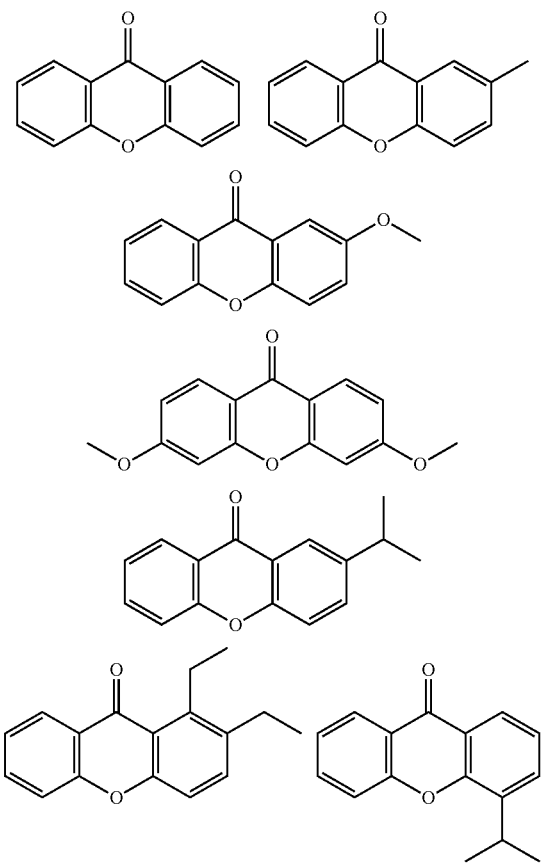
Examples of acridone and derivatives thereof include the following compounds.
[Chemical Formula 52]
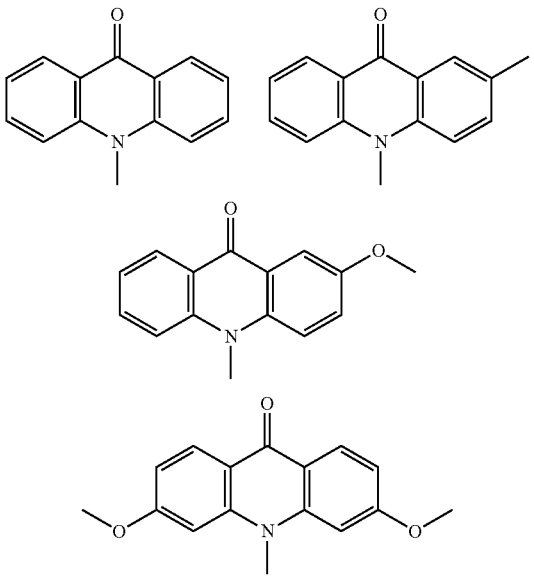
Examples of coumarin and derivatives thereof include the following compounds.
[Chemical Formula 53]
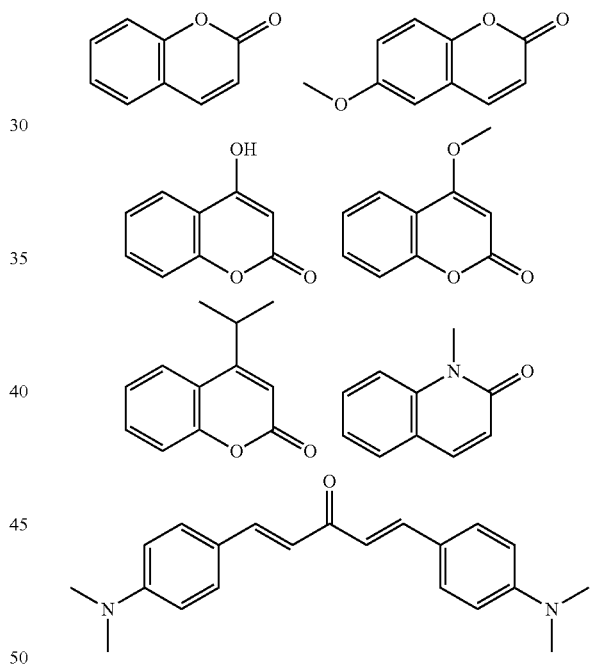
The above photosensitizers may contain the following compounds.
[Chemical Formula 54]
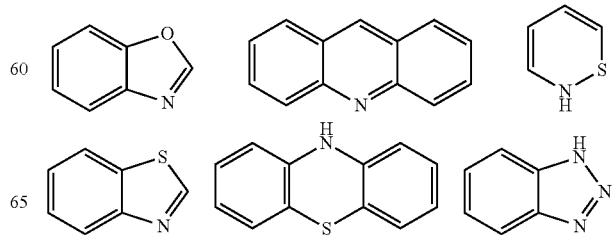

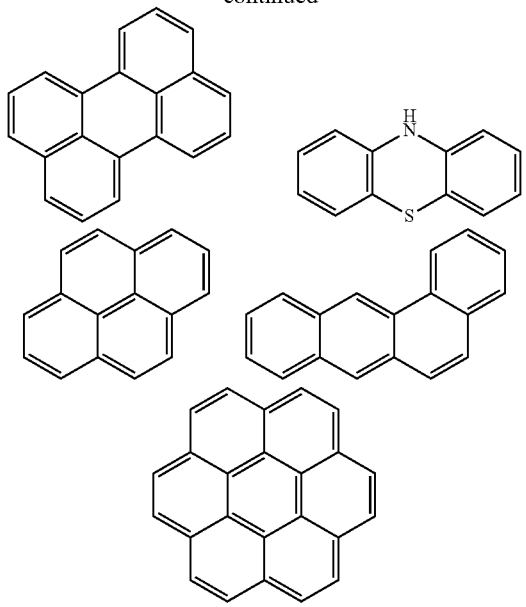

More specific examples of the above photosensitizers include acetophenone, 2,2-dimethoxy-2-phenylacetophenone, diethoxyacetophenone, 1-hydroxycyclohexylphenylketone, 1,2-hydroxy-2-methyl-1-phenylpropan-1-one, α-hydroxycyclohexylphenylketone, 2-hydroxy-2-methyl-1-phenylpropanone, 2-hydroxy-2-methyl-1-(4-isopropyphenyl)propanone, 2-hydroxy-2-methyl-1-(4-dodecylphenyl) propanone, 2-hydroxy-2-methyl-1-[(2-hydroxyethoxy) phenyl]propanone, benzophenone, 2-methylbenzophenone, 3-methylbenzophenone, 4-methylbenzhophenone, 4-methoxybenzophenone, 2-chlorobenzophenone, 4-chlorobenzophenone, 4-bromobenzophenone, 2-carboxybenzophenone, 2-ethoxycarbonylbenzophenone, 4-benzoyl-4'-methyldiphenyl sulfide, benzophenone tetracarboxylic acid or a tetramethyl ester thereof, 4,4'-bis(dimethylamino)benzophenone, 4,4'-bis(dicyclohexylamino)benzophenone, 4,4'-bis(diethylamino)benzophenone, 4,4'-bis(dihydroxyethylamino)benzophenone, 4-methoxy-4'-dimethylaminobenzophenone, 4,4'-dimethoxybenzophenone, 4-dimethyl aminobenzophenone, 4-dimethylaminoacetophenone, benzyl, anthraquinone, 2-t-butylanthraquinone, 2-methylanthraquinone, phenanthraquinone, fluorenone, 2-benzyl-2-dimethylamino-1-(4-morpholinophenyl)-1-butanone, 2-(dimethylamino)-2-[(4-methylphenyl)methyl]-1-[4-(4-morpholinyl)phenyl]-1-butanone, 2-methyl-1-[4-(methylthio)phenyl]-2-morpholino-1-propanone, 2-hydroxy-2-methyl-[4-(1-methylvinyl)phenyl]propanol oligomer, benzoin, benzoin methyl ether, benzoin ethyl ether, benzoin propyl ether, benzoin isopropyl ether, benzoin isobutyl ether, benzoin phenyl ether, benzyl dim ethyl ketal, acridone, chloroacridone, N-methylacridone, N-butylacridone, N-butyl-chloroacridone, 2,4,6-trimethylbenzoyldiphenylphosphine oxide, 2,6-dimethoxybenzoyldiphenylphosphine oxide, 2,6-dichlorobenzoyldiphenylphosphine oxide, 2,4,6-trimethylbenzoylmethoxyphenylphosphine oxide, 2,4,6-trimethylbenzoylethoxyphenylphosphine oxide, 2,3,5,6-tetramethylbenzoyldiphenylphosphine oxide, bis-(2,6-dichlorobenzoyl)phenylphosphine oxide, bis-(2,6-dichlorobenzoyl)-2,5-dimethylphenylphosphine oxide, bis-(2,6-dichlorobenzoyl)-4-propylphenylphosphine oxide, bis-(2,6-dichlorobenzoyl)-1-naphthylphosphine oxide, bis-(2,6-dimethoxybenzoyl)phenylphosphine oxide, bis-(2,6-dimethoxybenzoyl)-2,4,4-trimethylpentylphosphine oxide, bis-(2,6-dimethoxybenzoyl)-2,5-dimethylphenylphosphine oxide, bis-(2,4,6-trimethylbenzoyl)phenylphosphine oxide, (2,5,6-trimethylbenzoyl)-2,4,4-trimethylpentylphosphine oxide, 2-isopropylthioxanthone, 4-isopropylthioxanthone, 2,4-diethylthioxanthone, 2,4-dichlorothioxanthone, 1-chloro-4-propoxythioxanthone, benzoyl di-(2,6-dimethylphenyl)phosphonate, 1-[4-(phenylthio)phenyl]-1,2-octanedione-2-(O-benzoyloxime), 1-[9-ethyl-6-(2-methylbenzoyl)-9H-carbazol-3-yl]ethanone-1-(O-acetyloxime), 1-[9-ethyl-6-(2-methylbenzoyl)-9H-carbazol-3-yl]-3-cyclopentylpropanone-1-(O-acetyloxime), 1-[4-(phenylthio)phenyl]-3-cyclopentylpropane-1,2-dione-2-(O-benzoyloxime), 2,2-dimethoxy-1,2-diphenylethan-1-one, 1-[4-(2-hydroxyethoxy)-phenyl]-2-hydroxy-2-methyl-1-propan-1-one, 2-hyroxy-1-{4-[4-(2-hydroxy-2-methyl-propionyl)-benzyl]phenyl}-2-methyl-propan-1-one, a phenylglyoxylic acid methyl ester, 2-methyl-1-(4-methylthiophenyl)-2-morpholinopropan-1-one, 2-benzyl-2-dimethylamino-1-(4-morpholinophenyl)-butanone-1, 1,2-octanedione 1-[4-(phenylthio)-2-(O-benzoyloxime)], ethanone1-[9-ethyl-6-(2-methylbenzoyl)-9H-carbazol-3-yl]-1-(0-acetyloxime), and the like.

Hereinafter, examples of the photosensitizer and the (b) photosensitizer precursor generating the photosensitizer will be described, and an absorption ratio of the non-ionizing radiation (wavelength: 365 nm) of the photosensitizer to the (b) photosensitizer precursor will be described. The absorption ratio is calculated by taking the amount of the non-ionizing radiation absorbed by the (b) photosensitizer precursor as a denominator and the amount of the non-ionizing radiation absorbed by the photosensitizer as a numerator. By comparing the amounts of the non-ionizing radiation absorbed by the (b) photosensitizer precursor and the photosensitizer, it is understood that the amount of the non-ionizing radiation absorbed increases tenfold or more through the structure change from the (b) photosensitizer precursor to the photosensitizer.

TABLE 1

| Photosensitizer | (b) Photosensitizer precursor | Absorption ratio |
|---|---|---|
| Benzophenone derivative | Ketal structure | at least tenfold |
| Naphthyl phenyl ketone derivative | Ketal structure | at least tenfold |
| Thioxanthone derivative | Ketal structure | at least tenfold |
| Acridone derivative photosensitizer | Ketal structure | at least tenfold |
| Benzanthrone derivative photosensitizer | Ketal structure | at least tenfold |
| Naphthaldehyde derivative | Acetal structure | at least tenfold |
| Naphthalene carboxylic acid derivative | Orthoester structure | at least tenfold |

(c) Photoacid Generator

The photoacid generator is a component which generates an acid by being irradiated with ionizing radiation or non-ionizing radiation having a wavelength of equal to or less than 400 nm, preferably equal to or less than 250 nm, and more preferably equal to or less than 200 nm, and is different from the component (a). The photoacid generator is preferably a salt of a cation and an anion. It is desired that the photoacid generator absorbs sufficiently little the radiation having a wavelength of flood-exposure and does not directly generate an acid by the radiation at the time of flood-exposure. If such a demand is satisfied, it is possible to generate an acid only in a pattern-exposed portion within the resist material film by the photosensitization reaction at the time of flood-exposure.

Specific examples of the photoacid generator include an onium salt compound, a diazomethane compound, a sulfonimide compound, and the like. Examples of the onium salt compound include a sulfonium salt compound, a tetrahydrothiophenium salt compound, an iodoinum salt compound, and the like. The photoacid generator has a sufficiently high reduction potential for electron transfer and can generate an acid by being decomposed by receiving an electron from the photosensitizer excited through the flood-exposure. Furthermore, in a case where the energy level of the triplet-excited state of the photosensitizer is higher than the energy level of the triplet-excited state of the photoacid generator, a triplet sensitization reaction from the photosensitizer to the photoacid generator easily occurs. The photoacid generator preferably contains at least one compound selected from the group consisting of a sulfonium salt compound, an iodonium salt compound, a sulfonyldiazomethane, N-sulfonyloxyimide, and an oxime-O-sulfonate type photoacid generator, is more preferably at least one compound selected from the group consisting of a sulfonium salt compound and an iodonium salt compound, and even more preferably contains an iodonium salt compound.

Specific examples of the sulfonium salt compound include triphenylsulfonium trifluoromethanesulfonate, triphenylsulfonium nonafluoro-n-butanesulfonate, triphenylsulfonium perfluoro-n-octanesulfonate, triphenylsulfonium 2-bicyclo[2.2.1]hept-2-yl-1,1,2,2-tetrafluoroethanesulfonate, 4-cyclohexylphenyldiphenylsulfonium trifluoromethanesulfonate, 4-cyclohexylphenyldiphenylsulfonium nonafluoro-n-butanesulfonate, 4-cyclohexylphenyldiphenylsulfonium perfluoro-n-octanesulfonate, 4-cyclohexylphenyldiphenylsulfonium 2-bicyclo[2.2.1]hept-2-yl-1,1,2,2-tetrafluoroethanesulfonate, 4-methanesulfonylphenyldiphenylsulfonium trifluoromethanesulfonate, 4-methanesulfonylphenyldiphenylsulfonium nonafluoro-n-butanesulfonate, 4-methanesulfonylphenyldiphenylsulfonium perfluoro-n-octanesulfonate, 4-methanesulfonylphenyldiphenylsulfonium 2-bicyclo[2.2.1]hept-2-yl-1,1,2,2-tetrafluoroethanesulfonate, and the like.

Specific examples of the tetrahydrothiophenium salt compound include 1-(4-n-butoxynaphthalen-1-yl)tetrahydrothiophenium trifluoromethanesulfonate, 1-(4-n-butoxynaphthalen-1-yl)tetrahydrothiophenium nonafluoro-n-butanesulfonate, 1-(4-n-butoxynaphthalen-1-yl)tetrahydrothiophenium perfluoro-n-octanesulfonate, 1-(4-n-butoxynaphthalen-1-yl)tetrahydrothiophenium 2-bicyclo[2.2.1]hept-2-yl-1,1,2,2-tetrafluoroethanesulfonate, 1-(6-n-butoxynaphthalen-2-yl)tetrahydrothiophenium trifluoromethanesulfonate, 1-(6-n-butoxynaphthalen-2-yl)tetrahydrothiophenium nonafluoro-n-butanesulfonate, 1-(6-n-butoxynaphthalen-2-yl)tetrahydrothiophenium perfluoro-n-octanesulfonate, 1-(6-n-butoxynaphthalen-2-yl)tetrahydrothiophenium 2-bicyclo[2.2.1]hept-2-yl-1,1,2,2-tetrafluoroethanesulfonate, 1-(3,5-dimethyl-4-hydroxyphenyl)tetrahydrothiophenium trifluoromethanesulfonate, 1-(3,5-dimethyl-4-hydroxyphenyl)tetrahydrothiophenium nonafluoro-n-butanesulfonate, 1-(3,5-dimethyl-4-hydroxyphenyl)tetrahydrothiophenium perfluoro-n-octanesulfonate, 1-(3,5-dimethyl-4-hydroxyphenyl)tetrahydrothiophenium 2-bicyclo[2.2.1]hept-2-yl-1,1,2,2-tetrafluoroethanesulfonate, and the like.

Specific examples of the iodonium salt compound include diphenyliodonium trifluoromethanesulfonate, diphenyliodonium nonafluoro-n-butanesulfonate, diphenyliodonium perfluoro-n-octanesulfonate, diphenyliodonium 2-bicyclo[2.2.1]hept-2-yl-1,1,2,2-tetrafluoroethanesulfonate, bis(4-t-butylphenyl)iodonium trifluoromethanesulfonate, bis(4-t-butylphenyl)iodonium nonafluoro-n-butanesulfonate, bis(4-t-butylphenyl)iodonium perfluoro-n-octanesulfonate, bis(4-t-butylphenyl)iodonium 2-bicyclo[2.2.1]hept-2-yl-1,1,2,2-tetrafluoroethanesulfonate, and the like.

Specific examples of the sulfonimide compound include N-(trifluoromethanesulfonyloxy)bicyclo[2.2.1]hept-5-ene-2,3-dicarboximide, N-(nonafluoro-n-butanesulfonyloxy)bicyclo[2.2.1]hept-5-ene-2,3-dicarboximide, N-(perfluoro-n-octanesulfonyloxy)bicyclo[2.2.1]hept-5-ene-2,3-dicarboximide, N-(2-bicyclo[2.2.1]hept-2-yl-1,1,2,2-tetrafluoroethanesulfonyloxy)bicyclo[2.2.1]hept-5-ene-2,3-dicarboximide, and the like.

Specific examples of the diazomethane compound include bis(n-propylsulfonyl)diazomethane, bis(isopropylsulfonyl)diazomethane, bis(n-butylsulfonyl)diazomethane, bis(tert-butylsulfonium)diazomethane, bis(cyclopentylsulfonyl)diazomethane, bis(cyclohexylsulfonyl)diazomethane, bis(phenylsulfonyl)diazomethane, bis(4-chlorophenylsulfonyl)diazomethane, bis(p-tolylsulfonyl)diazomethane, bis(2,4-xylylsulfonyl)diazomethane, bis(4-isopropylphenylsulfonyl)diazomethane, bis(4-tert-butylphenylsulfonyl)diazomethane, bis(naphthylsulfonyl)diazomethane, bis(anthracenylsulfonyl)diazomethane, and the like.

(Other Components)

The resist material may appropriately contain (3) a first scavenger, (4) a second scavenger, (5) a cross-linking agent, (6) an additive, (7) a solvent, and the like in addition to the (1) base component and the component (2) described above.

(3) First Scavenger

The first scavenger is a component which captures an acid and a cation and functions as a quencher. If the resist material contains the first scavenger, the acid generated in the resist material can be neutralized, and hence the chemical contrast of the latent image of the acid between a pattern-exposed portion and a pattern-unexposed portion can be enhanced. In a case where the component (a) has a ketal compound group or an acetal compound group or in a case where the component (b) has a ketal compound or an acetal compound, the photosensitizer is generated through an acid-catalyzed reaction at normal temperature. If the resist material contains the first scavenger, the acid functioning as a catalyst in a photosensitizer generating reaction is captured, and hence the contrast of the generation of the photosensitizer from the acetal compound or the like can also be enhanced. Furthermore, in a case where the photosensitizer is generated by a reaction mechanism in which the resist material is photosensitized through a cationic intermediate generated by the pattern-exposure step, by capturing the cationic intermediate, the acid increases only in a pattern-exposed portion in a more selective manner at the time of flood-exposure, and an effect of improving the chemical contrast of the latent image of the acid is obtained. The first scavenger can be classified into a scavenger having optical reactivity and a scavenger without optical reactivity.

In a case where the first scavenger is a scavenger without optical reactivity, the scavenger is preferably a basic compound. Examples of the basic compound include a hydroxide compound, a carboxylate compound, an amine compound, an imine compound, an amide compound, and the like. More specifically, examples thereof include primary to tertiary aliphatic amines, aromatic amine, heterocyclic amine, a nitrogen-containing compound having a carboxyl group, a nitrogen-containing compound having a sulfonyl group, a nitrogen-containing compound having a hydroxyl group, a nitrogen-containing compound having a hydroxyphenyl group, an alcoholic nitrogen-containing compound, a nitrogen-containing compound having a carbamate group, an amide compound, an imide compound, and the like. The basic compound is preferably a nitrogen-containing compound having a carbamate group. The basic compound may be a Troger's base; hindered amine such as diazabicycloundecene (DBU) or diazabicyclononene (DBM); or an ionic quencher such as tetrabutylammoniumhydroxide (TBAH) or tetrabutylammoniumlactate.

Specific examples of the primary aliphatic amine include ammonia, methylamine, ethylamine, n-propylamine, isopropylamine, n-butylamine, isobutylamine, sec-butylamine, tert-butylamine, pentylamine, tert-amylamine, cyclopentylamine, hexylamine, cyclohexylamine, heptylamine, octylamine, nonylamine, decylamine, dodecylamine, cetylamine, methylenediamine, ethylenediamine, tetraethylenepentamine, and the like. Specific examples of the secondary aliphatic amine include dimethylamine, diethylamine, di-n-propylamine, diisopropylamine, di-n-butylamine, diisobutylamine, di-sec-butylamine, dipentylamine, dicyclopentylamine, dihexylamine, dicyclohexylamine, diheptylamine, dioctylamine, dinonylamine, didecylamine, didodecylamine, dicetylamine, N,N-dimethylmethylenediamine, N,N-dimethylethylenediamine, N,N-dimethyltetraethylenepentamine, and the like. Specific examples of the tertiary aliphatic amine include trimethylamine, triethylamine, tri-n-propylamine, triisopropylamine, tri-n-butylamine, triisobutylamine, tri-sec-butylamine, tripentylamine, tricyclopentylamine, trihexylamine, tricyclohexylamine, triheptylamine, trioctylamine, trinonylamine, tridecylamine, tridodecylamine, tricetylamine, N,N,N',N'-tetramethylmethylenediamine, N,N,N',N'-tetramethylethylenediamine, N,N,N',N'-tetramethyltetraethylenepentamine, and the like.

Specific examples of the aromatic amine and the heterocyclic amine include aniline derivatives such as aniline, N-methylaniline, N-ethylaniline, N-propylaniline, N,N-dimethylaniline, 2-methylaniline, 3-methylaniline, 4-methylaniline, ethylaniline, propylaniline, trimethylaniline, 2-nitroaniline, 3-nitroaniline, 4-nitroaniline, 2,4-dinitroaniline, 2,6-dinitroaniline, 3,5-dinitroaniline, and N,N-dimethyltoluidine; diphenyl(p-tolyl)amine; methyldiphenylamine; triphenylamine; phenylenediamine; naphthylamine; diaminonaphthalene; pyrrole derivatives such as pyrrole, 2H-pyrrole, 1-methylpyrrole, 2,4-dimethylpyrrole, 2,5-dimethylpyrrole, and N-methylpyrrole; oxazole derivatives such as oxazole and isoxazole; thiazole derivatives such as thiazole and isothiazole; imidazole derivatives such as imidazole, 4-methylimidazole, and 4-methyl-2-phenylimidazole; pyrazole derivatives; furazan derivatives; pyrroline derivatives such as pyrroline and 2-methyl-1-pyrroline; pyrrolidine derivatives such as pyrrolidine, N-methylpyrrolidine, pyrrolidinone, and N-methylpyrrolidone; imidazoline derivatives; imidazolidine derivatives; pyridine derivatives such as pyridine, methylpyridine, ethylpyridine, propylpyridine, butylpyridine, 4-(1-butylpentyl)pyridine, dimethylpyridine, trimethylpyridine, triethylpyridine, phenylpyridine, 3-methyl-2-phenylpyridine, 4-tert-butylpyridine, diphenylpyridine, benzylpyridine, methoxypyridine, butoxypyridine, dimethoxypyridine, 4-pyrrolidinopyridine, 2-(1-ethylpropyl)pyridine, aminopyridine, and dimethylaminopyridine; pyridazine derivatives; pyrimidine derivatives; pyrazine derivatives; pyrazoline derivatives; pyrazolidine derivatives; piperidine derivatives; piperazine derivatives; morpholine derivatives; indole derivatives; isoindole derivatives; 1H-indazole derivatives; indoline derivatives; quinoline derivatives such as quinoline and 3-quinolinecarbonitrile; isoquinoline derivatives; cinnoline derivatives; quinazoline derivatives; quinoxaline derivatives; phthalazine derivatives; purine derivatives; pteridine derivatives; carbazole derivatives; phenanthridine derivatives; acridine derivatives; phenazine derivatives; 1,10-phenanthroline derivatives; adenine derivatives; adenosine derivatives; guanine derivatives; guanosine derivatives; uracil derivatives; uridine derivatives; and the like.

Specific examples of the nitrogen-containing compound having a carboxy group include aminobenzoic acid; indolecarboxylic acid; amino acid derivatives such as nicotinic acid, alanine, arginine, aspartic acid, glutamic acid, glycine, histidine, isoleucine, glycyl leucine, leucine, methionine, phenylalanine, threonine, lysine, 3-aminopyrazine-2-carboxylic acid, and methoxyalanine; and the like.

Specific examples of the nitrogen-containing compound having a sulfonyl group include 3-pyrdinesulfonic acid, pyridinium p-toluenesulfonate, and the like.

Specific examples of the nitrogen-containing compound having a hydroxyl group, the nitrogen-containing compound having a hydroxyphenyl group, and the alcoholic nitrogen-containing compound include 2-hydroxypyridine, aminocresol, 2,4-quinolinediol, 3-indole methanol hydrate, monoethanolamine, diethanolamine, triethanolamine, N-ethyl diethanolamine, N,N-diethylethanolamine, triisopropanolamine, 2,2'-iminodiethanol, 2-aminoethanol, 3-amino-1-propanol, 4-amino-1-butanol, 4-(2-hydroxyethyl) morpholine, 2-(2-hydroxyethyl)pyridine, 1-(2-hydroxyethyl)piperazine, 1-[2-(2-hydroxyethoxy)ethyl]piperazine, piperidineethanol, 1-(2-hydroxyethyl)pyrrolidine, 1-(2-hydroxyethyl)-2-pyrrolidinone, 3-piperidino-1,2-propanediol, 3-pyrrolidino-1,2-propanediol, 8-hydroxyjulolidine, 3-quinuclidinol, 3-tropanol, 1-methyl-2-pyrrolidineethanol, 1-aziridine ethanol, N-(2-hydroxyethyl) phthalimide, N-(2-hydroxyethyl) isonicotinamide, and the like.

Specific examples of the nitrogen-containing compound having a carbamate group include N-(tert-butoxycarbonyl)-L-alanine, N-(tert-butoxycarbonyl)-L-alanine methyl ester, (S)-(−)-2-(tert-butoxycarbonylamino)-3-cyclohexyl-1-propanol, (R)-(+)-2-(tert-butoxycarbonylamino)-3-methyl-1-butanol, (R)-(+)-2-(tert-butoxycarbonylamino)-3-phenylpropanol, (S)-(−)-2-(tert-butoxycarbonylamino)-3-phenylpropanol, (R)-(+)-2-(tert-butoxycarbonylamino)-3-phenyl-1-propanol, (S)-(−)-2-(tert-butoxycarbonylamino)-3-phenyl-1-propanol, (R)-(+)-2-(tert-butoxycarbonylamino)-1-propanol, (S)-(−)-2-(tert-butoxycarbonylamino)-1-propanol, N-(tert-butoxycarbonyl)-L-aspartic acid 4-benzyl ester, N-(tert-butoxycarbonyl)-O-benzyl-L-threonine, (R)-(+)-1-(tert-butoxycarbonyl)-2-tert-butyl-3-methyl-4-imidazolidinone, (S)-(−)-1-(tert-butoxycarbonyl)-2-tert-butyl-3-methyl-4-imidazolidinone, N-(tert-butoxycarbonyl)-3-cyclohexyl-L-alanine methyl ester, N-(tert-butoxycarbonyl)-L-cysteinemethyl ester, N-(tert-butoxycarbonyl)ethanolamine, N-(tert-butoxycarbonylethylenediamine, N-(tert-butoxycarbonyl)-D-glucoseamine, Nα-(tert-butoxycarbonyl)-L-glutamine, 1-(tert-butoxycarbonyl)imidazole, N-(tert-butoxycarbonyl)-L-isoleucine, N-(tert-butoxycarbonyl)-L-isoleucine methyl ester, N-(tert-butoxycarbonyl)-L-leucinol, Nα-(tert-butoxycarbonyl)-L-lysine, N-(tert-butoxycarbonyl)-L-methionine, N-(tert-butoxycarbonyl)-3-(2-naphthyl)-L-alanine, N-(tert-butoxycarbonyl)-L-phenylalanine, N-(tert-butoxycarbonyl)-

L-phenylalanine methyl ester, N-(tert-butoxycarbonyl)-D-prolinal, N-(tert-butoxycarbonyl)-L-proline, N-(tert-butoxycarbonyl)-L-proline-N'-methoxy-N'-methylamide, N-(tert-butoxycarbonyl)-1H-pyrazole-1-carboxamidine, (S)-(−)-1-(tert-butoxycarbonyl)-2-pyrrolidinemethanol, (R)-(+)-1-(tert-butoxycarbonyl)-2-pyrrolidinemethanol, 1-(tert-butoxycarbonyl) 3-[4-(1-pyrrolyl) phenyl]-L-alanine, N-(tertbutoxycarbonyl)-L-serine, N-(tert-butoxycarbonyl)-L-serinemethyl ester, N-(tert-butoxycarbonyl)-L-threonine, N-(tert-butoxycarbonyl)-p-toluenesulfoneamide, N-(tert-butoxycarbonyl)-S-trityl-L-cysteine, Nα-(tert-butoxycarbonyl)-L-tryptophan, N-(tert-butoxycarbonyl)-L-tyrosine, N-(tert-butoxycarbonyl)-L-tyrosinemethyl ester, N-(tert-butoxycarbonyl)-L-valine, N-(tert-butoxycarbonyl)-L-valine methyl ester, N-(tert-butoxycarbonyl)-L-valinol, tert-butyl N-(3-hydroxypropyl) carbamate, tert-butyl N-(6-aminohexyl) carbamate, tert-butylcarbamate, tert-butylcarbazate, tert-butyl-N-(benzyloxy)carbamate, tert-butyl-4-benzyl-1-piperazinecarboxylate, tert-butyl(1S,4S)-(−)-2,5-diazabicyclo[2.2.1]heptane-2-carboxylate, tert-butyl-N-(2,3-dihydroxypropyl)carbamate, tert-butyl (S)-(−)-4-formyl-2,2-dimethyl-3-oxazolidinecarboxylate, tert-butyl[R—(R*, S*)]—N-[2-hydroxy-2-(3-hydroxyphenyl)-1-methylethyl] carbamate, tert-butyl-4-oxo-1-piperidinecarboxylate, tert-butyl-1-pyrrolecarboxylate, tert-butyl-1-pyrrolidinecarboxylate, tert-butyl(tetrahydro-2-oxo-3-furanyl) carbamate, and the like.

Specific examples of the amide compound include formamide, N-methyl formamide, N,N-dimethylformamide, acetamide, N-methyl acetamide, N,N-dimethylacetamide, propion amide, benzamide, 1-cyclohexylpyrrolidone, and the like.

Specific examples of the imide compound include phthalimide, succinimide, maleimide, and the like.

The scavenger having optical reactivity may be a compound (photodecomposition-type scavenger) which loses the function of a scavenger by being decomposed through an optical reaction or a compound (photogeneration-type scavenger) which obtains the function of a scavenger by being generated through an optical reaction.

In a case where the resist material contains the first scavenger which loses the function of a scavenger by being decomposed through an optical reaction, the first scavenger is decomposed in a pattern-exposed portion after the pattern-exposure step but is not decomposed in a pattern-unexposed portion. Accordingly, the function of capturing an acid and a cation is depressed in the pattern-exposed portion while it is maintained in the pattern-unexposed portion. Therefore, the chemical contrast of the latent image of the acid can be improved. In a case where the first scavenger is a compound which loses the function of a scavenger by being decomposed through an optical reaction, the first scavenger is preferably sulfonate or carboxylate of a photodecomposition-type cation. The sulfonic acid in the sulfonate is preferably a weak acid, and more preferably an acid having a hydrocarbon group which has 1 to 20 carbon atoms and does not contain a fluorine atom. Examples of the sulfonic acid include sulfonic acids such as alkylsulfonate, benzenesulfonate, and 10-camphorsulfonate. The carboxylic acid in the carboxylate is preferably a weak acid, and more preferably a carboxylic acid having 1 to 20 carbon atoms. Examples of the carboxylic acid include carboxylic acids such as formic acid, acetic acid, propionic acid, tartaric acid, succinic acid, cyclohexylcarboxylic acid, benzoic acid, and salicylic acid. The photodecomposition-type cation in the carboxylate of the photodecomposition-type cation is preferably an onium cation, and specific examples thereof include an iodonium cation, a sulfonium cation, and the like.

In a case where the resist material contains the first scavenger which obtains the function of a scavenger by being generated through an optical reaction, the first scavenger functions as a scavenger in a pattern-exposed portion at the time of pattern-exposure step but does not function in a pattern-unexposed portion. Accordingly, the function of capturing an acid and a cation is performed in a pattern-exposed portion while it is not performed in a pattern-unexposed portion. The photogeneration-type scavenger may be a compound which obtains the function of a scavenger at the time of flood-exposure. In this case, the exposure amount is greater at the time of flood-exposure than at the time of pattern-exposure, and the amount of the scavenger generated is relatively great at the time of flood-exposure. Therefore, in a case where the photosensitizer is generated through the cation as an intermediate from the component (b) and in a case where the photosensitizer is generated by the acid catalyst, it is possible to efficiently generate the photosensitizer while depressing the function of the scavenger of a cation and an acid as much as possible before the flood-exposure. In contrast, if most of the first scavenger is decomposed at the time of flood-exposure, the decomposed first scavenger sufficiently captures the unnecessary acid of the unexposed portion at the time of FPEB following the flood-exposure and inhibits the diffusion of the acid, and hence the chemical contrast of the latent image of the acid of the resist can be improved.

In a case where the first scavenger is a compound which obtains the function of a scavenger by being generated through an optical reaction, the carboxylate of the photodecomposition-type cation is preferably a compound (photobase generator) generating a base through the flood-exposure, and more preferably a nitrogen-containing compound generating an amino group. Furthermore, the carboxylate is preferably a carboxylic acid ester. In the photosensitization chemical-amplification type resist, in order to allow generation of an acid through photosensitization at the time of flood-exposure compared to a general resist. Therefore, it is desired to reduce the content of the first scavenger with respect to PAG at the time of pattern-exposure. That is, it is difficult for the resist material to contain the first scavenger at a high concentration. In contrast, it is desired to increase the amount of the first scavenger so as to inhibit the polarity changing reaction or the diffusion of the acid in the patter-unexposed portion. It is considered that the photogeneration-type scavenger generating a base at the time of flood-exposure satisfies both of the requirements described above. The generation of a base at the time of flood-exposure may be caused by the direct absorption of light of the flood-exposure or by photosensitization. In a case where the base is generated by photosensitization, the first scavenger also functions as a scavenger of an acid or a cation in the photosensitization reaction at the time of flood-exposure, and can inhibit the photosensitization reaction in a portion where the pattern-exposure amount is small. Consequently, the contrast of the latent image of the acid of the resist can be further improved.

Examples of the compound (photobase generator) generating a base through the flood-exposure include the compounds described in Japanese Unexamined Patent Publication Application Nos. H4-151156, H4-162040, H5-197148, H5-5995, H6-194834, H8-146608, and H10-83079 and European Patent No. 622682. Examples of the photobase generator include a compound containing a carbamate group (urethane bond), a compound containing an acyloxyimino group, an ion-based compound (anion-cation complex), a compound containing a carbamoyloxyimino group, and the like. Among these, a compound containing a carbamate group (urethane bond), a compound containing an acyloxyimino group, or an ion-based compound (anion-cation complex) is preferable. Furthermore, the photobase generator is preferably a compound having a cyclic structure in a molecule. Examples of the cyclic structure include benzene, naphthalene, anthracene, xanthone, thioxanthone, anthraquinone, fluorene, and the like.

In view of photodecomposition properties, the photobase generator is more preferably a compound represented by the following Formula (XLV). When the aforementioned compound is exposed, at least the bond between a nitrogen atom and a carbon atom of a carbonyl group adjacent to the nitrogen atom in Formula (XLV) is broken, and hence amine or ammonia and carbon dioxide are generated. It is preferable that the product having —N($R^{26}$)($R^{27}$) has a high boiling point after the decomposition. In addition, in view of controlling the diffusion at the time of PEB, it is preferable that the product having —N($R^{26}$)($R^{27}$) has a great molecular weight or has a bulky skeleton.

[Chemical Formula 55]

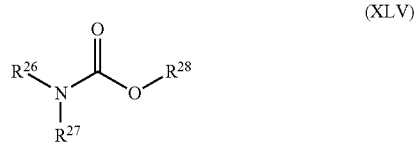

(XLV)

In the formula, each of $R^{26}$ and $R^{27}$ independently represents a hydrogen atom or a monovalent hydrocarbon group which may contain a heteroatom; $R^{26}$ and $R^{27}$ may form a cyclic structure together with a nitrogen atom adjacent thereto by being bonded to each other; and $R^{28}$ is a monovalent optical functional group.

Specific examples of the photobase generator include 2-nitrobenzyl carbamate, 2,5-dinitrobenzyl cyclohexylcarbamate, N-cyclohexyl-4-methylphenylsulfonamide, and 1,1-dimethyl-2-phenylethyl-N-isopropylcarbamate.

The first scavenger may be a compound (thermal generation-type scavenger) which obtains the function of a scavenger by being generated through the thermal reaction. In a case where the resist material contains a thermal generation-type scavenger, it is desired to bake the resist material after the flood-exposure and to generate the scavenger during the baking. Therefore, the baking temperature after the flood-exposure is preferably higher than the temperature of heating performed between the coating of the resist material and the pattern-exposure, and the temperature of baking performed between the pattern-exposure and the flood-exposure. In a case where the resist material contains the first scavenger which obtains the function of a scavenger by being generated through a thermal reaction or an optical reaction at the wavelength of the flood-exposure, the acid capturing ability of the first scavenger in a pattern-unexposed portion is improved, and the chemical contrast of the latent image of the acid can be improved.

(4) Second Scavenger

The second scavenger is a compound functioning as a free radical scavenger that captures a free radical. If the resist material contains the second scavenger, the generation of the photosensitizer through a radical reaction in the resist material is further suppressed in a portion in which the pattern-exposure amount is small, and hence an effect of further enhancing the contrast of the latent image of the photosensitizer is obtained. As a result, it is possible to obtain an effect of further increasing the contrast of the latent image of the acid between a pattern-exposed portion and a pattern-unexposed portion after the flood-exposure.

Specific examples of the second scavenger include a phenol-based compound, a quinone-based compound, an amine-based compound, and the like, and examples thereof include 2,6-di-t-butyl-p-cresol, 2,2-methylene-bis(4-methyl-6-t-butylphenol), 1,1,3-tris(2-methyl-4-hydroxy-5-t-butylphenyl)butane, 1,3,5-trimethyl-2,4,6-tris(3,5-di-t-butyl-4-hydroxybenzyl)benzene, 1,3,5-tris(3',5'-di-t-butyl-4-hydroxybenzyl)-S-triazine-2,4,6-(1H,3H,5H)trione, 2,2,6,6-tetramethyl-1-piperidinyloxy(TEMPO), 2-tert-butyl-4-hydroxyanisole, 3-tert-butyl-4-hydroxyanisole, 3,4,5-trihydroxybenzoic acid propyl ester, 2-(1,1-dimethylethyl)-1,4-benzenediol, diphenylpicrylhydrazyl, 4-tert-butylcatechol, N-methylaniline, p-methoxydiphenylamine, diphenylamine, N,N'-diphenyl-p-phenylenediamine, p-hydroxydiphenylamine, phenol, octadecyl-3-(3,5-di-tert-butyl-4-hydroxyphenyl)propionate, tetrakis(methylene(3,5-di-tert-butyl)-4-hydroxy-hydrocinnamate)methane, phenothiazine, isourea of alkylamide, thiodiethylene bis(3, 5-di-tert-butyl-4-hydroxy-hydrocinnamate, 1,2-bis(3,5-di-tert-butyl-4-hydroxyhydrocinnamoyl)hydrazine, tris(2-methyl-4-hydroxy-5-tert-butylphenyl)butane, cyclic neopentanetetrayl bis(octadecylphosphite), 4,4'-thiobis(6-tert-butyl-m-cresol), 2,2'-methylenebis(6-tert-butyl-p-cresol), oxalyl bis(benzylidenehydrazide)methyl 5-doxyl stearate, hydroquinone, 2-t-butylhydroquinone, hydroquinone monomethyl ether, metaquinone, benzoquinone, bis(2, 2,6,6-tetramethyl-4-piperidyl)-sebacate, phenothiazine, naturally occurring antioxidants such as unprocessed seed oil, wheat germ seed oil, tocopherol, and rubber, and the like.

(5) Cross-Linking Agent

The cross-linking agent is a component used for causing a cross-linking reaction between the base component molecules through the acid-catalyzed reaction during the baking step after the flood-exposure such that the molecular weight of the base component is increased and the base component becomes insoluble in the developer. The cross-linking agent is different from the (1) base component described above. If the resist material contains the cross-linking agent, polar moieties become nonpolar when the cross-linking occurs, and the base component becomes insoluble in the developer. Therefore, a negative resist material can be provided.

The cross-linking agent is a compound having two or more functional groups. Each of the functional groups is preferably at least one group selected from the group consisting of a (meth)acryloyl group, a hydroxymethyl group, an alkoxymethyl group, an epoxy group, and a vinyl ether group.

Specific examples of the compound having two or more (meth)acryloyl groups include trimethylolpropane tri(meth)acrylate, ditrimethylolpropane tetra(meth)acrylate, pentaerythritol tri(meth)acrylate, pentaerythritol tetra(meth)acrylate, dipentaerythritol penta(meth)acrylate, dipentaerythritol hexa(meth)acrylate, glycerin tri(meth)acrylate, tris(2-hydroxyethyl) isocyanurate tri(meth)acrylate, ethyleneglycol di(meth)acrylate, 1,3-butanediol di(meth)acrylate, 1,4-butanediol di(meth)acrylate, 1,6-hexanediol di(meth)acrylate, neopentyl glycol di(meth)acrylate, diethyleneglycol di(meth)acrylate, triethylene glycol di(meth)acrylate, dipropylene glycol di(meth)acrylate, bis(2-hydroxyethyl) isocyanurate di(meth)acrylate, and the like.

Specific examples of the compound having two or more alkoxymethyl groups or hydroxymethyl groups include a phenol compound containing hydroxymethyl groups, a phenol compound containing alkoxymethyl groups, alkoxymethylated melamine, an alkoxymethylated urea compound, and the like. All of the above alkoxy groups preferably have 1 to 5 carbon atoms. The compound having two or more alkoxymethyl groups or hydroxymethyl groups is preferably a phenol compound containing methoxymethyl groups, a phenol compound containing ethoxymethyl groups, methoxymethylated melamine, or a methoxymethylated urea compound, and more preferably methoxymethylated melamine or a methoxymethylated urea compound. Examples of the methoxymethylated melamine include compounds represented by the following Formulae (IX) to (X) and the like.

[Chemical Formula 56]

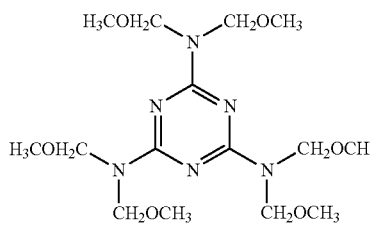

(IX)

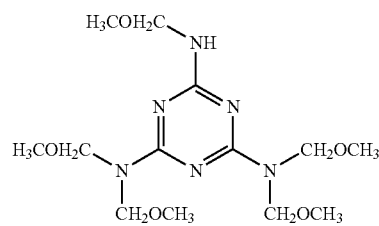

(X)

Examples of the methoxymethylated urea compound include compounds represented by the following Formulae (XI) to (XIII).

[Chemical Formula 57]

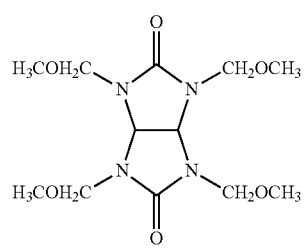

(XI)

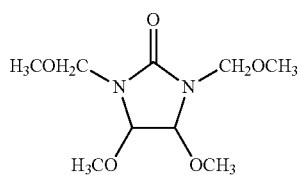

(XII)

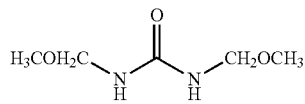

(XIII)

Specific examples of the compound having two or more epoxy groups include a novolac-type epoxy resin, a bisphenol-type epoxy resin, an alicyclic epoxy resin, an aliphatic epoxy resin, and the like.

Specific examples of the compound having two or more vinylether groups include bis(4-(vinyloxymethyl) cyclohexylmethyl)glutarate, tri(ethyleneglycol)divinylether, adipic acid divinyl ester, diethylene glycol divinyl ether, 1,2,4-tris(4-vinyloxybutyl) trimellitate, 1,3,5-tris(4-vinyloxybutyl) trimellitate, bis(4-(vinyloxy) butyl)terephthalate, bis(4-(vinyloxy) butyl)isophthalate, ethylene glycol divinyl ether, 1,4-butanediol divinyl ether, tetramethylene glycol divinyl ether, tetraethylene glycol divinyl ether, neopentyl glycol divinyl ether, trimethylolpropane trivinyl ether, trimethylolethane trivinyl ether, hexanediol divinyl ether, 1,4-cyclohexanediol divinyl ether, tetraethylene glycol divinyl ether, pentaerythritol divinyl ether, pentaerythritol trivinyl ether, and cyclohexanedimethanol divinyl ether.

(6) Additive

Examples of the additive include a surfactant, an antioxidant, a dissolution inhibitor, a plasticizer, a stabilizer, a colorant, a halation inhibitor, a dye, and the like. As the surfactant, the antioxidant, the dissolution inhibitor, the plasticizer, the stabilizer, the colorant, the halation inhibitor, and the dye, known materials can be selected. Specifically, as the surfactant, an ionic or nonionic fluorine-based surfactant and/or silicon-based surfactant can be used. Specific examples of the antioxidant include a phenol-based antioxidant, an antioxidant composed of an organic acid derivative, a sulfur-containing antioxidant, a phosphorus-based antioxidant, an amine-based antioxidant, an antioxidant composed of an amine-aldehyde condensate, an antioxidant composed of an amine-ketone condensate, and the like.

(7) Solvent

The solvent is a component used for dissolving the composition of the resist material and facilitating the formation of the resist material film by means of a coating machine used in a spin coating method or the like. Herein, the compound included in the aforementioned component (b) and the like is excluded from the solvent. Specific examples of the solvent include ketones such as cyclohexanone and methyl-2-amyl ketone; alcohols such as 3-methoxybutanol, 3-methyl-3-methoxybutanol, 1-methoxy-2-propanol, and 1-ethoxy-2-propanol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; and esters such as propylene glycol monomethyl ether acetate, propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, propylene glycol monomethyl ether acetate, and propylene glycol monotert-butyl ether acetate.

(Formulation Ratio)

The resist material is a photosensitive resin composition containing the above components. At the time of preparing the resist material, the formulation ratio between the respective components should be appropriately set according to the purpose, service conditions, and the like of the resist material.

The amount of the component (a) formulated is preferably 0.005 parts by mass to 50 parts by mass, and more preferably 0.1 parts by mass to 30 parts by mass, with respect to 100 parts by mass of the component (1). If the amount is equal to or greater than 0.005 parts by mass, sufficient sensitivity is easily obtained. In contrast, if the amount is equal to or less than 50 parts by mass, the compatibility between the resist and the component (a) is improved, and hence the resist material film is easily formed. The amount of the component (b) formulated is preferably 0.005 parts by mass to 50 parts by mass, and more preferably 0.1 parts by mass to 30 parts by mass, with respect to 100 parts by mass of the component (1). If the amount is equal to or greater than 0.005 parts by mass, sufficient sensitivity is easily obtained. In contrast, if the amount is equal to or less than 50 parts by mass, a rectangular resist pattern is easily obtained. The amount of the component (c) formulated is preferably 0.01 parts by mass to 50 parts by mass, and more preferably 0.1 parts by mass to 30 parts by mass, with respect to 100 parts by mass of the component (1). If the amount is equal to or greater than 0.01 parts by mass, sufficient sensitivity is easily obtained. In contrast, if the amount is equal to or less than 50 parts by mass, a rectangular resist pattern is easily obtained.

The amount of the (3) first scavenger formulated is preferably 0.001 parts by mass to 20 parts by mass, and more preferably 0.01 parts by mass to 10 parts by mass, with respect to 100 parts by mass of the component (1). If the amount is equal to or less than 20 parts by mass, excessive reduction of the sensitivity tends to be able to be inhibited. If the amount is equal to or greater than 0.001 parts by mass, the aforementioned effect resulting from formulating the first scavenger tends to be easily obtained. The ratio between the photoacid generator (total amount of the components (a) and (c)) and the first scavenger used in the resist material is preferably photoacid generator/first scavenger (molar ratio) =1.5 to 300. That is, in view of the sensitivity and the resolution, the molar ratio is preferably equal to or greater than 1.5. Furthermore, in view of inhibiting the resist pattern dimension from changing with the passage of time from the point after the exposure to the heating treatment, the molar ratio is preferably equal to or less than 300. The photoacid generator/first scavenger (molar ratio) is more preferably 5.0 to 200.

The amount of the (4) second scavenger formulated is preferably equal to or less than 10 parts by mass, and more preferably 0.0005 parts by mass to 5 parts by mass, with respect to 100 parts by mass of the component (1). If the amount is equal to or less than 10 parts by mass, the generation of the photosensitizer tends not to be easily inhibited, and the sensitivity tends to be easily increased during the flood-exposure due to the photosensitizer. If the amount is equal to or greater than 0.0005 parts by mass, the aforementioned effect resulting from formulating the second scavenger tends to be easily obtained.

The amount of the (5) cross-linking agent formulated is preferably equal to or less than 40 parts by mass, and more preferably 0.1 parts by mass to 25 parts by mass, with respect to 100 parts by mass of the component (1). If the amount is equal to or less than 40 parts by mass, the decrease in the contrast of an image resulting from the increase in the solubility of the resist material tends to be able to be inhibited. If the amount is equal to or greater than 0.1 parts by mass, the aforementioned effect resulting from formulating the cross-linking agent tends to be easily obtained.

The amount of the (6) additive formulated is preferably equal to or less than 30 parts by mass, and more preferably 0.1 parts by mass to 10 parts by mass, with respect to 100 parts by mass of the component (1). If the amount is equal to or less than 30 parts by mass, the characteristics of the resist materials do not easily deteriorate. If the amount is equal to or greater than 0.1 parts by mass, an excellent process window of the resist material tends to be able to be obtained.

The amount of the (7) solvent formulated is preferably 200 parts by mass to 10,000 parts by mass, and more preferably 300 parts by mass to 5,000 parts by mass, with respect to 100 parts by mass of the component (1). If the amount is equal to or less than 10,000 parts by mass, the characteristics of the resist materials do not easily deteriorate. If the amount is equal to or greater than 200 parts by mass, the resist material film is easily formed.

Second Embodiment

A photosensitization chemical-amplification type resist material (hereinafter, simply referred to as a "resist material" in some cases) of the present embodiment contains (1') a base component which makes a pattern-exposed portion soluble or insoluble in a developer after the baking step.

(1') Base Component

The (1') base component may be an organic compound or an inorganic compound. Furthermore, the organic compound may be a polymer compound or a low-molecular weight compound. The (1') base component has, among three groups consisting of (d) an acid-photosensitizer generating group, (e) a precursor group, and (f) a photoacid generating group, only the group (d), any two groups, or all of the groups (d) to (f) described below. That is, in the present embodiment, the base component is an organic or inorganic compound to which the following groups (d) to (f) are bonded. The base component may have the following groups (d) to (f) in a single molecule (or a single particle) or in each of a plurality of molecules (or particles).

The polymer compound as the (1') base component is a compound which has a weight average molecular weight of 3,000 to 200,000 and preferably 5,000 to 30,000 and makes a pattern-exposed portion soluble or insoluble in a developer in the developing step through the acid-catalyzed reaction during the baking step (see FIG. 4) after the flood-exposure. The low-molecular weight compound as the component (1') is a compound which has a molecular weight of 500 to 3,000 and preferably 1,000 to 3,000 and makes a pattern-exposed portion soluble or insoluble in a developer in the developing step through the acid-catalyzed reaction during the baking step (see FIG. 4) after the flood-exposure. Examples of the organic compound and the inorganic compound as the component (1') include the same ones exemplified above as the component (1). Hereinafter, the (1') base component will be specifically described by explaining the polymer compound for example.

The polymer compound used as the component (1') can have the groups (d) to (f) described above as, for example, the groups (protecting groups) represented by $R^{11}$ to $R^{13}$ in Formula (VII), $R^{11}$ or $R^{14}$ in Formula (VIII), $R^{15}$ or $R^{16}$ in Formula (XXV), and $R^{17}$ in Formula (XXVI) of the polymer compound used as the component (1) or as a portion of these groups. Furthermore, the low-molecular weight compound used as the component (1') can have the groups (d) to (f) described above on a side chain of a polymer compound, for example.

(d) Acid-Photosensitizer Generating Group

The acid-photosensitizer generating group is a group generating an acid and a photosensitizer, which absorbs non-ionizing radiation having a wavelength of greater than 200 nm and preferably greater than 250 nm, by being irradiated with ionizing radiation or non-ionizing radiation having a wavelength of equal to or less than 400 nm, preferably equal to or less than 250 nm, and more preferably equal to or less than 200 nm. The non-ionizing radiation that the photosensitizer absorbs preferably has a wavelength longer than the wavelength that the acid-photosensitizer generating group absorbs.

Examples of the acid-photosensitizer generating group include an onium salt compound group, a diazomethane compound group, a sulfonimide compound group, and the like. Examples of the onium salt compound group include a sulfonium salt compound group, an iodonium salt compound group, a tetrahydrothiophenium salt compound group, and the like. The acid-photosensitizer generating group is preferably a sulfonium salt compound group or an iodonium salt compound group, and more preferably an iodonium salt compound group, because these compounds have a high reduction potential. Furthermore, the acid-photosensitizer generating group is preferably an anion bound type in which an anion is bonded to the (1') base component. If the acid-photosensitizer generating group is an anion bound type, the diffusion of the generated acid to an unexposed portion tends to be able to be inhibited.

The sulfonium salt compound group is a group composed of a sulfonium cation and an acid anion. The sulfonium salt compound group is preferably at least one group selected from the group consisting of groups represented by the following Formulae (XIV) to (XVII). The groups represented by the following Formulae (XIV) to (XVII) are cation bound types in which a cation is bonded to the (1') base component.

[Chemical Formula 58]

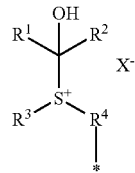
(XIV)

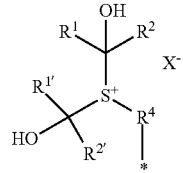
(XV)

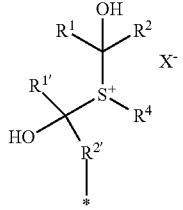
(XVI)

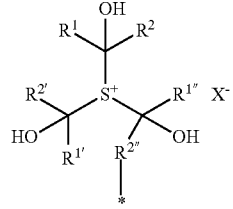
(XVII)

In Formulae (XIV) to (XVII), each of $R^1$, $R^2$, $R^{1'}$, $R^{2'}$, $R^{1''}$, $R^{2''}$, $R^3$, and $R^4$ independently represents a hydrogen atom; a phenyl group; a naphthyl group; an anthracenyl group; a phenoxy group; a naphthoxy group; an anthracenoxy group; an amino group; an amide group; a halogen atom; a linear, branched or cyclic and saturated or unsaturated hydrocarbon group (preferably an alkyl group) having 1 to 30 carbon atoms (preferably 1 to 5 carbon atoms); a phenoxy group substituted with an alkoxy group having 1 to 5 carbon atoms, a hydroxyl group, an amino group, an amide group, or an alkyl group having 1 to 5 carbon atoms; a phenyl group substituted with a linear, branched or cyclic and saturated or unsaturated hydrocarbon group (preferably an alkyl group) having 1 to 30 carbon atoms (preferably 1 to 5 carbon atoms), an alkoxy group having 1 to 5 carbon atoms, an amino group, an amide group, or a hydroxyl group; a naphthoxy group substituted with an alkoxy group having 1 to 5 carbon atoms, an alkyl group having 1 to 5 carbon atoms, an amino group, an amide group, or a hydroxyl group; an anthracenoxy group substituted with an alkoxy group having 1 to 5 carbon atoms, an alkyl group having 1 to 5 carbon atoms, an amino group, an amide group, or a hydroxyl group; a linear, branched or cyclic and saturated or unsaturated hydrocarbon group (preferably an alkyl group) having 1 to 30 carbon atoms (preferably 1 to 5 carbon atoms) substituted with an alkoxy group having 1 to 5 carbon atoms, a phenoxy group, a naphthoxy group, an anthracenoxy group, an amino group, an amide group, or a hydroxyl group; or a carbonyl group to which an alkyl group having 1 to 12 carbon atoms is bonded. In Formulae (XIV) to (XVII), the hydrogen atom of the hydroxyl group may be substituted with a phenyl group; a halogen atom; a linear, branched or cyclic and saturated or unsaturated hydrocarbon group (preferably an alkyl group) having 1 to 30 carbon atoms (preferably 1 to 5 carbon atoms); or a phenyl group substituted with a linear, branched or cyclic and saturated or unsaturated hydrocarbon group (preferably an alkyl group) having 1 to 30 carbon atoms (preferably 1 to 5 carbon atoms), an alkoxy group having 1 to 5 carbon atoms, or a hydroxyl group. When the hydrogen atom of the hydroxyl group is substituted, the sulfonium salt compound group contains a ketal compound group or an acetal compound group. In Formulae (XIV) to (XVII), any two or more groups among $R^1$, $R^2$, $R^{1'}$, $R^{2'}$, $R^{1''}$, $R^{2''}$, $R^3$, and $R^4$ may form a cyclic structure through a single bond, a double bond, or a bond containing —$CH_2$—, —O—, —S—, —$SO_2$—, —$SO_2NH$—, —C(=O)—, —C(=O)O—, —NHCO—, —NHC(=O)NH—, —$CHR^e$—, —$CR^e_2$—, —NH—, or —$NR^e$—. $R^e$ represents a phenyl group; a phenoxy group; a halogen atom; a linear, branched or cyclic and saturated or unsaturated hydrocarbon group (preferably an alkyl group) having 1 to 30 carbon atoms (preferably 1 to 5 carbon atoms); a phenoxy group substituted with an alkoxy group having 1 to 5 carbon atoms, a hydroxyl group, or an alkyl group having 1 to 5 carbon atoms; or a phenyl group substituted with a linear, branched or cyclic and saturated or unsaturated hydrocarbon group (preferably an alkyl group) having 1 to 30 carbon atoms (preferably 1 to 5 carbon atoms), an alkoxy group having 1 to 5 carbon atoms, or a hydroxyl group. Each of $R^1$, $R^2$, $R^{1'}$, $R^{2'}$, $R^{1''}$, $R^{2''}$, $R^3$, and $R^4$ independently preferably represents a phenyl group; a phenoxy group; a phenoxy group substituted with an alkoxy group having 1 to 5 carbon atoms, a hydroxyl group, or an alkyl group having 1 to 5 carbon atoms; or a phenyl group substituted with an alkoxy group having 1 to 5 carbon atoms or a hydroxyl group. In Formulae (XIV) to (XVII), $X^-$ represents an acid anion. The acid is preferably a strong acid, and more preferably a super strong acid. In Formulae (XIV) to (XVII), * represents a binding portion to the (1') base component. In a case where $R^{2'}$, $R^{2''}$, and $R^4$ bind to the (1') base component, each of $R^{2'}$, $R^{2''}$, and $R^4$ independently represents a divalent group obtained by removing one hydrogen atom from a phenyl group; a naphthyl group; an anthracenyl group; a phenoxy group; a naphthoxy group; an anthracenoxy group; a linear, branched or cyclic and saturated or unsaturated hydrocarbon group (preferably an alkyl group) having 1 to 30 carbon atoms (preferably 1 to 5 carbon atoms); a phenoxy group substituted with an alkoxy group having 1 to 5 carbon atoms, a hydroxyl group, or an alkyl group having 1 to 5 carbon atoms; a phenyl group substituted with a linear, branched or cyclic and saturated or unsaturated hydrocarbon group (preferably an alkyl group) having 1 to 30 carbon atoms (preferably 1 to 5 carbon atoms), an alkoxy group having 1 to 5 carbon atoms, or a hydroxyl group; a naphthoxy group substituted with an alkoxy group having 1 to 5 carbon atoms, an alkyl group having 1 to 5 carbon atoms, or a hydroxyl group; an anthracenoxy group substituted with an alkoxy group having 1 to 5 carbon atoms, an alkyl group having 1 to 5 carbon atoms, or a hydroxyl group; a linear, branched or cyclic and saturated or unsaturated hydrocarbon group (preferably an alkyl group) having 1 to 30 carbon atoms (preferably 1 to 5 carbon atoms) substituted with an alkoxy group having 1 to 5 carbon atoms, a phenoxy group, a naphthoxy group, an anthracenoxy group, or a hydroxyl group; or a carbonyl group to which an alkyl group having 1 to 12 carbon atoms is bonded. Each of $R^{2'}$, $R^{2''}$, and $R^4$ preferably represents a divalent group obtained by removing one hydrogen atom from an alkoxy group having 1 to 5 carbon atoms or a phenyl group substituted with an alkoxy group having 1 to 5 carbon atoms, an alkyl group having 1 to 5 carbon atoms, or a hydroxyl group.

The sulfonium salt compound group is preferably at least one group selected from the group consisting of groups represented by the following Formulae (XXXI) to (XXXIII). The groups represented by the following Formulae (XXXI) to (XXXIII) are anion bound types in which an anion is bonded to the (1') base component. If the acid anion remains bonded to the (1') base component after exposure, the diffusion of the acid after exposure tends to be able to be inhibited, and image blurring tends to be able to be reduced.

[Chemical Formula 59]

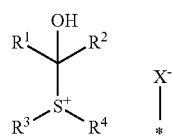
(XXXI)

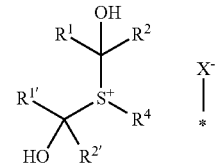
(XXXII)

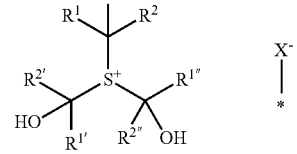
(XXXIII)

In Formulae (XXXI) to (XXXIII), each of $R^1$, $R^2$, $R^{1'}$, $R^{2'}$, $R^{1''}$, $R^{2''}$, $R^3$, and $R^4$ independently represents a hydrogen atom; a phenyl group; a naphthyl group; an anthracenyl group; a phenoxy group; a naphthoxy group; an anthracenoxy group; an amino group; an amide group; a halogen atom; a linear, branched or cyclic and saturated or unsaturated hydrocarbon group (preferably an alkyl group) having 1 to 30 carbon atoms (preferably 1 to 5 carbon atoms); a phenoxy group substituted with an alkoxy group having 1 to 5 carbon atoms, a hydroxyl group, an amino group, an amide group, or an alkyl group having 1 to 5 carbon atoms; a phenyl group substituted with a linear, branched or cyclic and saturated or unsaturated hydrocarbon group (preferably an alkyl group) having 1 to 30 carbon atoms (preferably 1 to 5 carbon atoms), an alkoxy group having 1 to 5 carbon atoms, an amino group, an amide group, or a hydroxyl group; a naphthoxy group substituted with an alkoxy group having 1 to 5 carbon atoms, an alkyl group having 1 to 5 carbon atoms, an amino group, an amide group, or a hydroxyl group; an anthracenoxy group substituted with an alkoxy group having 1 to 5 carbon atoms, an alkyl group having 1 to 5 carbon atoms, an amino group, an amide group, or a hydroxyl group; a linear, branched or cyclic and saturated or unsaturated hydrocarbon group (preferably an alkyl group) having 1 to 30 carbon atoms (preferably 1 to 5 carbon atoms) substituted with an alkoxy group having 1 to 5 carbon atoms, a phenoxy group, a naphthoxy group, an anthracenoxy group, an amino group, an amide group, or a hydroxyl group; or a carbonyl group to which an alkyl group having 1 to 12 carbon atoms is bonded. In the formulae, the hydrogen atom of the hydroxyl group may be substituted with a phenyl group; a halogen atom; a linear, branched or cyclic and saturated or unsaturated hydrocarbon group (preferably an alkyl group) having 1 to 30 carbon atoms (preferably 1 to 5 carbon atoms); or a phenyl group substituted with a linear, branched or cyclic and saturated or unsaturated hydrocarbon group (preferably an alkyl group) having 1 to 30 carbon atoms (preferably 1 to 5 carbon atoms), an alkoxy group having 1 to 5 carbon atoms, or a hydroxyl group. In Formulae (XXXI) to (XXXIII), any two or more groups among $R^1$, $R^2$, $R^{1'}$, $R^{2'}$, $R^{1''}$, $R^{2''}$, $R^3$, and $R^4$ may form a cyclic structure through a single bond, a double bond, or a bond containing —$CH_2$—, —O—, —S—, —$SO_2$—, —$SO_2NH$—, —C(=O)—, —C(=O)O—, —NHCO—, —NHC(=O)NH—, —$CHR^e$—, —$CR^e_2$—, —NH—, or —$NR^e$—. $R^e$ represents a phenyl group; a phenoxy group; a halogen atom; a linear, branched or cyclic and saturated or unsaturated hydrocarbon group (preferably an alkyl group) having 1 to 30 carbon atoms (preferably 1 to 5 carbon atoms); a phenoxy group substituted with an alkoxy group having 1 to 5 carbon atoms, a hydroxyl group, or an alkyl group having 1 to 5 carbon atoms; or a phenyl group substituted with a linear, branched or cyclic and saturated or unsaturated hydrocarbon group (preferably an alkyl group) having 1 to 30 carbon atoms (preferably 1 to 5 carbon atoms), an alkoxy group having 1 to 5 carbon atoms, or a hydroxyl group. Each of $R^1$, $R^2$, $R^{1'}$, $R^{2'}$, $R^{1''}$, $R^{2''}$, $R^3$, and $R^4$ independently preferably represents a phenyl group; a phenoxy group; a phenoxy group substituted with an alkoxy group having 1 to 5 carbon atoms, a hydroxyl group, or an alkyl group having 1 to 5 carbon atoms; or a phenyl group substituted with an alkoxy group having 1 to 5 carbon atoms or a hydroxyl group. In Formulae (XXXI) to (XXXIII), $X^-$ represents an acid anion group. The acid is preferably a strong acid, and more preferably a super strong acid. In the formulae, * represents a binding portion in the (1') base component.

Specific examples of the groups represented by —C(—OH)$R^1R^2$, —C(—OH)$R^{1'}R^{2'}$, and —C(—OH)$R^{1''}R^{2''}$ in Formulae (XIV) to (XVII) and (XXXI) to (XXXIII) include the same groups as exemplified above in Formulae (I) to (III).

The iodonium salt compound group is a group composed of an iodonium cation and an acid anion. The iodonium salt compound group is preferably at least one group selected from the group consisting of groups represented by the following Formulae (XVIII) to (XIX). The groups represented by the following Formulae (XVIII) to (XIX) are cation bound types in which a cation is bonded to the (1') base component.

[Chemical Formula 60]

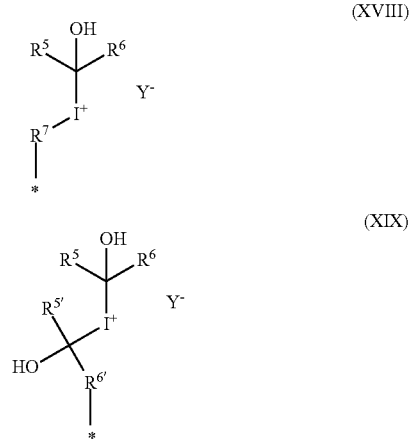

(XVIII)

(XIX)

In Formulae (XVIII) to (XIX), each of $R^5$, $R^6$, and $R^{5'}$ independently represents a hydrogen atom; a phenyl group; a naphthyl group; an anthracenyl group; a phenoxy group; a naphthoxy group; an anthracenoxy group; an amino group; an amide group; a halogen atom; a linear, branched or cyclic and saturated or unsaturated hydrocarbon group (preferably an alkyl group) having 1 to 30 carbon atoms (preferably 1 to 5 carbon atoms); a phenoxy group substituted with an alkoxy group having 1 to 5 carbon atoms, a hydroxyl group, an amino group, an amide group, or an alkyl group having 1 to 5 carbon atoms; a phenyl group substituted with a linear, branched or cyclic and saturated or unsaturated hydrocarbon group (preferably an alkyl group) having 1 to 30 carbon atoms (preferably 1 to 5 carbon atoms), an alkoxy group having 1 to 5 carbon atoms, an amino group, an amide group, or a hydroxyl group; a naphthoxy group substituted with an alkoxy group having 1 to 5 carbon atoms, an alkyl group having 1 to 5 carbon atoms, an amino group, an amide group, or a hydroxyl group; an anthracenoxy group substituted with an alkoxy group having 1 to 5 carbon atoms, an alkyl group having 1 to 5 carbon atoms, an amino group, an amide group, or a hydroxyl group; a linear, branched or cyclic and saturated or unsaturated hydrocarbon group (preferably an alkyl group) having 1 to 30 carbon atoms (preferably 1 to 5 carbon atoms) substituted with an alkoxy group having 1 to 5 carbon atoms, a phenoxy group, a naphthoxy group, an anthracenoxy group, an amino group, an amide group, or a hydroxyl group; or a carbonyl group to which an alkyl group having 1 to 12 carbon atoms is bonded. In Formulae (XVIII) to (XIX), the hydrogen atom of the hydroxyl group may be substituted with a phenyl group; a halogen atom; a linear, branched or cyclic and saturated or unsaturated hydrocarbon group (preferably an alkyl group) having 1 to 30 carbon atoms (preferably 1 to 5 carbon atoms); or a phenyl group substituted with a linear, branched or cyclic and saturated or unsaturated hydrocarbon group (preferably an alkyl group) having 1 to 30 carbon atoms (preferably 1 to 5 carbon atoms), an alkoxy group having 1 to 5 carbon atoms, or a hydroxyl group. When the hydrogen atom of the hydroxyl group is substituted, the iodonium salt compound group contains a ketal compound group or an acetal compound group. In Formulae (XVIII) to (XIX), any two or more groups among $R^5$, $R^6$, $R^{5'}$, $R^{6'}$, and $R^7$ may form a cyclic structure through a single bond, a double bond, or a bond containing —$CH_2$—, —O—, —S—, —$SO_2$—, —$SO_2NH$—, —C(=O)—, —C(=O)O—, —NHCO—, —NHC(=O)NH—, —$CHR^f$—, —$CR^f_2$—, —NH—, or —$NR^f$—. $R^f$ represents a phenyl group; a phenoxy group; a halogen atom; a linear, branched or cyclic and saturated or unsaturated hydrocarbon group (preferably an alkyl group) having 1 to 30 carbon atoms (preferably 1 to 5 carbon atoms); a phenoxy group substituted with an alkoxy group having 1 to 5 carbon atoms, a hydroxyl group, or an alkyl group having 1 to 5 carbon atoms; or a phenyl group substituted with a linear, branched or cyclic and saturated or unsaturated hydrocarbon group (preferably an alkyl group) having 1 to 30 carbon atoms (preferably 1 to 5 carbon atoms), an alkoxy group having 1 to 5 carbon atoms, or a hydroxyl group. Each of $R^5$, $R^6$, and $R^{5'}$ independently preferably represents a phenyl group; a phenoxy group; a phenoxy group substituted with an alkoxy group having 1 to 5 carbon atoms, a hydroxyl group, or an alkyl group having 1 to 5 carbon atoms; or a phenyl group substituted with an alkoxy group having 1 to 5 carbon atoms or a hydroxyl group. In Formulae (XVIII) to (XIX), $Y^-$ represents an acid, preferably represents a strong acid, and more preferably represents a super strong acid anion. In Formulae (XVIII) to (XIX), * represents a binding portion to the (1') base component. Each of $R^{6'}$ and $R^7$ independently represents a divalent group obtained by removing one hydrogen atom from a phenyl group; a naphthyl group; an anthracenyl group; a phenoxy group; a naphthoxy group; an anthracenoxy group; a linear, branched or cyclic and saturated or unsaturated hydrocarbon group (preferably an alkyl group) having 1 to 30 carbon atoms (preferably 1 to 5 carbon atoms); a phenoxy group substituted with an alkoxy group having 1 to 5 carbon atoms, an alkyl group having 1 to 5 carbon atoms, or a hydroxyl group; a phenyl group substituted with a linear, branched or cyclic and saturated or unsaturated hydrocarbon group (preferably an alkyl group) having 1 to 30 carbon atoms (preferably 1 to 5 carbon atoms), an alkoxy group having 1 to 5 carbon atoms, or a hydroxyl group; a naphthoxy group substituted with an alkoxy group having 1 to 5 carbon atoms, an alkyl group having 1 to 5 carbon atoms, or a hydroxyl group; an anthracenoxy group substituted with an alkoxy group having 1 to 5 carbon atoms, an alkyl group having 1 to 5 carbon atoms, or a hydroxyl group; a linear, branched or cyclic and saturated or unsaturated hydrocarbon group (preferably an alkyl group) having 1 to 30 carbon atoms (preferably 1 to 5 carbon atoms) substituted with an alkoxy group having 1 to 5 carbon atoms, a phenoxy group, a naphthoxy group, an anthracenoxy group, or a hydroxyl group; or a carbonyl group to which an alkyl group having 1 to 12 carbon atoms is bonded. Each of $R^{6'}$ and $R^7$ preferably represents a divalent group obtained by removing one hydrogen atom from an alkoxy group having 1 to 5 carbon atoms or a phenyl group substituted with an alkoxy group having 1 to 5 carbon atoms, an alkyl group having 1 to 5 carbon atoms, or a hydroxyl group.

The iodonium salt compound group is preferably at least one group selected from the group consisting of groups represented by the following Formulae (XXXIV) to (XXXV). The groups represented by the following Formulae (XXXIV) to (XXXV) are anion bound types in which an anion is bonded to the (1') base component. If the acid anion remains bonded to the (1') base component after exposure, the diffusion of the acid after exposure tends to be able to be inhibited, and image blurring tends to be able to be reduced.

[Chemical Formula 61]

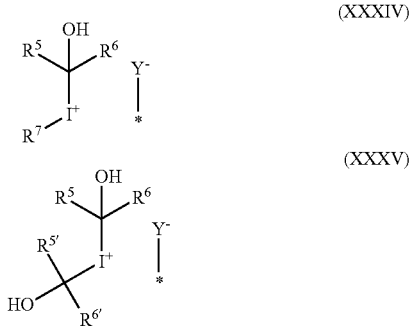

In Formulae (XXXIV) to (XXXV), each of $R^5$, $R^6$, $R^{5'}$, $R^{6'}$, and $R^7$ independently represents a hydrogen atom; a phenyl group; a naphthyl group; an anthracenyl group; a phenoxy group; a naphthoxy group; an anthracenoxy group; an amino group; an amide group; a halogen atom; a linear, branched or cyclic and saturated or unsaturated hydrocarbon group (preferably an alkyl group) having 1 to 30 carbon atoms (preferably 1 to 5 carbon atoms); a phenoxy group substituted with an alkoxy group having 1 to 5 carbon atoms, a hydroxyl group, an amino group, an amide group, or an alkyl group having 1 to 5 carbon atoms; a phenyl group substituted with a linear, branched or cyclic and saturated or unsaturated hydrocarbon group (preferably an alkyl group) having 1 to 30 carbon atoms (preferably 1 to 5 carbon atoms), an alkoxy group having 1 to 5 carbon atoms, an amino group, an amide group, or a hydroxyl group; a naphthoxy group substituted with an alkoxy group having 1 to 5 carbon atoms, an alkyl group having 1 to 5 carbon atoms, an amino group, an amide group, or a hydroxyl group; an anthracenoxy group substituted with an alkoxy group having 1 to 5 carbon atoms, an alkyl group having 1 to 5 carbon atoms, an amino group, an amide group, or a hydroxyl group; a linear, branched or cyclic and saturated or unsaturated hydrocarbon group (preferably an alkyl group) having 1 to 30 carbon atoms (preferably 1 to 5 carbon atoms) substituted with an alkoxy group having 1 to 5 carbon atoms, a phenoxy group, a naphthoxy group, an anthracenoxy group, an amino group, an amide group, or a hydroxyl group; or a carbonyl group to which an alkyl group having 1 to 12 carbon atoms is bonded. In Formulae (XXXIV) to (XXXV), the hydrogen atom of the hydroxyl group may be substituted with a phenyl group; a halogen atom; a linear, branched or cyclic and saturated or unsaturated hydrocarbon group (preferably an alkyl group) having 1 to 30 carbon atoms (preferably 1 to 5 carbon atoms); or a phenyl group substituted with a linear, branched or cyclic and saturated or unsaturated hydrocarbon group (preferably an alkyl group) having 1 to 30 carbon atoms (preferably 1 to 5 carbon atoms), an alkoxy group having 1 to 5 carbon atoms, or a hydroxyl group. When the hydrogen atom of the hydroxyl group is substituted, the iodonium salt compound group contains a ketal compound group or an acetal compound group. In Formulae (XXXIV) to (XXXV), any two or more groups among $R^5$, $R^6$, $R^{5'}$, $R^{6'}$, and $R^7$ may form a cyclic structure through a single bond, a double bond, or a bond containing —$CH_2$—, —O—, —S—, —$SO_2$—, —$SO_2NH$—, —C(=O)—, —C(=O)O—, —NHCO—, —NHC(=O)NH—, —$CHR^f$—, —$CR^f_2$—, —NH—, or —$NR^f$—. $R^f$ represents a phenyl group; a phenoxy group; a halogen atom; a linear, branched or cyclic and saturated or unsaturated hydrocarbon group (preferably an alkyl group) having 1 to 30 carbon atoms (preferably 1 to 5 carbon atoms); a phenoxy group substituted with an alkoxy group having 1 to 5 carbon atoms, a hydroxyl group, or an alkyl group having 1 to 5 carbon atoms; or a phenyl group substituted with a linear, branched or cyclic and saturated or unsaturated hydrocarbon group (preferably an alkyl group) having 1 to 30 carbon atoms (preferably 1 to 5 carbon atoms), an alkoxy group having 1 to 5 carbon atoms, or a hydroxyl group. Each of $R^5$, $R^6$, $R^{5'}$, $R^{6'}$, and $R^7$ independently preferably represents a phenyl group; a phenoxy group; a phenoxy group substituted with an alkoxy group having 1 to 5 carbon atoms, a hydroxyl group, or an alkyl group having 1 to 5 carbon atoms; or a phenyl group substituted with an alkoxy group having 1 to 5 carbon atoms or a hydroxyl group. In Formulae (XXXIV) to (XXXV), $Y^-$ represents a group of an acid anion, preferably represents a strong acid anion, and more preferably represents a super strong acid anion. In Formulae (XXXIV) to (XXXV), * represents a binding portion to the (1') base component and represents a binding portion in the (1') base component.

Specific examples of groups represented by —C(—OH)$R^5R^6$ and —C(—OH)$R^{5'}R^{6'}$ in Formulae (XVIII) to (XIX) and (XXXIV) to (XXXV) include the same groups as those represented by —C(—OH)$R^1R^2$—, —C(—OH)$R^{1'}R^{2'}$—, —C(—OH)$R^{1''}R^{2''}$—, and the like exemplified above in Formulae (I) to (III).

Examples of the super strong acid anions of the sulfonium salt compound group and the iodonium salt compound group include anions exemplified above for the aforementioned sulfonium salt compound and iodonium salt compound. The acid anion group of the sulfonium salt compound group and the iodonium salt compound group is a group that can function as an acid anion. Examples of the acid anion group include a sulfonate anion group, a carboxylate anion group, a bis(alkylsulfonyl)amide anion group, a tris(alkylsulfonyl)methide anion group, and the like. The acid anion group is preferably an acid anion group represented by the following Formula (XXXVII), (XXXVIII), or (XXXIX), and more preferably an acid anion group represented by the following Formula (XXXVII).

[Chemical Formula 62]

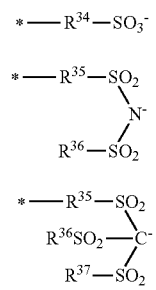

In Formulae (XXXVII), (XXXVIII), and (XXXIX), each of $R^{34}$ and $R^{35}$ independently represents a divalent organic group, and each of $R^{36}$ and $R^{37}$ represents a monovalent organic group. * represents a binding portion to the (1') base component. Examples of the divalent organic group include an alkylene group, an arylene group, a group in which a plurality of these groups is linked to each other, and the like. Specific examples of the monovalent organic group include an alkyl group, an aryl group, a group in which a plurality of these groups is linked to each other, and the like. The monovalent organic group is preferably an alkyl group in which the 1-position is substituted with a fluorine atom or a fluoroalkyl group, or a phenyl group which is substituted with a fluorine atom or a fluoroalkyl group. The divalent organic group is preferably an alkylene group in which the 1-position (anion side) is substituted with a fluorine atom or a fluoroalkyl group, or a phenylene group which is substituted with a fluorine atom or a fluoroalkyl group. If the organic group has a fluorine atom or a fluoroalkyl group, the acidity of an acid generated by exposure tends to be increased, and the sensitivity tends to be improved. Here, it is preferable that the monovalent organic group does not contain a fluorine atom as a substituent on the terminal. Furthermore, it is preferable that an atom of the divalent organic group bonded to the (1') base component is not bonded to a fluorine atom.

Examples of the chemical structure of the component (1') (polymer compound) having an anion bound-type sulfonium salt compound group will be shown below. Through the pattern-exposure, the sulfonium salt compound group is decomposed, the anion remains bonded to the polymer compound, the cation is decomposed, and as a result, an acid is generated.

[Chemical Formula 63]

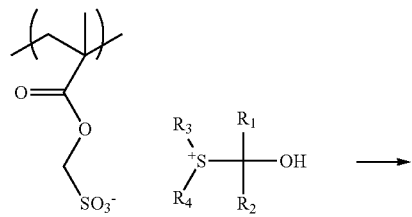

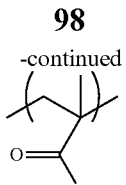

(e) Precursor Group

The precursor group is a component becoming a group having the function of a photosensitizer, which absorbs non-ionizing radiation having a wavelength of greater than 200 nm and preferably greater than 250 nm, by being irradiated with ionizing radiation or non-ionizing radiation having a wavelength of equal to or less than 400 nm, preferably equal to or less than 250 nm, and more preferably equal to or less than 200 nm. The precursor group is different from the group (d) described above. In the method for forming a pattern of the present embodiment, the structure of the precursor group is changed due to a direct or indirect reaction during the pattern-exposure step and becomes a group having the function of a photosensitizer assisting the generation of an acid in the flood-exposure step. Particularly, in a case where the precursor group is bonded to the polymer compound, the group having the function of a photosensitizer is fixed to the polymer compound. Therefore, the diffusion of the precursor group from a pattern-exposed portion is inhibited, and hence an effect of further enhancing the contrast of the latent image of the acid between a pattern-exposed portion and a pattern-unexposed portion after the flood-exposure is obtained.

It is preferable that the precursor group becomes a carbonyl compound group (group obtained by removing a hydrogen atom from a carbonyl compound) absorbing non-ionizing radiation, which has a wavelength of greater than 200 nm and preferably greater than 250 nm, by being irradiated with ionizing radiation or non-ionizing radiation having a wavelength of equal to or less than 400 nm, preferably equal to or less than 250 nm, and more preferably equal to or less than 200 nm. Furthermore, it is preferable that the carbonyl compound group remain bonded to the (1') base component after exposure. If the carbonyl compound group remains bonded to the (1') base component after exposure, the diffusion of the photosensitizer after exposure tends to be able to be inhibited, and image blurring tends to be able to be reduced. It is more preferable that the precursor group is an alcohol compound group represented by the following Formula (XXIV).

[Chemical Formula 64]

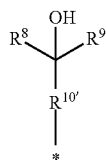
(XXIV)

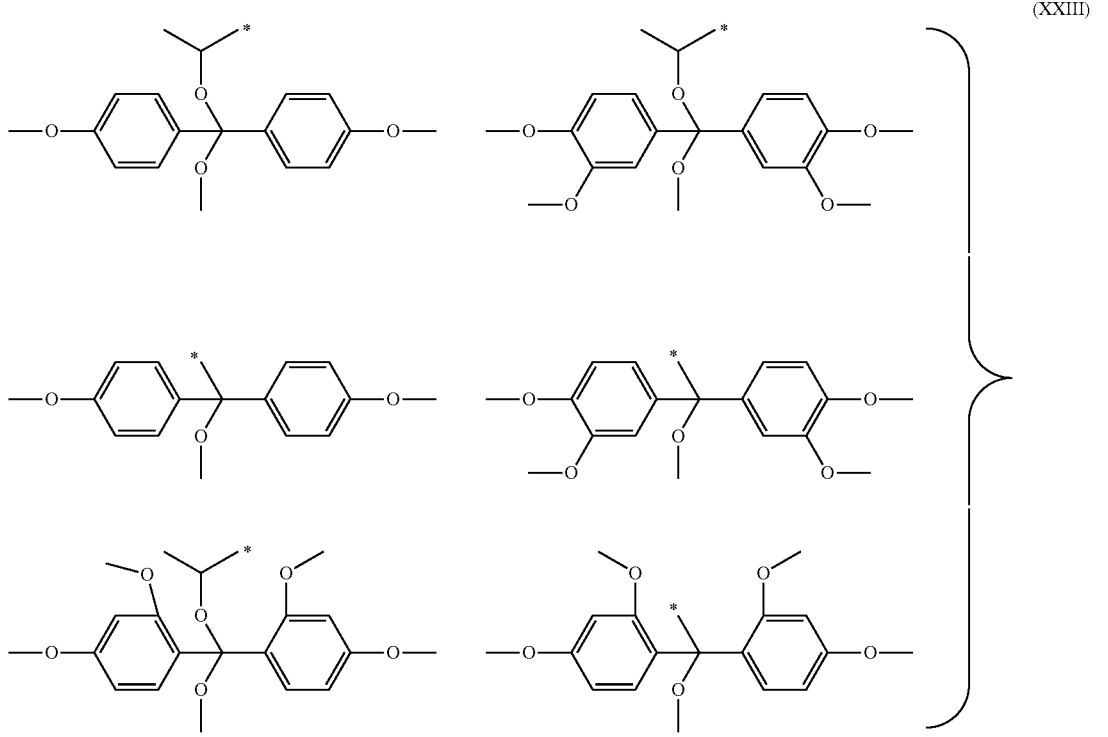
(XXIII)

In Formula (XXIV), each of $R^8$ and $R^9$ independently represents a hydrogen atom; a phenyl group; a naphthyl group; an anthracenyl group; an alkoxy group having 1 to 5 carbon atoms; an alkylthio group having 1 to 5 carbon atoms; a phenoxy group; a naphthoxy group; an anthracenoxy group; an amino group; an amide group; a halogen atom; a linear, branched or cyclic and saturated or unsaturated hydrocarbon group (preferably an alkyl group) having 1 to 30 carbon atoms (preferably 1 to 5 carbon atoms); an alkoxy group having 1 to 5 carbon atoms substituted with a linear, branched or cyclic and saturated or unsaturated hydrocarbon group (preferably an alkyl group) having 1 to 30 carbon atoms (preferably 1 to 5 carbon atoms), an alkoxy group having 1 to 5 carbon atoms, an amino group, an amide group, or a hydroxyl group; an alkylthio group having 1 to 5 carbon atoms substituted with a linear, branched or cyclic and saturated or unsaturated hydrocarbon group (preferably an alkyl group) having 1 to 30 carbon atoms (preferably 1 to 5 carbon atoms), an alkoxy group having 1 to 5 carbon atoms, an amino group, an amide group, or a hydroxyl group; a phenoxy group substituted with an alkoxy group having 1 to 5 carbon atoms, a hydroxyl group, an amino group, an amide group, or an alkyl group having 1 to 5 carbon atoms; a phenyl group substituted with a linear, branched or cyclic and saturated or unsaturated hydrocarbon group (preferably an alkyl group) having 1 to 30 carbon atoms (preferably 1 to 5 carbon atoms), an alkoxy group having 1 to 5 carbon atoms, an amino group, an amide group, or a hydroxyl group; a naphthoxy group substituted with an alkoxy group having 1 to 5 carbon atoms, an alkyl group having 1 to 5 carbon atoms, an amino group, an amide group, or a hydroxyl group; an anthracenoxy group substituted with an alkoxy group having 1 to 5 carbon atoms, an alkyl group having 1 to 5 carbon atoms, an amino group, an amide group, or a hydroxyl group; a linear, branched or cyclic and saturated or unsaturated hydrocarbon group (preferably an alkyl group) having 1 to 30 carbon atoms (preferably 1 to 5 carbon atoms) substituted with an alkoxy group having 1 to 5 carbon atoms, a phenoxy group, a naphthoxy group, an anthracenoxy group, an amino group, an amide group, or a hydroxyl group; or a carbonyl group bonded to an alkyl group having 1 to 12 carbon atoms. $R^{10'}$ represents a divalent group obtained by removing one hydrogen atom from a phenyl group; a naphthyl group; an anthracenyl group; a phenoxy group; a naphthoxy group; an anthracenoxy group; an amino group; a linear, branched or cyclic and saturated or unsaturated hydrocarbon group (preferably an alkyl group) having 1 to 30 carbon atoms (preferably 1 to 5 carbon atoms); a phenoxy group substituted with an alkoxy group having 1 to 5 carbon atoms, a hydroxyl group, an amino group, an amide group, or an alkyl group having 1 to 5 carbon atoms; a phenyl group substituted with a linear, branched or cyclic and saturated or unsaturated hydrocarbon group (preferably an alkyl group) having 1 to 30 carbon atoms (preferably 1 to 5 carbon atoms), an alkoxy group having 1 to 5 carbon atoms, an amino group, an amide group, or a hydroxyl group; a naphthoxy group substituted with an alkoxy group having 1 to 5 carbon atoms, an alkyl group having 1 to 5 carbon atoms, an amino group, an amide group, or a hydroxyl group; an anthracenoxy group substituted with an alkoxy group having 1 to 5 carbon atoms, an alkyl group having 1 to 5 carbon atoms, an amino group, an amide group, or a hydroxyl group; a linear, branched or cyclic and saturated or unsaturated hydrocarbon group (preferably an alkyl group) having 1 to 30 carbon atoms (preferably 1 to 5 carbon atoms) substituted with an alkoxy group having 1 to 5 carbon atoms, a phenoxy group, a naphthoxy group, an anthracenoxy group, an amino group, an amide group, or a hydroxyl group, or a carbonyl group to which an alkyl group having 1 to 12 carbon atoms is bonded. The alcohol compound group may be a thiol compound group in which an alcoholic hydroxyl group in Formula (XXIV) has become a thiol group. In Formula (XXIV), the hydrogen atom of the hydroxyl group or the thiol group may be substituted with a phenyl group; a halogen atom; a linear, branched or cyclic and saturated or unsaturated hydrocarbon group (preferably an alkyl group) having 1 to 30 carbon atoms (preferably 1 to 5 carbon atoms); a linear, branched or cyclic and saturated or unsaturated hydrocarbon group (preferably an alkyl group) having 1 to 30 carbon atoms (preferably 1 to 5 carbon atoms); or a phenyl group substituted with an alkoxy group having 1 to 5 carbon atoms or a hydroxyl group. When the hydrogen atom of the hydroxyl group is substituted, the alcohol compound group contains a ketal compound group or an acetal compound group. Furthermore, when the hydrogen atom of the thiol group is substituted, the thiol compound group contains a thioketal compound group or a thioacetal compound group. In the formulae, any two or more groups among $R^8$, $R^9$, and $R^{10'}$ may form a cyclic structure through a single bond, a double bond, or a bond containing —$CH_2$—, —O—, —S—, —$SO_2$—, —$SO_2NH$—, —C(=O)—, —C(=O)O—, —NHCO—, —NHC(=O)NH—, —$CHR^g$—, —$CR^g_2$—, —NH—, or —$NR^g$—. $R^g$ represents a phenyl group; a phenoxy group; a halogen atom; a linear, branched or cyclic and saturated or unsaturated hydrocarbon group (preferably an alkyl group) having 1 to 30 carbon atoms (preferably 1 to 5 carbon atoms); a phenoxy group substituted with an alkoxy group having 1 to 5 carbon atoms, a hydroxyl group, or an alkyl group having 1 to 5 carbon atoms; a linear, branched or cyclic and saturated or unsaturated hydrocarbon group (preferably an alkyl group) having 1 to 30 carbon atoms (preferably 1 to 5 carbon atoms); or a phenyl group substituted with an alkoxy group having 1 to 5 carbon atoms or a hydroxyl group. Each of $R^8$ and $R^9$ independently preferably represents a hydrogen atom; a phenyl group; a phenoxy group; a phenoxy group substituted with an alkoxy group having 1 to 5 carbon atoms, a hydroxyl group, or an alkyl group having 1 to 5 carbon atoms; or a phenyl group substituted with an alkoxy group having 1 to 5 carbon atoms or a hydroxyl group. $R^{10'}$ preferably represents a divalent group obtained by removing one hydrogen atom from a phenyl group; a phenoxy group; a phenoxy group substituted with an alkoxy group having 1 to 5 carbon atoms, a hydroxyl group, or an alkyl group having 1 to 5 carbon atoms; or a phenyl group substituted with an alkoxy group having 1 to 5 carbon atoms or a hydroxyl group. In Formula (XXIV), * represents a binding portion to the (1') base component.

It can be said that the ketal compound group or the acetal compound group in which the hydrogen atom of the hydroxyl group in Formula (XXIV) is substituted is preferably a compound group represented by the following Formula (XL). That is, the precursor group may be the compound group represented by the following Formula (XL). In a case where either $R^8$ or $R^9$ is a hydrogen atom, it can be said that the compound group represented by the following Formula (XL) is an acetal compound group.

[Chemical Formula 65]

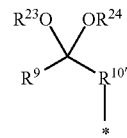

(XL)

In Formula (XL), each of $R^9$ and $R^{10'}$ has the same definition as each of $R^9$ and $R^{10'}$ in Formula (XXIV). As described above, $R^9$ and $R^{10'}$ may form a cyclic structure. In Formula (XL), each of $R^{23}$ and $R^{24}$ independently represents a phenyl group; a halogen atom; a linear, branched or cyclic and saturated or unsaturated hydrocarbon group (preferably an alkyl group) having 1 to 30 carbon atoms (preferably 1 to 5 carbon atoms); or a phenyl group substituted with a linear, branched or cyclic and saturated or unsaturated hydrocarbon group (preferably an alkyl group) having 1 to 30 carbon atoms (preferably 1 to 5 carbon atoms), an alkoxy group having 1 to 5 carbon atoms, or a hydroxyl group. $R^{23}$ and $R^{24}$ may form a cyclic structure through a single bond, a double bond, or a bond containing —$CH_2$—, —O—, —S—, —$SO_2$—, —$SO_2NH$—, —C(=O)—, —C(=O)O—, —NHCO—, —NHC(=O)NH—, —$CHR^g$—, —$CR^g_2$—, —NH—, or —$NR^g$—. $R^g$ has the same definition as $R^g$ in Formula (XXIV). The ketal compound group or the acetal compound group may be a thioketal compound group or a thioacetal compound group in which an oxygen atom bonded to $R^{23}$ and/or $R^{24}$ in Formula (XL) is substituted with sulfur.

Each of the ketal compound group and the acetal compound group bonded to the (1') base component can be obtained by reacting the carbonyl compound group bonded to the (1') base component with an alcohol. This reaction can be said to be a reaction for protecting a carbonyl group contributing to the photosensitization action. It can be said that $R^{23}$ and $R^{24}$ in Formula (XL) are protecting groups of the carbonyl group. Furthermore, it can be said that, in this case, the reaction is a deprotection reaction in which the precursor group becomes a group having the function of a photosensitizer by radiation or the like. The reactivity of the protecting groups is as described above in relation to the photosensitizer precursor.

The precursor group may be a compound group represented by any of the following Formulae (XLI) to (XLIV) or a derivative group thereof.

[Chemical Formula 66]

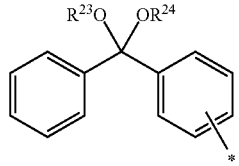

(XLI)

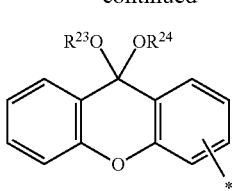

(XLII)

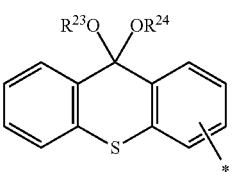

(XLIII)

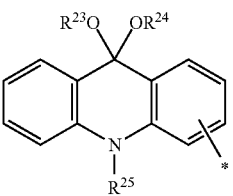

(XLIV)

In Formulae (XLI) to (XLIV), each of $R^{23}$ and $R^{24}$ has the same definition as each of $R^{23}$ and $R^{24}$ in Formula (XL). In Formulae (XLI) to (XLIV), a hydrogen atom of an aromatic ring may be substituted with an alkoxy group having 1 to 5 carbon atoms or an alkyl group having 1 to 5 carbon atoms, and the aromatic ring may form a naphthalene ring or an anthracene ring by being bonded to another aromatic ring. $R^{25}$ represents an alkyl group having 1 to 5 carbon atoms. In Formulae (XLI) to (XLIV), * represents a binding portion to the (1') base component. Herein, in Formula (XLIV), $R^{25}$ may be bonded to the (1') base component. In a case where the (1') base component to which the compound group represented by any of Formulae (XLI) to (XLIV) or the derivative group thereof is bonded is used, the shift of the absorption wavelength of the radiation at the time when the precursor group becomes a group having the function of a photosensitizer is further increased, and the sensitization reaction can be caused in a pattern-exposed portion in a more selective manner.

It can be said that the orthoester compound group in which the hydrogen atom of the alcoholic hydroxyl group in Formula (XXIV) is substituted is preferably a compound group represented by the following Formula (XLVIII). That is, the precursor group may be a compound group represented by the following Formula (XLVIII).

[Chemical Formula 67]

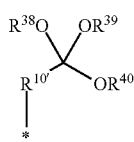

(XLVIII)

In Formula (XLVIII), each of $R^{38}$ to $R^{40}$ has the same definition as each of $R^{38}$ to $R^{40}$ in Formula (XXIV). In Formula (XLVIII), $R^{10'}$ has the same definition as $R^{10'}$ in Formula (XXIV). Any two or more groups among $R^{38}$ to $R^{40}$ may form a cyclic structure through a single bond, a double bond, or a bond containing —$CH_2$—, —O—, —S—, —$SO_2$—, —$SO_2NH$—, —C(=O)—, —C(=O)O—, —NHCO—, —NHC(=O)NH—, —$CHR^g$—, —$CR^g_2$—, —NH—, or —$NR^g$—. $R^g$ has the same definition as $R^g$ in Formula (VI).

The orthoester compound group is decomposed through the deprotection reaction in the pattern-exposure and becomes, for example, a carboxylic acid ester group or a carboxylic acid group containing a carbonyl group. The orthoester compound group is preferably, for example, an OBO ester compound group represented by the following Formula (XLIX) in which the portion of carboxyl group of the photosensitizer having a carboxyl group is substituted (protected) with OBO (for example, 4-methyl2,6,7-trioxabicyclo[2.2.2]-octan-1-yl). The precursor group in which a carboxyl group is protected with OBO generates a carboxylic acid group by an acid catalyst generated at the time of pattern-exposure so as to cause the shift of the absorption wavelength of radiation and functions as a group having the function of a photosensitizer at the time of flood-exposure. Due to the generation of the carboxylic acid group from the precursor group, the change of polarity of the resist (for example, change of a nonpolar resist to a polar resist) occurs in a pattern-exposed portion. Therefore, the orthoester compound group also functions as a dissolution accelerator in the developing step and contributes to the enhancement of resist contrast. If the precursor group contains the OBO ester compound group, the generation of the group having the function of a photosensitizer and the polarity changing reaction can be simultaneously caused.

[Chemical Formula 68]

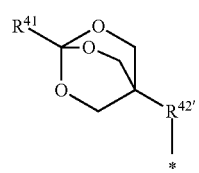

(XLIX)

In Formula (XLIX), $R^{41}$ has the same definition as $R^{41}$ in Formula (XLVII). $R^{42'}$ represents a divalent group obtained by removing one hydrogen atom from a phenyl group; a naphthyl group; an anthracenyl group; a phenoxy group; a naphthoxy group; an anthracenoxy group; an amino group; a linear, branched or cyclic and saturated or unsaturated hydrocarbon group (preferably an alkyl group) having 1 to 30 carbon atoms (preferably 1 to 5 carbon atoms); a phenoxy group substituted with an alkoxy group having 1 to 5 carbon atoms, a hydroxyl group, an amino group, an amide group, or an alkyl group having 1 to 5 carbon atoms; a phenyl group substituted with a linear, branched or cyclic and saturated or unsaturated hydrocarbon group (preferably an alkyl group) having 1 to 30 carbon atoms (preferably 1 to 5 carbon atoms), an alkoxy group having 1 to 5 carbon atoms, an amino group, an amide group, or a hydroxyl group; a naphthoxy group substituted with an alkoxy group having 1 to 5 carbon atoms, an alkyl group having 1 to 5 carbon atoms, an amino group, an amide group, or a hydroxyl group; an anthracenoxy group substituted with an alkoxy group having 1 to 5 carbon atoms, an alkyl group having 1 to 5 carbon atoms, an amino group, an amide group, or a hydroxyl group; a linear, branched or cyclic and saturated or unsaturated hydrocarbon group (preferably an alkyl group) having 1 to 30 carbon atoms (preferably 1 to 5 carbon atoms) substituted with an alkoxy group having 1 to 5 carbon atoms, a phenoxy group, a naphthoxy group, an anthracenoxy group, an amino group, an amide group or a hydroxyl group; or a carbonyl group to which an alkyl group having 1 to 12 carbon atoms is bonded. $R^{41}$ preferably represents a hydrogen atom; a phenyl group; a phenoxy group; a phenoxy group substituted with an alkoxy group having 1 to 5 carbon atoms, a hydroxyl group, or an alkyl group having 1 to 5 carbon atoms; or a phenyl group substituted with an alkoxy group having 1 to 5 carbon atoms or a hydroxyl group. $R^{42'}$ preferably represents a divalent group obtained by removing one hydrogen atom from a phenyl group; a phenoxy group; a phenoxy group substituted with an alkoxy group having 1 to 5 carbon atoms, a hydroxyl group, or an alkyl group having 1 to 5 carbon atoms; or a phenyl group substituted with an alkoxy group having 1 to 5 carbon atoms or a hydroxyl group.

Specific examples of the precursor group include groups obtained by removing one hydrogen atom from the compounds exemplified above as the photosensitizer precursor.

Examples of the chemical structure of the component (1') (polymer compound) having the (e) precursor group will be shown below. At the time of pattern-exposure, due to the acid catalyst generated by the pattern-exposure, the protecting group is removed from the precursor group, and a carbonyl group is generated. That is, the (1') base component to which a group having the function of a photosensitizer is bonded is generated. Because a group having the function of a photosensitizer is bonded to the (1') base component, the diffusion of the photosensitizer during the flood-exposure can be inhibited, and the contrast of the latent image of the acid in the resist material film can be improved.

[Chemical Formula 69]

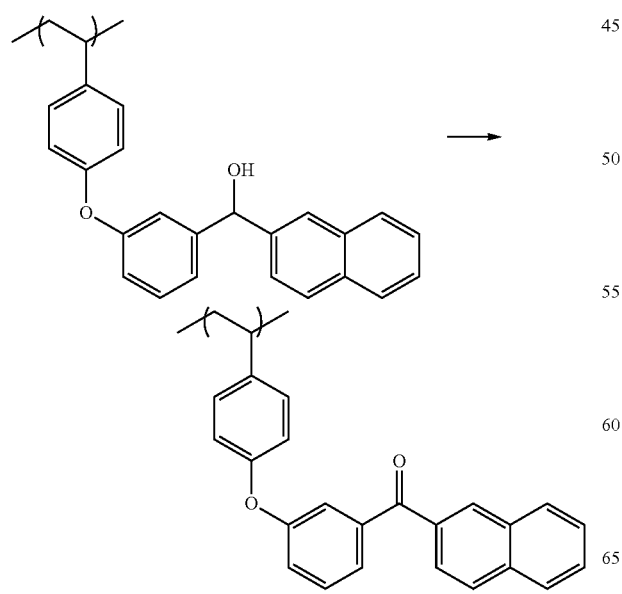

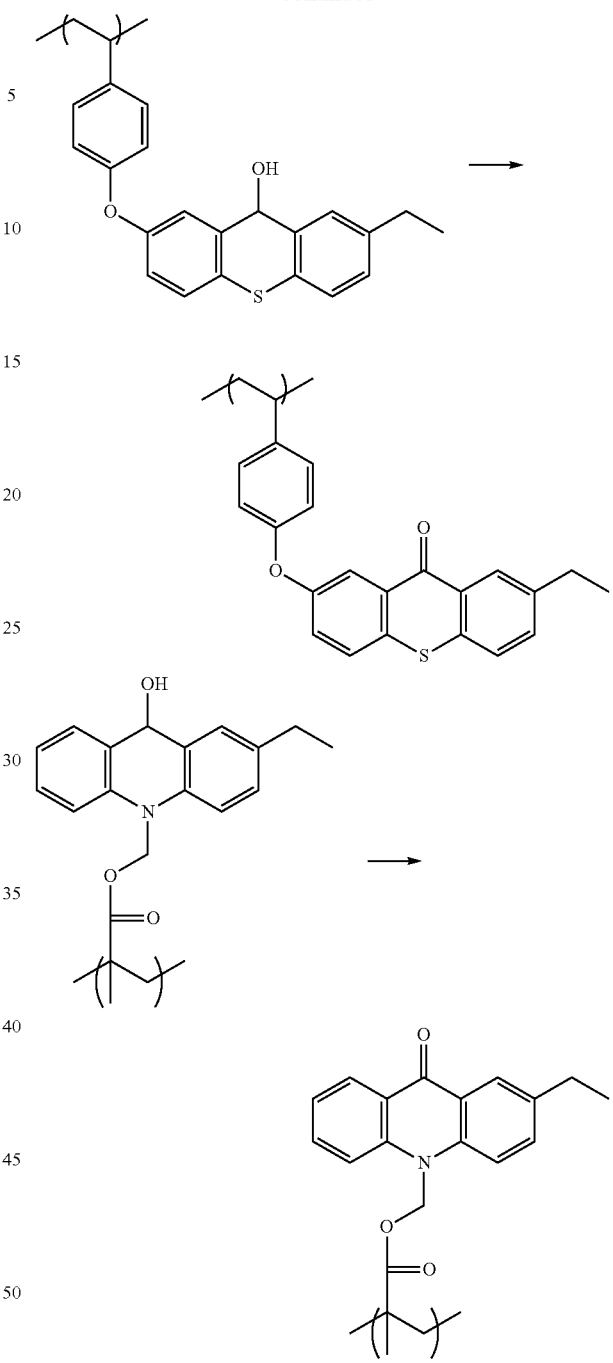

[Chemical Formula 70]

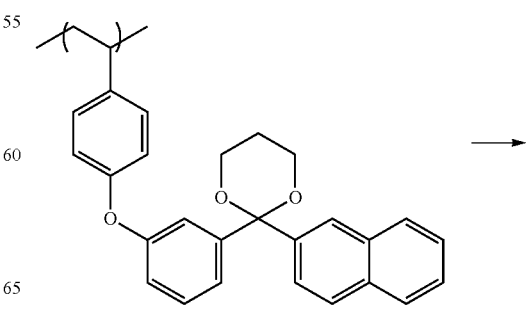

107
-continued
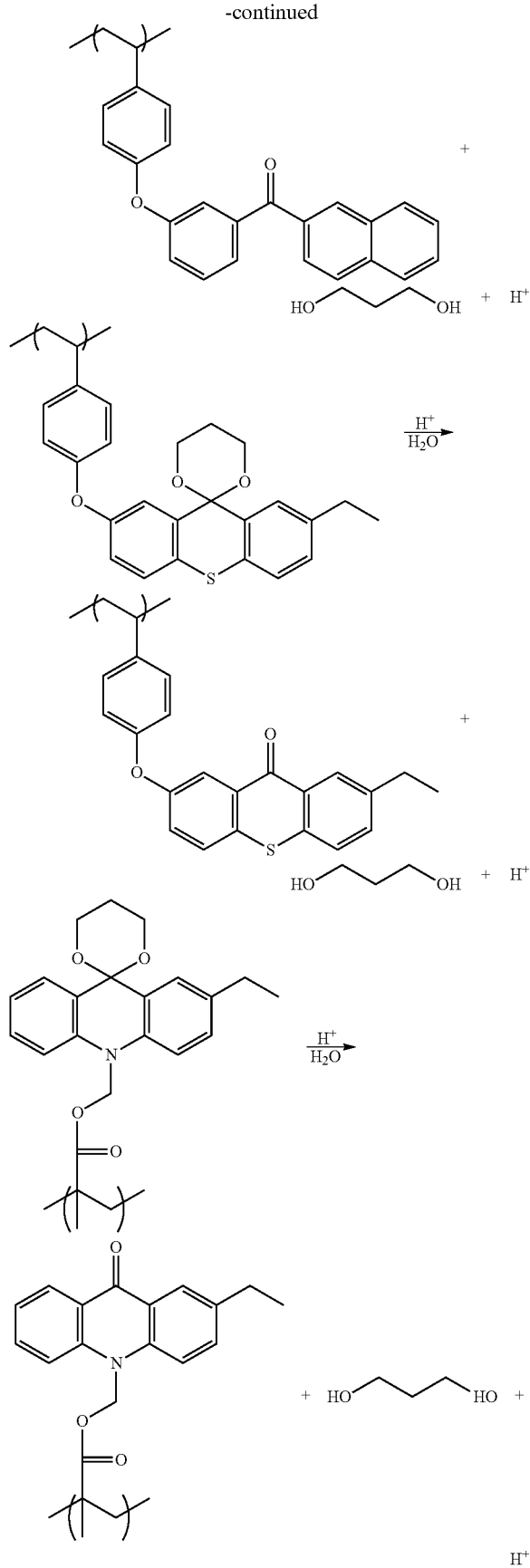
108
-continued
[Chemical Formula 71]
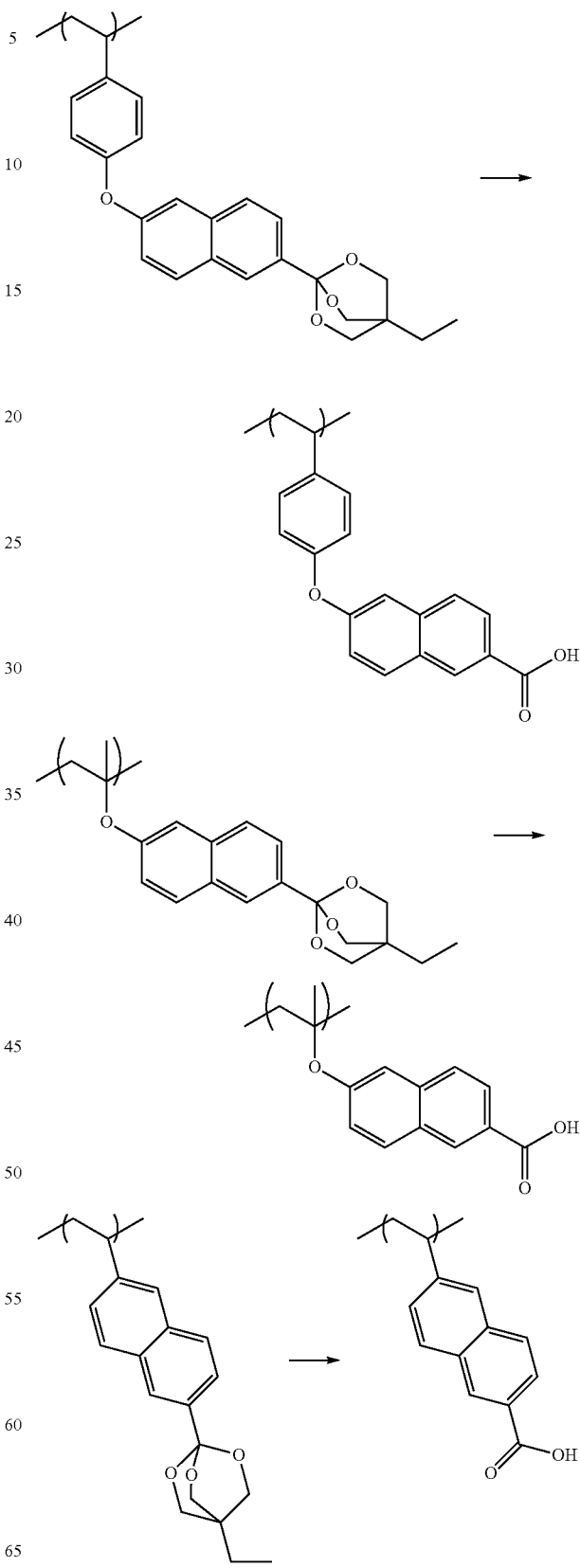

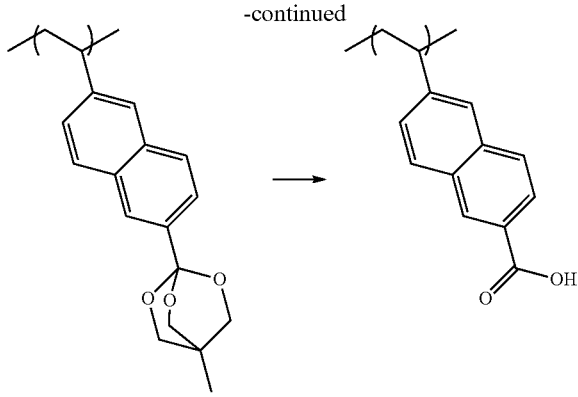

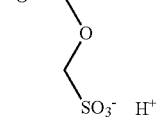

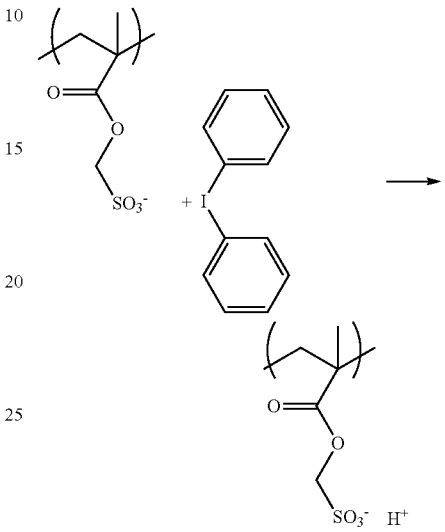

(f) Photoacid Generating Group

The photoacid generating group is a group generating an acid by being irradiated with ionizing radiation or non-ionizing radiation having a wavelength of equal to or less than 400 nm, preferably equal to or less than 250 nm, and more preferably equal to or less than 200 nm. The photoacid generating group is different from the group (d) described above.

The photoacid generating group preferably has the same structure (salt constituted with a cation and an anion) as the compound exemplified above in relation to the component (c). The photoacid generating group is preferably bonded to the (1') base component through a portion of a cation or anion, and more preferably bonded to the (1') base component through a portion of an anion (the photoacid generating group is preferably an anion bound type). Furthermore, in the group (f), a portion of the anion more preferably remains bonded to the (1') base component after exposure. If the acid anion remains bonded to the (1') base component after exposure, the diffusion of the acid after exposure tends to be able to be inhibited, and image blurring tends to be able to be reduced.

Specific examples of the photoacid generating group include groups obtained by removing one hydrogen atom from the compound exemplified above as the photoacid generator.

Examples of the chemical structure of the component (1') (polymer compound) having the (f) photoacid generating group will be shown below. In the following example, through the pattern-exposure, the photoacid generating group is decomposed, and the anion group remains in the base portion after the decomposition.

[Chemical Formula 72]

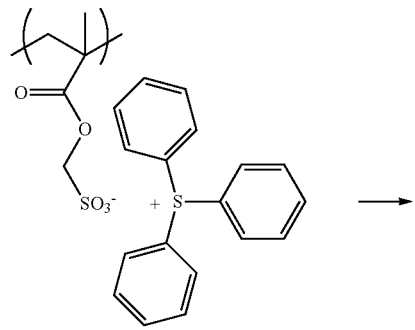

The amount of each of the groups (d) to (f) bonded to the base component is preferably 0.1 by mass to 30% by mass, and more preferably 0.2% by mass to 10% by mass, with respect to the total mass of the base component.

In a case where the (1') base component is a polymer compound, the amount of the group (d) contained in the polymer compound is preferably 0.001 moles to 0.5 moles, more preferably 0.002 moles to 0.3 moles, and even more preferably 0.01 moles to 0.3 moles, with respect to 1 mole of the polymer compound. If the amount of the group (d) contained in the (1') base component is equal to or less than 0.5 moles, a resist pattern having an excellent shape is easily obtained. In contrast, if the amount is equal to or greater than 0.001 moles, sufficient sensitivity is easily obtained. The amount of the group (e) contained in the (1') base component is preferably 0.001 moles to 0.95 moles, more preferably 0.002 moles to 0.3 moles, and even more preferably 0.01 moles to 0.3 moles, with respect to 1 mole of the polymer compound. If the amount of the group (e) contained in the (1') base component is equal to or less than 0.5 moles, a resist pattern having an excellent shape is easily obtained. In contrast, if the amount is equal to or greater than 0.001 moles, sufficient sensitivity is easily obtained. The amount of the group (f) contained in the (1') base component is preferably 0.001 moles to 0.5 moles, more preferably 0.002 moles to 0.3 moles, and even more preferably 0.01 moles to 0.3 moles, with respect to 1 mole of the polymer compound. If the amount of the group (f) contained in the (1') base component is equal to or less than 0.5 moles, a resist pattern having an excellent shape is easily obtained. In contrast, if the amount is equal to or greater than 0.001 moles, sufficient sensitivity is easily obtained.

In a case where the (1') base component is a low-molecular weight compound, the amount of the group (d) contained in the low-molecular weight compound is preferably 0.001 moles to 0.5 moles, more preferably 0.002 moles to 0.3 moles, and even more preferably 0.01 moles to 0.3 moles, with respect to 1 mole of the low-molecular weight compound. If the amount of the group (d) contained in the (1') base component is equal to or less than 0.5 moles, a resist pattern having an excellent shape is easily obtained. In contrast, if the amount is equal to or greater than 0.001 moles, sufficient sensitivity is easily obtained. The amount of the group (e) contained in the (1') base component is preferably 0.001 moles to 0.5 moles, more preferably 0.002 moles to 0.3 moles, and even more preferably 0.01 moles to 0.3 moles, with respect to 1 mole of the low-molecular weight compound. If the amount of the group (e) contained in the (1') base component is equal to or less than 0.5 moles, a resist pattern having an excellent shape is easily obtained. In contrast, if the amount is equal to or greater than 0.001 moles, sufficient sensitivity is easily obtained. The amount of the group (f) contained in the (1') base component is preferably 0.001 moles to 0.5 moles, more preferably 0.002 moles to 0.3 moles, and even more preferably 0.01 moles to 0.3 moles, with respect to 1 mole of the low-molecular weight compound. If the amount of the group (f) contained in the (1') base component is equal to or less than 0.5 moles, a resist pattern having an excellent shape is easily obtained. In contrast, if the amount is equal to or greater than 0.001 moles, sufficient sensitivity is easily obtained. Herein, the amount of the group contained in the polymer compound or the low-molecular weight compound equals to the number of moles of monomers having the groups (d) to (f) with respect to 1 mole of all the monomers used for synthesis.

(Other Components)

The resist material may appropriately contain the component (2), (3) first scavenger, (4) second scavenger, (5) cross-linking agent, (6) additive, (7) solvent, and the like described above in the first embodiment, in addition to the (1') base component.

The amount of other components formulated is the same as in the first embodiment, and those other components exert the same effect as in the first embodiment. Here, the amount of the component (2) formulated is preferably 0.005 parts by mass to 35 parts by mass, and more preferably 0.1 parts by mass to 15 parts by mass, with respect to 100 parts by mass of the (I') base component. If the amount is equal to or less than 15 parts by mass, the compatibility between the component (2) and other components in the resist material becomes excellent, a resist material film is easily formed, and a resist pattern having an excellent shape is obtained. In contrast, if the amount is equal to or greater than 0.1 parts by mass, sufficient sensitivity is easily obtained. The amount of the (3) first scavenger formulated is preferably 0.001 parts by mass to 10 parts by mass, and more preferably 0.01 parts by mass to 5 parts by mass, with respect to 100 parts by mass of the (1') base component. If the amount is equal to or greater than 0.01 parts by mass, the aforementioned effect resulting from formulating the first scavenger tends to be easily obtained. The ratio between the photoacid generator (total amount of the components (a) and (c)) and the first scavenger used in the resist material is preferably photoacid generator/first scavenger (molar ratio)=1.5 to 300. That is, in view of the sensitivity and the resolution, the molar ratio is preferably equal to or greater than 1.5. Furthermore, in view of inhibiting the resist pattern dimension from changing with the passage of time from the point after the exposure to the heating treatment, the molar ratio is preferably equal to or less than 300. The photoacid generator/first scavenger (molar ratio) is more preferably 5.0 to 200.

The resist material may be constituted with the first and second embodiments in combination. That is, the action of generating a photosensitizer and an acid by exposure in the manner described in any of the first and second embodiments should be obtained. For example, the resist material according to the present embodiment may contain the (1') base component having the group (e) and the component (2) containing the component (c), or may contain the (1') base component having the group (f) and the component (2) containing the component (b).

Specifically, the resist materials according to the first embodiment, the second embodiment, and the embodiment as a combination of the first and second embodiments are as follows.

A. a composition in which the (1) base component is blended with the component (2).

B. a composition containing the (1') first base component to which the group (d) is bonded, any two groups among the groups (d) to (f) are bonded, or all of the groups (d) to (f) are bonded.

C. a composition in which the (1') first base component to which the group (e) is bonded is blended with the (1') second base component to which the group (f) is bonded.

D. a composition in which the (1') base component to which the group (e) is bonded is blended with the component (c) as the component (2).

E. a composition in which the (1') base component to which the group (f) is bonded is blended with the component (b) as the component (2).

In the composition C described above, the first base component and the second base component may be constituted with the same base component or constituted with different base components. Furthermore, the resist material may be obtained by further blending any of the compositions A to E with another (1') base component, another component (2), and the like.

The resist material of the present embodiment can be manufactured by mixing the aforementioned components (1) to (7) together by a known method. Specifically, the (1') base component can be manufactured as below.

In a case where the (1') base component is a polymer compound, as one of the methods for synthesizing the polymer compound, there is a method of performing heating polymerization by adding a polymerization initiator (for example, a radical initiator) to a monomer, which has an unsaturated bond for obtaining a repeating unit, in an organic solvent. The polymer compound can be obtained by this method. Examples of the organic solvent used at the time of polymerization include toluene, benzene, tetrahydrofuran, diethylether, dioxane, and the like. Examples of the polymerization initiator include 2,2'-azobisisobutyronitrile (AIBN), 2,2'-azobis(2,4-dimethylvaleronitrile), dimethyl 2,2-azobis(2-methylpropionate), benzoyl peroxide, lauroyl peroxide, and the like. The monomer can be polymerized by being heated preferably to a temperature of 50° C. to 80° C. The reaction time is 2 hours to 100 hours and preferably 5 hours to 20 hours. The groups (d) to (f) may be used as they are in a state of being introduced into the monomer. Alternatively, the acid-labile group thereof may be eliminated using an acid catalyst, and then the groups (d) to (f) may be protected or partially protected such that a bond is formed.

In a case where the (1') base component is a low-molecular weight compound, the groups (d) to (f) may be used as they are for the reactive group of the low-molecular weight compound. Alternatively, the acid-labile group thereof may be eliminated using an acid catalyst, and then groups (d) to (f) may be protected or partially protected such that a bond is formed.

<Method for Forming Pattern>

The resist material is suitably used in a two-stage exposure lithography process. That is, a lithography process (method for forming a pattern) according to the present embodiment includes a film forming step of forming a resist material film formed using the resist material on a substrate, a pattern-exposure step of irradiating the resist material film with ionizing radiation or non-ionizing radiation having a wavelength of equal to or less than 400 nm, preferably equal to or less than 250 nm, and more preferably equal to or less than 200 nm, through a mask, a flood-exposure step of irradiating the resist material film having undergone the pattern-exposure step with non-ionizing radiation having a wavelength which is longer than the wavelength of the non-ionizing radiation in the pattern-exposure step and is greater than 200 nm and preferably greater than 250 nm, a baking step of heating the resist material film having undergone the flood-exposure step, and a step of bringing the resist material film having undergone the baking step into contact with a developer.

Figure 4:
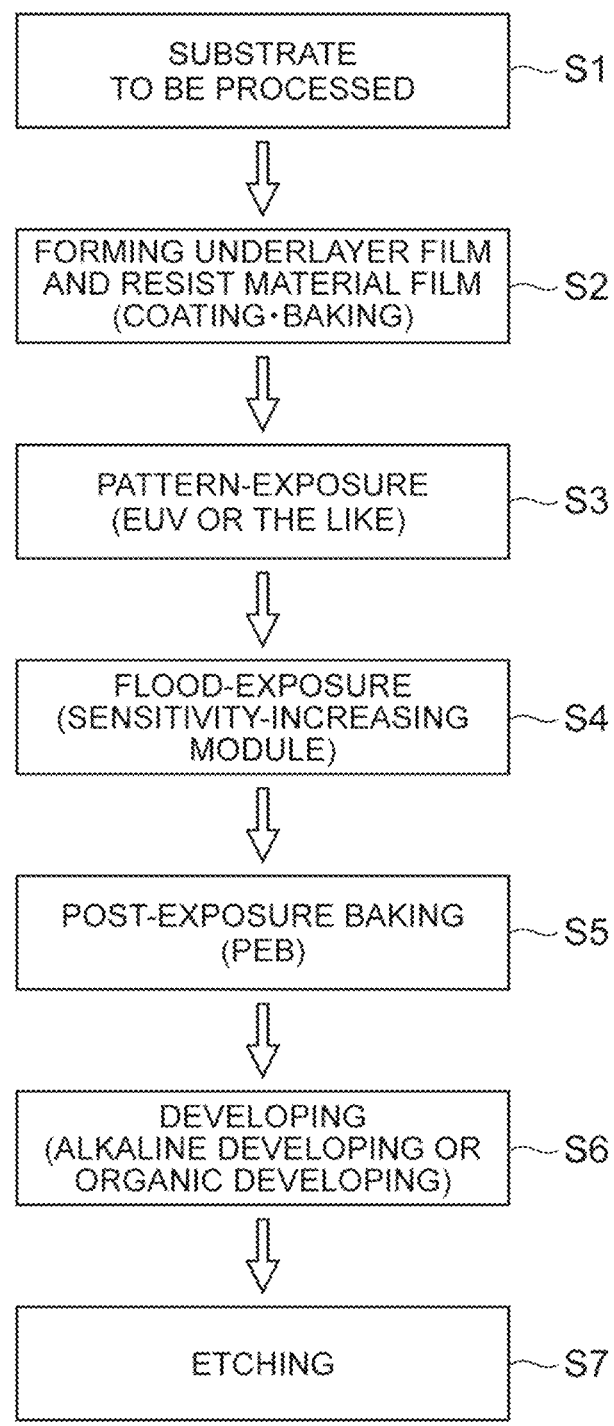
FIG. 4 is a flowchart showing an embodiment of a method for forming a pattern using a photosensitization chemical-amplification type resist material according to the present invention.
Figure 7:
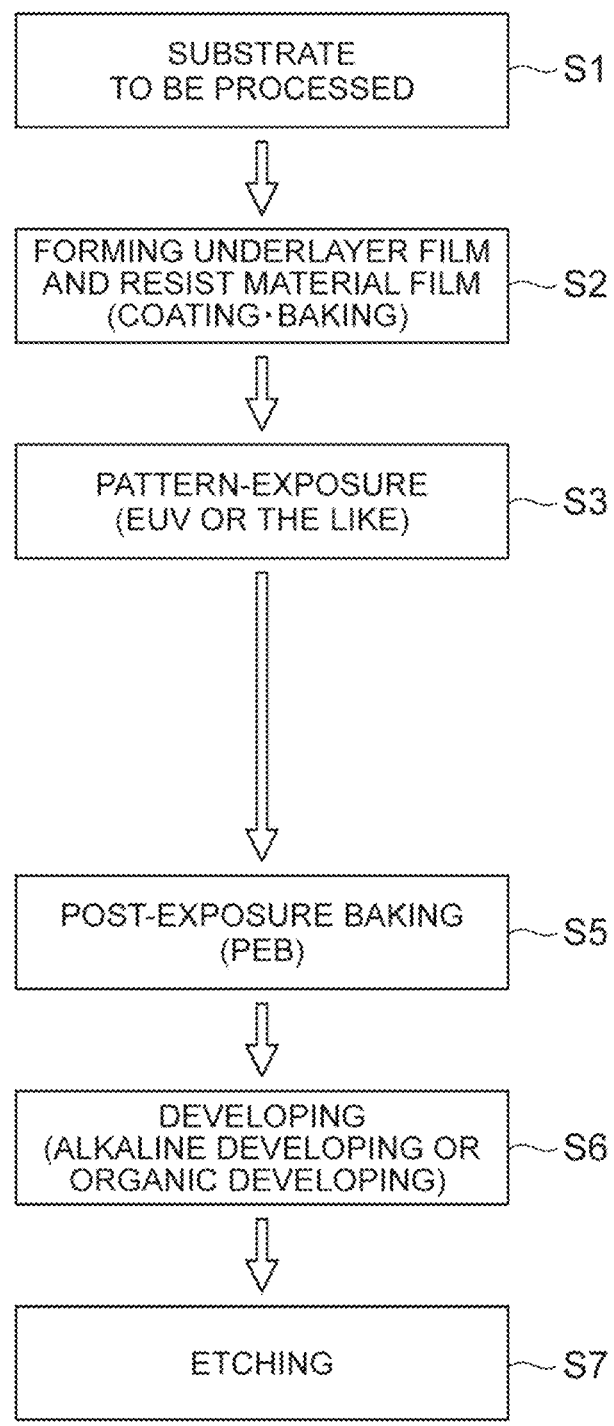
FIG. 7 is a flowchart showing an example of a method for forming a pattern using a conventional chemical-amplification type resist material.

FIG. 4 is a flowchart showing the lithography process according to the present embodiment. As shown in FIG. 4, the process includes the following steps. FIG. 7 is a flowchart showing an example of a method for forming a pattern using a conventional chemical-amplification type resist material.

Step S1: a step of preparing a substrate to be processed.

Step S2: a step of forming an underlayer film and a resist material film (film forming step).

Step S3: a step of generating an acid in an exposed portion by pattern-exposure (pattern-exposure step).

Step S4: a step of causing the acid to increase only in a pattern-exposed portion by flood-exposure (flood-exposure step).

Step S5: a step of causing a polarity changing reaction in a pattern-exposed portion by an acid catalyst through post-exposure baking (baking step).

Step S6: a step of forming a resist pattern by a developing treatment (developing step).

Step S7: a step of transferring the pattern by etching.

(Step S1) (Step S2: Film Forming Step)

In the following steps, the substrate as a processing target (substrate to be processed) may be a substrate constituted with a semiconductor wafer such as a silicon substrate, a silicon dioxide substrate, a glass substrate, or an ITO substrate, or may be a substrate in which an insulating film layer is formed on the semiconductor wafer.

A resist material film is formed on the substrate, and the resist material film is formed using the resist material of the present embodiment. Specific examples of the method for forming the resist material film include a method of coating the substrate with a liquid resist material by using a spin coater or the like, a method of putting a film-like (solid) resist material on the substrate, and the like. In a case where the substrate is coated with the liquid resist material, the resist material may be heated (pre-baked) after coating such that the solvent in the resist material volatilizes. The resist material film-forming conditions are appropriately selected according to the properties of the resist material, the thickness of the resist material film to be obtained, and the like. The thickness of the resist material film is preferably 1 nm to 5,000 nm, more preferably 10 nm to 1,000 nm, and even more preferably 30 nm to 200 nm.

Before the resist material film is formed on the substrate, an underlayer film (an antireflection film, a film for improving resist adhesiveness and resist shape, and the like) may be formed on the substrate. If the antireflection film is formed, it is possible to inhibit the occurrence of standing waves resulting from the reflection of radiation from the substrate or the like during the pattern-exposure step. If the film for improving the resist adhesiveness is formed, the adhesiveness between the substrate and the resist material film can be improved. If the film for improving the resist shape is formed, it is possible to further improve the shape of the resist having undergone development (that is, the footing shape or constricted shape of the resist). Meanwhile, in order to prevent the resist shape from deteriorating due to the occurrence of the standing waves of the radiation of the flood-exposure, it is desired to set the thickness of the underlayer film such that the reflection of the radiation of the flood-exposure is suppressed. It is desired that the underlayer film is a film that does not absorb the radiation of the flood-exposure. In a case where the underlayer film absorbs the radiation of the flood-exposure, in order to prevent an acid from being generated in an unexposed portion at the time of pattern-exposure due to photosensitization of the photosensitizer in the resist material film by the transfer of energy or electrons from the underlayer film, a buffering layer not transmitting the photosensitization reaction may be disposed between the resist material film and the underlayer so as to prevent sensitization starting from the underlayer film absorbing the radiation.

A protective film may be additionally formed on the resist material film. If the protective film is formed, it is possible to inhibit the deactivation of the photosensitizer, the acid, and reaction intermediates of these generated in the pattern-exposure step S3 and to improve the process stability. In order to prevent the occurrence of an acid generating reaction in an unexposed portion at the time of flood-exposure, the protective film may be an absorption film which absorbs at least a portion of the wavelengths of the non-ionizing radiation directly absorbed by the photoacid generator (acid-photosensitizer generator) as the component (a) or (c) described above or the photoacid generating group (acid-photosensitizer generating group) as the group (d) or (f) described above. If the absorption film is used, it is possible to inhibit the out-of-band light (OOB light), which is the radiation of an ultraviolet region generated at the time of EUV exposure, from entering the resist material film and to prevent a photoacid generator or a photoacid generating group from being decomposed in a pattern-unexposed portion. Furthermore, in a case where the absorption film is directly formed on the resist material film, in order to prevent the generation of an acid by the photosensitization reaction in a pattern-exposed portion within the resist material film, it is preferable to use a film which does not induce the photosensitization reaction from the protective film at the wavelength of the flood-exposure. In addition, in order to prevent the photosensitizer in the resist material film from being sensitized due to the transfer of energy, electrons, and the like from the protective film, a buffering layer may be disposed between the resist material film and the protective film so as to prevent the sensitization starting from the absorption layer absorbing the radiation. If the absorption film is formed on the resist material film after the pattern-exposure step S3 before the flood-exposure step S4 is performed, it is possible to further inhibit the photoacid generator or the photoacid generating group remaining in the resist material film after the pattern-exposure step S3 from directly generating an acid by being irradiated with the non-ionizing radiation in the flood-exposure step S4.

(Step S3: Pattern-Exposure Step)

In the pattern-exposure step S3, a light shielding mask having a predetermined pattern is disposed on the resist material film formed in the film forming step S2. Then, from an exposure device (radiation irradiation module) having a projector lens, an electro-optical system mirror, or a reflecting mirror, ionizing radiation or non-ionizing radiation having a wavelength of equal to or less than 400 nm, preferably equal to or less than 250 nm, and more preferably equal to or less than 200 nm, is radiated to the resist material film through the mask described above (pattern-exposure). As a light source of the pattern-exposure, for example, electron beams at 1 keV to 200 keV, extreme ultraviolet rays (EUV) having a wavelength of 13.5 nm, excimer laser beams at 193 nm (ArF excimer laser beams), or excimer laser beams at 248 nm (KrF excimer laser beams) are used in many cases. The exposure amount at the time of pattern-exposure may be smaller than the exposure amount at the time of performing flood-exposure by using the photosensitization chemical-amplification type resist of the present embodiment. Through the pattern-exposure, the aforementioned components (a) to (c) or groups (d) to (f) in the resist material film are decomposed, and an acid and a photosensitizer which absorbs non-ionizing radiation having a wavelength of greater than 200 nm are generated.

For the exposure, an exposure device using a step-and-scan method called "scanner" is widely used. In this method, by performing scanning exposure on the mask and the substrate in synchronization, a pattern of each shot is formed. Through the exposure, a reaction selectively occurs at exposed portions in the resist.

Before the following flood-exposure step S4 is performed, an absorption film, which absorbs at least a portion of the wavelengths of the non-ionizing radiation directly absorbed by the photoacid generator as the component (a) or (c) described above or the photoacid generating group as the component (d) or (f) described above, may be formed on the resist material film having undergone the pattern-exposure step S3. If the absorption film is formed, it is possible to further inhibit the photoacid generator or the photoacid generating group remaining in the resist material film after the pattern-exposure step S3 from directly generating an acid by being irradiated with the non-ionizing radiation in the flood-exposure step S4 described below.

In a case where a photosensitizer precursor (or a precursor group) having an alcoholic hydroxyl group, in which a hydrogen atom is not substituted, is used, while the resist material film having undergone the pattern-exposure step S3 is being allowed to stand until the following flood-exposure step S4 is performed, it is preferable that the atmosphere in which the resist material film is present is an atmosphere with reduced pressure or an inert atmosphere containing nitrogen or argon. If the resist material film is placed in the atmosphere described above, it is possible to inhibit the resist material film from being exposed to oxygen during the exposure, to inhibit the radical reaction from stopping due to oxygen, and to inhibit the acid from being quenched due to a trace amount of basic compound, and accordingly, the process tends to be able to be further stabilized. The time period (storage time) during which the resist material film having undergone the pattern-exposure step S3 is allowed to stand until the flood-exposure step S4 is performed is preferably equal to or less than 30 minutes, and more preferably equal to or less than 10 minutes. If the storage time is equal to or less than 30 minutes, the deterioration of sensitivity tends to be able to be inhibited. Meanwhile, in a case where the photosensitizer precursor (that is, a ketal compound, an acetal compound, an orthoester compound, or the like) having an alcoholic hydroxyl group, in which a hydrogen atom is substituted, is used, while the resist material film having undergone the pattern-exposure step S3 is being allowed to stand until the following flood-exposure step S4 is performed, the atmosphere in which the resist material film is present may be the air atmosphere cleaned using an amine removing filter. In a case where the photosensitizer precursor is used, the resist material film is not easily affected by oxygen as described above, and hence the resist material film may be processed in an air atmosphere cleaned with an amine removing filter. If the resist material film is placed in the aforementioned atmosphere, it is possible to inhibit the acid from being quenched due to a trace amount of basic compound, and accordingly, the process tends to be able to be further stabilized. The time period (storage time) during which the resist material film having undergone the pattern-exposure step S3 is allowed to stand until the flood-exposure step S4 is performed is preferably equal to or less than 30 minutes, and more preferably equal to or less than 10 minutes. If the storage time is equal to or less than 30 minutes, the deterioration of sensitivity tends to be able to be inhibited.

Figure 5:
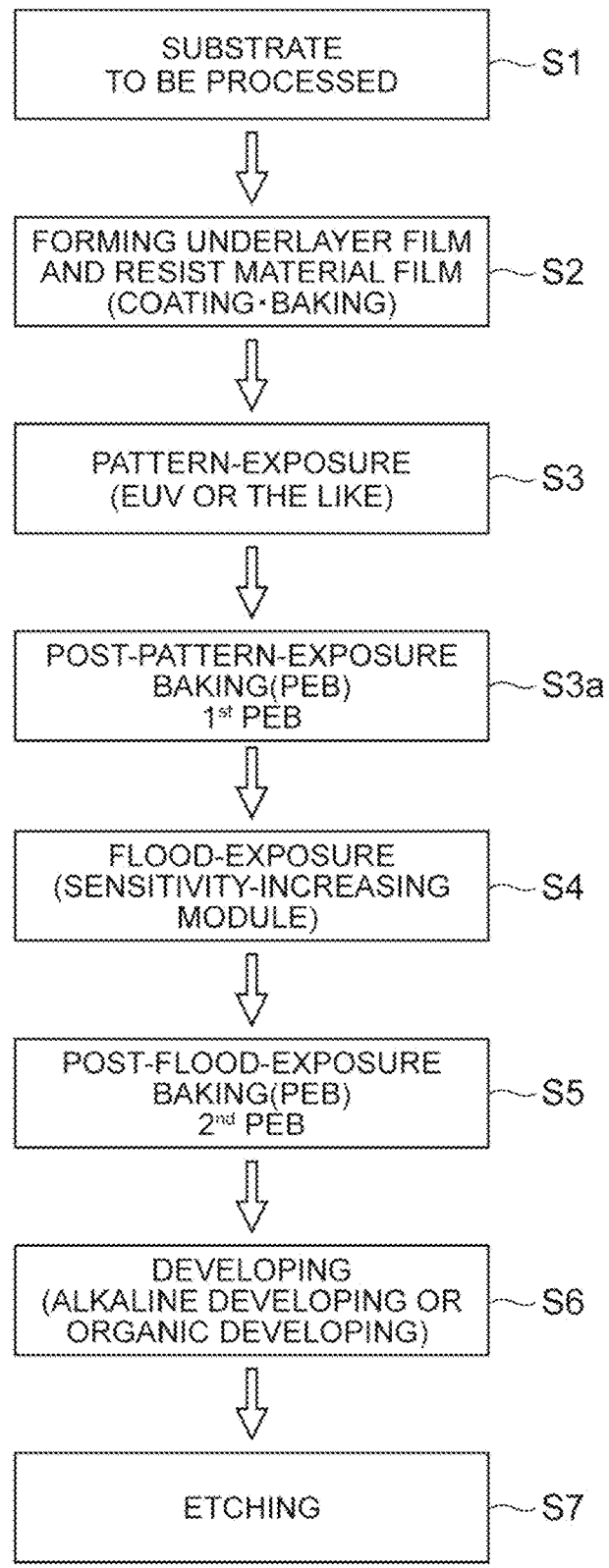
FIG. 5 is a flowchart showing another embodiment of the method for forming a pattern using a photosensitization chemical-amplification type resist material according to the present invention.

The method for forming a pattern of the present embodiment may further include a step of transporting the substrate from the exposure device performing the pattern-exposure step S3 into the exposure device performing the flood-exposure step S4, between the pattern-exposure step S3 and the following flood-exposure step S4. Furthermore, the flood-exposure may be performed in a coating/developing device connected in line or in a module corresponding to the interface with the exposure device. In a case where the component (2) or the (1') base component contains a ketal compound, an acetal compound, or an orthoester compound or contains a ketal compound group, an acetal compound group, or an orthoester compound group, the method for forming a pattern of the present embodiment may include a baking step S3a (referred to as post-pattern-exposure baking (PPEB or PEB) in some cases) between the pattern-exposure step S3 and the following flood-exposure step S4 (see FIG. 5). The heating temperature in the baking step is preferably 30° C. to 150° C., more preferably 50° C. to 120° C., and even more preferably 60° C. to 100° C. The heating time is preferably 5 seconds to 3 minutes, and more preferably 10 seconds to 60 seconds. Furthermore, the baking is preferably performed in a humidity-controlled environment. This is because the humidity affects the reaction rate in a case where a hydrolysis reaction is used as the deprotection reaction generating the photosensitizer. If the method for forming a pattern includes the baking step described above, it is possible to accelerate the generation of the photosensitizer resulting from the hydrolysis reaction into a carbonyl compound from the acetal compound, the orthoester compound, the ketal compound, or the like.

(Step S4: Flood-Exposure Step)

In the flood-exposure step S4, from a sensitivity-increasing module (referred to as an exposure device or a radiation irradiation module in some cases) having a projector lens (or a light source), non-ionizing radiation having a wavelength, which is longer than the wavelength of the non-ionizing radiation in the pattern-exposure and is greater than 200 nm and preferably greater than 250 nm, is radiated (flood-exposure) to the entire surface (entire surface encompassing pattern-exposed portions and portions not being pattern-exposed) of the resist material film having undergone the pattern-exposure step S3. The exposure amount in the flood-exposure may mean that the entire wafer surface is exposed at once, the portions of the wafer surface are exposed in combination, or the wafer surface is exposed over and over. As a light source for the flood-exposure, a general light source can be used. In addition to ultraviolet rays from a mercury lamp, a xenon lamp, or the like controlled to have a desired wavelength by being passed through a band pass filter or a cutoff filter, narrowband ultraviolet rays from a LED light source, a laser diode, a laser light source, or the like may also be used. In the flood-exposure, only the photosensitizer generated in a pattern-exposed portion within the resist material film absorbs the radiation. Therefore, in the flood-exposure, selective absorption of radiation occurs in the pattern-exposed portion. Accordingly, during the flood-exposure, an acid can be continuously generated only in the pattern-exposed portion, and hence the sensitivity can be greatly improved. In contrast, an acid is not generated in a pattern-unexposed portion, and accordingly, it is possible to improve the sensitivity while maintaining the chemical contrast in the resist material film. In the flood-exposure step, in order to suppress the occurrence of an acid generating reaction in a pattern-unexposed portion, radiation having a wavelength longer than the wavelength that the base component, the photoacid generator, and the photosensitizer precursor can absorb needs to be used for exposure. Considering this, the wavelength of the non-ionizing radiation in the flood-exposure is preferably equal to or greater than 280 nm, and more preferably equal to or greater than 320 nm. In a case where a photosensitizer which can absorb radiation with a longer wavelength is generated, the wavelength of the non-ionizing radiation may be equal to or greater than 350 nm. Here, in a case where the wavelength of the non-ionizing radiation is too long, the efficiency of the photosensitization reaction is reduced. Therefore, it is desired to avoid radiation having such a wavelength that the base component, the photoacid generator, and the photosensitizer precursor can absorb and to use non-ionizing radiation having a wavelength as short as possible such that the photosensitizer can absorb it. From this standpoint, specifically, the wavelength of the non-ionizing radiation is preferably 450 nm, and more preferably equal to or less than 400 nm.

The pattern-exposure step S3 and/or the flood-exposure step S4 may be performed by immersion lithography (immersion exposure) or dry lithography (dry exposure). The immersion lithography refers to exposure performed in a state where a liquid is interposed between the resist material film and the projector lens. In contrast, the dry lithography refers to exposure performed in a state where a gas is interposed between the resist material film and the projector lens, under reduced pressure, or in a vacuum.

The immersion lithography in the pattern-exposure step S3 and/or the flood-exposure step S4 may be performed in a state where a liquid having a refractive index of equal to or greater than 1.0 is interposed between the resist material film or the protective film formed in the film forming step S2 and the projector lens. The protective film is preferably an antireflection film or a film for improving reaction stability. Furthermore, the protective film is preferably a film which can prevent defects resulting from the liquid in the immersion exposure by preventing the permeation of the liquid and improving the water repellency of the film.

During the immersion lithography in the flood-exposure step S4, the liquid may absorb at least a portion of the wavelengths of the non-ionizing radiation directly absorbed by the photoacid generator (acid-photosensitizer generator) as the component (a) or (c) described above or the photoacid generating group (acid-photosensitizer generating group) as the group (d) or (f) described above. If such a liquid is used in the immersion lithography, it is possible to further inhibit the photoacid generator or the photoacid generating group remaining in the resist material film having undergone the pattern-exposure step S3 from directly generating an acid by being irradiated with the non-ionizing radiation in the flood-exposure step S4.

In a case where either or both of the pattern-exposure step S3 and the flood-exposure step S4 are performed by dry lithography, the dry lithography may be performed in any of an air atmosphere, an atmosphere with reduced pressure, and an inert atmosphere. However, the dry lithography is preferably performed in an atmosphere with reduced pressure or in an inert atmosphere containing nitrogen or argon, furthermore, preferably performed in an atmosphere with a basic compound concentration of equal to or less than 20 ppb, more preferably performed in an atmosphere with a basic compound concentration of equal to or less than 5 ppb, and particularly preferably performed in an atmosphere with a basic compound concentration of equal to or less than 1 ppb.

(Step S5: Baking Step)

In the baking step S5, the resist material film having undergone the flood-exposure step S4 is subjected to heating (hereinafter, referred to as post-flood-exposure baking (PFEB) or simply referred to as post-exposure baking (PEB) in some cases). In a case where the method for forming a pattern of the present embodiment includes the baking step S3a between the pattern-exposure and the flood-exposure, the baking step S3a and the baking step S5 are referred to as a 1st PEB step and a 2nd PEB step respectively in some cases (see FIG. 5). The heating can be performed in, for example, an air atmosphere or an atmosphere of an inert gas such as nitrogen or argon for 10 seconds to 300 seconds at 50° C. to 200° C. If the heating conditions are within the above range, the diffusion of an acid tends to be able to be controlled, and the processing rate of the semiconductor wafer tends to be able to be assured. In the baking step S5, due to the acid generated in the pattern-exposure step S3 and the flood-exposure step S4, a polarity changing reaction such as the deprotection reaction of the (1) base component or the (1') base component and a cross-linking reaction occur. The side walls of the resist are corrugated in some cases by being affected by the standing waves of the radiation in the resist material film. However, in the baking step S5, the corrugation can be suppressed due to the diffusion of the reactants.

(Step S6: Developing Step)

In the developing step S6, the resist material film having undergone the baking step S5 is brought into contact with a developer. Due to the reaction occurring in the resist material film in the baking step S5, the solubility in the developer is selectively changed in a pattern-exposed portion. The developing is performed by exploiting such a phenomenon, and hence a resist pattern is formed. The developer can be classified into a positive developer and a negative developer.

The positive developer is preferably an alkaline developer. The alkaline developer selectively dissolves a highly polar portion of the resist material film having undergone exposure. Specific examples of the alkaline developer include potassium hydroxide, sodium hydroxide, sodium carbonate, potassium carbonate, sodium phosphate, sodium silicate, ammonia, amines (ethanolamine and the like), and tetraalkylammonium hydroxide (TAAH). The alkaline developer is preferably TAAH. Examples of TAAH include tetramethylammonium hydroxide (TMAH), tetraethyl ammonium hydroxide, tetrapropylammonium hydroxide, tetrabutylammonium hydroxide, methyltriethylammonium hydroxide, trimethyl ethyl ammonium hydroxide, dimethyl diethyl ammonium hydroxide, trimethyl (2-hydroxyethyl) ammonium hydroxide (that is, choline), triethyl(2-hydroxyethyl)ammonium hydroxide, dimethyl di(2-hydroxyethyl) ammonium hydroxide, diethyl di(2-hydroxyethyl) ammonium hydroxide, methyl tri(2-hydroxyethyl) ammonium hydroxide, ethyl tri(2-hydroxyethyl)ammonium hydroxide, tetra(2-hydroxyethyl)ammonium hydroxide, and the like.

As the positive developer, a 2.38% by mass aqueous solution of tetramethylammonium hydroxide (TMAH) is widely used.

In an alkaline developing process, carboxylic acid or a hydroxyl group generated in the resist material film after exposure is ionized or dissolved in an alkaline developer, and by exploiting such a phenomenon, a pattern is formed. After the developing process, in order to remove the developer remaining on the substrate, a washing treatment using water, called rinsing, is performed.

The negative developer is preferably an organic developer. The organic developer selectively dissolves a lowly polar portion of the resist material film having undergone exposure. The organic developer is used for improving the resolution performance and the process window in hollow patterns such as holes or trenches (grooves). In this case, due to the difference in affinity for the solvent in the resist material film and the organic developer, dissolution contrast between a pattern-exposed portion and a pattern-unexposed portion is obtained. A highly polar portion exhibits low solubility in the organic developer and remains as a resist pattern. Specific examples of the organic developer include 2-octanone, 2-nonanone, 2-heptanone, 3-heptanone, 4-heptanone, 2-hexanone, 3-hexanone, diisobutyl ketone, methylcyclohexanone, acetophenone, methylacetophenone, propyl acetate, butyl acetate, isobutyl acetate, amyl acetate, butenyl acetate, isoamyl acetate, propyl formate, butyl formate, isobutyl formate, amyl formate, isoamyl formate, methyl valerate, methyl pentenoate, methyl crotonate, ethyl crotonate, methyl propionate, ethyl propionate, ethyl 3-ethoxypropionate, methyl lactate, ethyl lactate, propyl lactate, butyl lactate, isobutyl lactate, amyl lactate, isoamyl lactate, methyl 2-hydroxy isobutyrate, ethyl 2-hydroxy isobutyrate, methyl benzoate, ethyl benzoate, phenyl acetate, benzyl acetate, phenylmethyl acetate, benzyl formate, phenylethyl formate, 3-phenylmethyl propionate, benzyl propionate, phenylethyl acetate, 2-phenylethyl acetate, and the like.

In some cases, the resist pattern having undergone the developing step S6 (including the rinsing step) is subjected to heating (referred to as post-baking in some cases). By the post-baking, it is possible to gasify and remove the rinsing solution remaining after the rinsing treatment and to cure the resist pattern.

(Step S7)

In the step S7, the resist pattern having undergone the developing step S6 is used as a mask, and the substrate as a base is subjected to etching or ion injection, thereby forming a pattern. The etching may be dry etching performed in an atmosphere such as a plasma excitation atmosphere or may be wet etching in which the substrate is dipped into a chemical solution. After a pattern is formed on the substrate, the resist pattern is removed.

<Mechanism of Reaction>

Hereinafter, mechanisms of reactions caused in the lithography process according to the present embodiment will be described.

First, the typical lithography process for a conventional chemical-amplification type resist is as follows. The photoacid generator (PAG) in the resist material film is decomposed, subjected to pattern-exposure, and then generates an acid. Then, through an acid-catalyzed reaction accompanied by heating, the dissolution characteristics of the base component of the resist change. As a result, the solubility of the resist material film in a developer changes, and hence developing becomes possible.

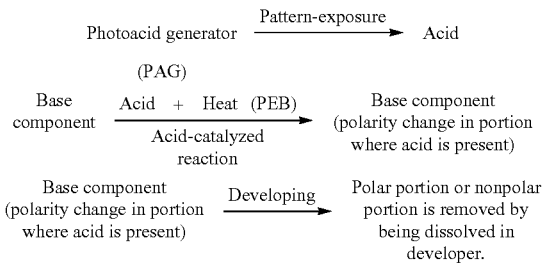

In contrast, in the lithography process according to the present embodiment, photosensitization is utilized for generating an acid, and accordingly, the amount of acid generated can be further increased, and the sensitivity can be greatly amplified than ever before.

The reaction system in the lithography process according to the present embodiment can be roughly classified into the following three systems. In order to further improving characteristics, these systems may be used in combination.

A first reaction system in the lithography process according to the present embodiment is a system applied in a case where the resist material contains the (a) acid-photosensitizer generator as the component (2) or contains the (1') base component having the (d) acid-photosensitizer generating group. In this system, both of an acid and a photosensitizer are generated from the component (a) at the time of exposure. Because the generated photosensitizer contains a carbonyl group or the like, the wavelength of the radiation to be absorbed shifts and becomes longer than the wavelength of radiation absorbed by the component (a). By performing flood-exposure by using non-ionizing radiation having a wavelength, which only the generated photosensitizer can absorb, and at which the component (a) can be decomposed through photosensitization, the amount of acid generated can be selectively amplified in a pattern-exposed portion. The acid-catalyzed reaction of the base component that occurs after the generation of an acid is the same as the reaction in the conventional lithography process.

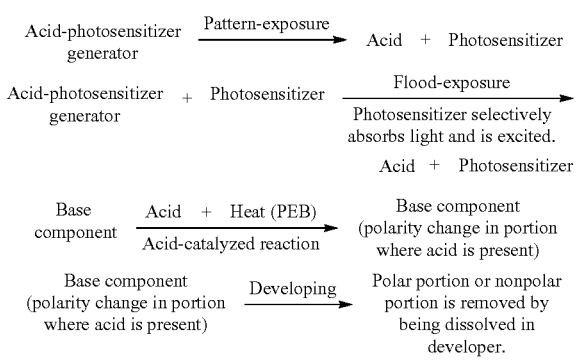

A second reaction system in the lithography process according to the present embodiment is a system applied in a case where the resist material contains the (b) photosensitizer precursor and the (c) photoacid generator as the component (2) or contains the (1') base component having the (e) precursor group and the (f) photoacid generating group, and the component (b) (or the group (e)) has an alcoholic hydroxyl group, in which a hydrogen atom is not substituted. In this system, an acid is generated from the component (c) (or the group (f)) at the time of pattern-exposure, and a photosensitizer is generated from the component (b) (or the group (e)). In a case where the component (b) (or the group (e)) has an alcoholic hydroxyl group, in which a hydrogen atom is not substituted, the alcoholic hydroxyl group and a carbon atom bonded to the alcoholic hydroxyl group become a carbonyl group contributing to the photosensitization action. In this reaction, a photosensitizer is generated through an intermediate having a short life such as a radical or a cation, and the reaction can be caused at normal temperature within a sufficiently short time such as several seconds. Because the generated photosensitizer contains a carbonyl group or the like, the wavelength of the radiation to be absorbed shifts and becomes longer than the wavelength of radiation absorbed by the components (b) and (c) and the groups (e) and (f). By performing flood-exposure by using non-ionizing radiation having a wavelength, which only the generated photosensitizer can absorb, and at which the component (c) or the group (f) can be decomposed through photosensitization, the amount of acid generated can be selectively amplified in a pattern-exposed portion. The acid-catalyzed reaction of the base component that occurs after the generation of an acid is the same as the reaction in the conventional lithography process.

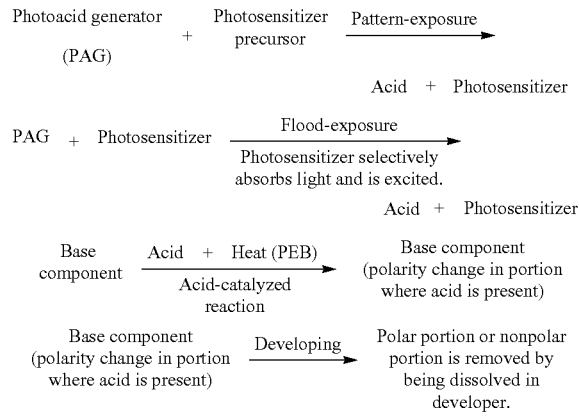

A third reaction system in the lithography process according to the present embodiment is a system applied in a case where the resist material contains the (b) photosensitizer precursor and the (c) photoacid generator as the component (2) or contains the (1') base component having the (e) precursor group and the (f) photoacid generating group, and the component (b) (or the group (e)) has an alcoholic hydroxyl group, in which a hydrogen atom is substituted. In this system, first, an acid is generated from the component (c) (or the group (f)) at the time of pattern-exposure, the generated acid functions as a catalyst, and a photosensitizer is generated from the component (b) (or the group (e)). Examples of the component (b) having an alcoholic hydroxyl group, in which a hydrogen atom is substituted, include an acetal compound, a ketal compound, an orthoester compound, and the like. Through the acid-catalyzed reaction, the acetal compound and the ketal compound generate aldehyde and ketone respectively as a photosensitizer. Furthermore, through the acid-catalyzed reaction, the orthoester compound generates a carboxylic acid ester as a photosensitizer. Through a deprotection reaction of carboxylic acid protected with OBO, carboxylic acid as a photosensitizer may be generated. In this reaction system, because the acid generated through the pattern-exposure functions as a catalyst, and hence a photosensitizer is generated, it is possible to control the photosensitizer generation reaction by inhibiting the deactivation of the acid as a catalyst. Because the generated photosensitizer becomes a carbonyl group-containing compound such as aldehyde, ketone, a carboxylic acid ester, or carboxylic acid, the wavelength of radiation to be absorbed shifts and becomes longer than the wavelength of radiation absorbed by the components (b) and (c) and the groups (e) and (f). By performing flood-exposure by using non-ionizing radiation having a wavelength, which only the generated photosensitizer can absorb, and at which the component (c) or the group (f) can be decomposed through photosensitization, the amount of acid generated can be selectively increased in a pattern-exposed portion. The acid-catalyzed reaction of the base component that occurs after the generation of an acid is the same as the reaction in the conventional lithography process.

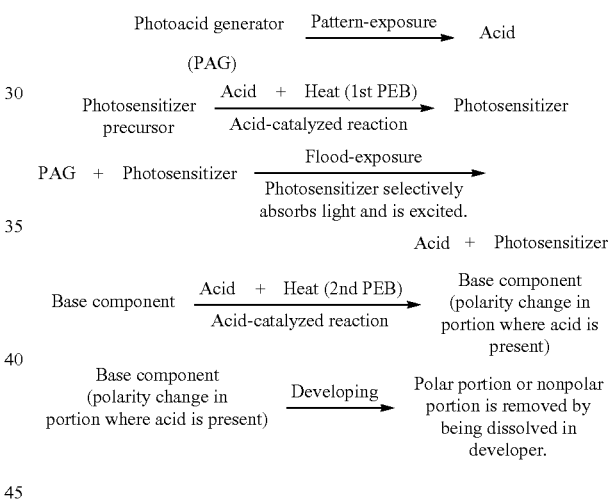

Next, the reaction in the lithography process according to the present embodiment will be described for each step. In the following section, the reaction will be described mainly based on the second reaction system, and if necessary, the reaction in the first and third reaction systems will be additionally described.

(Reaction in Pattern-Exposure Step S3)

In the pattern-exposure step S3, the resist material film is irradiated with ionizing radiation or non-ionizing radiation having a wavelength of equal to or less than 400 nm, preferably equal to or less than 250 nm, and more preferably equal to or less than 200 nm (pattern-exposure). Hereinafter, an example of a reaction assumed to occur in a case where the resist material film is irradiated with ionizing radiation will be described mainly based on the second reaction system. Here, the reaction assumed to occur in the aforementioned case is not limited to the reaction described below.

In the pattern-exposure step S3, regarding the component (c) or the group (f), the following reaction (first acid generation mechanism) occurs. Although the following reaction will be described based on the component (c) for example, the first acid generation mechanism also operates in the same manner even when the group (f) is used.

[Chemical Formula 73]

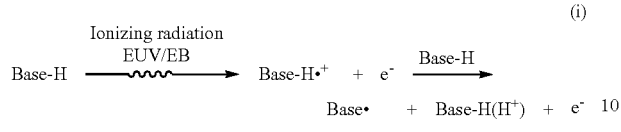
(i)

In the above Formula (i), . represents a free radical. In the above reaction, by being irradiated with ionizing radiation such as extreme ultraviolet ray (EUV)/electron beam (EB), the base component (Base) is ionized and generates an electron.

[Chemical Formula 74]

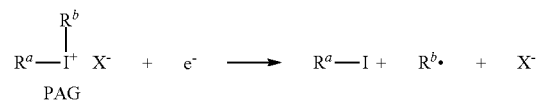
(ii)

In the above Formula (ii), $R^aR^bI^+X^-$ is an iodonium salt compound as an example of the component (c) (PAG). $X^-$ is an acid anion, and each of $R^a$ and $R^b$ has the same definition as each of $R^3$ and $R^4$ in Formula (I). In the above reaction, the electron generated as in Formula (i) is captured by the component (c) or the group (f), and the component (c) or the group (f) is decomposed as shown in the above formula. As a result, the acid anion $X^-$ is generated.

[Chemical Formula 75]

(iii)

In the above reaction, a proton adduct of the base component generated as in Formula (i) reacts with the acid anion $X^-$ generated as in Formula (ii) or the like, and hence an acid is generated. The above mechanism is the first acid generation mechanism in the pattern-exposure step S3.

[Chemical Formula 76]

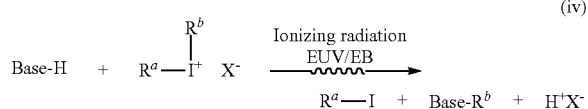
(iv)

If the acid generation mechanism in the pattern-exposure step S3 is summarized into one formula, the above formula (iv) can be obtained.

In contrast, in the pattern-exposure step S3, regarding the component (b) or the group (e), for example, the following reaction (first photosensitizer generation mechanism) occurs. However, the reaction described herein is merely a partial reaction and does not show the entire reaction mechanism. Although the following reaction will be described based on the component (b) for example, the first photosensitizer generation mechanism also operates in the same manner even when the group (e) is used. Furthermore, in the following reaction, an example of a reaction of the component (b) in the second reaction system, that is, in case that the component (b) is an alcohol compound and a hydrogen atom in the hydroxyl group is not substituted, will be described.

[Chemical Formula 77]

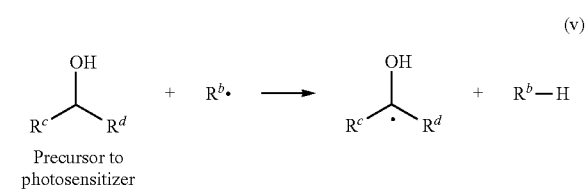
(v)

In the above Formula (v), $R^cR^dCH(OH)$ is a secondary alcohol compound as an example of the component (b) (Precursor to photosensitizer). Each of $R^c$ and $R^d$ has the same definition as each of $R^8$ to $R^{10}$ and the like in Formula the (VI). In the above reaction, $R^b$. having a free radical generated in Formula (ii) or the like reacts with the secondary alcohol compound. As a result, hydrogen is withdrawn from the secondary alcohol compound, and a secondary alcohol compound having a carbon radical on a root base of a hydroxyl group is generated.

[Chemical Formula 78]

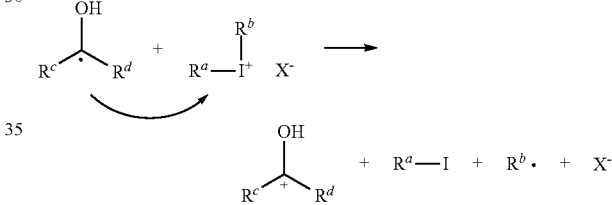
(vi)

In the above reaction, the carbon radical of the secondary alcohol compound delivers an electron to the component (c) or the base component to which the group (f) are bonded, such that these are decomposed. $R^b$. having a free radical generated by the decomposition is then supplied to the reaction shown in Formula (v), and the reactions of Formulae (v) and (vi) proceed in series. The serial reaction mechanism of Formulae (v) and (vi) is also referred to as a radical chain-type acid generation mechanism.

[Chemical Formula 79]

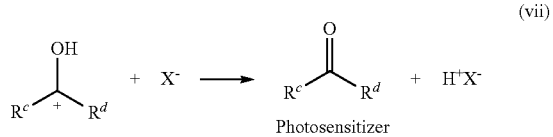
(vii)

The cation of the secondary alcohol compound generated in Formula (vi) reacts with the acid anion $X^-$ generated in Formula (vi) or the like, and as a result, a ketone compound as a photosensitizer and an acid are generated. The generated ketone compound functions as a photosensitizer in the flood-exposure step S4. The above mechanism is the first photosensitizer generation mechanism in the pattern-exposure step S3.

[Chemical Formula 80]

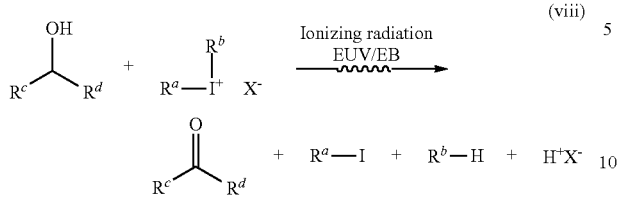 (viii)

If the photosensitizer generation mechanism of the alcohol compound in the pattern-exposure step S3 is summarized into one formula, the above Formula (viii) can be obtained.

Next, an example of a reaction will be described which occurs in a case where the resist material film is irradiated with non-ionizing radiation having a wavelength of equal to or less than 400 nm, preferably equal to or less than 250 nm, and more preferably equal to or less than 200 nm.

In the pattern-exposure step S3, regarding the component (c) or the group (f), the following reaction (second acid generation mechanism) additionally occurs. Although the following reaction will be described based on the component (c) for example, the second acid generation mechanism also operates in the same manner even when the group (f) is used.

[Chemical Formula 81]

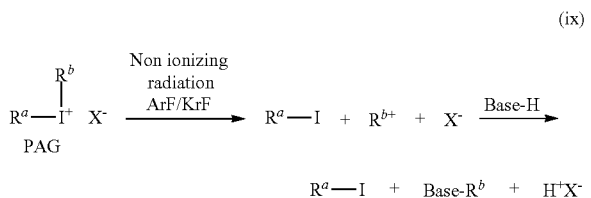 (ix)

In the above reaction, by the irradiation of an iodonium salt compound as an example of the component (c) (PAG) with non-ionizing radiation such as ArF/KrF, the photoacid generator is directly excited and decomposed, and an acid is generated. The above mechanism is the second acid generation mechanism in the pattern-exposure step S3.

In contrast, in the pattern-exposure step S3, regarding the component (b) or the group (e), the following reaction (photosensitizer generation mechanism) occurs. Although the following reaction will be described based on the component (b) for example, the second photosensitizer generation mechanism also operates in the same manner even when the group (e) is used.

[Chemical Formula 82]

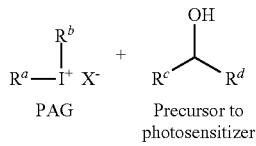

Precursor to photosensitizer

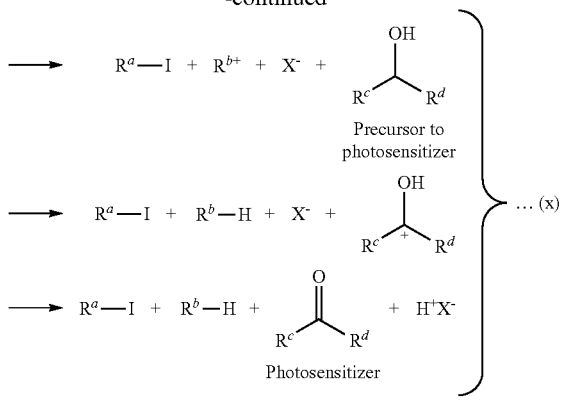 ...(x)

In the above reaction, due to the $R^{b+}$ cation generated from an iodonium salt compound, hydrogen is withdrawn from a carbon atom on the root base of a hydroxyl group of the secondary alcohol compound as the component (b), and a carbocation of the secondary alcohol compound is generated. The acid anion $X^-$ and a hydrogen ion from the carbocation form a pair and generate an acid, and a ketone compound as a photosensitizer is generated. The above mechanism is an example of the second photosensitizer generation mechanism in the pattern-exposure step S3. From an alcohol compound having an acetal compound group or a ketal compound group, a ketone compound (carbonyl compound) functioning as a photosensitizer can be generated in the same manner through a hydrolysis deprotection reaction or the like by a photogenerated acid catalyst.

In a case where the component (b) in a third reaction system, that is, the component (b) is an acetal compound or a ketal compound, the photosensitizer generation mechanism is partially different from the first photosensitizer generation mechanism. First, by the first and second photoacid generation mechanisms, an acid is generated. The generated acid acts on the acetal compound or the ketal compound, and hence a ketone compound as a photosensitizer is generated. That is, the acid generated by the first and second photoacid generation mechanisms functions a catalyst in a reaction for generating the ketone compound from the acetal compound or the ketal compound. The generated ketone compound functions as a photosensitizer in the flood-exposure step S4. The above mechanism is the third photosensitizer generation mechanism in the pattern-exposure step S3.

The third photosensitizer generation mechanism in the pattern-exposure step S3 in the third reaction system will be more specifically described. First, as in the second system described above, an acid is generated as shown in the following Formula (xxvii).

[Chemical Formula 83]

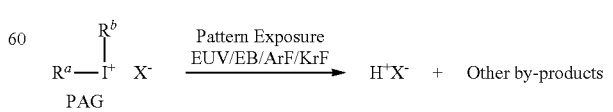 (xxvii)

The acid generated by pattern-exposure functions a catalyst, hence the structure of the component (b) or the group (e) changes, and a photosensitizer is generated as below. The structure changing reaction (deprotection reaction) can be accelerated by performing baking after the pattern-exposure before the flood-exposure. Furthermore, if the baking is performed after the reaction rate is reduced by increasing the activation energy of the structure changing reaction, and the acid in a pattern-unexposed portion is captured (neutralized) by a scavenger, the contrast of the latent image of the acid in the resist material film can be further enhanced. In addition, the increase of the activation energy of the deprotection reaction (addition of a protecting group which is not easily eliminated) also results in the improvement of the storage stability of the photochemical-amplification type resist material at normal temperature.

In the third reaction system, for example, a carbonyl group is substituted (protected) with a protecting group in the component (b) or the group (e). The acid generated through pattern-exposure functions a catalyst, and as a result, a deprotection reaction occurs, and a carbonyl compound as a photosensitizer is generated. The wavelength of the radiation to be absorbed by the photosensitizer generated by the reaction shifts and becomes longer than the wavelength of the radiation absorbed by the components (b) and (c) and the groups (e) and (f). By performing flood-exposure using non-ionizing radiation having a wavelength that only the generated photosensitizer can absorb, the photosensitizer can be selectively excited in a pattern-exposed portion.

Examples of the photosensitizer precursor that can be formed by protecting a carbonyl compound include an acetal compound, a ketal compound, an orthoester compound, and the like.

When a ketal compound is used as the photosensitizer precursor, a photosensitizer is generated by a deprotection reaction (acid-catalyzed hydrolysis reaction) as shown in the following Formula (xviii).

[Chemical Formula 84]

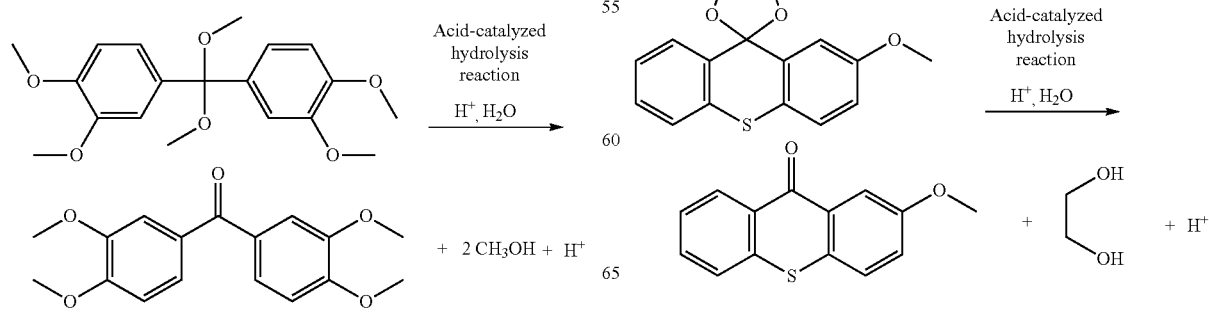

(xviii)

More specifically, by the following acid-catalyzed hydrolysis reaction, the ketal compound undergoes structural change and becomes a ketone compound.

[Chemical Formula 85]

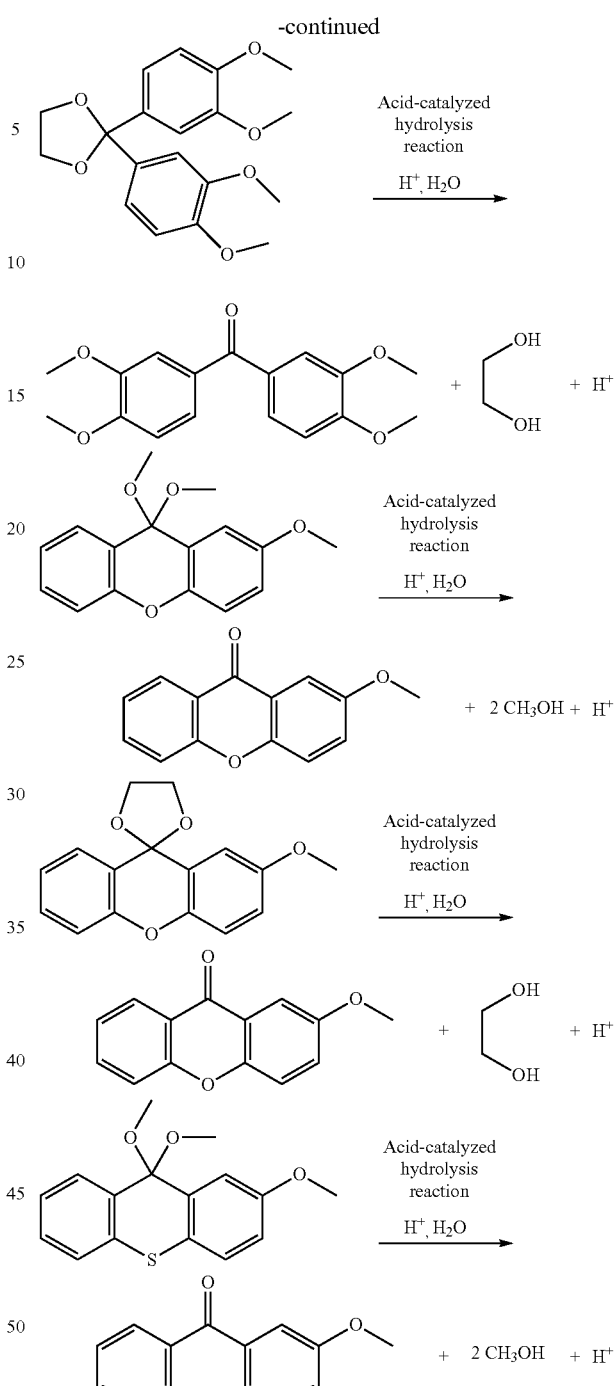

When an acetal compound is used as the photosensitizer precursor, a photosensitizer is generated by a deprotection reaction (acid-catalyzed hydrolysis reaction) as shown in the following Formula (xix).

[Chemical Formula 86]

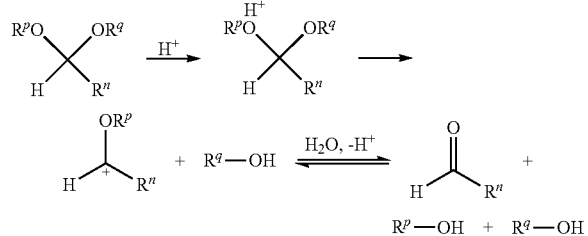

(xix)

More specifically, by the following acid-catalyzed hydrolysis reaction, the acetal compound undergoes structural change and becomes an aldehyde compound.

[Chemical Formula 87]

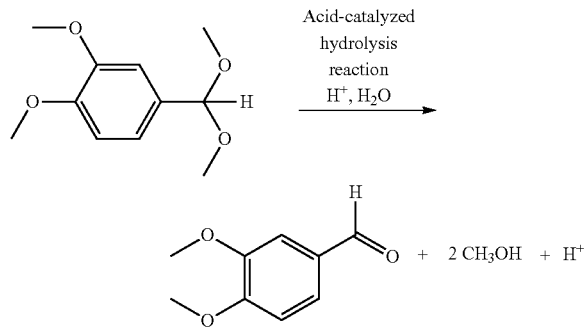

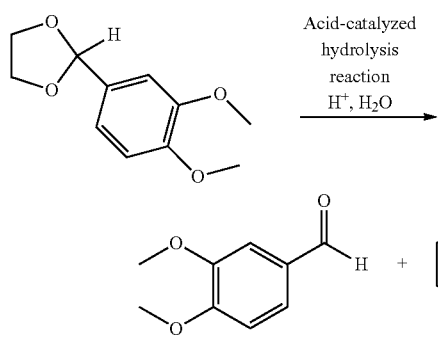

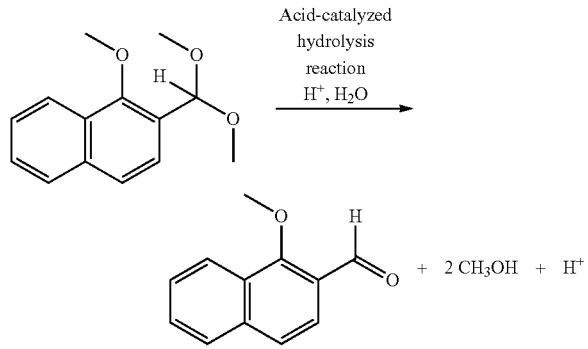

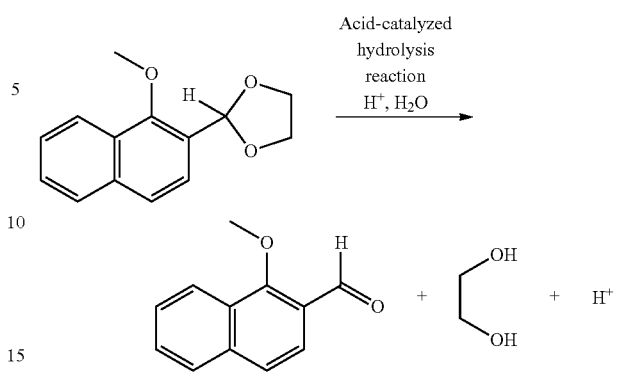

When an orthoester compound is used as the photosensitizer precursor, a photosensitizer is generated by a deprotection reaction (acid-catalyzed hydrolysis reaction) as shown in the following Formula (xx). The orthoester compound is decomposed into a carboxylic acid ester compound through the deprotection reaction.

[Chemical Formula 88]

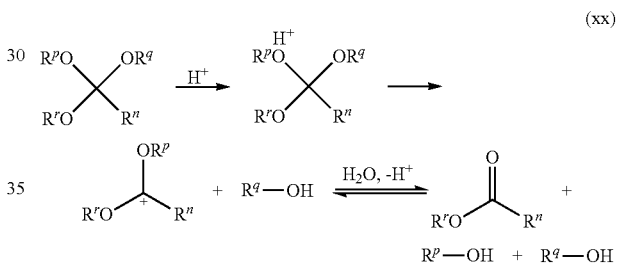

(xx)

More specifically, by the following acid-catalyzed hydrolysis reaction, the orthoester compound undergoes structural change and becomes a carboxylic acid ester compound.

[Chemical Formula 89]

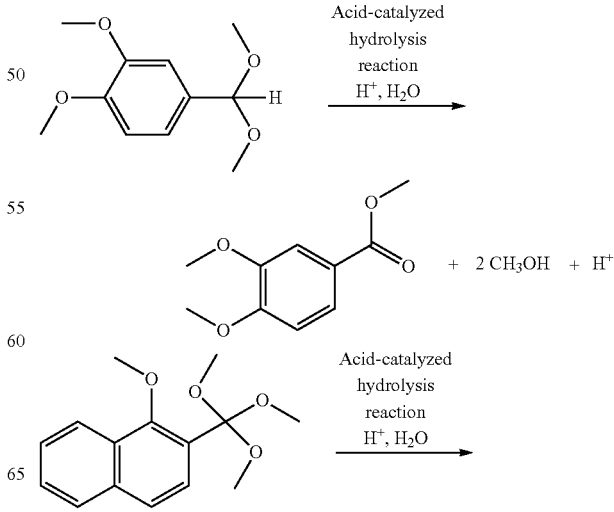

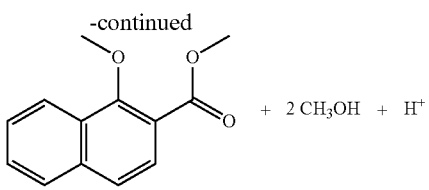

Among orthoester compounds, an OBO ester compound in which carboxylic acid is protected with OBO (4-methyl-2,6,7-trioxabicyclo[2.2.2.2]octan-1-yl) generates carboxylic acid as shown in the following Formula (xxi) through a deprotection reaction. Accordingly, the photosensitizer precursor obtained by the protection with OBO can generate a photosensitizer having a carboxyl group. If the photosensitizer is used, the polarity increase of the resist material film is caused simultaneously with the generation of the photosensitizer, and hence the dissolution contrast of the resist material film can be improved.

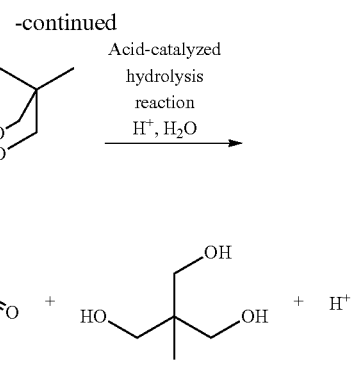

In the first reaction system, a photosensitizer is generated by the following reaction. In the first reaction system, the component (a) generating an acid and a photosensitizer through pattern-exposure generates both of an acid and a

[Chemical Formula 90]

(xxi)

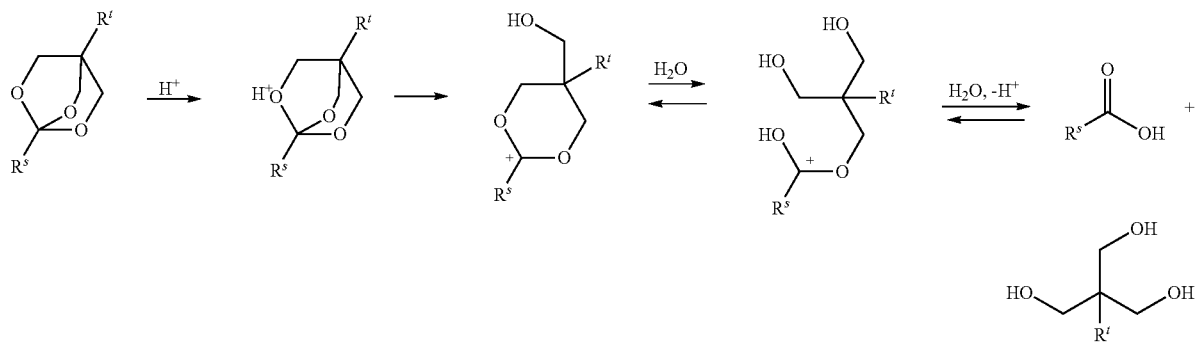

More specifically, by the following acid-catalyzed hydrolysis reaction, the OBO ester compound undergoes structural change and becomes carboxylic acid.

photosensitizer at the time of pattern-exposure. The following is an example of the reaction (sixth acid generation mechanism).

[Chemical Formula 91]

[Chemical Formula 92]

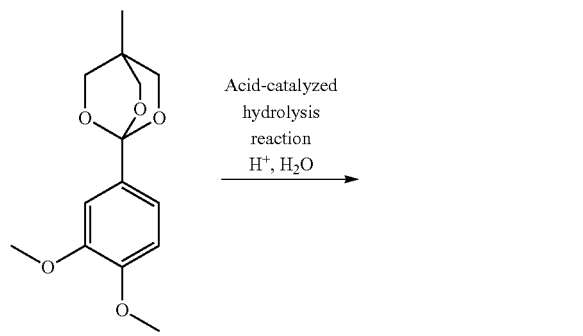

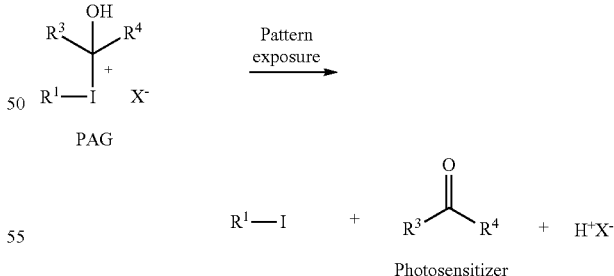

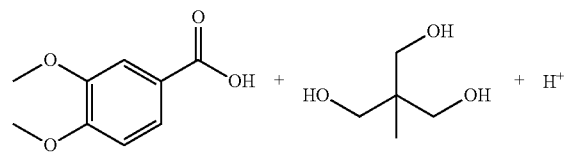

In the pattern-exposure step S3, regarding the component (a) and the base component bonded to which the group (d) are bonded, both of the acid generation mechanism and the photosensitizer generation mechanism operate.

In the first embodiment, the component (2) contains only the component (a), contains any two components, or contains all of the components (a) to (c). Accordingly, during the pattern-exposure step S3 in the first embodiment, both of the acid generation mechanism and the photosensitizer generagroups among the groups (d) to (f), or contains all of the groups (d) to (f). Accordingly, during the pattern-exposure step S3 in the second embodiment, both of the acid generation mechanism and the photosensitizer generation mechanism operate.

(Reaction in Flood-Exposure Step S4)

In the flood-exposure step S4, the resist material film is irradiated with non-ionizing radiation having a wavelength which is longer than the wavelength of the non-ionizing radiation in the pattern-exposure and is greater than 200 nm and preferably greater than 250 nm (flood-exposure). Although the photosensitizer precursor needs to absorb sufficiently little the energy of the pattern-exposure at the time of pattern-exposure, the photosensitizer precursor undergoes the change of chemical structure due to the energy of the pattern-exposure and generates a photosensitizer. Due to the change of chemical structure, the light absorption spectrum is changed, and hence the photosensitizer absorbs long wavelength in the ultraviolet region. Examples of the chemical change include the change of an alcohol compound (or a ketal compound) into a ketone compound. Therefore, for example, it is desired to select a material which causes a great light absorption shift when a structural change from an alcohol to a ketone is caused. Hereinafter, the reaction in the flood-exposure step S4 will be described. Although the following reaction will be described based on the components (b) and (c) for example, the same reaction also occurs even when the component (a) and the groups (d) to (f) are used. That is, regarding the amplification of the amount of acid generated by the photosensitization commonly occurring in the first to third reaction systems, first, the second and third reaction systems will be mainly described for example. These reactions consist of the excitation of the photosensitizer through flood-exposure and the generation of an acid through the decomposition of the photoacid generator caused by the excited photosensitizer. The reaction mechanism in which the excited photosensitizer decomposes the photoacid generator is roughly classified into a mechanism operating mainly by electron transfer and a mechanism operating by excitation transfer. Because theses sensitization reactions occur in series, the amount of acid generated can be greatly amplified through flood-exposure, and hence the sensitivity of the resist is greatly improved.

In Formula (xi), $R^cR^dC=O$ is a ketone compound generated in the pattern-exposure step S3, and $R^aR^bI^+X^-$ is an iodonium salt compound as an example of the component (c) (PAG) partially remaining even after the pattern-exposure step S3. Furthermore, in Formula (xi), * represents an excitation state, *(S) is a singlet-excited state, and *(T) is a triplet-excited state. In the above reaction, the ketone compound as a photosensitizer generated in the pattern-exposure step S3 is excited by being irradiated with non-ionizing radiation. The excited ketone compound is in a singlet-excited state first, but a portion thereof becomes in a triplet-excited state through intersystem crossing.

[Chemical Formula 94]

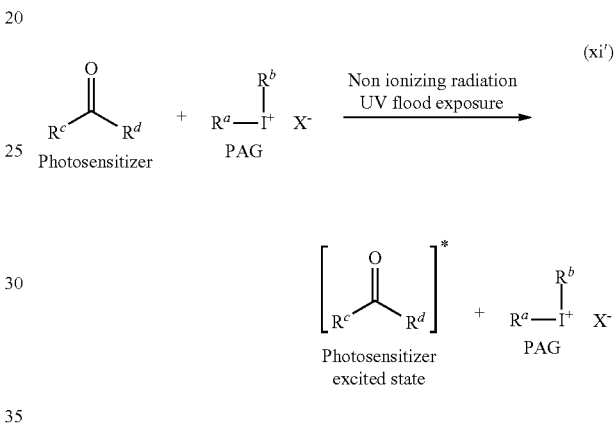

The reaction of the above Formula (xi) can also be described as Formula (xi') without specifying the singlet-excited state and the triplet-excited state.

In the flood-exposure step S4, due to the excited photosensitizer, the component (c) (PAG) is indirectly decomposed, and hence an acid is generated. Examples of the

[Chemical Formula 93]

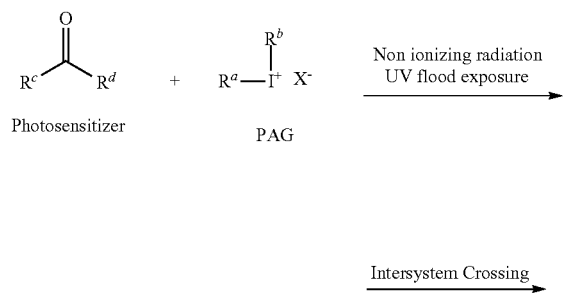

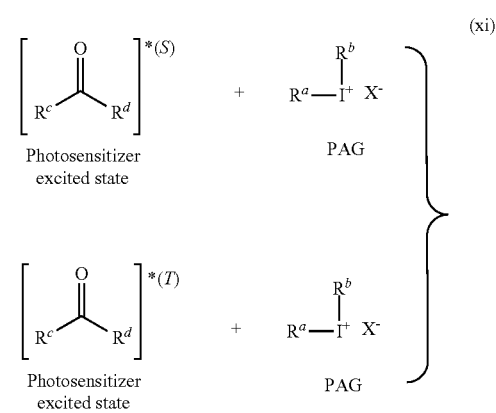

(S): Excitation to Singlet State,
(T): Excitation to Triplet State aforementioned acid generation mechanism in the flood-exposure step S4 mainly include a third acid generation mechanism (electron transfer sensitization-type acid generation mechanism), a fourth acid generation mechanism (energy transfer sensitization-type acid generation mechanism), and a fifth acid generation mechanism (hydrogen withdrawal-type acid generation mechanism).

enough for causing electron transfer; and hence the free energy of the electron transfer reaction for photosensitization needs to become negative such that the reaction spontaneously proceeds. Presumably, in order to reduce the oxidation potential of the photosensitizer, it is desired to use a compound in which conjugation is extended in the portion of ketone and to introduce a group having high electron-donating properties.

[Chemical Formula 96]

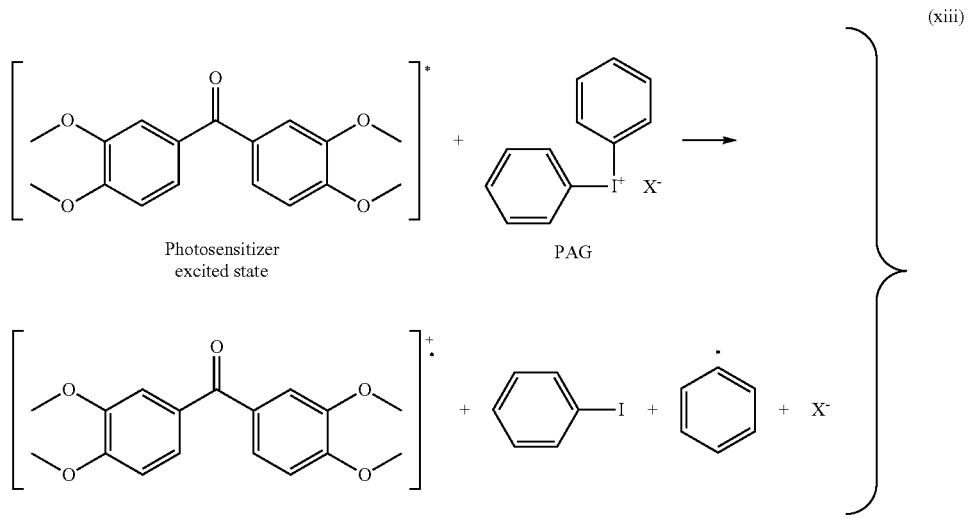

[Chemical Formula 95]

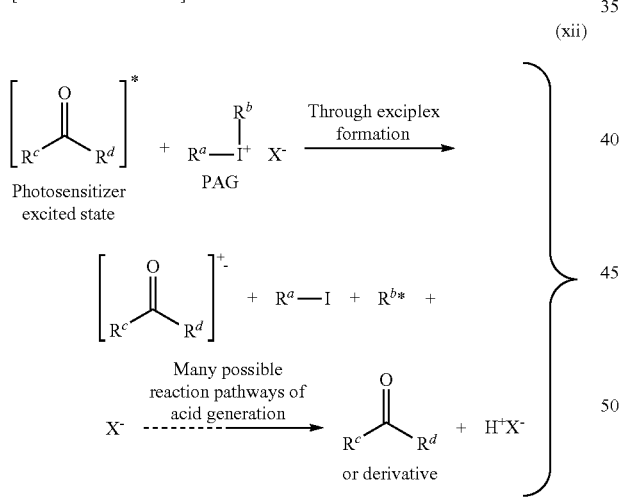

Formula (xii) is a reaction formula showing the third acid generation mechanism (electron transfer sensitization-type acid generation mechanism). In the above reaction, from the excited ketone compound, an electron is transferred to the iodonium salt compound (PAG) remaining even after the pattern-exposure step S3, hence the iodonium salt compound is decomposed, and as a result, a photosensitizer and an acid are generated. In order to realize the third acid generation mechanism by electron transfer, the oxidation potential of the photosensitizer needs to be sufficiently low; the reduction potential of PAG needs to be sufficiently high; the energy level of the flood-exposure needs to be high The above Formula (xiii) shows a specific example of electron transfer occurring in the third acid generation mechanism.

Through electron transfer, a cation radical of the photosensitizer is generated. The product of Formula (xiii) generates an acid by causing the following reaction. In a case where the cation radical of the photosensitizer reacts with a phenyl radical, the third acid generation mechanism (electron transfer sensitization-type acid generation mechanism) is as follows.

[Chemical Formula 97]

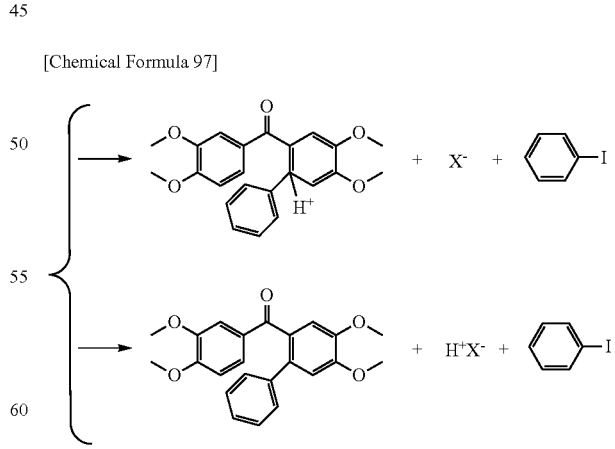

In a case where the cation radical of the photosensitizer reacts with a polymer (POLY-H), the third acid generation mechanism (electron transfer sensitization-type acid generation mechanism) is as follows.

[Chemical Formula 98]

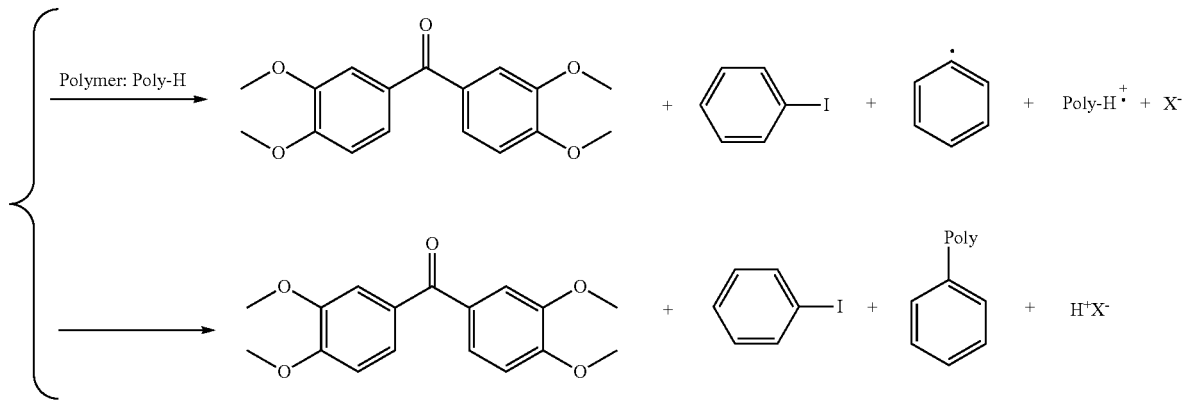

[Chemical Formula 99]

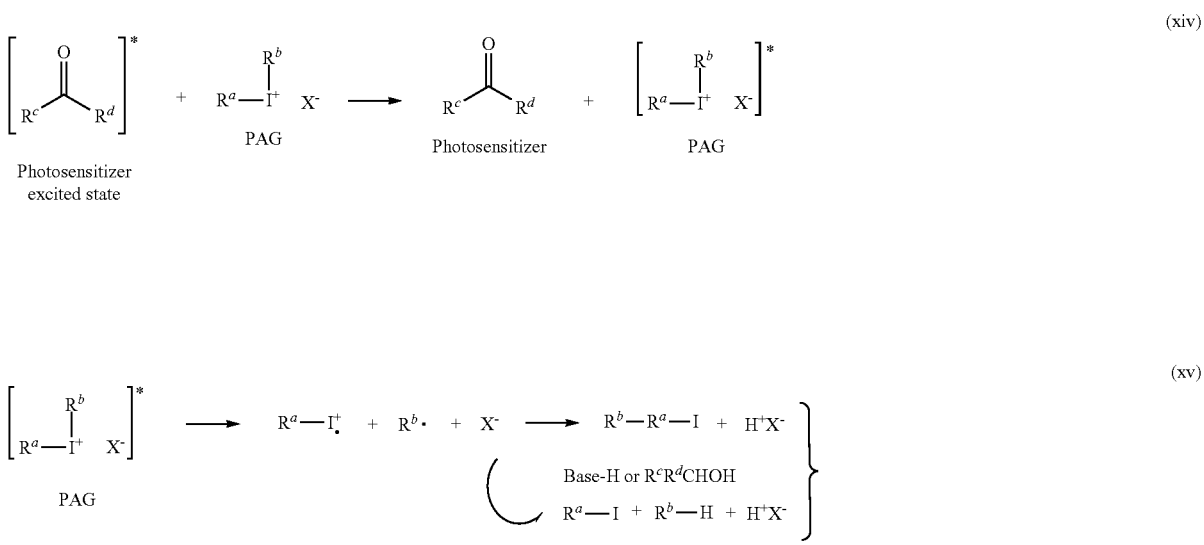

Each of Formulae (xiv) and (xv) is a reaction formula showing the fourth acid generation mechanism (energy transfer sensitization-type acid generation mechanism). In Formula (xiv), the excitation state shifts from the ketone compound to the iodonium salt compound (triplet-excited state), and a photosensitizer is generated. In Formula (xv), the excited iodonium salt compound is decomposed, and hence an acid is generated. In a case where triplet sensitization reaction from the photosensitizer to PAG is used, the photosensitizer needs to be able to be excited to be in a singlet-excited state at the wavelength of the flood-exposure, and the energy level of the triplet-excited state of the photosensitizer needs to be higher than the energy level of the triplet-excited state of PAG.

[Chemical Formula 100]

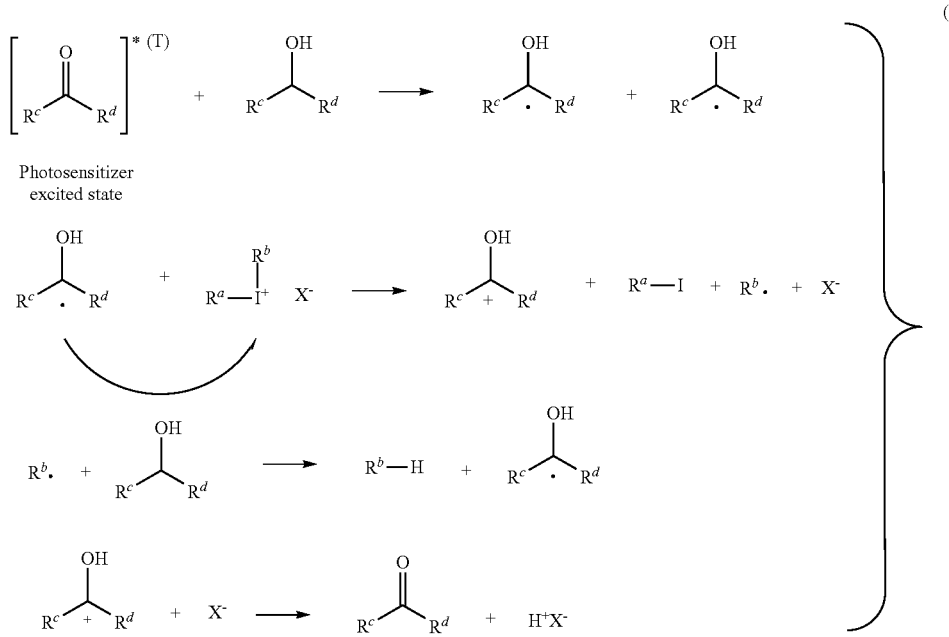

Formula (xvi) is a reaction formula showing the fifth acid generation mechanism (hydrogen withdrawal-type acid generation mechanism) that operates in a case where the component (b) is a photosensitizer precursor having a hydroxyl group. In the above reaction, the excited ketone compound withdraws hydrogen of the secondary alcohol compound remaining even after the pattern-exposure step S3, a free radical is generated. From the generated radical, an electron is transferred to the iodonium salt compound, and as a result, a photosensitizer and an acid are generated.

In the first reaction system, at the time of flood-exposure, exposure is performed using radiation having a wavelength that is mainly absorbed not by the photoacid generator (PAG) as the component (c) but by the photosensitizer. As a result, the acid and the photosensitizer are additionally generated only in the portion where the photosensitizer is generated (seventh acid generation mechanism). Although an iodonium salt is used as the photoacid generator (PAG) in the following formula, the acid is also generated in the same manner even in a case where other photoacid generators such as a sulfonium salt are used.

[Chemical Formula 101]

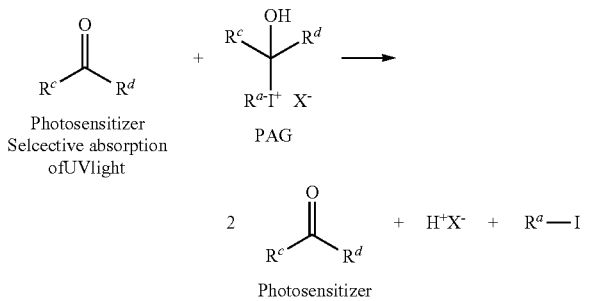

By including the pattern-exposure step S3 and the flood-exposure step S4, the method for forming a pattern of the present embodiment can greatly increase the amount of acid generated after exposure only in a pattern-exposed portion.

FIG. 1 is graph showing the absorbances of a pattern-exposed portion and an unexposed portion of the resist material film at the time of flood-exposure. In a portion not being subjected to pattern-exposure (pattern-unexposed portion) within the resist material film, the absorption of ultraviolet rays having a relatively short wavelength is caused while the absorption of ultraviolet rays having a relatively long wavelength is not caused. In contrast, in a portion subjected to pattern-exposure (pattern-exposed portion) within the resist material film, an acid and a photosensitizer are generated as described above. The generated photosensitizer is a substance absorbing non-ionizing radiation having a wavelength of greater than 200 nm, and absorbs ultraviolet rays having a relatively long wavelength. During the flood-exposure, the entire surface of the resist material film is irradiated with radiation without using a mask unlike in the pattern-exposure, but a pattern-unexposed portion absorbs little the second radiation used in the flood-exposure step S4. Therefore, in the flood-exposure step S4, mainly the third to fifth and seventh acid generation mechanisms operate in a pattern-exposed portion. Accordingly, an acid can be continuously generated only in a pattern-exposed portion during the flood-exposure, and it is possible to improve the sensitivity while maintaining the lithography characteristics.

Figure 2A:
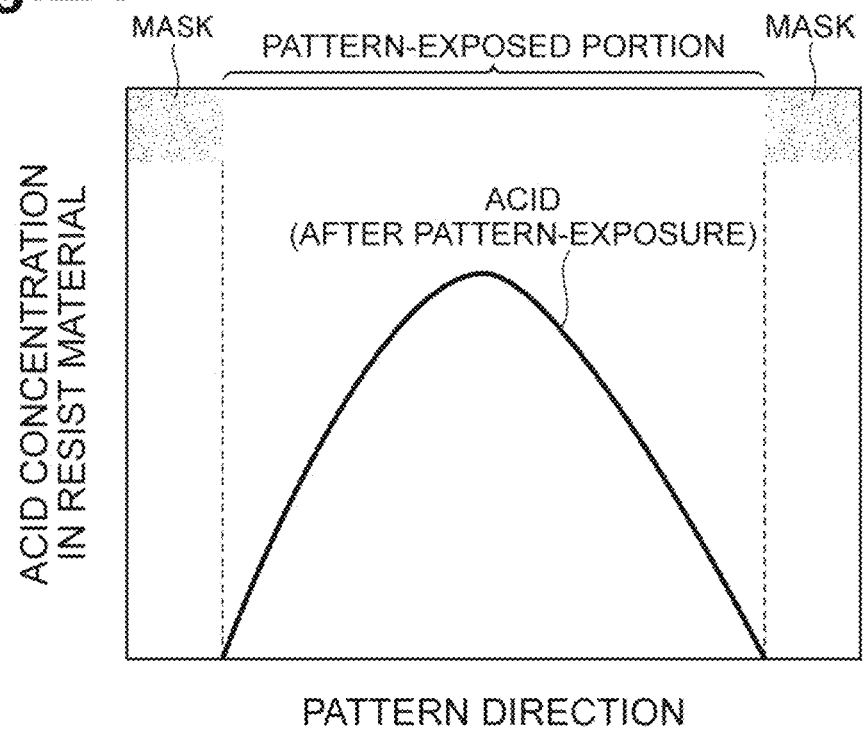
FIG. 2A is a schematic view graphically showing an acid concentration distribution in a conventional chemical-amplification type resist material.
Figure 2B:
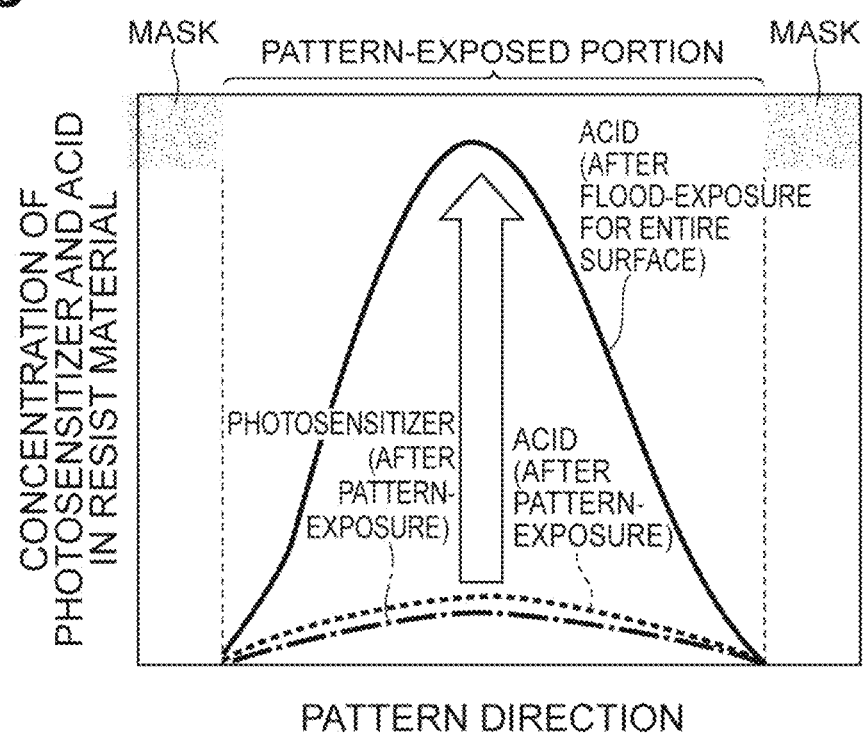
FIG. 2B is a schematic view graphically showing a photosensitizer concentration distribution and an acid concentration distribution in a photosensitization chemical-amplification type resist material according to an embodiment of the present invention.

FIG. 2A is a graph showing an acid concentration distribution in a conventional chemical-amplification type resist material. In a case where only pattern-exposure is performed using extreme ultraviolet rays (EUV) or the like as shown in FIG. 7, an acid cannot be sufficiently generated, and hence the sensitivity is reduced. If the exposure amount is increased to improve the sensitivity, the latent image of the resist pattern deteriorates (deterioration of lithography characteristics), and accordingly, it is difficult to achieve both of the sensitivity and the lithography characteristics. FIG. 2B is a graph showing a photosensitizer concentration distribution and an acid concentration distribution in the photosensitization chemical-amplification type resist material according to the present embodiment. During the pattern-exposure, the latent image of the resist pattern becomes excellent, but an acid is not sufficiently generated. However, after the flood-exposure, the amount of acid can be increased only in a pattern-exposed portion due to the photosensitizer generated by the pattern-exposure, and it is possible to improve the sensitivity in a small exposure amount while maintaining the excellent latent image of the resist pattern. Because the photosensitizer-induced acid generation mechanism at the time of flood-exposure operates at room temperature, blurring of the latent image at the time of generating an acid can be suppressed, and it is possible to greatly increase the sensitivity while maintaining resolution.

Figure 3A:
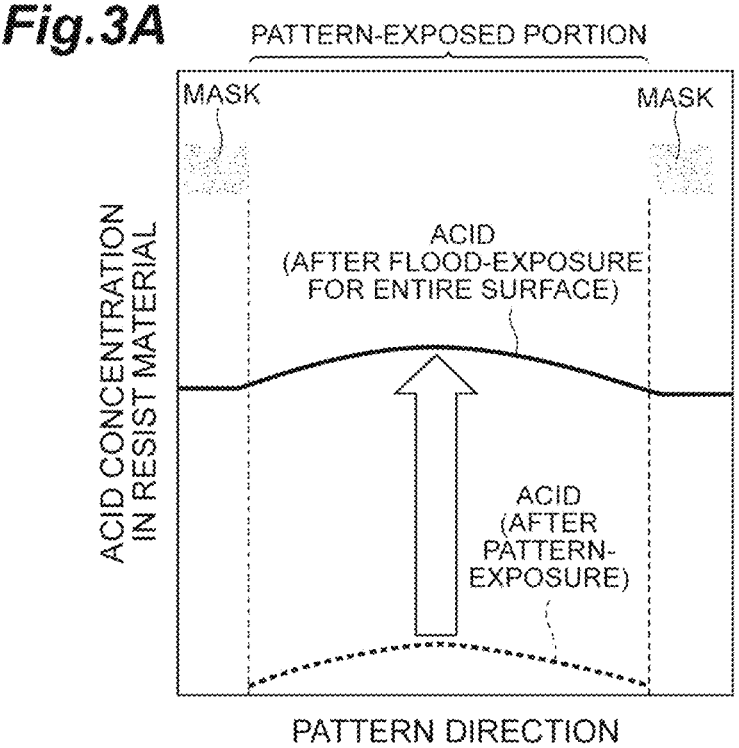
FIG. 3A is a schematic view graphically showing an acid concentration distribution in a conventional chemical-amplification type resist material.
Figure 3B:
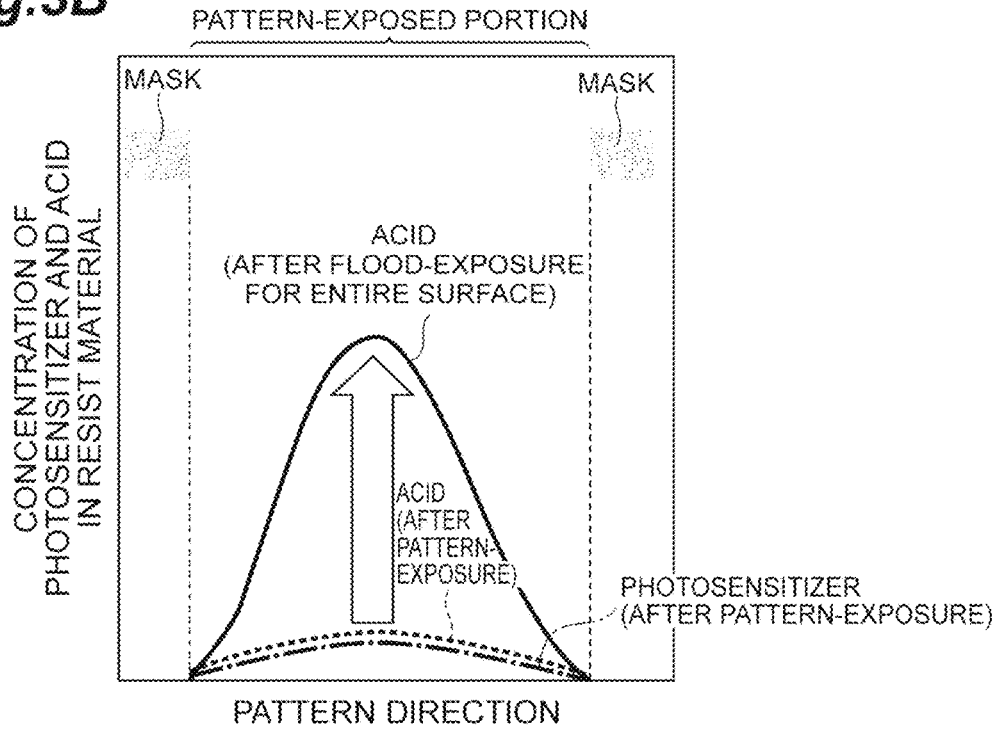
FIG. 3B is a schematic view graphically showing a photosensitizer concentration distribution and an acid concentration distribution in a photosensitization chemical-amplification type resist material according to an embodiment of the present invention.

FIG. 3A is a graph showing an acid concentration distribution in a conventional chemical-amplification type resist material film, and shows an acid concentration distribution obtained in a case where both of the pattern-exposure and the flood-exposure are performed using extreme ultraviolet rays (EUV) or the like. In the pattern-exposure, the amount of acid generated is small, but the excellent latent image of the resist pattern is maintained. However, in the flood-exposure, an acid is generated across the entire surface of the resist material film. If the exposure amount is increased to improve the sensitivity, the latent image of the resist pattern greatly deteriorates (deterioration of lithography characteristics), and it is difficult to achieve both of the sensitivity and the lithography characteristics. Similarly to FIG. 2B, FIG. 3B is a graph showing a photosensitizer concentration distribution and an acid concentration distribution in a photosensitization chemical-amplification type resist material according to the present embodiment. In FIG. 3B, the amount of acid can be increased only in a pattern-exposed portion as in FIG. 2B, and it is possible to improve the sensitivity in a small exposure amount while maintaining the excellent latent image of the resist pattern.

<Semiconductor Device>

Figure 6A:
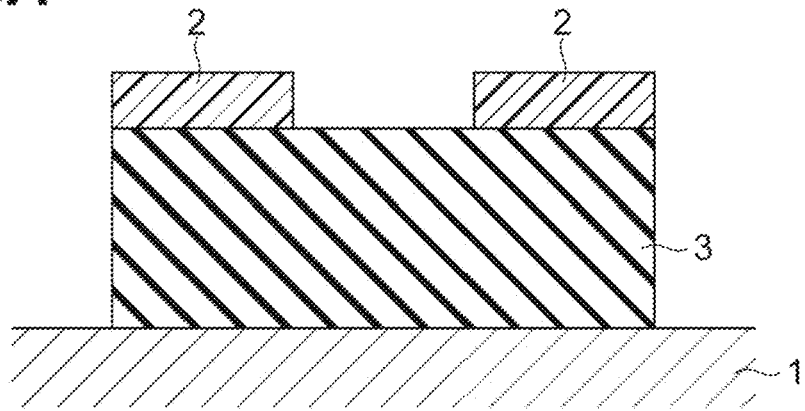
FIGS. 6A, 6B, and 6C are cross-sectional views illustrating an example of a process for manufacturing a semiconductor device according to an embodiment of the present invention.
Figure 6B:
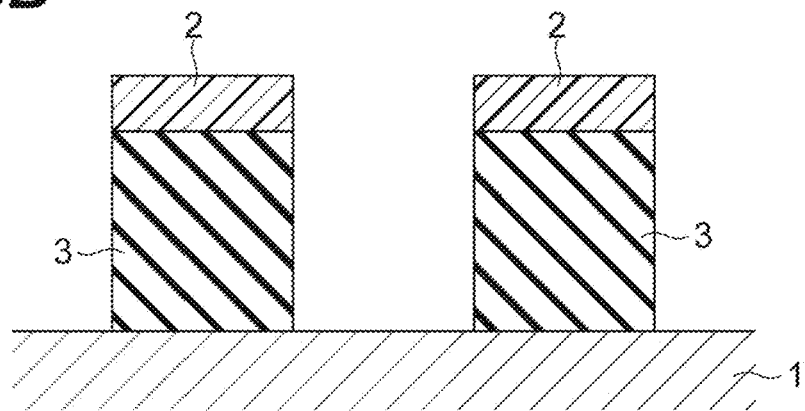
Figure 6C:
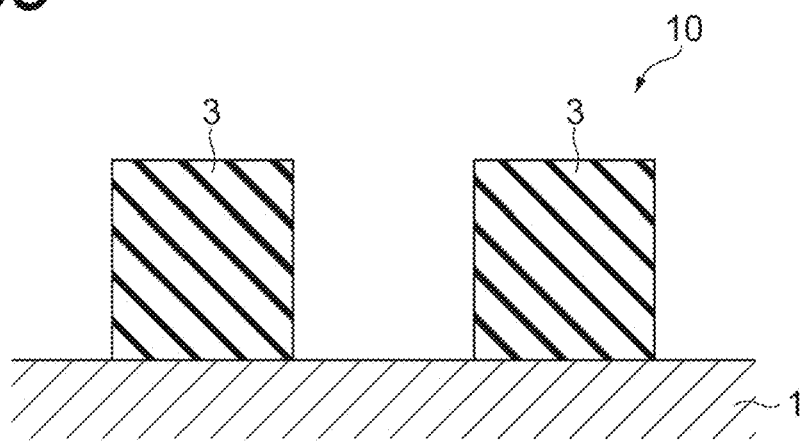

A semiconductor device according to the present embodiment can be manufactured using the pattern formed by the aforementioned method. FIGS. 6A, 6B and 6C are cross-sectional views showing an example of a process for manufacturing the semiconductor device of the present embodiment.

FIG. 6A is a cross-sectional view showing a resist pattern forming step and illustrating a semiconductor wafer 1, a film to be etched 3 which is formed on the semiconductor wafer 1, and a resist pattern 2 which is formed on the film to be etched 3 by the method for forming a pattern described above (FIG. 6A corresponds to the state after the developing step S6). Examples of the film to be etched include an active layer, a lower insulating layer, a gate electrode film, an upper insulating layer, and the like. Between the film to be etched 3 and the resist pattern 2, an antireflection film or a film for improving resist adhesiveness or resist shape may be disposed. Furthermore, a multilayer mask structure may be adopted. FIG. 6B is a cross-sectional view showing an etching step and illustrating the semiconductor wafer 1, the resist pattern 2, and the film to be etched 3 which is etched using the resist pattern 2 as a mask. The film to be etched 3 is etched in the shape of the opening portion of the resist pattern 2. FIG. 6C is a cross-sectional view of a patterned substrate 10 including the semiconductor wafer 1 and the pattern of the film to be etched 3 having undergone etching from which the resist pattern 2 has been removed. The pattern of the film to be etched 3, from which the resist pattern 2 has been removed, is flattened due to wiring embedded therein for example, and device elements are laminated on the substrate, thereby manufacturing a semiconductor device.

<Mask for Lithography>

A mask for lithography according to the present embodiment is manufactured by processing a substrate by using a resist pattern formed by the same method as described above. In many cases, the mask for lithography is manufactured by etching a substrate surface or a hard mask on a glass substrate by using a resist pattern. The mask mentioned herein includes a transmission type mask using ultraviolet rays or electron beams, a reflection type mask using EUV light, and the like. The transmission type mask is used for masking a light-shielded portion or a phase shift portion with a resist pattern and processing the resultant by etching. The reflection type mask is used for masking a light-absorbing substance with a resist pattern and processing the resultant by etching.

<Template for Nanoimprinting>

A template for nanoimprinting according to the present embodiment is also manufactured using the resist pattern formed by the same method as described above. The resist pattern is formed on a glass surface or a hard mask surface of a substrate such as a glass substrate, and the resultant is processed by etching, thereby forming the template for nanoimprinting.

EXAMPLES

Hereinafter, the present invention will be specifically described based on examples, but the scope of the present invention is not limited thereto.

Example 1

32.19 parts by mass (0.44 parts by mole) of the following GBLMA, 23.86 parts by mass (0.24 parts by mole) of the following MAMA, and 21.29 parts by mass (0.21 parts by mole) of the following HAMA as methyl methacrylates to which a protecting group was bonded and 22.66 parts by mass (0.11 parts by mole) of the following PBpS-F2MAS as methyl methacrylate to which a photoacid generating group was bonded were mixed together and radically polymerized, thereby synthesizing a methyl methacrylate-based polymer compound (polymer compound P) having the (f) photoacid generating group as the component (1'). The obtained methyl methacrylate-based polymer compound had a weight average molecular weight (Mw) of 24,800 and a molecular weight distribution (Mw/Mn) of 3.08. Herein, the above Mw and Mw/Mn were measured through gel permeation chromatography (GPC) under the following conditions by using a calibration curve based on standard polystyrene.

Device: HPLC (manufactured by Shimadzu Corporation)
Column: Shodex KF-805L(x) with KF-G
Detector: RID-10A, SPD-M10AVP
Column temperature: 40° C.
Flow rate: 1.0 mL/min
Eluant: tetrahydrofuran solution

[Chemical Formula102]

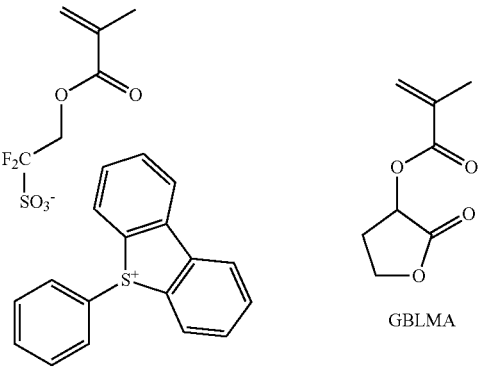

PBpS-F2MAS

GBLMA

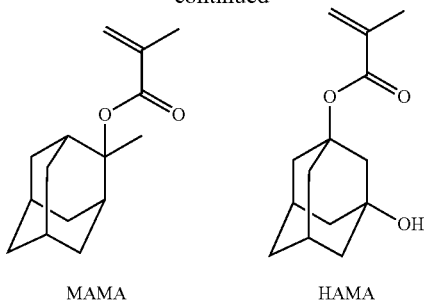

MAMA  HAMA 29.0 mg (0.1 mole with respect to 1 mole of the polymer compound P) of a dimethoxybenzhydrol derivative as the (b) photosensitizer precursor and 1.77 mg (0.005 moles with respect to 1 mole of the polymer compound P) of trioctylamine (TOA, manufactured by Sigma-Aldrich Co, LLC.) as the (3) first scavenger (quencher) were added to 7.91 mg (7 mL) of a 5% by mass cyclohexanone solution of the obtained polymer compound P, thereby preparing a resist material. Herein, the dimethoxybenzhydrol derivative is an acetal compound in which two methoxy groups are bonded to carbon atoms of a carbonyl group in p-dimethoxybenzhydrol functioning as a photosensitizer. The dimethoxybenzhydrol derivative generates ketone (p-dimethoxybenzophenone) functioning as a photosensitizer in the following deprotection reaction after pattern-exposure.

[Chemical Formula 103]

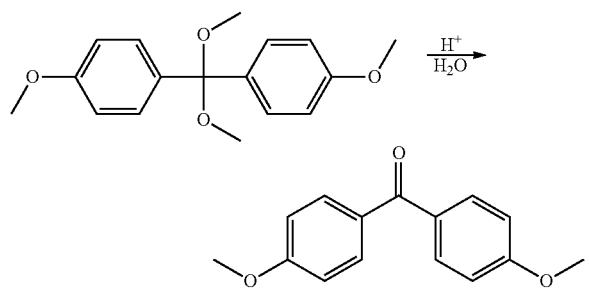

By using a spin coater (manufactured by MIKASA CO., LTD.), a silicon substrate having undergone a surface treatment using hexamethyldisilazane (HMDS) was spin-coated with the prepared resist material for 60 seconds at a rotation frequency of 4,000 rpm. After the spin coating, the coating film was heated for 60 seconds at 110° C., thereby forming a resist material film on the silicon substrate (film forming step). As a result of measuring the thickness of the resist material film by using an atomic force microscope (AFM, trade name: NanoNavi II SPA-300HV, manufactured by Hitachi High-Tech Science Corporation), it was found that the thickness was 51 nm.

By using a patterning device (vector scanning method, trade name: ELS-7700T, manufactured by ELIONIX INC.), the substrate on which the resist material film was formed was irradiated with electron beams in a vacuum (equal to or less than $2.9 \times 10^{-5}$ Pa) at a irradiation current of 10 pA and an acceleration voltage of 75 kV (pattern-exposure step). Then, in a state where the vacuum was maintained, through a quartz window of an exposure device (UV lamp, power of light source: 0.8 mW/h, trade name: SLUV-6, manufactured by AS ONE Corporation), ultraviolet rays having a wavelength of 365 nm was radiated to the entire surface of the resist material film for 30 minutes immediately after the pattern-exposure (flood-exposure step).

The resist material film having undergone the flood-exposure was heated for 60 seconds at 110° C. in a nitrogen gas stream (baking step). The resist material film having undergone the baking step was subjected to a developing treatment by being brought into contact with 2.38% by mass tetramethylammonium hydroxide (TMAH) for 60 seconds at 25° C., thereby obtaining a resist pattern (developing step).

Example 2

A resist pattern was obtained in the same manner as in Example 1, except that the resist material film was irradiated with ultraviolet rays for 10 minutes in the flood-exposure step.

Comparative Example 1

A resist pattern was obtained in the same manner as in Example 1, except that flood-exposure was not performed.

<Evaluation of Sensitivity>

Figure 8:
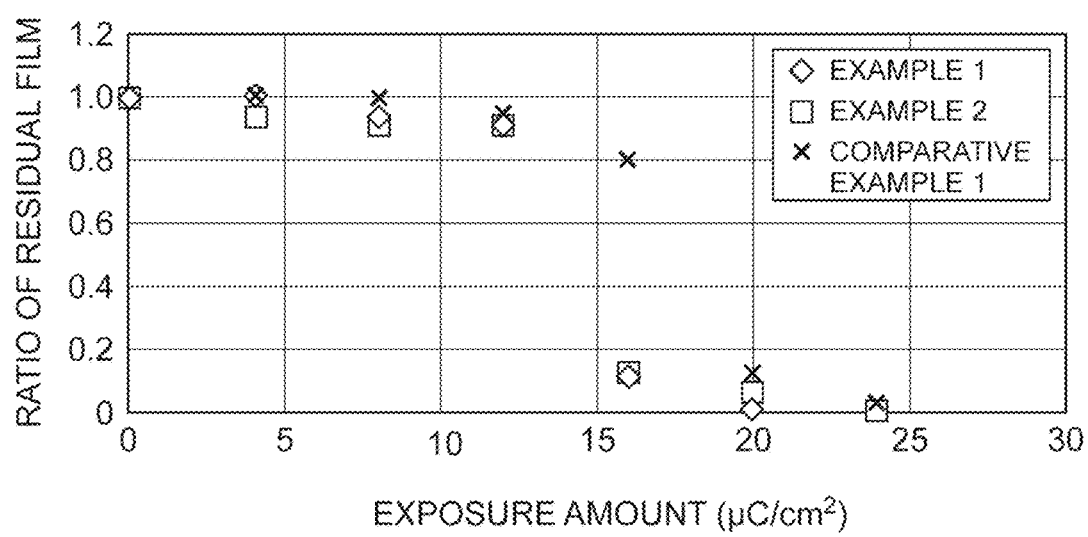
FIG. 8 is a graph showing a sensitivity curve of resist materials obtained in Examples 1 and 2 and Comparative Example 1.

The exposure amount in the pattern-exposure step of Examples 1 and 2 and Comparative Example 1 was varied within a range of 0 $\mu C/cm^2$ to 200 $\mu C/cm^2$, the resist material film was exposed in a 2 m×100 m rectangular shape at each exposure amount, and then the resist material film was subjected to the developing treatment. Thereafter, a ratio of a residual film in a pattern-exposed portion was measured. FIG. 8 is a graph (sensitivity curve) in which the ordinate shows the ratio of a residual film and the abscissa shows the exposure amount. Herein, the ratio of a residual film was determined based on the following equation by measuring the thickness of the resist material film remaining on the substrate before and after the developing treatment at room temperature and in the air atmosphere by using an atomic force microscope (AFM, trade name: NanoNavi II SPA-300HV, manufactured by Hitachi High-Tech Science Corporation).

Ratio of residual film=[(thickness of resist material film before developing treatment)−(thickness of resist material film after developing treatment)]/(thickness of resist material film before developing treatment)

The exposure amount necessary for the ratio of a residual film to become zero (0) was calculated as sensitivity ($E_0$) by being extrapolated from a curve approximate to the graph of FIG. 8. As a result, the sensitivities of Example 1, Example 2, and Comparative Example 1 were found to be 15.8 $\mu C/cm^2$, 20.2 $\mu C/cm^2$, and 24.3 $\mu C/cm^2$ respectively. It was confirmed that higher sensitivity was obtained in Examples 1 and 2 than in Comparative Example 1 by performing flood-exposure. Herein, as described above, the "sensitivity $E_0$" means the exposure amount necessary for the ratio of a residual film to become zero (0). Therefore, if the value of the sensitivity $E_0$ is small, it means that the generally used "sensitivity" is high, and inversely, if the value of the sensitivity $E_0$ is great, it means that the generally used "sensitivity" is low.

<Evaluation of Lithography Characteristics>

Within the resist patterns obtained in Examples 1 and 2 and Comparative Example 1, the portions developed for contact holes having a diameter of 50 nm and a pitch of 150 nm were observed using a high-resolution scanning electron microscope (SEM, trade name: NVision 40D, manufactured by Carl Zeiss). As a result, it was confirmed that in all of Examples 1 and 2 and Comparative Example 1, a resist pattern for contact holes having a diameter of 48 nm to 51 nm was formed with excellent regularity. Herein, in Example 1, Example 2, and Comparative Example 1, the exposure amounts (sensitivity $E_{size}$) at the time when the ratio of a residual resist material film for forming a resist pattern for contact holes having a diameter of 50 nm became zero (0) were 48.0 µC/cm², 60.0 µC/cm², and 76.0 µC/cm² respectively.

Within the resist patterns obtained in Examples 1 and 2 and Comparative Example 1, a portion in which lines of 50 nm line/100 nm space were formed at a pitch of 150 nm were observed using a high-resolution scanning electron microscope (SEM, trade name: NVision 40D, manufactured by Carl Zeiss). As a result, it was confirmed that in all of Examples 1 and 2 and Comparative Example 1, a resist pattern for lines was formed with excellent regularity. The line edge roughness (LER) of Example 1, Example 2, and Comparative Example 1 was 8.9 nm, 9.2 nm, and 8.2 nm respectively. Herein, in Example 1, Example 2, and Comparative Example 1, the exposure amounts (sensitivity $E_{size}$ ($E_{50\ nm}$)) at the time when the ratio of a residual resist material film for forming a resist pattern for lines having a width of 50 nm became zero (0) were 44.0 µC/cm², 56.0 µC/cm², and 72.0 µC/cm² respectively. Accordingly, it was confirmed that, in all of the patterns including contact holes and line-and-space patterns, the sensitivity was further improved in Examples 1 and 2 than in Comparative Example 1, in a state of maintaining resolution.

Comparative Example 2

As the (1) base component, 600 mg of a methyl methacrylate-based polymer compound Q (weight average molecular weight: 16,000) having a constitutional unit represented by the following formula was dissolved in 45 mL of cyclohexanone. To the solution, 29.0 mg (0.05 moles with respect to 1 mole of the polymer compound) of an iodonium salt compound (trade name: DPI-PFBS, manufactured by Midori Kagaku Co., Ltd.) as the (c) photoacid generator, 28.83 mg (0.1 moles with respect to 1 mole of the polymer compound) of a dimethoxybenzhydrol derivative as the (b) photosensitizer precursor, and 1.77 mg (0.005 moles with respect to 1 mole of the polymer compound) of trioctylamine (TOA, manufactured by Sigma-Aldrich Co, LLC.) as the (3) first scavenger (quencher) were added, thereby preparing a resist material.

[Chemical Formula 104]

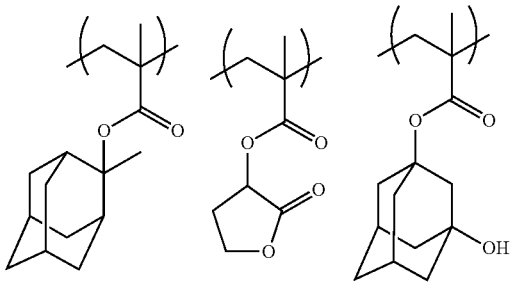

By using a spin coater (manufactured by MIKASA CO., LTD.), a silicon substrate having undergone a surface treatment using hexamethyldisilazane (HMDS) was spin-coated with the prepared resist material for 120 seconds at a rotation frequency of 1,200 rpm. After the spin coating, the coating film was heated for 60 seconds at 110° C., thereby forming a resist material film on the silicon substrate (film forming step). As a result of measuring the thickness of the resist material film by using an atomic force microscope (AFM, trade name: NanoNavi II SPA-300HV, manufactured by Hitachi High-Tech Science Corporation), it was found that the thickness was 43 nm.

By using a patterning device (equipped with a beam blanker, raster scanning method, trade name: JSM-6500F, manufactured by JEOL Ltd.), the substrate on which the resist material film was formed was irradiated with electron beams in a vacuum at an irradiation current of 30 pA and an acceleration voltage of 30 kV (pattern-exposure step). After the pattern-exposure, the substrate on which the resist material film was formed was temporarily taken out into the air atmosphere in which the amount of amine as a basic substance was not controlled, and then stored for 0 minutes to 30 minutes in a dry nitrogen atmosphere.

The resist material film after storage was taken out into the air atmosphere and heated for 60 seconds at 110° C. in a nitrogen gas stream (baking step). The resist material film having undergone the baking step was subjected to a developing treatment by being brought into contact with 2.38% by mass tetramethylammonium hydroxide (TMAH) for 60 seconds at 25° C., thereby obtaining a resist pattern (developing step).

<Evaluation of Sensitivity>

Figure 9:
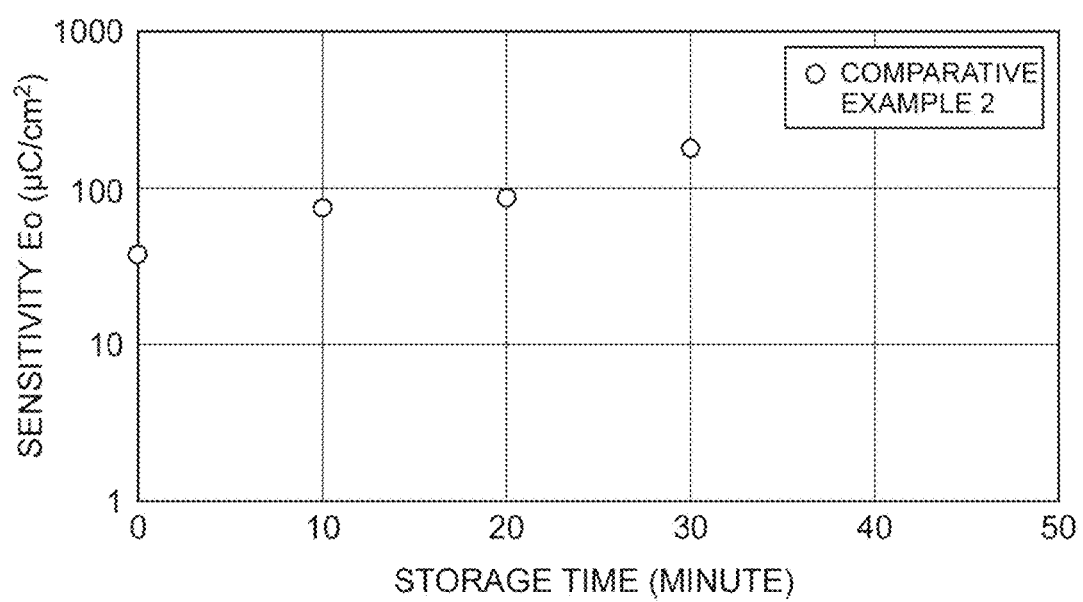
FIG. 9 is a graph showing a relationship between sensitivity and storage time in a resist material obtained in Comparative Example 2.

The ratio of a residual film at the time when the storage time after the pattern-exposure was set to be 0, 10, 20, and 30 minutes was measured, and the sensitivity ($E_0$) was calculated in the same manner as in Example 1. FIG. 9 is a graph in which the ordinate shows the logarithm of sensitivity and the abscissa shows the storage time. When being subjected to developing immediately after the pattern-exposure (storage time: 0 minutes), the resist material film had a sensitivity of 40.3 µC/cm². When the resist material film was stored for 10 minutes in a nitrogen atmosphere, the sensitivity thereof became 68.4 µC/cm², and when it was stored for 30 minutes in a nitrogen atmosphere, the sensitivity thereof became 188.5 µC/cm². Therefore, it was confirmed that the longer the storage time after the pattern-exposure, the further the sensitivity was reduced.

<Evaluation of Lithography Characteristics>

The resist pattern obtained in Comparative Example 2 was observed in the same manner as in Example 1. As a result, it was found that, in any storage times, a resist pattern for contact holes having a diameter of 50 nm and a pitch of 150 nm and a resist pattern for lines of 50 nm line/100 nm space were formed with excellent regularity. Furthermore, it was confirmed that as the storage time was increased, the size of the contact holes became nonuniform, the formed resist patterns did not have excellent regularity, the line edge roughness of the resist pattern for lines was increased, and some of the lines were broken.

Example 3

As the (1) base component, 600 mg of the methyl methacrylate-based polymer compound Q was dissolved in 45 mL of cyclohexanone. To the solution, 29.0 mg (0.05 moles with respect to 1 mole of the polymer compound) of an iodonium salt compound (trade name: DPI-PFBS, manufactured by Midori Kagaku Co., Ltd.) as the (c) photoacid generator, 28.83 mg (0.1 moles with respect to 1 mole of the polymer compound) of a dimethoxybenzhydrol derivative as the (b) photosensitizer precursor, and 1.77 mg (0.005 moles with respect to 1 mole of the polymer compound) of trioctylamine (TOA, manufactured by Sigma-Aldrich Co, LLC.) as the (3) first scavenger (quencher) were added, thereby preparing a resist material.

By using a spin coater (manufactured by MIKASA CO., LTD.), a silicon substrate having undergone a surface treatment using hexamethyldisilazane (HMDS) was spin-coated with the prepared resist material for 120 seconds at a rotation frequency of 1,200 rpm. After the spin coating, the coating film was heated for 60 seconds at 110° C., thereby forming a resist material film on the silicon substrate (film forming step). As a result of measuring the thickness of the resist material film by using an atomic force microscope (AFM, trade name: NanoNavi II SPA-300HV, manufactured by Hitachi High-Tech Science Corporation), it was found that the thickness was 43 nm.

By using a patterning device (equipped with a beam blanker, raster scanning method, trade name: JSM-6500F, manufactured by JEOL Ltd.), the substrate on which the resist material film was formed was irradiated with electron beams in a vacuum at an irradiation current of 30 pA and an acceleration voltage of 30 kV (pattern-exposure step). Thereafter, in an air atmosphere in which the amount of amine as a basic substance was not controlled, by using an exposure device (UV lamp, power of light source: 0.78 mW/h, trade name: SLUV-6, manufactured by AS ONE Corporation), the entire surface of the resist material film immediately after the pattern-exposure was irradiated with ultraviolet rays having a wavelength of 365 nm for 10 minutes (flood-exposure step).

The resist material film having undergone the flood-exposure was heated for 60 seconds at 110° C. in a nitrogen gas stream (baking step). The resist material film having undergone the baking step was subjected to a developing treatment by being brought into contact with 2.38% by mass tetramethylammonium hydroxide (TMAH) for 60 seconds at 25° C., thereby obtaining a resist pattern (developing step).

Example 4

A resist pattern was obtained in the same manner as in Example 3, except that the flood-exposure step was performed as below.

The substrate having undergone the pattern-exposure step was temporarily taken out into an air atmosphere in which the amount of amine as a basic substance was not controlled. Then, in a dry nitrogen environment, by using an exposure device (LED light source, power of light source: 0.72 mW/h, trade name: 3D LIMELIGHT manufactured by NITRIDE SEMICONDCUTOR Co., Ltd.), the entire surface of the resist material film having undergone the pattern-exposure step was irradiated with ultraviolet rays having a wavelength of 365 nm for 15 minutes (flood-exposure step).

Example 5

A resist pattern was obtained in the same manner as in Example 3, except that the flood-exposure step was performed as below.

The substrate having undergone the pattern-exposure step was temporarily taken out into an air atmosphere in which the amount of amine as a basic substance was not controlled, and stored for 10 minutes in a dry nitrogen atmosphere. Then, in a dry nitrogen environment, by using an exposure device (LED light source, power of light source: 0.72 mW/h, trade name: 3D LIMELIGHT manufactured by NITRIDE SEMICONDCUTOR Co., Ltd.), the entire surface of the resist material film after storage step was irradiated with ultraviolet rays having a wavelength of 365 nm for 15 minutes (flood-exposure step).

<Evaluation of Sensitivity>

The sensitivity ($E_0$) was calculated in the same manner as in Example 1. As a result, in Examples 3 and 4 in which flood-exposure was performed but storage was not performed, a sensitivity of 29.5 µC/cm$^2$ and 37.6 µC/cm$^2$ was obtained respectively. In contrast, in Comparative Example 2 in which none of flood-exposure and storage was performed, a sensitivity of 43.3 µC/cm$^2$ was obtained as described above. Therefore, it was understood that the sensitivity was increased due to flood-exposure. In addition, in Example 5 in which both of flood-exposure and storage were performed, a sensitivity of 48.1 µC/cm$^2$ was obtained. However, in Comparative Example 2 in which flood-exposure was not performed but storage was performed, a sensitivity of 68.4 µC/cm$^2$ was obtained as described above. Therefore, it was understood that the sensitivity was increased due to the flood-exposure.

<Evaluation of Lithography Characteristics>

Figure 10:
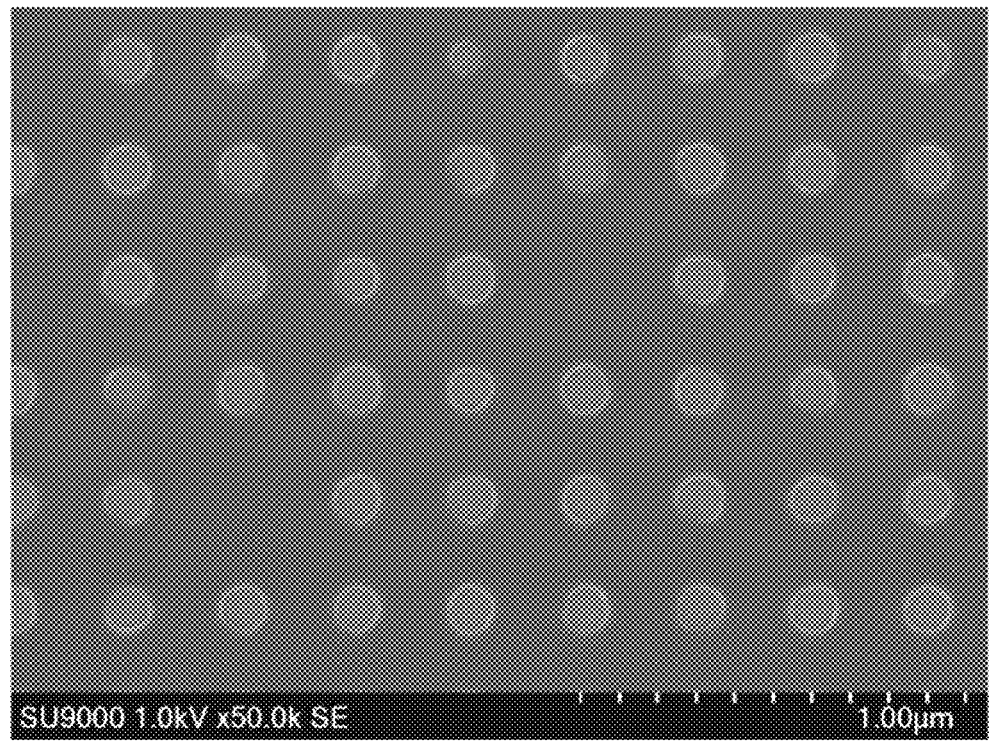
FIG. 10 is an SEM image of a resist pattern obtained in Comparative Example 2.
Figure 11:
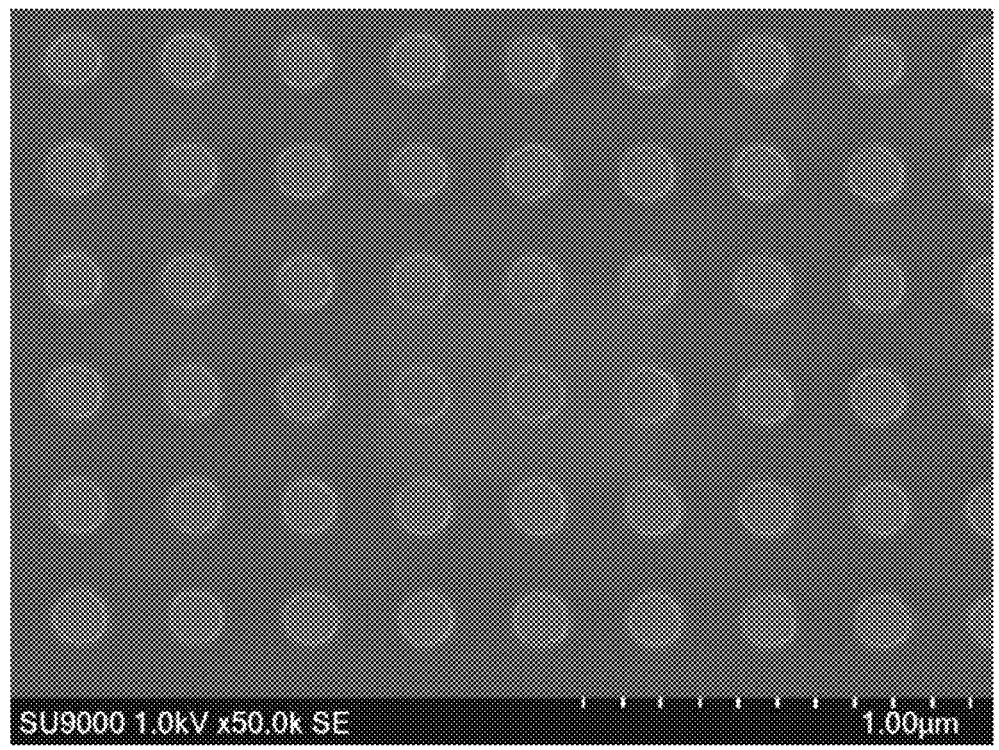
FIG. 11 is an SEM image of a resist pattern obtained in Example 3.

Within the resist patterns obtained in Example 3 and Comparative Example 2, the portions developed for contact holes having a diameter of 100 nm and a pitch of 200 nm were observed using a high-resolution scanning electron microscope (SEM, trade name: SU9000, manufactured by Hitachi High-Technologies Co., Ltd.). FIG. 10 is an SEM image of the resist patterns obtained in Comparative Example 2 (storage time: 10 minutes). As is evident from FIG. 10, the resist pattern for contact holes was not formed in some portions in Comparative Example 2 (storage time: 10 minutes), and there were many holes having a diameter less than 100 nm. FIG. 11 is an SEM image of the resist patterns obtained in Example 3. As is evident from FIG. 11, overall, a resist pattern for contact holes maintaining a pitch of 200 nm and having a diameter of 98 nm to 102 nm was formed with excellent regularity.

In Example 3 and Comparative Example 2, the exposure amount (sensitivity $E_{size}$) at the time when the ratio of a residual resist material film for forming a resist pattern for contact holes having a diameter of 75 nm became zero (0) was 60.0 µC/cm$^2$ and 112.5 µC/cm$^2$ respectively. Therefore, it was confirmed that, due to the flood-exposure, the sensitivity was improved in a state where resolution was maintained.

Within the resist patterns obtained in Examples 3 and 4 and Comparative Example 2, the portions formed as lines of 75 nm line/75 nm space having a pitch of 150 nm were observed using a high-resolution scanning electron microscope (SEM, trade name: NVision 40D, manufactured by Carl Zeiss). As a result, it was found that in all of Examples 3 and 4 and Comparative Example 2, resist patterns for lines having a width of 74 nm to 76 nm were formed with excellent regularity while maintaining a pitch of 150 nm. The line edge roughness (LER) of Example 3, Example 4, and Comparative Example 2 was 11.0 nm, 10.8 nm, and 11.3 nm respectively. Herein, in Example 3, Example 4, and Comparative Example 2 (storage time: 10 minutes), the exposure amount (sensitivity $E_{size}$) at the time when the ratio of a residual resist material film for forming a resist pattern for lines having a width of 50 nm became zero (0) was 67.5 PC/cm$^2$, 87.5 µC/cm$^2$, and 97.5 µC/cm$^2$ respectively. Accordingly, it was confirmed that in any patterns of contact holes and line-and-space, the sensitivity was further improved in a state of maintaining resolution in Examples 3 and 4 than in Comparative Example 2.

In the flood-exposure of Example 3, the power of the light source was 0.78 mW/h, and the exposure time was 10 minutes. Furthermore, in the flood-exposure of Example 4, the power of the light source was 0.72 mW/h and the exposure time was 15 minutes. Presumably, because of the wavelength of the non-ionizing radiation used in the flood-exposure, the obtained sensitivity was higher in Example 3 than in Example 4 even if the exposure time was relatively short in Example 3. The UV lamp used in examples was black light that was ultraviolet rays having a distribution within a wide wavelength range. The UV lamp emits ultraviolet rays which is centered on 365 nm but covers a wide wavelength range from about 320 nm to about 400 nm. As a result, an acid is generated by a photosensitizer absorbing short wavelength components, the improved sensitivity is achieved thereby, compared to LED having a single wavelength of 365 nm.

In Example 5, the exposure amount (sensitivity $E_{size}$) at the time when the ratio of a residual resist material film for forming a resist pattern for lines having a width of 50 nm became zero (0) was 150 µC/cm$^2$ and LER was 14 nm. The resolution and sensitivity were lower in Example 5 than in Example 4 in which storage was not performed.

Comparative Example 3

600 mg of the methyl methacrylate-based polymer compound Q as the (1) base component was dissolved in 48 mL of cyclohexanone. To the solution, 29.0 mg (0.05 moles with respect to 1 mole of the polymer compound) of an iodonium salt compound (trade name: DPI-PFBS, manufactured by Midori Kagaku Co., Ltd.) as the (c) photoacid generator, 28.83 mg (0.1 moles with respect to 1 mole of the polymer compound) of a dimethoxybenzhydrol derivative as the (b) photosensitizer precursor, and 3.54 mg (0.01 moles with respect to 1 mole of the polymer compound) of trioctylamine (TOA, manufactured by Sigma-Aldrich Co, LLC.) as the (3) first scavenger (quencher) were added, thereby preparing a resist material.

By using a spin coater (manufactured by MIKASA CO., LTD.), a silicon substrate having undergone a surface treatment using hexamethyldisilazane (HMDS) was spin-coated with the prepared resist material for 60 seconds at a rotation frequency of 1,200 rpm. After the spin coating, the coating film was heated for 60 seconds at 110° C., thereby forming a resist material film on the silicon substrate (film forming step). As a result of measuring the thickness of the resist material film by using an atomic force microscope (AFM, trade name: NanoNavi II SPA-300HV, manufactured by Hitachi High-Tech Science Corporation), it was found that the thickness was 41 nm.

By using a patterning device (equipped with a beam blanker, raster scanning method, trade name: JSM-6500F, manufactured by JEOL Ltd.), the substrate on which the resist material film was formed was irradiated with electron beams in a vacuum at an irradiation current of 30 pA and an acceleration voltage of 30 kV (pattern-exposure step). After the pattern-exposure, the substrate on which the resist material film was formed was temporarily taken out into the air atmosphere in which the amount of amine as a basic substance was not controlled, and then stored for 0 minutes to 30 minutes in a dry nitrogen atmosphere.

The resist material film after storage was taken out into the air atmosphere and heated for 60 seconds at 110° C. in a nitrogen gas stream (baking step). The resist material film having undergone the baking step was subjected to a developing treatment by being brought into contact with 2.38% by mass tetramethylammonium hydroxide (TMAH) for 60 seconds at 25° C., thereby obtaining a resist pattern (developing step).

<Evaluation of Sensitivity>

The ratio of a residual film at the time when the storage time after the pattern-exposure was set to be 0, 10, 20, and 30 minutes was measured, and the sensitivity was calculated in the same manner as in Example 1. Table 2 shows the change of sensitivity with the storage time. It was confirmed that the longer the storage time after the pattern-exposure, the lower the sensitivity.

<Evaluation of Lithography Characteristics>

The resist pattern obtained in Comparative Example 3 was observed in the same manner as in Example 1. As a result, it was confirmed that, regardless of the storage time, a resist pattern for contact holes having a diameter of 50 nm and a pitch of 150 nm and a resist pattern for lines of 50 nm line/100 nm space were obtained; however, as in Comparative Example 2, as the storage time was increased, the size of the contact holes became nonuniform, and excellently regular patterns were not obtained. It was also confirmed that the line edge roughness of the line shape was poor, and some of the line were broken.

TABLE 2

| Storage time | 0 minutes | 10 minutes | 20 minutes | 30 minutes |
| --- | --- | --- | --- | --- |
| Sensitivity (µC/cm$^2$) | 38 | 68 | 125 | 130 |

Example 6

By using a patterning device (equipped with a beam blanker, raster scanning method, trade name: JSM-6500F, manufactured by JEOL Ltd.), the resist material film formed on the substrate in Comparative Example 3 was irradiated with electron beams in a vacuum at an irradiation current of 30 pA and an acceleration voltage of 30 kV (pattern-exposure step). Thereafter, in an air atmosphere in which the amount of amine as a basic substance was not controlled, by using an exposure device (UV lamp, 0.78 mW/h, trade name: SLUV-6, manufactured by AS ONE Corporation), the entire surface of the resist material film immediately after the pattern-exposure was irradiated with ultraviolet rays having a wavelength of 365 nm for 10 minutes (flood-exposure step).

The resist material film having undergone the flood-exposure was heated for 60 seconds at 110° C. in a nitrogen gas stream (baking step). The resist material film having undergone the baking step was subjected to a developing treatment by being brought into contact with 2.38% by mass tetramethylammonium hydroxide (TMAH) for 60 seconds at 25° C., thereby obtaining a resist pattern (developing step).

<Evaluation of Sensitivity>

The sensitivity ($E_0$) was calculated in the same manner as in Example 1. As a result, in Example 6, a sensitivity of 50 µC/cm$^2$ was obtained, but in Comparative Example 3 in which the resist material film was stored for 10 minutes (hereinafter, described as Comparative Example 3-(a)), a sensitivity of 68 µC/cm$^2$ was obtained. Therefore, it was understood that the sensitivity was increased due to the flood-exposure.

<Evaluation of Lithography Characteristics>

Within the resist patterns obtained in Example 6 and Comparative Example 3-(a), the portions developed for contact holes having a diameter of 50 nm and a pitch of 150 nm were observed using a high-resolution scanning electron microscope (SEM, trade name NVision 40D, manufactured by Carl Zeiss). As a result, it was found that in Example 6 and Comparative Example 3, a resist pattern for contact holes having a diameter of 48 nm to 55 nm was formed with excellent regularity while maintaining a pitch of 150 nm. Herein, in Example 6 and Comparative Example 3, the exposure amount (sensitivity $E_{size}(E_{50\ nm})$) at the time when the ratio of the resist material film for forming the resist pattern for contact holes having a diameter of 50 nm became zero (0) was 129.0 µC/cm² and 150.0 µC/cm² respectively. Therefore, it was confirmed that due to the flood-exposure, the sensitivity was improved in a state where resolution was maintained.

Within the resist patterns obtained in Example 6 and Comparative Example 3-(a), the portions formed as lines of 50 nm line/50 nm space at a pitch of 100 nm were observed using a high-resolution scanning electron microscope (SEM, trade name NVision 40D, manufactured by Carl Zeiss). As a result, it was found that in Example 6 and Comparative Example 3, a resist pattern for lines of 49 nm to 52 nm were formed with excellent regularity while maintaining a pitch of 100 nm. In Example 6 and Comparative Example 3-(a), the line edge roughness (LER) was 9.8 nm and 12.8 nm respectively. Herein, in Example 6 and Comparative Example 3-(a), the exposure amount (sensitivity $E_{size}$ ($E_{50\ nm}$)) at the time when the ratio of the resist material film for forming the resist pattern for lines having a width of 50 nm became zero (0) was 120.0 µC/cm² and 145.0 µC/cm² respectively. Accordingly, it was confirmed that in all of contact holes and line-and-space patterns, the sensitivity was further improved in Example 6 in a state of maintaining resolution than in Comparative Example 3-(a).

Example 7

600 mg of the methyl methacrylate-based polymer compound Q as the (1) base component was dissolved in 45 mL of cyclohexanone. To the solution, 58.0 mg (0.1 moles with respect to 1 mole of the polymer compound) of an iodonium salt compound (trade name: DPI-PFBS, manufactured by Midori Kagaku Co., Ltd.) as the (c) photoacid generator, 57.7 mg (0.1 moles with respect to 1 mole of the polymer compound) of a dimethoxybenzhydrol derivative as the (b) photosensitizer precursor, and 3.54 mg (0.01 moles with respect to 1 mole of the polymer compound) of trioctylamine (TOA, manufactured by Sigma-Aldrich Co, LLC.) as the (3) first scavenger (quencher) were added, thereby preparing a resist material.

By using a spin coater (manufactured by MIKASA CO., LTD.), a silicon substrate having undergone a surface treatment using hexamethyldisilazane (HMDS) was spin-coated with the prepared resist material for 60 seconds at a rotation frequency of 1,200 rpm. After the spin coating, the coating film was heated for 60 seconds at 110° C., thereby forming a resist material film on the silicon substrate (film forming step). As a result of measuring the thickness of the resist material film by using an atomic force microscope (AFM, trade name: NanoNavi II SPA-300HV, manufactured by Hitachi High-Tech Science Corporation), it was found that the thickness was 44 nm.

By using a patterning device (equipped with a beam blanker, raster scanning method, trade name: JSM-6500F, manufactured by JEOL Ltd.), the substrate on which the resist material film was formed was irradiated with electron beams in a vacuum at an irradiation current of 30 pA and an acceleration voltage of 30 kV (pattern-exposure step). Then, in an air atmosphere in which the amount of amine as a basic substance was not controlled, by using an exposure device (UV lamp, 0.78 mW/h, trade name: SLUV-6, manufactured by AS ONE Corporation), the entire surface of the resist material film immediately after the pattern-exposure was irradiated with ultraviolet rays having a wavelength of 365 nm for 10 minutes (flood-exposure step).

The resist material film having undergone flood-exposure was taken out into the air atmosphere and heated for 60 seconds at 110° C. in a nitrogen gas stream (baking step). The resist material film having undergone the baking step was subjected to a developing treatment by being brought into contact with 2.38% by mass tetramethylammonium hydroxide (TMAH) for 60 seconds at 25° C., thereby obtaining a resist pattern (developing step).

Example 8

A resist pattern was obtained in the same manner as in Example 7, except that the ultraviolet ray irradiation was performed for 5 minutes during flood-exposure.

Comparative Example 4

A resist pattern was obtained in the same manner as in Example 7, except that flood-exposure was not performed.

Comparative Example 5

A resist pattern was obtained in the same manner as in Comparative Example 4, except that after the pattern-exposure step, the resist material film was temporarily taken out into an air atmosphere before the baking step and then stored for 3 minutes in a dry nitrogen atmosphere.

<Evaluation of Sensitivity>

The sensitivity ($E_0$) was calculated in the same manner as in Example 1. As a result, in Comparative Example 4, a sensitivity of 24 µC/cm² was obtained, while in Example 7 and Example 8, a sensitivity of 3 µC/cm² and 4 µC/cm² was obtained respectively. Therefore, it was understood that the sensitivity was increased not less than sextuple due to flood-exposure.

<Evaluation of Lithography Characteristics>

Within the resist patterns obtained in Example 7 and Comparative Example 4, the portions developed for contact holes having a diameter of 100 nm and a pitch of 200 nm were observed using a high-resolution scanning electron microscope (SEM, trade name: NVision 40D, manufacturing Carl Zeiss). As a result, it was found that in Example 7 and Comparative Example 4, a resist pattern for contact holes having a diameter of 99 nm to 102 nm was formed with excellent regularity while maintaining a pitch of 200 nm. Herein, in Example 7 and Comparative Example 4, the exposure amount (sensitivity $E_{size}$) at the time when the ratio of the resist material film for forming the resist pattern for contact holes having a diameter of 100 nm became zero (0) was 6.0 µC/cm² and 45.0 µC/cm² respectively. Therefore, it was confirmed that due to the flood-exposure, the sensitivity was improved sevenfold in a state where resolution was maintained.

Within the resist patterns obtained in Examples 7 and 8 and Comparative Example 4, the portions formed as lines of 100 nm line/100 nm space at a pitch of 200 nm were observed using an atomic force microscope (AFM, trade name: NanoNavi II SPA-300HV, manufactured by Hitachi High-Tech Science Corporation). As a result, it was found that in Example 7, Example 8, and Comparative Example 4, a resist pattern for lines of 101 nm to 102 nm was formed with excellent regularity while maintaining a pitch of 200 nm. In Example 7, Example 8, and Comparative Example 4, the line edge roughness (LER) was 9.8 nm, 10.1 nm, and 10.3 nm respectively. Herein, in Example 7, Example 8, and Comparative Example 4, the exposure amount (sensitivity $E_{size}$) at the time when the ratio of the resist material film for forming the resist pattern for lines having a width of 100 nm became zero (0) was 6.0 $\mu C/cm^2$, 9.0 $\mu C/cm^2$, and 42.0 $\mu C/cm^2$ respectively. Accordingly, it was confirmed that in any of contact holes and line-and-space patterns, the sensitivity was further improved in Examples 7 and 8 in a state of maintaining resolution than in Comparative Example 4. In Comparative Example 5, the exposure amount (sensitivity $E_{size}$) at the time when the ratio of the resist material film for forming the resist pattern for lines having a width of 100 nm became zero (0) was 52.5 $\mu C/cm^2$, and LER was 13.3 nm. In Comparative Example 5, the sensitivity and resolution were lower than in Comparative Example 4 because Comparative Example 5 included the storage step.

Example 9

50 parts by mass of a polyhydroxystyrene (PHS)-based polymer compound as the (1) base component was dissolved in cyclohexanone. To the solution, 5 parts by mass of a sulfonium salt compound as the (c) photoacid generator, 5 parts by mass of dimethoxybis(4-methoxyphenyl)methane as the (b) photosensitizer precursor, and 1 part by mass of the (3) first scavenger (quencher) were added, thereby preparing a resist material. Dimethoxybis(4-methoxyphenyl)methane generates a ketone (p-dimethoxybenzophenone) as a photosensitizer through the following deprotection reaction after pattern-exposure.

[Chemical Formula 105]

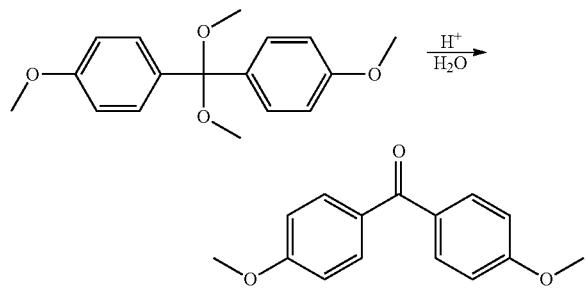

On a silicon substrate having undergone a surface treatment using a $SO_2$ polymer (TPU-2014) described in the journal of Microelectronic Engineering, No. 122, 70-76 (2014), an underlayer film having a thickness of 61 nm was formed. By using a spin coater (manufactured by MIKASA CO., LTD.), the underlayer film was spin-coated with the prepared resist material for 60 seconds at a rotation frequency of 1,200 rpm. After the spin coating, the coating film was heated for 60 seconds at 130° C. in a nitrogen gas stream, thereby forming a resist material film on the silicon substrate (film forming step). As a result of measuring the thickness of the resist material film by using an atomic force microscope (AFM, trade name: NanoNavi II SPA-300HV, manufactured by Hitachi High-Tech Science Corporation), it was found that the thickness was 50.3 nm.

By using a patterning device (vector scanning method, trade name: ELS-100T, manufactured by ELIONIX INC.), the substrate on which the resist material film was formed was irradiated with electron beams in a vacuum at a irradiation current of 50 pA and an acceleration voltage of 125 kV (pattern-exposure step). Then, in an air atmosphere, by using an exposure device (LED light source, power of light source: 41 mW/h, trade name: LHPUV 365/2501, manufactured by IWASAKI ELECTRIC CO., LTD.), the entire surface of the resist material film was irradiated with ultraviolet rays having a wavelength of 365 nm immediately after pattern-exposure (flood-exposure step). During the flood-exposure, the exposure amount was changed to 2.4, 4.8, and 7.2 $J/cm^2$, and a resist material film was obtained under each condition.

Each of the resist material films having undergone flood-exposure was heated for 60 seconds at 110° C. in a nitrogen gas stream (baking step). Each of the resist material films having undergone the baking step was subjected to a developing treatment by being brought into contact with 2.38% by mass tetramethylammonium hydroxide (TMAH) for 60 seconds at 24° C. and then rinsed with ultrapure water, thereby obtaining a resist pattern (developing step).

Example 10

A resist pattern was obtained in the same manner as in Example 9, except that the amount of dimethoxybis(4-methoxyphenyl)methane added as the (b) photosensitizer precursor was changed to 10 parts by mass from 5 parts by mass, and the exposure amount of flood-exposure was set to be 1.2, 2.4, and 4.8 $J/cm^2$.

Example 11

A resist pattern was obtained in the same manner as in Example 9, except that the amount of dimethoxybis(4-methoxyphenyl)methane added as the (b) photosensitizer precursor was changed to 15 parts by mass from 5 parts by mass, and the exposure amount of flood-exposure was set to be 1.2, 2.4, and 4.8 $J/cm^2$.

Example 12

A resist pattern was obtained in the same manner as in Example 9, except that the amount of dimethoxybis(4-methoxyphenyl)methane added as the (b) photosensitizer precursor was changed to 20 parts by mass from 5 parts by mass, and the exposure amount of flood-exposure was set to be 1.2, 2.4, and 3.6 $J/cm^2$.

Comparative Examples 6 to 9

Resist patterns of Comparative Examples 6 to 9 were obtained in the same manner as in Examples 9 to 12 respectively, except that flood-exposure was not performed.

Comparative Example 10

A resist pattern of Comparative Example 10 was obtained in the same manner as in Example 9, except that the resist material was prepared without adding the (b) photosensitizer precursor, and flood-exposure was not performed.

<Evaluation of Sensitivity>

Figure 12:
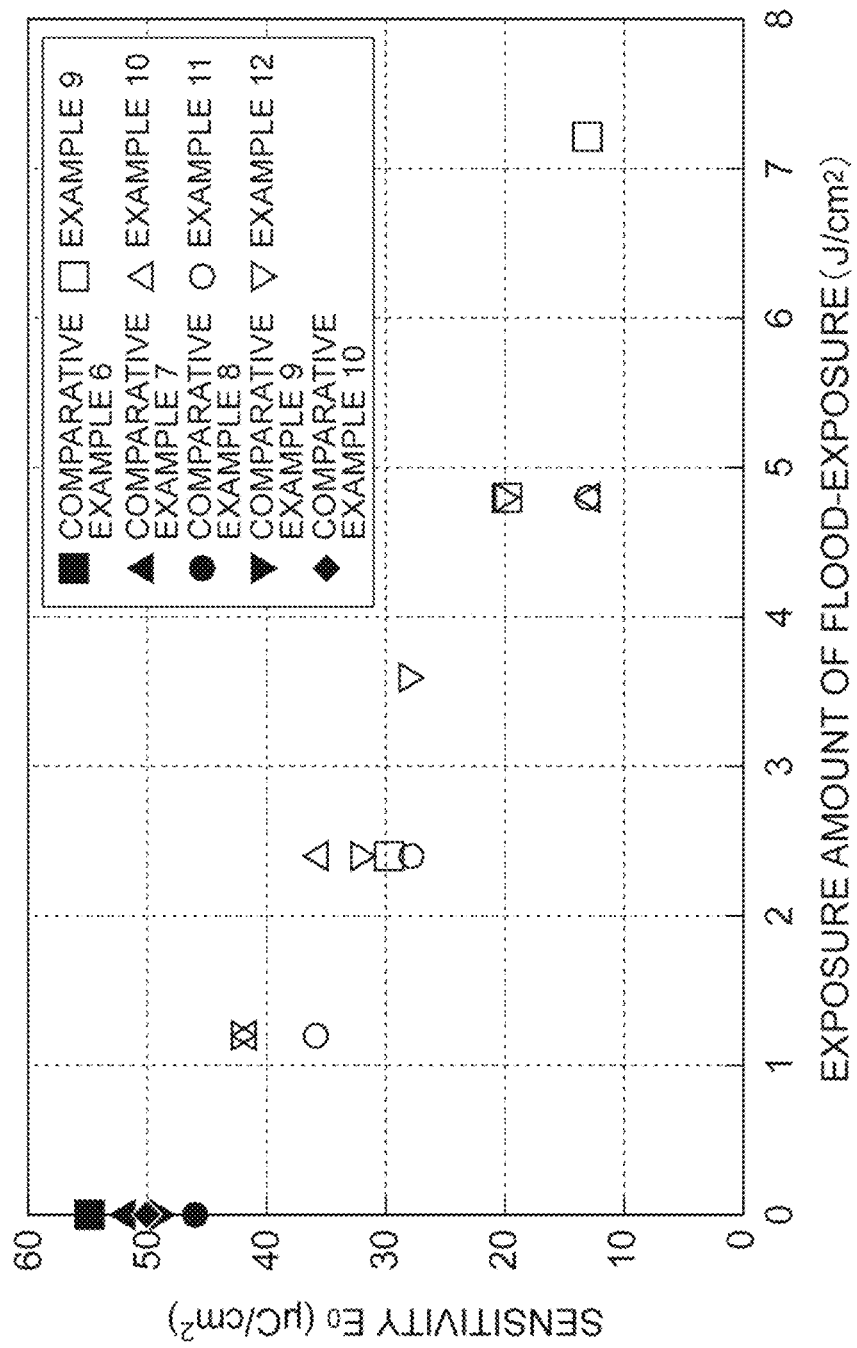
FIG. 12 is a graph showing a relationship between sensitivity and an exposure amount of flood-exposure in resist materials obtained in Examples 9 to 12 and Comparative Examples 6 to 10.

The sensitivities ($E_0$) of Examples 9 to 12 and Comparative Examples 6 to 10 were calculated in the same manner as in Example 1. FIG. 12 is a graph plotted by showing the dose of the sensitivity ($E_0$) during the pattern-exposure in each of the examples and Comparative Examples on the ordinate and showing the exposure amount of the flood-exposure in each of the examples and Comparative Examples on the abscissa. The graph shows a relationship between the sensitivity and the exposure amount. As is evident from FIG. 12, in Comparative Examples 6 to 10 in which flood-exposure was not performed, the value of the sensitivity $E_0$ (the exposure amount of pattern-exposure necessary for the ratio of a residual film to become zero (0)) was great. In contrast, in Examples 9 to 12 in which flood-exposure was performed, as the exposure amount of the flood-exposure increased, the value of the sensitivity $E_0$ was reduced.

<Evaluation of Lithography Characteristics>

Figure 13A:
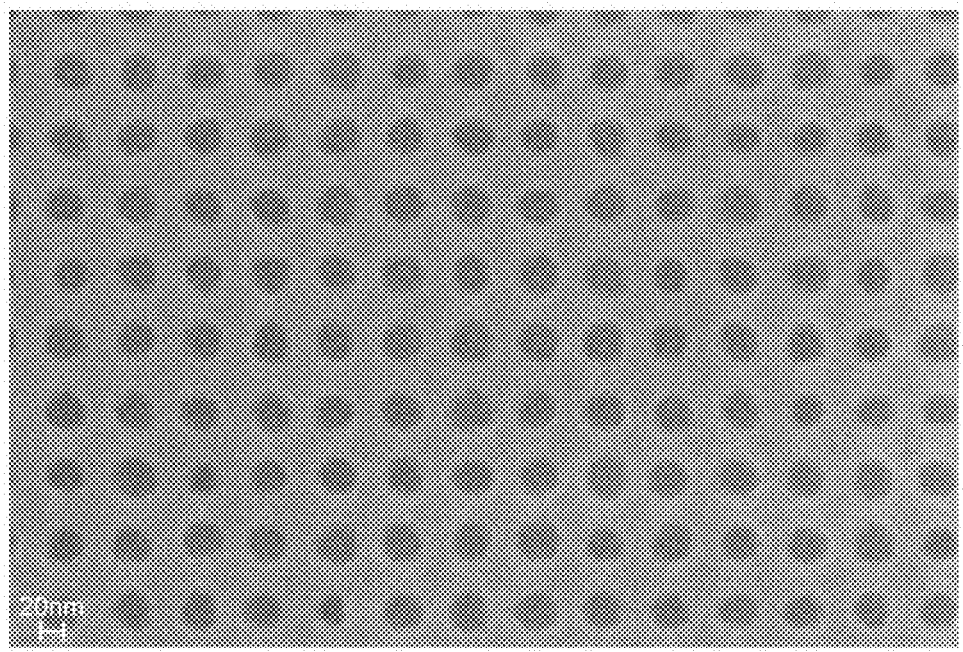
FIG. 13A is an SEM image of a resist pattern obtained in Comparative Example 6.
Figure 13B:
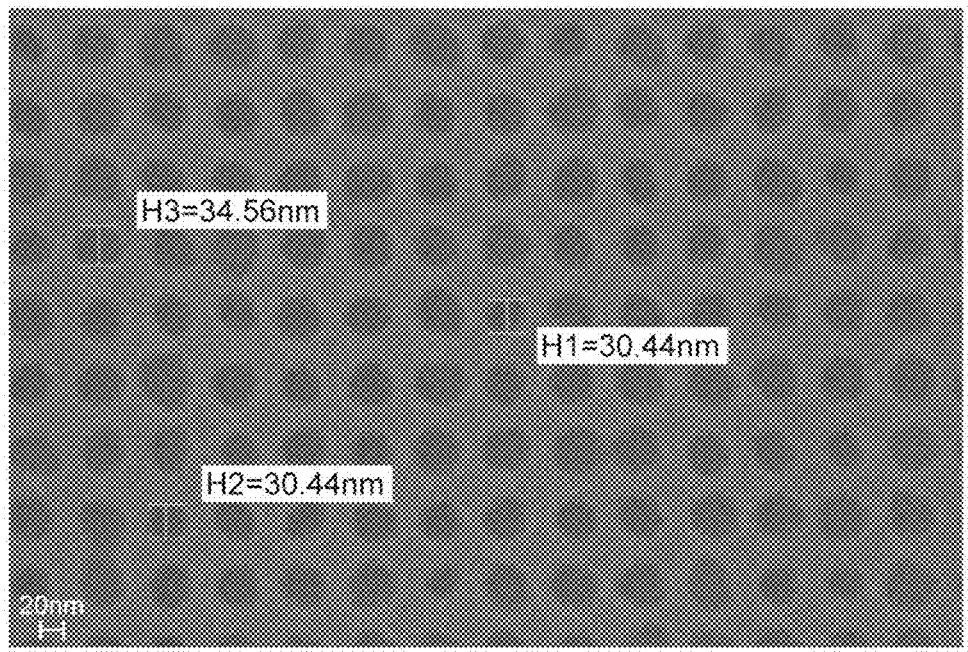
FIG. 13B is an SEM image of a resist pattern obtained in Example 9 by setting the exposure amount of flood-exposure to be 7.2 J/cm$^2$.

Within the resist patterns obtained in Example 9 and Comparative Example 6, the portions developed for contact holes having a diameter of 30 nm and a pitch of 60 nm were observed using a high-resolution scanning electron microscope (SEM, trade name: NVision 40D, manufactured by Carl Zeiss). FIG. 13A is an SEM image of the resist pattern obtained in Comparative Example 6, and FIG. 13B is an SEM image of the resist pattern obtained in Example 9 by setting the exposure amount of flood-exposure to be 7.2 J/cm². In all of the resist patterns, resist patterns for contact holes having a diameter of fairly close to 30 nm were formed with excellent regularity while maintaining a pitch of 60 nm. Herein, in Example 9 and Comparative Example 6, the exposure amount (sensitivity $E_{size}$) at the time when the ratio of a residual resist material film for forming a resist pattern for contact holes having a diameter of 30 nm became zero (0) was 70 μC/cm² and 120 μC/cm² respectively. Therefore, it was confirmed that due to the flood-exposure, the exposure amount (value of the sensitivity $E_{size}$) necessary for the ratio of a residual film to become zero (0) in a state of maintaining resolution could be reduced by about half.

REFERENCE SIGNS LIST

1 ... semiconductor wafer, 2 ... resist pattern, 3 ... film to be etched, 10 ... patterned substrate.

The invention claimed is:

1. A photosensitization chemical-amplification type resist material used as a photosensitive resin composition in a lithography process including a pattern-exposure step of irradiating a predetermined site of a resist material film formed using the photosensitive resin composition with ionizing radiation or non-ionizing radiation having a wavelength of equal to or less than 400 nm, a flood-exposure step of irradiating the resist material film having undergone the pattern-exposure step with non-ionizing radiation having a wavelength which is longer than the wavelength of the non-ionizing radiation used in the pattern-exposure and is greater than 200 nm, a baking step of heating the resist material film having undergone the flood-exposure step, and a developing step of forming a resist pattern by bringing the resist material film having undergone the baking step into contact with a developer, the photosensitization chemical-amplification type resist material comprising:

(1) a base component which makes a portion subjected to the pattern-exposure soluble or insoluble in the developer after the baking step; and (2) a component generating a photosensitizer and an acid through exposure; and (3) a photodecomposition-type scavenger as a first scavenger capturing an acid and a cation, wherein the component (2) is the following component (a), contains any two components among the following components (a) to (c), or contains all of the following components (a) to (c), (a) an acid-photosensitizer generator generating an acid and a photosensitizer, which absorbs non-ionizing radiation having a wavelength of greater than 200 nm, by being irradiated with ionizing radiation or non-ionizing radiation having a wavelength of equal to or less than 400 nm, (b) a photosensitizer precursor becoming a photosensitizer, which absorbs non-ionizing radiation having a wavelength of greater than 200 nm, by being irradiated with ionizing radiation or non-ionizing radiation having a wavelength of equal to or less than 400 nm, and (c) a photoacid generator generating an acid by being irradiated with ionizing radiation or non-ionizing radiation having a wavelength of equal to or less than 400 nm, wherein the component (b) includes a ketal compound or an acetal compound represented by the following Formula (XXXVI),

(XXXVI)

wherein, in the Formula (XXXVI), each of $R^9$ and $R^{10}$ independently represents a hydrogen atom; a phenyl group; a naphthyl group; an anthracenyl group; an alkoxy group having 1 to 5 carbon atoms; an alkylthio group having 1 to 5 carbon atoms; a phenoxy group; a naphthoxy group; an anthracenoxy group; an amino group; an amide group; a linear, branched or cyclic and saturated or unsaturated hydrocarbon group having 1 to 30 carbon atoms; an alkoxy group having 1 to 5 carbon atoms substituted with a linear, branched or cyclic and saturated or unsaturated hydrocarbon group having 1 to 30 carbon atoms, an alkoxy group having 1 to 5 carbon atoms, an amino group, an amide group, or a hydroxyl group; an alkylthio group having 1 to 5 carbon atoms substituted with a linear, branched or cyclic and saturated or unsaturated hydrocarbon group having 1 to 30 carbon atoms, an alkoxy group having 1 to 5 carbon atoms, an amino group, an amide group, or a hydroxyl group; a phenoxy group substituted with an alkoxy group having 1 to 5 carbon atoms, a hydroxyl group, an amino group, an amide group, or an alkyl group having 1 to 5 carbon atoms; a phenyl group substituted with a linear, branched or cyclic and saturated or unsaturated hydrocarbon group having 1 to 30 carbon atoms, an alkoxy group having 1 to 5 carbon atoms, an amino group, an amide group, or a hydroxyl group; a naphthoxy group substituted with an alkoxy group having 1 to 5 carbon atoms, an alkyl group having 1 to 5 carbon atoms, an amino group, an amide group, or a hydroxyl group; an anthracenoxy group substituted with an alkoxy group having 1 to 5 carbon atoms, an alkyl group having 1 to 5 carbon atoms, an amino group, an amide group, or a hydroxyl group; a linear, branched or cyclic and saturated or unsaturated hydrocarbon group having 1 to 30 carbon atoms substituted with an alkoxy group having 1 to 5 carbon atoms, a phenoxy group, a naphthoxy group, an anthracenoxy group, an amino group, an amide group, or a hydroxyl group; or a carbonyl group to which an alkyl group having 1 to 12 carbon atoms is bonded, in the Formula (XXXVI), each of $R^{23}$ and $R^{24}$ independently represents a phenyl group; a linear, branched or cyclic and saturated or unsaturated hydrocarbon group having 1 to 30 carbon atoms; or a phenyl group substituted with a linear, branched or cyclic and saturated or unsaturated hydrocarbon group having 1 to 30 carbon atoms, an alkoxy group having 1 to 5 carbon atoms, or a hydroxyl group, in the Formula (XXXVI), $R^9$ and $R^{10}$ or $R^{23}$ and $R^{24}$ may form a cyclic structure through a single bond, a double bond, or a bond containing —$CH_2$—, —O—, —S—, —$SO_2$—, —$SO_2NH$—, —C(=O)—, —C(=O)O—, —NHCO—, —NHC(=O)NH—, —$CHR^g$—, —$CR^g_2$—, —NH—, or —$NR^g$—; and $R^g$ represents a phenyl group; a phenoxy group; a halogen atom; a linear, branched or cyclic and saturated or unsaturated hydrocarbon group having 1 to 30 carbon atoms; a phenoxy group substituted with an alkoxy group having 1 to 5 carbon atoms, a hydroxyl group, or an alkyl group having 1 to 5 carbon atoms; or a phenyl group substituted with a linear, branched or cyclic and saturated or unsaturated hydrocarbon group having 1 to 30 carbon atoms, an alkoxy group having 1 to 5 carbon atoms, or a hydroxyl group.

2. The resist material according to claim 1, wherein the photosensitizer generated from the component (2) through exposure contains a carbonyl compound.

3. The resist material according to claim 2, wherein the carbonyl compound is at least one compound selected from the group consisting of benzophenone derivatives, xanthone derivatives, thioxanthone derivatives, coumarin derivatives, and acridone derivatives.

4. The resist material according to claim 2, wherein the carbonyl compound is an acridone derivative.

5. The resist material according to claim 2, wherein the carbonyl compound is a naphthalene derivative or an anthracene derivative.

6. The resist material according to claim 1, wherein the component (a) contains at least one compound selected from the group consisting of sulfonium salt compounds represented by the following Formulae (I) to (III),

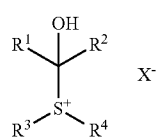

(I)

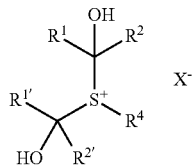

(II)

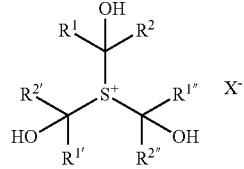

(III)

wherein, in the Formulae (I) to (III), each of $R^1$, $R^2$, $R^{1'}$, $R^{2'}$, $R^{1''}$, and $R^{2''}$ independently represents a hydrogen atom; a phenyl group; a naphthyl group; an anthracenyl group; a phenoxy group; a naphthoxy group; an anthracenoxy group; an amino group; an amide group; a halogen atom; a linear, branched or cyclic and saturated or unsaturated hydrocarbon group having 1 to 30 carbon atoms; a phenoxy group substituted with an alkoxy group having 1 to 5 carbon atoms, a hydroxyl group, an amino group, an amide group, or an alkyl group having 1 to 5 carbon atoms; a phenyl group substituted with a linear, branched or cyclic and saturated or unsaturated hydrocarbon group having 1 to 30 carbon atoms, an alkoxy group having 1 to 5 carbon atoms, an amino group, an amide group, or a hydroxyl group; a naphthoxy group substituted with an alkoxy group having 1 to 5 carbon atoms, an alkyl group having 1 to 5 carbon atoms, an amino group, an amide group, or a hydroxyl group; an anthracenoxy group substituted with an alkoxy group having 1 to 5 carbon atoms, an alkyl group having 1 to 5 carbon atoms, an amino group, an amide group, or a hydroxyl group; a linear, branched or cyclic and saturated or unsaturated hydrocarbon group having 1 to 30 carbon atoms substituted with an alkoxy group having 1 to 5 carbon atoms, a phenoxy group, a naphthoxy group, an anthracenoxy group, an amino group, an amide group, or a hydroxyl group; or a carbonyl group to which an alkyl group having 1 to 12 carbon atoms is bonded, in the Formulae (I) to (III), $R^3$ and $R^4$ independently represents a phenyl group; a naphthyl group; an anthracenyl group; a phenoxy group; a naphthoxy group; an anthracenoxy group; an amino group; an amide group; a linear, branched or cyclic and saturated or unsaturated hydrocarbon group having 1 to 30 carbon atoms; a phenoxy group substituted with an alkoxy group having 1 to 5 carbon atoms, a hydroxyl group, an amino group, an amide group, or an alkyl group having 1 to 5 carbon atoms; a phenyl group substituted with a linear, branched or cyclic and saturated or unsaturated hydrocarbon group having 1 to 30 carbon atoms, an alkoxy group having 1 to 5 carbon atoms, an amino group, an amide group, or a hydroxyl group; a naphthoxy group substituted with an alkoxy group having 1 to 5 carbon atoms, an alkyl group having 1 to 5 carbon atoms, an amino group, an amide group, or a hydroxyl group; an anthracenoxy group substituted with an alkoxy group having 1 to 5 carbon atoms, an alkyl group having 1 to 5 carbon atoms, an amino group, an amide group, or a hydroxyl group; a linear, branched or cyclic and saturated or unsaturated hydrocarbon group having 1 to 30 carbon atoms substituted with an alkoxy group having 1 to 5 carbon atoms, a phenoxy group, a naphthoxy group, an anthracenoxy group, an amino group, an amide group, or a hydroxyl group; or a carbonyl group to which an alkyl group having 1 to 12 carbon atoms is bonded, in the Formulae (I) to (III), the hydrogen atom of the hydroxyl group may be substituted with a phenyl group; a linear, branched or cyclic and saturated or unsaturated hydrocarbon group having 1 to 30 carbon atoms; or a phenyl group substituted with a linear, branched or cyclic and saturated or unsaturated hydrocarbon group having 1 to 30 carbon atoms, an alkoxy group having 1 to 5 carbon atoms, or a hydroxyl group, in the Formulae (I) to (III), any two or more groups among $R^1$, $R^2$, $R^{1'}$, $R^{2'}$, $R^{1''}$, $R^{2''}$, $R^3$, and $R^4$ may form a cyclic structure by being bonded to each other through a single bond, a double bond, or a bond containing —$CH_2$—, —O—, —S—, —$SO_2$—, —$SO_2NH$—, —C(=O)—, —C(=O)O—, —NHCO—, —NHC(=O)NH—, —$CR^e_2$—, —NH—, or —$NR^e$—, and $R^e$ represents a phenyl group; a phenoxy group; a halogen atom; a linear, branched or cyclic and saturated or unsaturated hydrocarbon group having 1 to 30 carbon atoms; a phenoxy group substituted with an alkoxy group having 1 to 5 carbon atoms, a hydroxyl group, or an alkyl group having 1 to 5 carbon atoms; or a phenyl group substituted with a linear, branched or cyclic and saturated or unsaturated hydrocarbon group having 1 to 30 carbon atoms, an alkoxy group having 1 to 5 carbon atoms, or a hydroxyl group, in the Formulae (I) to (III), $X^-$ represents an acid anion.

7. The resist material according to claim 1,
wherein the component (a) contains at least one of iodonium salt compounds represented by the following Formulae (IV) and (V),

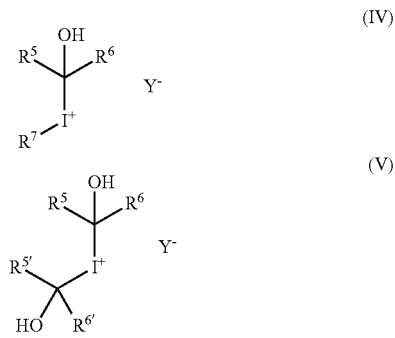

wherein, in the Formulae (IV) and (V), each of $R^5$, $R^6$, $R^{5'}$, and $R^{6'}$ independently represents a hydrogen atom; a phenyl group; a naphthyl group; an anthracenyl group; a phenoxy group; a naphthoxy group; an anthracenoxy group; an amino group; an amide group; a halogen atom; a linear, branched or cyclic and saturated or unsaturated hydrocarbon group having 1 to 30 carbon atoms; a phenoxy group substituted with an alkoxy group having 1 to 5 carbon atoms, a hydroxyl group, an amino group, an amide group, or an alkyl group having 1 to 5 carbon atoms; a phenyl group substituted with a linear, branched or cyclic and saturated or unsaturated hydrocarbon group having 1 to 30 carbon atoms, an alkoxy group having 1 to 5 carbon atoms, an amino group, an amide group, or a hydroxyl group; a naphthoxy group substituted with an alkoxy group having 1 to 5 carbon atoms, an alkyl group having 1 to 5 carbon atoms, an amino group, an amide group, or a hydroxyl group; an anthracenoxy group substituted with an alkoxy group having 1 to 5 carbon atoms, an alkyl group having 1 to 5 carbon atoms, an amino group, an amide group, or a hydroxyl group; a linear, branched or cyclic and saturated or unsaturated hydrocarbon group having 1 to 30 carbon atoms substituted with an alkoxy group having 1 to 5 carbon atoms, a phenoxy group, a naphthoxy group, an anthracenoxy group, an amino group, an amide group, or a hydroxyl group; or a carbonyl group to which an alkyl group having 1 to 12 carbon atoms is bonded, in the Formulae (IV) and (V), $R^7$ represents a phenyl group; a naphthyl group; an anthracenyl group; a phenoxy group; a naphthoxy group; an anthracenoxy group; an amino group; an amide group; a linear, branched or cyclic and saturated or unsaturated hydrocarbon group having 1 to 30 carbon atoms; a phenoxy group substituted with an alkoxy group having 1 to 5 carbon atoms, a hydroxyl group, an amino group, an amide group, or an alkyl group having 1 to 5 carbon atoms; a phenyl group substituted with a linear, branched or cyclic and saturated or unsaturated hydrocarbon group having 1 to 30 carbon atoms, an alkoxy group having 1 to 5 carbon atoms, an amino group, an amide group, or a hydroxyl group; a naphthoxy group substituted with an alkoxy group having 1 to 5 carbon atoms, an alkyl group having 1 to 5 carbon atoms, an amino group, an amide group, or a hydroxyl group; an anthracenoxy group substituted with an alkoxy group having 1 to 5 carbon atoms, an alkyl group having 1 to 5 carbon atoms, an amino group, an amide group, or a hydroxyl group; a linear, branched or cyclic and saturated or unsaturated hydrocarbon group having 1 to 30 carbon atoms substituted with an alkoxy group having 1 to 5 carbon atoms, a phenoxy group, a naphthoxy group, an anthracenoxy group, an amino group, an amide group, or a hydroxyl group; or a carbonyl group to which an alkyl group having 1 to 12 carbon atoms is bonded, in the Formulae (IV) and (V), the hydrogen atom of the hydroxyl group may be substituted with a phenyl group; a linear, branched or cyclic and saturated or unsaturated hydrocarbon group having 1 to 30 carbon atoms; or a phenyl group substituted with a linear, branched or cyclic and saturated or unsaturated hydrocarbon group having 1 to 30 carbon atoms, an alkoxy group having 1 to 5 carbon atoms, or a hydroxyl group, in the Formulae (IV) and (V), any two or more groups among $R^5$, $R^6$, $R^{5'}$, $R^{6'}$, and $R^7$ may form a cyclic structure through a single bond, a double bond, or a bond containing —$CH_2$—, —O—, —S—, —$SO_2$—, —$SO_2NH$—, —C(=O)—, —C(=O)O—, —NHCO—, —NHC(=O)NH—, —NH—, or —$NR^f$—, and $R^f$ represents a phenyl group; a phenoxy group; a halogen atom; a linear, branched or cyclic and saturated or unsaturated hydrocarbon group having 1 to 30 carbon atoms; a phenoxy group substituted with an alkoxy group having 1 to 5 carbon atoms, a hydroxyl group, or an alkyl group having 1 to 5 carbon atoms; or a phenyl group substituted with a linear, branched or cyclic and saturated or unsaturated hydrocarbon group having 1 to 30 carbon atoms, an alkoxy group having 1 to 5 carbon atoms, or a hydroxyl group, in the Formulae (IV) and (V), $Y^-$ represents an acid anion.

8. The resist material according to claim 1,
wherein the component (b) is at least one kind of compound selected from the group consisting of an acetal compound and a ketal compound represented by the following Formulae (XXVII) to (XXX),

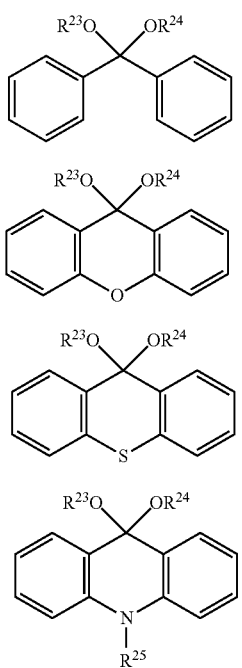

(XXVII)

(XXVIII)

(XXIX)

(XXX)

wherein, in the Formulae (XXVII) to (XXX), each of $R^{23}$ and $R^{24}$ independently represents a phenyl group; a linear, branched or cyclic and saturated or unsaturated hydrocarbon group having 1 to 30 carbon atoms; or a phenyl group substituted with a linear, branched or cyclic and saturated or unsaturated hydrocarbon group having 1 to 30 carbon atoms, an alkoxy group having 1 to 5 carbon atoms, or a hydroxyl group, in the Formulae (XXVII) to (XXX), $R^{23}$ and $R^{24}$ may form a cyclic structure through a single bond, a double bond, or a bond containing —CH$_2$—, —O—, —S—, —SO$_2$—, —SO$_2$NH—, —C(=O)—, —C(=O)O—, —NHCO—, —NHC(=O)NH—, —CHR$^g$—, —CR$^g_2$—, —NH—, or —NR$^g$—, and R$^g$ represents a phenyl group; a phenoxy group; a halogen atom; a linear, branched or cyclic and saturated or unsaturated hydrocarbon group having 1 to 30 carbon atoms; a phenoxy group substituted with an alkoxy group having 1 to 5 carbon atoms, a hydroxyl group, or an alkyl group having 1 to 5 carbon atoms; or a phenyl group substituted with a linear, branched or cyclic and saturated or unsaturated hydrocarbon group having 1 to 30 carbon atoms, an alkoxy group having 1 to 5 carbon atoms, or a hydroxyl group, in the Formulae (XXVII) to (XXX), the hydrogen atom of the aromatic ring may be substituted with an alkoxy group having 1 to 5 carbon atoms or an alkyl group having 1 to 5 carbon atoms, and the aromatic ring may form a naphthalene ring or an anthracene ring by being bonded to another aromatic ring, in the Formulae (XXVII) to (XXX), $R^{25}$ represents an alkyl group having 1 to 5 carbon atoms.

9. The resist material according to claim 1,
wherein the component (c) contains at least one kind of compound selected from the group consisting of sulfonium salt compounds, iodonium salt compounds, sulfonyldiazomethane, N-sulfonyloxyimide, and an oxime-O-sulfonate type photoacid generators.

10. The resist material according to claim 1,
wherein the base component is a polymer compound containing at least one of constitutional units represented by the following Formulae (VII) and (VIII), a polymer compound containing a constitutional unit represented by the following Formula (XXV), or a polymer compound containing a constitutional unit represented by the following Formula (XXVI),

[Chemical Formula 11]

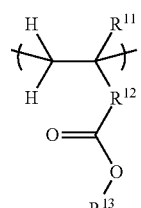

(VII)

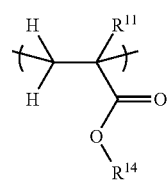

(VIII)

wherein, in the Formulae (VII) and (VIII), $R^{11}$ represents a hydrogen atom; a fluorine atom; a methyl group; a trifluoromethyl group; a linear, branched, or cyclic alkyl group having 1 to 20 carbon atoms that may have a hydroxyl group, an ether bond, an ester bond, or a lactone ring; a phenyl group; or a naphthyl group, in the Formulae (VII) and (VIII), $R^{12}$ represents a methylene group, a phenylene group, a naphthylene group, or a divalent group represented by (main chain) —C(=O)—O—R$^{12'}$—, in the Formulae (VII) and (VIII), each of $R^{13}$ and $R^{14}$ independently represents a hydrogen atom; a hydroxyl group; a cyano group; a carbonyl group; a carboxyl group; an alkyl group having 1 to 35 carbon atoms; or a protecting group having at least one structure selected from the group consisting of an ether bond, an ester bond, a sulfonic acid ester bond, a carbonate bond, a lactone ring, a sultone ring, and two carboxyl groups dehydrated,

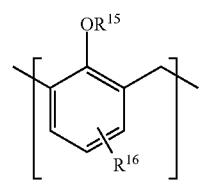

(XXV)

in the Formula (XXV), $R^{15}$ represents a hydrogen atom; a hydroxyl group; a cyano group; a carbonyl group; a carboxyl group; an alkyl group having 1 to 35 carbon atoms; or a protecting group having at least one structure selected from the group consisting of an ether bond, an ester bond, a sulfonic acid ester bond, a carbonate bond, a lactone ring, a sultone ring, and two carboxyl groups dehydrated, in the Formula (XXV), $R^{16}$ represents a hydrogen atom or an alkyl group having 1 to 35 carbon atoms,

[Chemical Formula 13]

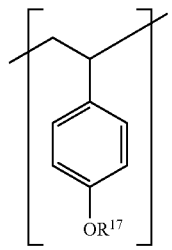

(XXVI)

in the Formula (XXVI), $R^{17}$ represents a hydrogen atom; a hydroxyl group; a cyano group; a carbonyl group; a carboxyl group; an alkyl group having 1 to 35 carbon atoms; or a protecting group having at least one structure selected from the group consisting of an ether bond, an ester bond, a sulfonic acid ester bond, a carbonate bond, a lactone ring, a sultone ring, and two carboxyl groups dehydrated.

11. The resist material according to claim 1, wherein the base component is an inorganic compound.

12. The resist material according to claim 1, wherein the first scavenger includes a basic compound.

13. The resist material according to claim 1, wherein the (3) first scavenger capturing an acid and a cation includes a photogeneration-type scavenger.

14. The resist material according to claim 1, further comprising (4) a second scavenger capturing free radicals.

15. The resist material according to claim 1 that is a negative resist material, further comprising (5) a cross-linking agent, wherein the cross-linking agent is methoxymethylated melamine or a methoxymethylated urea compound.

16. A photosensitization chemical-amplification type resist material used as a photosensitive resin composition in a lithography process including a pattern-exposure step of irradiating a predetermined site of a resist material film formed using the photosensitive resin composition with ionizing radiation or non-ionizing radiation having a wavelength of equal to or less than 400 nm, a flood-exposure step of irradiating the resist material film having undergone the pattern-exposure step with non-ionizing radiation having a wavelength which is longer than the wavelength of the non-ionizing radiation used in the pattern-exposure and is greater than 200 nm, a baking step of heating the resist material film having undergone the flood-exposure step, and a developing step of forming a resist pattern by bringing the resist material film having undergone the baking step into contact with a developer, the photosensitization chemical-amplification type resist material comprising:

(1') a base component which makes a portion subjected to the pattern-exposure soluble or insoluble in the developer after the baking step;
wherein the base component has only the following group (d), has any two groups among the following groups (d) to (f), or has all of the following groups (d) to (f),
(d) an acid-photosensitizer generating group, generating an acid, and a photosensitizer which absorbs non-ionizing radiation having a wavelength of greater than 200 nm, by being irradiated with ionizing radiation or non-ionizing radiation having a wavelength of equal to or less than 400 nm,
(e) a precursor group becoming a group having the function of a photosensitizer which absorbs non-ionizing radiation having a wavelength of greater than 200 nm by being irradiated with ionizing radiation or non-ionizing radiation having a wavelength of equal to or less than 400 nm, and
(f) a photo acid generating group generating an acid by being irradiated with ionizing radiation or non-ionizing radiation having a wavelength of equal to or less than 400 nm.

17. The resist material according to claim 16, wherein the group (d) contains at least one group selected from the group consisting of groups represented by the following Formulae (XIV) to (XVII),

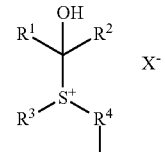

(XIV)

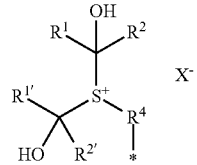

(XV)

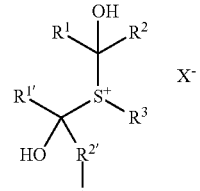

(XVI)

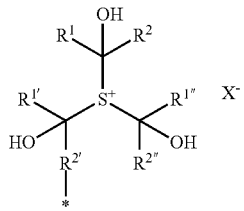

(XVII)

wherein, in the Formulae (XIV) to (XVII), each of $R^1$, $R^2$, $R^{1'}$, $R^{2'}$, $R^{1''}$, and $R^{2''}$ independently represents a hydrogen atom; a phenyl group; a naphthyl group; an anthracenyl group; a phenoxy group; a naphthoxy group; an anthracenoxy group; an amino group; an amide group; a halogen atom; a linear, branched or cyclic and saturated or unsaturated hydrocarbon group having 1 to 30 carbon atoms; a phenoxy group substituted with an alkoxy group having 1 to 5 carbon atoms, a hydroxyl group, an amino group, an amide group, or an alkyl group having 1 to 5 carbon atoms; a phenyl group substituted with a linear, branched or cyclic and saturated or unsaturated hydrocarbon group having 1 to 30 carbon atoms, an alkoxy group having 1 to 5 carbon atoms, an amino group, an amide group, or a hydroxyl group; a naphthoxy group substituted with an alkoxy group having 1 to 5 carbon atoms, an alkyl group having 1 to 5 carbon atoms, an amino group, an amide group, or a hydroxyl group; an anthracenoxy group substituted with an alkoxy group having 1 to 5 carbon atoms, an alkyl group having 1 to 5 carbon atoms, an amino group, an amide group, or a hydroxyl group; a linear, branched or cyclic and saturated or unsaturated hydrocarbon group having 1 to 30 carbon atoms substituted with an alkoxy group having 1 to 5 carbon atoms, a phenoxy group, a naphthoxy group, an anthracenoxy group, an amino group, an amide group, or a hydroxyl group; or a carbonyl group to which an alkyl group having 1 to 12 carbon atoms is bonded, in the Formulae (XIV) to (XVII), $R^3$ represents a phenyl group; a naphthyl group; an anthracenyl group; a phenoxy group; a naphthoxy group; an anthracenoxy group; an amino group; an amide group; a linear, branched or cyclic and saturated or unsaturated hydrocarbon group having 1 to 30 carbon atoms; a phenoxy group substituted with an alkoxy group having 1 to 5 carbon atoms, a hydroxyl group, an amino group, an amide group, or an alkyl group having 1 to 5 carbon atoms; a phenyl group substituted with a linear, branched or cyclic and saturated or unsaturated hydrocarbon group having 1 to 30 carbon atoms, an alkoxy group having 1 to 5 carbon atoms, an amino group, an amide group, or a hydroxyl group; a naphthoxy group substituted with an alkoxy group having 1 to 5 carbon atoms, an alkyl group having 1 to 5 carbon atoms, an amino group, an amide group, or a hydroxyl group; an anthracenoxy group substituted with an alkoxy group having 1 to 5 carbon atoms, an alkyl group having 1 to 5 carbon atoms, an amino group, an amide group, or a hydroxyl group; a linear, branched or cyclic and saturated or unsaturated hydrocarbon group having 1 to 30 carbon atoms substituted with an alkoxy group having 1 to 5 carbon atoms, a phenoxy group, a naphthoxy group, an anthracenoxy group, an amino group, an amide group, or a hydroxyl group; or a carbonyl group to which an alkyl group having 1 to 12 carbon atoms is bonded, in the Formulae (XIV) to (XVII), the hydrogen atom of the hydroxyl group may be substituted with a phenyl group; a linear, branched or cyclic and saturated or unsaturated hydrocarbon group having 1 to 30 carbon atoms; or a phenyl group substituted with a linear, branched or cyclic and saturated or unsaturated hydrocarbon group having 1 to 30 carbon atoms, an alkoxy group having 1 to 5 carbon atoms, or a hydroxyl group, in the Formulae (XIV) to (XVII), any two or more groups among $R^1$, $R^2$, $R^{1'}$, $R^{2'}$, $R^{1''}$, $R^{2''}$, $R^3$, and $R^4$ may form a cyclic structure through a single bond, a double bond, or a bond containing —$CH_2$—, —O—, —S—, —$SO_2$—, —$SO_2NH$—, —C(=O)—, —C(=O)O—, —NHCO—, —NHC(=O)NH—, —$CR^e_2$—, —NH—, or —$NR^e$, and $R^e$ represents a phenyl group; a phenoxy group; a halogen atom; a linear, branched or cyclic and saturated or unsaturated hydrocarbon group having 1 to 30 carbon atoms; a phenoxy group substituted with an alkoxy group having 1 to 5 carbon atoms, a hydroxyl group, or an alkyl group having 1 to 5 carbon atoms; or a phenyl group substituted with a linear, branched or cyclic and saturated or unsaturated hydrocarbon group having 1 to 30 carbon atoms, an alkoxy group having 1 to 5 carbon atoms, or a hydroxyl group, in the Formulae (XIV) to (XVII), * represents a binding portion to the (1') base component, and in a case where $R^{2'}$, and $R^{2''}$ in the formulae in the Formulae (XIV) to (XVII) have the binding portion described above, each of $R^{2'}$, $R^{2''}$, and $R^4$ independently represents a divalent group obtained by removing one hydrogen atom from a phenyl group; a naphthyl group; an anthracenyl group; a phenoxy group; a naphthoxy group; an anthracenoxy group; an amino group; a linear, branched or cyclic and saturated or unsaturated hydrocarbon group having 1 to 30 carbon atoms; a phenoxy group substituted with an alkoxy group having 1 to 5 carbon atoms, a hydroxyl group, an amino group, an amide group, or an alkyl group having 1 to 5 carbon atoms; a phenyl group substituted with a linear, branched or cyclic and saturated or unsaturated hydrocarbon group having 1 to 30 carbon atoms, an alkoxy group having 1 to 5 carbon atoms, an amino group, an amide group, or a hydroxyl group; a naphthoxy group substituted with an alkoxy group having 1 to 5 carbon atoms, an alkyl group having 1 to 5 carbon atoms, an amino group, an amide group, or a hydroxyl group; an anthracenoxy group substituted with an alkoxy group having 1 to 5 carbon atoms, an alkyl group having 1 to 5 carbon atoms, an amino group, an amide group, or a hydroxyl group; a linear, branched or cyclic and saturated or unsaturated hydrocarbon group having 1 to 30 carbon atoms substituted with an alkoxy group having 1 to 5 carbon atoms, a phenoxy group, a naphthoxy group, an anthracenoxy group, an amino group, an amide group, or a hydroxyl group; or a carbonyl group to which an alkyl group having 1 to 12 carbon atoms is bonded, in the Formulae (XIV) to (XVII), $X^-$ represents an acid anion.

18. The resist material according to claim 16,
wherein the group (d) contains at least one kind of group selected from the group consisting of groups represented by the following Formulae (XXXI) to (XXXIII),

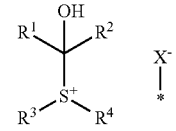

(XXXI)

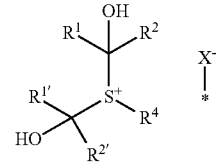

(XXXII)

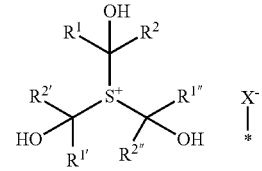

(XXXIII)

wherein, in the Formulae (XXXI) to (XXXIII), each of $R^1$, $R^2$, $R^{1'}$, $R^{2'}$, $R^{1'''}$, and $R^{2''}$ independently represents a hydrogen atom; a phenyl group; a naphthyl group; an anthracenyl group; a phenoxy group; a naphthoxy group; an anthracenoxy group; an amino group; an amide group; a halogen atom; a linear, branched or cyclic and saturated or unsaturated hydrocarbon group having 1 to 30 carbon atoms; a phenoxy group substituted with an alkoxy group having 1 to 5 carbon atoms, a hydroxyl group, an amino group, an amide group, or an alkyl group having 1 to 5 carbon atoms; a phenyl group substituted with a linear, branched or cyclic and saturated or unsaturated hydrocarbon group having 1 to 30 carbon atoms, an alkoxy group having 1 to 5 carbon atoms, an amino group, an amide group, or a hydroxyl group; a naphthoxy group substituted with an alkoxy group having 1 to 5 carbon atoms, an alkyl group having 1 to 5 carbon atoms, an amino group, an amide group, or a hydroxyl group; an anthracenoxy group substituted with an alkoxy group having 1 to 5 carbon atoms, an alkyl group having 1 to 5 carbon atoms, an amino group, an amide group, or a hydroxyl group; a linear, branched or cyclic and saturated or unsaturated hydrocarbon group having 1 to 30 carbon atoms substituted with an alkoxy group having 1 to 5 carbon atoms, a phenoxy group, a naphthoxy group, an anthracenoxy group, an amino group, an amide group, or a hydroxyl group; or a carbonyl group to which an alkyl group having 1 to 12 carbon atoms is bonded, in the Formulae (XXXI) to (XXXIII), each of $R^3$ and $R^4$ independently represents a phenyl group; a naphthyl group; an anthracenyl group; a phenoxy group; a naphthoxy group; an anthracenoxy group; an amino group; an amide group; a linear, branched or cyclic and saturated or unsaturated hydrocarbon group having 1 to 30 carbon atoms; a phenoxy group substituted with an alkoxy group having 1 to 5 carbon atoms, a hydroxyl group, an amino group, an amide group, or an alkyl group having 1 to 5 carbon atoms; a phenyl group substituted with a linear, branched or cyclic and saturated or unsaturated hydrocarbon group having 1 to 30 carbon atoms, an alkoxy group having 1 to 5 carbon atoms, an amino group, an amide group, or a hydroxyl group; a naphthoxy group substituted with an alkoxy group having 1 to 5 carbon atoms, an alkyl group having 1 to 5 carbon atoms, an amino group, an amide group, or a hydroxyl group; an anthracenoxy group substituted with an alkoxy group having 1 to 5 carbon atoms, an alkyl group having 1 to 5 carbon atoms, an amino group, an amide group, or a hydroxyl group; a linear, branched or cyclic and saturated or unsaturated hydrocarbon group having 1 to 30 carbon atoms substituted with an alkoxy group having 1 to 5 carbon atoms, a phenoxy group, a naphthoxy group, an anthracenoxy group, an amino group, an amide group, or a hydroxyl group; or a carbonyl group to which an alkyl group having 1 to 12 carbon atoms is bonded, in the Formulae (XXXI) to (XXXIII), the hydrogen atom of the hydroxyl group may be substituted with a phenyl group; a linear, branched or cyclic and saturated or unsaturated hydrocarbon group having 1 to 30 carbon atoms; or a phenyl group substituted with a linear, branched or cyclic and saturated or unsaturated hydrocarbon group having 1 to 30 carbon atoms, an alkoxy group having 1 to 5 carbon atoms, or a hydroxyl group, In the formulae, any two or more groups among $R^1$, $R^2$, $R^{1'}$, $R^{2'}$, $R^{1''}$, $R^{2''}$, $R^3$, and $R^4$ may form a cyclic structure through a single bond, a double bond, or a bond containing —CH$_2$—, —O—, —S—, —SO$_2$—, —SO$_2$NH—, —C(=O)—, —C(=O)O—, —NHCO—, —NHC(=O)NH—, —CR$^e_2$—, or —NR$^e$, and R$^e$ represents a phenyl group; a phenoxy group; a halogen atom; a linear, branched or cyclic and saturated or unsaturated hydrocarbon group having 1 to 30 carbon atoms; a phenoxy group substituted with an alkoxy group having 1 to 5 carbon atoms, a hydroxyl group, or an alkyl group having 1 to 5 carbon atoms; or a phenyl group substituted with a linear, branched or cyclic and saturated or unsaturated hydrocarbon group having 1 to 30 carbon atoms, an alkoxy group having 1 to 5 carbon atoms, or a hydroxyl group, in the Formulae (XXXI) to (XXXIII), X$^-$ represents an acid anion group, and * represents a binding portion to the (1') base component.

19. The resist material according to claim 16, wherein the group (d) contains at least one of groups represented by the following Formulae (XVIII) and (XIX),

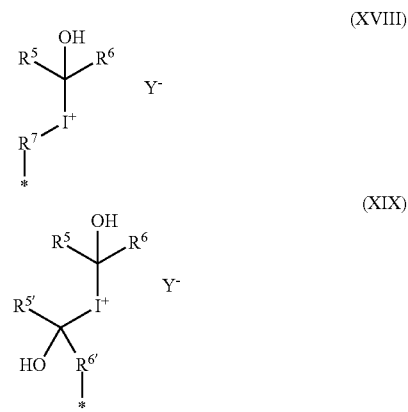

wherein, in the Formulae (XVIII) and (XIX), each of $R^5$, $R^6$, and $R^{5'}$ independently represents a hydrogen atom; a phenyl group; a naphthyl group; an anthracenyl group; a phenoxy group; a naphthoxy group; an anthracenoxy group; an amino group; an amide group; a halogen atom; a linear, branched or cyclic and saturated or unsaturated hydrocarbon group having 1 to 30 carbon atoms; a phenoxy group substituted with an alkoxy group having 1 to 5 carbon atoms, a hydroxyl group, an amino group, an amide group, or an alkyl group having 1 to 5 carbon atoms; a phenyl group substituted with a linear, branched or cyclic and saturated or unsaturated hydrocarbon group having 1 to 30 carbon atoms, an alkoxy group having 1 to 5 carbon atoms, an amino group, an amide group, or a hydroxyl group; a naphthoxy group substituted with an alkoxy group having 1 to 5 carbon atoms, an alkyl group having 1 to 5 carbon atoms, an amino group, an amide group, or a hydroxyl group; an anthracenoxy group substituted with an alkoxy group having 1 to 5 carbon atoms, an alkyl group having 1 to 5 carbon atoms, an amino group, an amide group, or a hydroxyl group; a linear, branched or cyclic and saturated or unsaturated hydrocarbon group having 1 to 30 carbon atoms substituted with an alkoxy group having 1 to 5 carbon atoms, a phenoxy group, a naphthoxy group, an anthracenoxy group, an amino group, an amide group, or a hydroxyl group; or a carbonyl group to which an alkyl group having 1 to 12 carbon atoms is bonded, in the Formulae (XVIII) and (XIX), the hydrogen atom of the hydroxyl group may be substituted with a phenyl group; a linear, branched or cyclic and saturated or unsaturated hydrocarbon group having 1 to 30 carbon atoms; or a phenyl group substituted with a linear, branched or cyclic and saturated or unsaturated hydrocarbon group having 1 to 30 carbon atoms, an alkoxy group having 1 to 5 carbon atoms, or a hydroxyl group, in the Formulae (XVIII) and (XIX), each of $R^{6'}$ and $R^7$ independently represents a divalent group obtained by removing one hydrogen atom from a phenyl group; a naphthyl group; an anthracenyl group; a phenoxy group; a naphthoxy group; an anthracenoxy group; an amino group; a linear, branched or cyclic and saturated or unsaturated hydrocarbon group having 1 to 30 carbon atoms; a phenoxy group substituted with an alkoxy group having 1 to 5 carbon atoms, a hydroxyl group, an amino group, an amide group, or an alkyl group having 1 to 5 carbon atoms; a phenyl group substituted with a linear, branched or cyclic and saturated or unsaturated hydrocarbon group having 1 to 30 carbon atoms, an alkoxy group having 1 to 5 carbon atoms, an amino group, an amide group, or a hydroxyl group; a naphthoxy group substituted with an alkoxy group having 1 to 5 carbon atoms, an alkyl group having 1 to 5 carbon atoms, an amino group, an amide group, or a hydroxyl group; an anthracenoxy group substituted with an alkoxy group having 1 to 5 carbon atoms, an alkyl group having 1 to 5 carbon atoms, an amino group, an amide group, or a hydroxyl group; a linear, branched or cyclic and saturated or unsaturated hydrocarbon group having 1 to 30 carbon atoms substituted with an alkoxy group having 1 to 5 carbon atoms, a phenoxy group, a naphthoxy group, an anthracenoxy group, an amino group, an amide group, or a hydroxyl group; or a carbonyl group to which an alkyl group having 1 to 12 carbon atoms is bonded, in the Formulae (XVIII) and (XIX), any two or more groups among $R^5$, $R^6$, $R^{5'}$, $R^{6'}$, and $R^7$ may form a cyclic structure through a single bond, a double bond, or a bond containing —$CH_2$—, —O—, —S—, —$SO_2$—, —$SO_2NH$—, —C(═O)—, —C(═O)O—, —NHCO—, —NHC(═O)NH—, —$CHR^f$—, —$CR^f_2$—, —NH—, or —$NR^f$—, and $R^f$ represents a phenyl group; a phenoxy group; a halogen atom; a linear, branched or cyclic and saturated or unsaturated hydrocarbon group having 1 to 30 carbon atoms; a phenoxy group substituted with an alkoxy group having 1 to 5 carbon atoms, a hydroxyl group, or an alkyl group having 1 to 5 carbon atoms; or a phenyl group substituted with a linear, branched or cyclic and saturated or unsaturated hydrocarbon group having 1 to 30 carbon atoms, an alkoxy group having 1 to 5 carbon atoms, or a hydroxyl group, in the Formulae (XVIII) and (XIX), $Y^-$ represents an acid anion, and * represents a binding portion to the (1') base component.

20. The resist material according to claim 16,
wherein the group (d) contains at least one of groups represented by the following Formulae (XXXIV) and (XXXV),

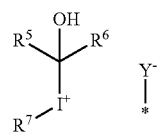

(XXXIV)

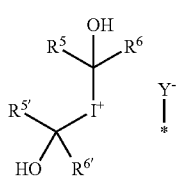

(XXXV)

wherein, in the Formulae (XXXIV) and (XXXV), each of $R^5$, $R^6$, $R^{5'}$, and $R^{6'}$ independently represents a hydrogen atom; a phenyl group; a naphthyl group; an anthracenyl group; a phenoxy group; a naphthoxy group; an anthracenoxy group; an amino group; an amide group; a halogen atom; a linear, branched or cyclic and saturated or unsaturated hydrocarbon group having 1 to 30 carbon atoms; a phenoxy group substituted with an alkoxy group having 1 to 5 carbon atoms, a hydroxyl group, an amino group, an amide group, or an alkyl group having 1 to 5 carbon atoms; a phenyl group substituted with a linear, branched or cyclic and saturated or unsaturated hydrocarbon group having 1 to 30 carbon atoms, an alkoxy group having 1 to 5 carbon atoms, an amino group, an amide group, or a hydroxyl group; a naphthoxy group substituted with an alkoxy group having 1 to 5 carbon atoms, an alkyl group having 1 to 5 carbon atoms, an amino group, an amide group, or a hydroxyl group; an anthracenoxy group substituted with an alkoxy group having 1 to 5 carbon atoms, an alkyl group having 1 to 5 carbon atoms, an amino group, an amide group, or a hydroxyl group; a linear, branched or cyclic and saturated or unsaturated hydrocarbon group having 1 to 30 carbon atoms substituted with an alkoxy group having 1 to 5 carbon atoms, a phenoxy group, a naphthoxy group, an anthracenoxy group, an amino group, an amide group, or a hydroxyl group; or a carbonyl group to which an alkyl group having 1 to 12 carbon atoms is bonded, in the Formulae (XXXIV) and (XXXV), the hydrogen atom of the hydroxyl group may be substituted with a phenyl group; a linear, branched or cyclic and saturated or unsaturated hydrocarbon group having 1 to 30 carbon atoms; or a phenyl group substituted with a linear, branched or cyclic and saturated or unsaturated hydrocarbon group having 1 to 30 carbon atoms, an alkoxy group having 1 to 5 carbon atoms, or a hydroxyl group, in the Formulae (XXXIV) and (XXXV), any two or more groups among $R^5$, $R^6$, $R^{5'}$, $R^{6'}$, and $R^7$ may form a cyclic structure through a single bond, a double bond, or a bond containing —$CH_2$—, —O—, —S—, —$SO_2$—, —$SO_2NH$—, —C(═O)—, —C(═O)O—, —NHCO—, —NHC(═O)NH—, —$CHR^f$—, —$CR^f_2$—, —NH—, or —$NR^f$, and $R^f$ represents a phenyl group; a phenoxy group; a halogen atom; a linear, branched or cyclic and saturated or unsaturated hydrocarbon group having 1 to 30 carbon atoms; a phenoxy group substituted with an alkoxy group having 1 to 5 carbon atoms, a hydroxyl group, or an alkyl group having 1 to 5 carbon atoms; or a phenyl group substituted with a linear, branched or cyclic and saturated or unsaturated hydrocarbon group having 1 to 30 carbon atoms, an alkoxy group having 1 to 5 carbon atoms, or a hydroxyl group, in the Formulae (XXXIV) and (XXXV), Y⁻ represents an acid anion group, and * represents a binding portion to the (1') base component.

21. The resist material according to claim 16,
wherein the group (e) has a carbonyl compound group, and the carbonyl compound group remains bonded to the (1') base component after exposure.

22. The resist material according to claim 16,
wherein the group (f) has an acid anion, and the anion remains bonded to the (1') base component after exposure.

23. The photosensitization chemical-amplification type resist material according to claim 16, further comprising (2) a component generating a photosensitizer and an acid through exposure,
wherein the component (2) contains at least one component selected from the group consisting of the following components (a) to (c),
(a) an acid-photosensitizer generator generating an acid and a photosensitizer, which absorbs non-ionizing radiation having a wavelength of greater than 200 nm, by being irradiated with ionizing radiation or non-ionizing radiation having a wavelength of equal to or less than 400 nm,
(b) a photosensitizer precursor becoming a photosensitizer, which absorbs non-ionizing radiation having a wavelength of greater than 200 nm, by being irradiated with ionizing radiation or non-ionizing radiation having a wavelength of equal to or less than 400 nm, and
(c) a photoacid generator generating an acid by being irradiated with ionizing radiation or non-ionizing radiation having a wavelength of equal to or less than 400 nm.

24. A method for forming a pattern, comprising:
a film forming step of forming a resist material film formed using the resist material according to claim 1 on a substrate;
a pattern-exposure step of irradiating the resist material film with ionizing radiation or non-ionizing radiation having a wavelength of equal to or less than 400 nm through a mask;
a flood-exposure step of irradiating the resist material film having undergone the pattern-exposure step with non-ionizing radiation having a wavelength which is longer than the wavelength of the non-ionizing radiation in the pattern-exposure step and is greater than 200 nm;
a baking step of heating the resist material film having undergone the flood-exposure step; and
a step of bringing the resist material film having undergone the baking step into contact with a developer.

25. The method for forming a pattern according to claim 24, further comprising a baking step of heating the resist material film having undergone the pattern-exposure step, before the flood-exposure step.

26. The method for forming a pattern according to claim 24,
wherein the pattern-exposure step is performed using an exposure device having a projector lens by immersion lithography in which a liquid having a refractive index of equal to or greater than 1.0 is interposed between the resist material film and the projector lens.

27. The method for forming a pattern according to claim 24,
wherein in the film forming step, a protective film is additionally formed on the resist material film, and
the pattern-exposure step is performed using an exposure device having a projector lens by immersion lithography in which a liquid having a refractive index of equal to or greater than 1.0 is interposed between the protective film and the projector lens.

28. The method for forming a pattern according to claim 27,
wherein the protective film is an antireflection film or a film for improving reaction stability.

29. The method for forming a pattern according to claim 24,
wherein in the film forming step, a protective film which is an antireflection film or a film for improving reaction stability is additionally formed on the resist material film, and
the pattern-exposure step is performed by dry lithography.

30. The method for forming a pattern according to claim 24,
wherein in the film forming step, before the resist material film is formed on the substrate, an antireflection film or a film for improving resist adhesiveness or resist shape is formed on the substrate.

31. The method for forming a pattern according to claim 24, further comprising a step of forming an absorption film, which absorbs at least a portion of the wavelengths of the non-ionizing radiation that a photoacid generator directly absorbs, on the resist material film, before the flood-exposure step, such that the photoacid generator in the component (a) or (c), remaining in the resist material film having undergone the pattern-exposure step, is prevented from directly generating an acid by being irradiated with the non-ionizing radiation having a wavelength of greater than 200 nm in the flood-exposure step.

32. The method for forming a pattern according to claim 24,
wherein the flood-exposure step is performed in an air atmosphere by dry lithography.

33. The method for forming a pattern according to claim 24,
wherein the flood-exposure step is performed using an exposure device having a projector lens by immersion lithography in which a liquid, which absorbs at least a portion of the wavelengths of the non-ionizing radiation that a photoacid generator directly absorbs, is interposed between the resist material film and the projector lens, such that the photoacid generator in the component (a) or (c), remaining in the resist material film having undergone the pattern-exposure step, is prevented from directly generating an acid by being irradiated with the non-ionizing radiation having a wavelength of greater than 200 nm in the flood-exposure step.

34. The method for forming a pattern according to claim 24, further comprising a step of changing the atmosphere in which the resist material film is present to an atmosphere with reduced pressure or an inert atmosphere containing nitrogen or argon, after the pattern-exposure step, until the flood-exposure step.

35. The method for forming a pattern according to claim 24,
wherein either or both of the pattern-exposure step and the flood-exposure step are performed in an atmosphere with reduced pressure or an inert atmosphere containing nitrogen or argon.

36. The method for forming a pattern according to claim 24, further comprising a step of transporting the substrate from the exposure device performing the pattern-exposure step to the exposure device performing the flood-exposure step.

37. A semiconductor device manufactured using a pattern formed by the method for forming a pattern according to claim 24.

38. A mask for lithography manufactured using a pattern formed by the method for forming a pattern according to claim 24.

39. A template for nanoimprinting manufactured using a pattern formed by the method for forming a pattern according to claim 24.

40. A photosensitization chemical-amplification type resist material used as a photosensitive resin composition in a lithography process including a pattern-exposure step of irradiating a predetermined site of a resist material film formed using the photosensitive resin composition with ionizing radiation or non-ionizing radiation having a wavelength of equal to or less than 400 nm, a flood-exposure step of irradiating the resist material film having undergone the pattern-exposure step with non-ionizing radiation having a wavelength which is longer than the wavelength of the non-ionizing radiation used in the pattern-exposure and is greater than 200 nm, a baking step of heating the resist material film having undergone the flood-exposure step, and a developing step of forming a resist pattern by bringing the resist material film having undergone the baking step into contact with a developer, the photosensitization chemical-amplification type resist material comprising:
(1) a base component which makes a portion subjected to the pattern-exposure soluble or insoluble in the developer after the baking step;
(2) a component generating a photosensitizer and an acid through exposure; and
(3) a photodecomposition-type scavenger as a first scavenger capturing an acid and a cation,
wherein the component (2) is the following component (a), contains any two components among the following components (a) to (c), or contains all of the following components (a) to (c),
(a) an acid-photosensitizer generator generating an acid and a photosensitizer, which absorbs non-ionizing radiation having a wavelength of greater than 200 nm, by being irradiated with ionizing radiation or non-ionizing radiation having a wavelength of equal to or less than 400 nm,
(b) a photosensitizer precursor becoming a photosensitizer, which absorbs non-ionizing radiation having a wavelength of greater than 200 nm, by being irradiated with ionizing radiation or non-ionizing radiation having a wavelength of equal to or less than 400 nm, and
(c) a photoacid generator generating an acid by being irradiated with ionizing radiation or non-ionizing radiation having a wavelength of equal to or less than 400 nm,
wherein the component (b) includes an orthoester compound represented by the following Formula (XLVI),

(XLVI)

wherein, in the Formula (XLVI), $R^9$ represents a hydrogen atom; a phenyl group; a naphthyl group; an anthracenyl group; an alkoxy group having 1 to 5 carbon atoms; an alkylthio group having 1 to 5 carbon atoms; a phenoxy group; a naphthoxy group; an anthracenoxy group; an amino group; an amide group; a linear, branched or cyclic and saturated or unsaturated hydrocarbon group having 1 to 30 carbon atoms; an alkoxy group having 1 to 5 carbon atoms substituted with a linear, branched or cyclic and saturated or unsaturated hydrocarbon group having 1 to 30 carbon atoms, an alkoxy group having 1 to 5 carbon atoms, an amino group, an amide group, or a hydroxyl group; an alkylthio group having 1 to 5 carbon atoms substituted with a linear, branched or cyclic and saturated or unsaturated hydrocarbon group having 1 to 30 carbon atoms, an alkoxy group having 1 to 5 carbon atoms, an amino group, an amide group, or a hydroxyl group; a phenoxy group substituted with an alkoxy group having 1 to 5 carbon atoms, a hydroxyl group, an amino group, an amide group, or an alkyl group having 1 to 5 carbon atoms; a phenyl group substituted with a linear, branched or cyclic and saturated or unsaturated hydrocarbon group having 1 to 30 carbon atoms, an alkoxy group having 1 to 5 carbon atoms, an amino group, an amide group, or a hydroxyl group; a naphthoxy group substituted with an alkoxy group having 1 to 5 carbon atoms, an alkyl group having 1 to 5 carbon atoms, an amino group, an amide group, or a hydroxyl group; an anthracenoxy group substituted with an alkoxy group having 1 to 5 carbon atoms, an alkyl group having 1 to 5 carbon atoms, an amino group, an amide group, or a hydroxyl group; a linear, branched or cyclic and saturated or unsaturated hydrocarbon group having 1 to 30 carbon atoms substituted with an alkoxy group having 1 to 5 carbon atoms, a phenoxy group, a naphthoxy group, an anthracenoxy group, an amino group, an amide group, or a hydroxyl group; or a carbonyl group to which an alkyl group having 1 to 12 carbon atoms is bonded,
in the Formula (XLVI), each of $R^{38}$ to $R^{40}$ independently represents a phenyl group; a linear, branched or cyclic and saturated or unsaturated hydrocarbon group having 1 to 30 carbon atoms; or a phenyl group substituted with a linear, branched or cyclic and saturated or unsaturated hydrocarbon group having 1 to 30 carbon atoms, an alkoxy group having 1 to 5 carbon atoms, or a hydroxyl group,
in the Formula (XLVI), $R^{38}$ to $R^{40}$ may form a cyclic structure through a single bond, a double bond, or a bond containing —$CH_2$—, —O—, —S—, —$SO_2$—, —$SO_2NH$—, —C(=O)—, —C(=O)O—, —NHCO—, —NHC(=O)NH—, —$CHR^g$—, —$CR^g_2$—, —NH—, or —$NR^g$—, and $R^g$ represents a phenyl group; a phenoxy group; a halogen atom; a linear, branched or cyclic and saturated or unsaturated hydrocarbon group having 1 to 30 carbon atoms; a phenoxy group substituted with an alkoxy group having 1 to 5 carbon atoms, a hydroxyl group, or an alkyl group having 1 to 5 carbon atoms; or a phenyl group substituted with a linear, branched or cyclic and saturated or unsaturated hydrocarbon group having 1 to 30 carbon atoms, an alkoxy group having 1 to 5 carbon atoms, or a hydroxyl group.

41. A photosensitization chemical-amplification type resist material used as a photosensitive resin composition in a lithography process including a pattern-exposure step of irradiating a predetermined site of a resist material film formed using the photosensitive resin composition with ionizing radiation or non-ionizing radiation having a wavelength of equal to or less than 400 nm, a flood-exposure step of irradiating the resist material film having undergone the pattern-exposure step with non-ionizing radiation having a wavelength which is longer than the wavelength of the non-ionizing radiation used in the pattern-exposure and is greater than 200 nm, a baking step of heating the resist material film having undergone the flood-exposure step, and a developing step of forming a resist pattern by bringing the resist material film having undergone the baking step into contact with a developer, the photosensitization chemical-amplification type resist material comprising:

(1) a base component which makes a portion subjected to the pattern-exposure soluble or insoluble in the developer after the baking step;
(2) a component generating a photosensitizer and an acid through exposure; and
(3) a photodecomposition-type scavenger as a first scavenger capturing an acid and a cation,
wherein the component (2) is the following component (a), contains any two components among the following components (a) to (c), or contains all of the following components (a) to (c),
(a) an acid-photosensitizer generator generating an acid and a photosensitizer, which absorbs non-ionizing radiation having a wavelength of greater than 200 nm, by being irradiated with ionizing radiation or non-ionizing radiation having a wavelength of equal to or less than 400 nm,
(b) a photosensitizer precursor becoming a photosensitizer, which absorbs non-ionizing radiation having a wavelength of greater than 200 nm, by being irradiated with ionizing radiation or non-ionizing radiation having a wavelength of equal to or less than 400 nm, and
(c) a photoacid generator generating an acid by being irradiated with ionizing radiation or non-ionizing radiation having a wavelength of equal to or less than 400 nm,
wherein the component (b) includes an OBO ester compound represented by the following Formula (XLVII),

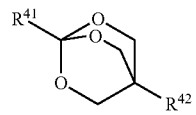

(XLVII)

wherein, in the Formula (XLVII), each of $R^{41}$ and $R^{42}$ independently represents a hydrogen atom; a phenyl group; a naphthyl group; an anthracenyl group; a phenoxy group; a naphthoxy group; an anthracenoxy group; an amino group; an amide group; a linear, branched or cyclic and saturated or unsaturated hydrocarbon group having 1 to 30 carbon atoms; a phenoxy group substituted with an alkoxy group having 1 to 5 carbon atoms, a hydroxyl group, an amino group, an amide group, or an alkyl group having 1 to 5 carbon atoms; a phenyl group substituted with a linear, branched or cyclic and saturated or unsaturated hydrocarbon group having 1 to 30 carbon atoms, an alkoxy group having 1 to 5 carbon atoms, an amino group, an amide group, or a hydroxyl group; a naphthoxy group substituted with an alkoxy group having 1 to 5 carbon atoms, an alkyl group having 1 to 5 carbon atoms, or a hydroxyl group; an anthracenoxy group substituted with an alkoxy group having 1 to 5 carbon atoms, an alkyl group having 1 to 5 carbon atoms, an amino group, an amide group, or a hydroxyl group; a linear, branched or cyclic and saturated or unsaturated hydrocarbon group having 1 to 30 carbon atoms substituted with an alkoxy group having 1 to 5 carbon atoms, a phenoxy group, a naphthoxy group, an anthracenoxy group, an amino group, an amide group, or a hydroxyl group; or a carbonyl group to which an alkyl group having 1 to 12 carbon atoms is bonded.

* * * * *